US012570639B2

(12) United States Patent
Asaba et al.

(10) Patent No.: US 12,570,639 B2
(45) Date of Patent: Mar. 10, 2026

(54) TETRAHYDROQUINOLINE DERIVATIVE AND MEDICINAL USE THEREOF

(71) Applicant: Toray Industries, Inc., Tokyo (JP)

(72) Inventors: Ken Nunettsu Asaba, Kamakura (JP); Takehiro Takahashi, Kamakura (JP); Masashi Yamamoto, Kamakura (JP); Kozue Takagaki, Kamakura (JP); Marina Nogami, Kamakura (JP); Riichiro Tsuji, Kamakura (JP); Hiroyuki Meguro, Kamakura (JP); Naoya Ukegawa, Kamakura (JP)

(73) Assignee: Toray Industries, Inc., Tokyo (JP)

( * ) Notice: Subject to any disclaimer, the term of this patent is extended or adjusted under 35 U.S.C. 154(b) by 420 days.

(21) Appl. No.: 18/268,667

(22) PCT Filed: Dec. 24, 2021

(86) PCT No.: PCT/JP2021/048081

§ 371 (c)(1),
(2) Date: Jun. 21, 2023

(87) PCT Pub. No.: WO2022/138888

PCT Pub. Date: Jun. 30, 2022

(65) Prior Publication Data

US 2024/0116903 A1 Apr. 11, 2024

(30) Foreign Application Priority Data

Dec. 25, 2020 (JP) ................................ 2020-215976

(51) Int. Cl.

| | |
|---|---|
| ***C07D 405/04*** | (2006.01) |
| ***A61P 37/02*** | (2006.01) |
| ***C07D 215/06*** | (2006.01) |
| ***C07D 401/04*** | (2006.01) |
| ***C07D 401/06*** | (2006.01) |
| ***C07D 413/04*** | (2006.01) |
| ***C07D 417/04*** | (2006.01) |

(52) U.S. Cl.

CPC ............ *C07D 405/04* (2013.01); *A61P 37/02* (2018.01); *C07D 215/06* (2013.01); *C07D 401/04* (2013.01); *C07D 401/06* (2013.01); *C07D 413/04* (2013.01); *C07D 417/04* (2013.01)

(58) Field of Classification Search

CPC .. C07D 405/04; C07D 215/06; C07D 401/04; C07D 401/06; C07D 413/04; C07D 417/04; A61P 37/02

See application file for complete search history.

(56) References Cited

U.S. PATENT DOCUMENTS

| | | | |
|---|---|---|---|
| 4,801,593 | A | 1/1989 | Hodson et al. |
| 5,359,076 | A | 10/1994 | Kohno et al. |
| 2007/0203167 | A1 | 8/2007 | Schiemann |
| 2008/0194615 | A1 | 8/2008 | Schiemann et al. |

FOREIGN PATENT DOCUMENTS

| | | | |
|---|---|---|---|
| CN | 1817863 | A | 8/2006 |
| CN | 110372614 | A | 10/2019 |
| CN | 110464727 | A | 11/2019 |
| CN | 111848675 | A | 10/2020 |
| DE | 102 36 910 | A1 | 3/2004 |
| JP | S56-51456 | A | 5/1981 |
| JP | H5-125052 | A | 5/1993 |
| WO | 2005/063735 | A1 | 7/2005 |
| WO | 2007/054138 | A1 | 5/2007 |
| WO | 2019/106434 | A1 | 6/2019 |
| WO | 2020/185738 | A1 | 9/2020 |

OTHER PUBLICATIONS

Wu, J Cell Mol Med, 2024;28:e18396, 1-16. (Year: 2024).*
Jian, Front Biosci (Landmark Ed) 2025, 30(1): 26265, 1-17. (Year: 2025).*
Gore, Bioorg & Med Chem Lett, vol. 20, 2010, 3573-3578. (Year: 2010).*
Extended European Search Report dated Jan. 7, 2025, from counterpart European Application No. EP 21911025.1.
Felicetti, T. et al., "Searching for Novel Inhibitors of the *S. aureus* NorA Efflux Pump: Synthesis and Biological Evaluation of the 3-Phenyl-1,4-benzothiazine Analogues," ChemMedChem, Wiley-VCH, DE, Jul. 2017, vol. 12, No. 16, pp. 1293-1302.
Li, X. et al., "Spiro-Bicyclic Bisborane Catalysts for Metal-Free Chemoselective and Enantioselective Hydrogenation of Quinolines," Angewandte Chemie International Edition, Verlag Chemie, Hoboken, USA, Mar. 5, 2019, vol. 58, No. 14, pp. 4664-4668.
Wang, Y. et al., "Silver-Catalyzed Reduction of Quinolines in Water," Organic Letters, May 7, 2019, vol. 21, No. 10, pp. 3631-3634.
Kaku, T. et al., "Atophan Derivatives. II. Reductions of 2-Anisyl- and 2-Phenylquionolines," Yakugaku Zasshi: Journal of the Pharmaceutical Society of Japan, Jan. 1, 1928, vol. 48, pp. 693-702. Machine Translation of Summary only.

(Continued)

*Primary Examiner* — D Margaret M Seaman
(74) *Attorney, Agent, or Firm* — DLA Piper LLP (US)

(57) ABSTRACT

A compound has a tetra-hydroquinoline skeleton, the compound having inhibitory action against ferroptosis, and exerting therapeutic or preventive effect on diseases, disorders or syndromes related to ferroptosis inhibition, such as multiple sclerosis. This disclosure provides a tetrahydroquinoline derivative represented by the following formula or a pharmaceutically acceptable salt thereof:

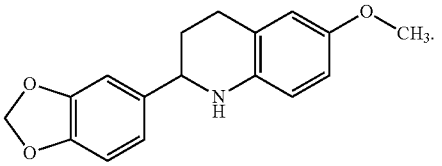

17 Claims, 3 Drawing Sheets

(56) References Cited

OTHER PUBLICATIONS

Lex Nagelkerken et al., "IL-4 abrogates the inhibitory effect of IL-10 on the development of experimental allergic encephalomyelitis in SJL mice," International Immunology, vol. 9, No. 9, pp. 1243-1251, May 13, 1997.
Juan M. Urbina et al., "Inhibitors of the fungal cell wall. Synthesis of 4-ary1-4-N-arylamine-1-butenes and related compounds with inhibitory activities on B(1-3) glucan and chitin synthases," Bioorganic & Medicinal Chemistry, vol. 8, Issue 4, pp. 691-698, Apr. 2000 (Abstract).
Leonor Y. Vargas M et al., "In vitro antifungal activity of new series of homoallylamines and related compounds with inhibitory properties of the synthesis of fungal cell wall polymers," Bioorganic & Medicinal Chemistry, vol. 11, Issue 7, pp. 1531-1550, Apr. 2003 (Abstract).
Owen B. Wallace et al., "Tetrahydroquinoline-Based selective estrogen receptor modulators (SERMS)," Bioorganic & Medicinal Chemistry Letters, vol. 13, Issue 11, pp. 1907-1910, Jun. 2, 2003 (Abstract).
Claudia Hindinger et al., "Liver X receptor activation decreases the severity of experimental autoimmune encephalomyelitis," Journal of Neuroscience Research, vol. 84, Issue 6, pp. 1225-1234, Sep. 5, 2006 (Abstract).
Hans Vander Mierde et al., "Base-mediated synthesis of quinolines: an unexpected cyclization reaction between 2-aminobenzylalcohol and ketones," Tetrahedron Letters, vol. 49, Issue 48, pp. 6893-6895, Nov. 24, 2008 (Abstract).
Leonor Y. Vargas Méndez et al., "Synthesis of New 4-Methyl-2-(4-pyridy1)-1,2,3,4-tetrahydroquinolines as Potent Antifungal Compounds," Journal of the Brazilian Chemical Society, vol. 21, No. 1, pp. 105-111, 2010.
Vijay K. Gore et al., "Structure-activity relationship (SAR) investigations of tetrahydroquinolines as BKCa agonists," Bioorgani & Medicinal Chemistry Letters, vol. 20, Issue 12, pp. 3573-3578, Jun. 15, 2010 (Abstract).
Scott J Dixon et al., "Ferroptosis: An Iron-Dependent Form of Nonapoptotic Cell Death," Cell 149, pp. 1060-1072, May 25, 2012.
Xin-Yuan Liu et al., "Highly regio-, diastereo- and enantioselective one-pot gold/chiral Brønsted acid-catalysed cascade synthesis of bioactive diversely substituted tetrahydroquinolines," Organic & Biomolecular Chemistry, vol. 10, No. 35, pp. 7208-7219, Sep. 21, 2012 (Abstract).
Jose Pedro Friedmann Angeli et al., "Inactivation of the ferroptosis regulator Gpx4 triggers acute renal failure in mice," Nature Cell Biology, vol. 16, pp. 1180-1191, Nov. 17, 2014 (Abstract).
Ganesh V. More et al., "Chiral phosphoric acid catalyzed asymmetric transfer hydrogenation of quinolines in a sustainable solvent," Tetrahedron: Asymmetry, vol. 26, Issue 20, pp. 1174-1179, Nov. 1, 2015 (Abstract).
Jennifer Yinuo Cao et al., "Mechanisms of ferroptosis," Cellular and Molecular Life Sciences, vol. 73, pp. 2195-2209, 2016.
Jingxiu Xu et al., "Palladium-catalyzed synthesis of quinolines from allyl alcohols and anilines," RSC Advances, vol. 7, pp. 36242-36245, Jul. 15, 2017.
Lars Devisscher et al., "Discovery of Novel, Drug-Like Ferroptosis Inhibitors with in Vivo Efficacy," Journal of Medicinal Chemistry, vol. 61, No. 22, pp. 10126-10140, Oct. 25, 2018 (Abstract).
Shinya Tsurusaki et al., "Hepatic Ferroptosis plays an important role as the trigger for initiating inflammation in nonalcoholic steatohepatitis," Cell Death and Disease, vol. 10, No. 449, pp. 1-14, 2019.
Che-Lin Hu et al., "Reduced expression of the ferroptosis inhibitor glutathione peroxidase-4 in multiple sclerosis and experimental autoimmune encephalomyelitis," Journal of Neurochemistry, vol. 148, pp. 426-439, 2019.
Xuexian Fang et al., "Ferroptosis as a target for protection against cardiomyopathy," Proceedings of the National Academy of Sciences of the United States of America, vol. 116, No. 7, pp. 2672-2680, Feb. 12, 2019 (Abstract).
Shashank Masaldan et al., "Striking while the iron is hot: Iron metabolism and ferroptosis in neurodegeneration," Free Radical Biology and Medicine, vol. 133, pp. 221-233, Mar. 2019 (Abstract).
Youran Liu et al., "Enantioselective synthesis of tunable chiral pyridine-aminophosphine ligands and their applications in asymmetric hydrogenation," Organic & Biomolecular Chemistry, vol. 17, Issue 20, pp. 5099-5105, May 28, 2019 (Abstract).
Yu-Zhen Li et al., "Reactions of the Lipid Hyroperoxides With Aminic Antioxidants: The Influence of Stereoelectronic and Resonance Effects on Hydrogen Atom Transfer," Frontiers in Chemistry, vol. 7, Article 850, pp. 1-11, Dec. 17, 2019.
Madeline Bross et al., "Approved and Emerging Disease Modifying Therapies on Neurodegeneration in Multiple Sclerosis," International Journal of Molecular Science, vol. 21, 4312, pp. 1-15, Jun. 17, 2020.
Hong-fa Yan et al., "Ferroptosis: mechanisms and links with diseases," Signal Transduction and Targeted Therapy, vol. 6, No. 49, pp. 1-16, 2021.
Hong-Xu Lei et al., "A quantum-chemical approach to develop tetrahydroquinoxaline as potent ferroptosis inhibitors," Journal of Molecular Structure, vol. 1228, 129485, Mar. 15, 2021 (Abstract).
International Search Report dated Feb. 15, 2022 in counterpart International Application No. PCT/JP2021/048081 w/English translation.
Written Opinion dated Feb. 15, 2022 in counterpart International Application No. PCT/JP2021/048081.
Masahiro Yoshida et al., "Involvement of cigarette smoke-induced epithelial cell ferroptosis in COPD pathogenesis," Nature Communications, vol. 10, pp. 1-14, 2019.

* cited by examiner

TETRAHYDROQUINOLINE DERIVATIVE AND MEDICINAL USE THEREOF

TECHNICAL FIELD

This disclosure relates to a tetrahydroquinoline derivative and pharmaceutical uses thereof.

BACKGROUND

Recently, various forms of regulated cell death have been discovered, and ferroptosis is reported as one of new cell deaths having the form of regulated cell death which is dependent on ferrous iron (Dixon et al., Cell, 2012, Vol. 149, pp 1060-10). Ferroptosis is a reaction in which antioxidative function is decreased by various stimuli such as reduction of intracellular glutathione amount or reduction of glutathione peroxidase 4 (GPX4), and a ferrous iron-dependent reaction progresses to increase intracellular lipid peroxides to a lethal level, thereby causing the cell death.

A relationship has been reported between inhibitory action against ferroptosis and therapeutic effects on kidney disease, amyotrophic lateral sclerosis, Parkinson's disease, Alzheimer's disease, Huntington's disease, non-alcoholic steatohepatitis, chronic obstructive pulmonary disease, Friedreich's ataxia, cardiomyopathy, and multiple sclerosis (Friedmann et al., Nature Cell Biology, 2014, Vol. 16, pp 1180-1191; Masaldan et al., Free Radical Biology and Medicine, 2019, Vol. 133, pp 221-233; Tsurusaki et al., Cell Death and Disease, 2019, Vol. 10, 449; Yoshida et al., Nature Communications, 2019, Vol. 10; and Xuexian et al., Proceedings of the National Academy of Sciences of the United States of America, 2019, Vol. 116, pp 2672-2680).

For example, multiple sclerosis, which is reported to reduce the level of GPX4 in the brain of patients and is suggested to have some relationship with ferroptosis, is characterized by demyelination which causes damage to the myelin sheath surrounding nerve fibers of the brain, spinal cord, optic nerve, and the like, and is a disease in which disturbances proceed during repeated cycles of relapse and remission. It has been known that multiple sclerosis shows different pathologies depending on the sites of lesion, including various neurological symptoms such as vision disturbances, quadriplegia, sensory disturbances, and gait disturbances (Madeline et al., International Journal of Molecular Sciences, 2020, Vol. 21, 4312 and Che-Lin et al., Journal of Neurochemistry, 2019, Vol. 148, pp 426-439).

Aniline derivatives such as ferrostatin-1 are known as compounds that show inhibitory action against ferroptosis (Dixon et al. and Lars et al., Journal of Medicinal Chemistry, 2018, Vol. 61, pp 10126-10140). Also, tetrahydroquinoxaline derivatives and 3,4-dihydro-2H-benzo-[1,4]oxazine derivatives are disclosed to have inhibitory action against ferroptosis (CN 110372614 A and CN 110464727 A).

It is reported that radical scavenging action is important to exert inhibitory action against ferroptosis (Jennifer Yinus Cao et al., Cellular and Molecular Life Science, 2016, Vol. 73, pp 2195-2209). Additionally, tetrahydroquinoxaline derivatives described in CN '614 are disclosed to have strong radical scavenging action and consequently to exert inhibitory action against ferroptosis (YTu-Zhen Li et al., Frontiers in Chemistry, 2019, Vol. 7, 850 and Hong-Xu Lei et al., Journal of Molecular Structure, 2021, Vol. 1228, 129485).

Moreover, tetrahydroquinoline derivatives with antiviral, antitumor, pain relief, or immunomodulatory actions are disclosed in JP S56-051456 A, WO 2007/054138, JP H5-125052 A, WO 2005/063735 and DE 10236910 A.

However, CN '614, CN '727, JP '456, WO '138, JP '052, WO '735 and DE '910 and Dixon et al., Friedmann et al., Masaldan et al., Tsurusaki et al., Yoshida et al., Xuexian et al., Madeline et al., Che-Lin et al., Lars et al., Jennifer Yinus Cao et al., Yu-Zhen Li et al. and Hong-Xu Lei et al., do not disclose the inhibitory action against ferroptosis of the tetrahydroquinoline derivatives, and do not suggest the possibility thereof.

Thus, it could be helpful to provide compounds having inhibitory action against ferroptosis and exerting therapeutic or preventive effect on diseases, disorders or syndromes related to ferroptosis inhibition such as multiple sclerosis.

SUMMARY

We intensively studied to solve the above problem and consequently found that compounds having a tetrahydroquinoline skeleton have inhibitory action against ferroptosis and a pharmacological action based on the inhibitory action, thereby completing this disclosure.

That is, this disclosure includes the following:

[1] A tetrahydroquinoline derivative represented by the general formula (I) below or a pharmaceutically acceptable salt thereof,

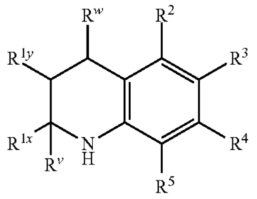

(I)

wherein $R^{1x}$ is hydrogen, phenyl (optionally, the phenyl group is substituted with a substituent as described below or forms a fused ring group as described below), or 5- or 6-membered heteroaryl selected from the group consisting of furyl, thienyl, pyrrolyl, imidazolyl, pyrazolyl, thiazolyl, isothiazolyl, oxazolyl, isoxazolyl, and pyridyl (the heteroaryl is optionally substituted with a substituent as described below);

$R^{1y}$ is hydrogen, 4-hydroxymethylphenyl, 4-aminocarbonylphenyl, 4-acetamidophenyl, 4-aminosulfonylphenyl, or 4-methylsulfonylphenyl (provided that $R^{1y}$ is a substituent other than hydrogen when $R^{1x}$ is hydrogen, or that $R^{1y}$ is hydrogen when $R^{1x}$ is a substituent other than hydrogen);

for the combination of $R^2$, $R^4$, and $R^5$, all of $R^2$, $R^4$, and $R^5$ represent hydrogen; otherwise, one of $R^2$ and $R^4$ is fluorine, chlorine, methoxy, or methyl in which one hydrogen atom is optionally replaced by a hydroxy group, and both the other and $R^5$ represent hydrogen; otherwise, both $R^2$ and $R^4$ represent hydrogen, and $R^5$ is fluorine or chlorine;

$R^3$ is hydrogen, halogen, $C_1$-$C_3$ alkyl in which any one to three hydrogen atoms are each independently optionally replaced by a hydroxy group(s) or a fluorine atom(s), 3-hydroxyoxetan-3-yl, hydroxy, $C_1$-$C_3$ alkoxy in which any one to three hydrogen atoms are optionally replaced by a fluorine atom(s), methoxycarbonyl, $—NR^9R^{10}$, $—CH_2NR^{11}R^{12}$, or $—CH_2CONR^{13}R^{14}$;

$R^v$ is hydrogen; and $R^w$ is hydrogen;

wherein, when $R^{1x}$ is phenyl (any one hydrogen atom in the phenyl group is optionally replaced by one substituent selected from the group consisting of halogen, $C_1$-$C_3$ alkyl in which any one to three hydrogen atoms are optionally replaced by a fluorine atom(s), $C_1$-$C_3$ alkoxy in which any one to three hydrogen atoms are optionally replaced by a fluorine atom(s), cyano, methoxycarbonyl, and —$NHCOR^8$, provided that m-cyanophenyl and p-(trifluoromethoxy)phenyl are excluded) or 5- or 6-membered heteroaryl (any one hydrogen atom in the 5- or 6-membered heteroaryl is optionally replaced by a $C_1$-$C_3$ alkyl or $C_1$-$C_3$ alkoxy group, provided that 1-methyl-1H-pyrazol-4-yl and 6-methoxypyridin-3-yl are excluded), $R^3$ is $C_1$-$C_3$ alkyl in which any one to three hydrogen atoms are replaced by a fluorine atom(s), $C_1$-$C_3$ alkyl in which any one hydrogen atom is replaced by a hydroxy group, ethyl, propyl, isopropyl, 3-hydroxyoxetan-3-yl, methoxy in which any one to three hydrogen atoms are replaced by a fluorine atom(s), methoxycarbonyl, —$NR^9R^{10}$, —$CH_2NR^{11}R^{12}$, or —$CH_2CONR^{13}R^{14}$ (wherein, when both $R^2$ and $R^4$ represent hydrogen and $R^5$ is fluorine or chlorine, $R^3$ is optionally hydrogen or fluorine, or when both $R^2$ and $R^5$ represent hydrogen and $R^4$ is fluorine or chlorine, $R^3$ is optionally fluorine, or when $R^2$ is methyl in which one hydrogen atom is optionally replaced by a hydroxy group, and both $R^4$ and $R^5$ represent hydrogen, $R^3$ is optionally hydrogen);

$R^8$ is hydrogen or $C_1$-$C_3$ alkyl;

$R^9$ is hydrogen;

$R^{10}$ is hydrogen, —$COR^{15}$, or $C_1$-$C_3$ alkylsulfonyl, or $R^9$ and $R^{10}$ together represent —$(CH_2)_n$—;

n is 4 or 5;

$R^{11}$ and $R^{12}$ together represent —$(CH_2)_m$—;

m is 4 or 5, wherein any one of the methylene groups is optionally replaced by an oxygen atom;

$R^{13}$ is hydrogen or methyl;

$R^{14}$ is hydrogen, methyl, ethyl, isopropyl, tert-butyl, 2-hydroxyethyl, $C_3$ or $C_4$ cycloalkyl in which any one carbon atom is optionally replaced by an oxygen atom, or methyl which is substituted with a $C_3$ or $C_4$ cycloalkyl group in which any one carbon atom is optionally replaced by a nitrogen or oxygen atom, or $R^{13}$ and $R^{14}$, together with the nitrogen atom which is bound to $R^{13}$ and $R^{14}$, optionally form a pyrrolidine ring, a piperidine ring, a piperazine ring, a morpholine ring, a piperazinone ring, or an azetidine ring in which any two hydrogen atoms are optionally replaced by a methyl group(s) and/or a fluorine atom(s) or in which any one hydrogen atom is optionally replaced by a hydroxy or methoxy group;

$R^{15}$ is $C_1$-$C_5$ alkyl, $C_1$-$C_5$ alkoxy, or —$NHR^{16}$; and $R^{16}$ is hydrogen or $C_1$-$C_5$ alkyl; or when $R^{1x}$ is hydrogen, phenyl (any one hydrogen atom in the phenyl group is replaced by a $C_1$-$C_3$ alkyl group in which any one hydrogen atom is replaced by a hydroxy group, —$CONR^6R^7$, aminosulfonyl, methylsulfonylamino, aminosulfonylamino, or $C_1$-$C_3$ alkyl-sulfonyl group; otherwise, the hydrogen atom at the meta-position of the phenyl group is re-placed by a cyano group; otherwise, the hydrogen atom at the para-position of the phenyl group is replaced by a trifluoromethoxy group), 1-methyl-1H-pyrazol-4-yl, or 6-methoxypyridin-3-yl, or when $R^{1x}$ is a fused ring group formed by fusing of a phenyl group and one ring selected from the group consisting of pyrrolidin-2-one, piperidin-2-one, and 1,3-dioxolane (wherein any one hydrogen atom in the fused ring group is optionally replaced by a methyl group), $R^3$ is hydrogen, fluorine, chlorine, bromine, $C_1$-$C_3$ alkyl in which any one to three hydrogen atoms are optionally replaced by a fluorine atom(s) or any one hydrogen atom is optionally replaced by a hydroxy group, 3-hydroxyoxetan-3-yl, hydroxy, methoxy in which any one to three hydrogen atoms are optionally replaced by a fluorine atom(s), methoxycarbonyl, —$NR^9R^{10}$, —$CH_2NR^{11}R^{12}$, or —$CH_2CONR^{13}R^{14}$;

$R^6$ and $R^7$ each independently represent hydrogen or $C_1$-$C_3$ alkyl, or $R^6$ and $R^7$, together with the nitrogen atom which is bound to $R^6$ and $R^7$, optionally form a piperidine ring, a morpholine ring, a piperazine ring, or an N-methylpiperazine ring;

$R^9$ is hydrogen;

$R^{10}$ is hydrogen, —$COR^{15}$, or $C_1$-$C_3$ alkylsulfonyl, or $R^9$ and $R^{10}$ together represent —$(CH_2)_n$—;

n is 4 or 5;

$R^{11}$ and $R^{12}$ together represent —$(CH_2)_m$—;

m is 4 or 5, wherein any one of the methylene groups is optionally replaced by an oxygen atom;

$R^{13}$ is hydrogen or methyl;

$R^{14}$ is hydrogen, methyl, ethyl, isopropyl, tert-butyl, 2-hydroxyethyl, $C_3$ or $C_4$ cycloalkyl in which any one carbon atom is optionally replaced by an oxygen atom, or methyl which is substituted with a $C_3$ or $C_4$ cycloalkyl group in which any one carbon atom is optionally replaced by a nitrogen or oxygen atom, or $R^{13}$ and $R^{14}$, together with the nitrogen atom which is bound to $R^{13}$ and $R^{14}$, optionally form a pyrrolidine ring, a piperidine ring, a piperazine ring, a morpholine ring, a piperazinone ring, or an azetidine ring in which any two hydrogen atoms are optionally replaced by a methyl group(s) and/or a fluorine atom(s) or in which any one hydrogen atom is optionally replaced by a hydroxy or methoxy group;

$R^{15}$ is $C_1$-$C_5$ alkyl, $C_1$-$C_5$ alkoxy, or —$NHR^{16}$; and $R^{16}$ is hydrogen or $C_1$-$C_5$ alkyl (provided that methyl 2-(4-methoxyphenyl)-1,2,3,4-tetrahydroquinoline-6-carboxylate and 2-(benzo[d][1,3]dioxol-5-yl)-1,2,3,4-tetrahydroquinoline are excluded).

[2] The tetrahydroquinoline derivative or a pharmaceutically acceptable salt thereof according to [1], wherein $R^{1x}$ is phenyl (optionally, the phenyl group is substituted with a substituent as described below or forms a fused ring group as described below) or 5- or 6-membered heteroaryl selected from the group consisting of furyl, thienyl, pyrrolyl, imidazolyl, pyrazolyl, thiazolyl, isothiazolyl, oxazolyl, isoxazolyl, and pyridyl (the heteroaryl is optionally substituted with a substituent as described below);

for the combination of $R^2$, $R^4$, and $R^5$, all of $R^2$, $R^4$, and $R^5$ hydrogen; otherwise, one of $R^2$ and $R^4$ is fluorine, chlorine, methoxy, or methyl in which one hydrogen atom is optionally replaced by a hydroxy group, and both the other and $R^5$ represent hydrogen; otherwise, both $R^2$ and $R^4$ represent hydrogen, and $R^5$ is fluorine or chlorine;

$R^v$ is hydrogen; and $R^w$ is hydrogen;

wherein, when $R^{1x}$ is phenyl (any one hydrogen atom in the phenyl group is optionally replaced by one substituent selected from the group consisting of halogen, $C_1$-$C_3$ alkyl in which any one to three hydrogen atoms are optionally replaced by a fluorine atom(s), $C_1$-$C_3$ alkoxy in which any one to three hydrogen atoms are optionally replaced by a fluorine atom(s), cyano, methoxycarbonyl, and —NHCOR$^8$, provided that m-cyanophenyl and p-(trifluoromethoxy)phenyl are excluded) or 5- or 6-membered heteroaryl (any one hydrogen atom in the 5- or 6-membered heteroaryl is optionally replaced by a $C_1$-$C_3$ alkyl or $C_1$-$C_3$ alkoxy group, provided that 1-methyl-1H-pyrazol-4-yl and 6-methoxypyridin-3-yl are excluded), $R^3$ is $C_1$-$C_3$ alkyl in which any one to three hydrogen atoms are replaced by a fluorine atom(s), $C_1$-$C_3$ alkyl in which any one hydrogen atom is replaced by a hydroxy group, ethyl, propyl, isopropyl, 3-hydroxyoxetan-3-yl, methoxy in which any one to three hydrogen atoms are replaced by a fluorine atom(s), methoxycarbonyl, —NR$^9$R$^{10}$, —CH$_2$NR$^{11}$R$^{12}$, or —CH$_2$CONR$^{13}$R$^{14}$ (wherein, when both $R^2$ and $R^4$ represent hydrogen and $R^5$ is fluorine or chlorine, $R^3$ is optionally hydrogen or fluorine, or when both $R^2$ and $R^5$ represent hydrogen and $R^4$ is fluorine or chlorine, $R^3$ is optionally fluorine, or when $R^2$ is methyl in which one hydrogen atom is optionally replaced by a hydroxy group, and both $R^4$ and $R^5$ represent hydrogen, $R^3$ is optionally hydrogen);

$R^8$ is hydrogen or $C_1$-$C_3$ alkyl;

$R^9$ is hydrogen;

$R^{10}$ is hydrogen, —COR$^{15}$, or $C_1$-$C_3$ alkylsulfonyl, or $R^9$ and $R^{10}$ together represent —(CH$_2$)$_n$—;

n is 4 or 5;

$R^{11}$ and $R^{12}$ together represent —(CH$_2$)$_m$—;

m is 4 or 5, wherein any one of the methylene groups is optionally replaced by an oxygen atom;

$R^{13}$ is hydrogen;

$R^{14}$ is hydrogen, methyl, ethyl, isopropyl, or tert-butyl, or $R^{13}$ and $R^{14}$, together with the nitrogen atom which is bound to $R^{13}$ and $R^{14}$, optionally form an azetidine ring in which any one hydrogen atom is optionally replaced by a hydroxy group;

$R^{15}$ is $C_1$-$C_5$ alkyl, $C_1$-$C_5$ alkoxy, or —NHR$^{16}$; and $R^{16}$ is hydrogen or $C_1$-$C_5$ alkyl; or when $R^{1x}$ is phenyl (any one hydrogen atom in the phenyl group is replaced by a $C_1$-$C_3$ alkyl in which any one hydrogen atom is replaced by a hydroxy group, —CONR$^6$R$^7$, aminosulfonyl, or $C_1$-$C_3$ alkylsulfonyl group; otherwise, the hydrogen atom at the meta-position of the phenyl group is replaced by a cyano group; otherwise, the hydrogen atom at the para-position of the phenyl group is replaced by a trifluoromethoxy group), 1-methyl-1H-pyrazol-4-yl, or 6-methoxypyridin-3-yl, or when $R^{1x}$ is a fused ring group formed by fusing of a phenyl group and one ring selected from the group consisting of pyrrolidin-2-one, piperidin-2-one, and 1,3-dioxolane (wherein any one hydrogen atom in the fused ring group is optionally replaced by a methyl group), $R^3$ is hydrogen, fluorine, chlorine, bromine, $C_1$-$C_3$ alkyl in which any one to three hydrogen atoms are optionally replaced by a fluorine atom(s) or any one hydrogen atom is optionally replaced by a hydroxy group, 3-hydroxyoxetan-3-yl, hydroxy, methoxy in which any one to three hydrogen atoms are optionally replaced by a fluorine atom(s), methoxycarbonyl, —NR$^9$R$^{10}$, —CH$_2$NR$^{11}$R$^{12}$, or —CH$_2$CONR$^{13}$R$^{14}$;

$R^6$ and $R^7$ each independently represent hydrogen or $C_1$-$C_3$ alkyl, or $R^6$ and $R^7$, together with the nitrogen atom which is bound to $R^6$ and $R^7$, optionally form a piperidine ring, a morpholine ring, a piperazine ring, or an N-methylpiperazine ring;

$R^9$ is hydrogen;

$R^{10}$ is hydrogen, —COR$^{15}$, or $C_1$-$C_3$ alkylsulfonyl, or $R^9$ and $R^{10}$ together represent —(CH$_2$)$_n$—;

n is 4 or 5;

$R^{11}$ and $R^{12}$ together represent —(CH$_2$)$_m$—;

m is 4 or 5, wherein any one of the methylene groups is optionally replaced by an oxygen atom;

$R^{13}$ is hydrogen;

$R^{14}$ is hydrogen, methyl, ethyl, isopropyl, or tert-butyl, or $R^{13}$ and $R^{14}$, together with the nitrogen atom which is bound to $R^{13}$ and $R^{14}$, optionally form an azetidine ring in which any one hydrogen atom is optionally replaced by a hydroxy group;

$R^{15}$ is $C_1$-$C_5$ alkyl, $C_1$-$C_5$ alkoxy, or —NHR$^{16}$; and $R^{16}$ is hydrogen or $C_1$-$C_5$ alkyl (provided that methyl 2-(4-methoxyphenyl)-1,2,3,4-tetrahydroquinoline-6-carboxylate and 2-(benzo[d][1,3]dioxol-5-yl)-1,2,3,4-tetrahydroquinoline are excluded).

[3] The tetrahydroquinoline derivative or a pharmaceutically acceptable salt thereof according to [1] or [2], wherein the tetrahydroquinoline derivative or the pharmaceutically acceptable salt thereof is selected from the group consisting of:

(2-phenyl-1,2,3,4-tetrahydroquinolin-6-yl)methanol,
tert-butyl (2-phenyl-1,2,3,4-tetrahydroquinolin-6-yl)carbamate,
2-phenyl-1,2,3,4-tetrahydroquinoline-6-amine,
2-(benzo[d][1,3]dioxol-5-yl)-6-methoxy-1,2,3,4-tetrahydroquinoline,
(2-phenyl-1,2,3,4-tetrahydroquinolin-7-yl)methanol,
2-phenyl-6-(trifluoromethoxy)-1,2,3,4-tetrahydroquinoline,
2-(4-(trifluoromethoxy)phenyl)-1,2,3,4-tetrahydroquinoline,
(2-phenyl-1,2,3,4-tetrahydroquinolin-5-yl)methanol,
(2-(1,2,3,4-tetrahydroquinolin-2-yl)phenyl)methanol,
(3-(1,2,3,4-tetrahydroquinolin-2-yl)phenyl)methanol,
(4-(1,2,3,4-tetrahydroquinolin-2-yl)phenyl)methanol,
6,7-difluoro-2-phenyl-1,2,3,4-tetrahydroquinoline,
N-methyl-3-(1,2,3,4-tetrahydroquinolin-2-yl)benzamide,
4-(1,2,3,4-tetrahydroquinolin-2-yl)benzamide,
4-(1,2,3,4-tetrahydroquinolin-2-yl)benzenesulfonamide,
3-(1,2,3,4-tetrahydroquinolin-2-yl)benzamide,
3-(1,2,3,4-tetrahydroquinolin-2-yl)benzonitrile,
6-isopropyl-2-phenyl-1,2,3,4-tetrahydroquinoline,
2-(1-methyl-1H-pyrazol-4-yl)-1,2,3,4-tetrahydroquinoline,
2-(6-methoxypyridin-3-yl)-1,2,3,4-tetrahydroquinoline,
4-((2-phenyl-1,2,3,4-tetrahydroquinolin-6-yl)methyl)morpholine,
2-(2-phenyl-1,2,3,4-tetrahydroquinolin-6-yl)propan-2-ol,
2-(2-phenyl-1,2,3,4-tetrahydroquinolin-6-yl)acetamide,
N-(tert-butyl)-2-(2-phenyl-1,2,3,4-tetrahydroquinolin-6-yl)acetamide,
3-(2-phenyl-1,2,3,4-tetrahydroquinolin-6-yl)oxetan-3-ol,
N-(2-phenyl-1,2,3,4-tetrahydroquinolin-6-yl)acetamide,
1-(3-hydroxyazetidin-1-yl)-2-(2-phenyl-1,2,3,4-tetrahydroquinolin-6-yl)ethan-1-one,
2-phenyl-6-(piperidin-1-yl)-1,2,3,4-tetrahydroquinoline,
N-(2-phenyl-1,2,3,4-tetrahydroquinolin-6-yl)methanesulfonamide, 4-(6-(3-(tert-butyl)ureido)-1,2,3,4-tetrahydroquinolin-2-yl)benzamide, 2-(4-(methylsulfonyl)phenyl)-1,2,3,4-tetrahydroquinoline, 3,3-dimethyl-N-(2-phenyl-1,2,3,4-tetrahydroquinolin-6-yl)butanamide, 1-(tert-butyl)-3-(2-phenyl-1,2,3,4-tetrahydroquinolin-6-yl)urea, 2-(4-(1,2,3,4-tetrahydroquinolin-2-yl)phenyl)propan-2-ol, 3-(1,2,3,4-tetrahydroquinolin-2-yl)benzenesulfonamide, 2-(1,2,3,4-tetrahydroquinolin-2-yl)benzenesulfonamide, N-(2-phenyl-1,2,3,4-tetrahydroquinolin-6-yl)pivalamide, 1-(2-phenyl-1,2,3,4-tetrahydroquinolin-6-yl)urea, 1,2,3,3',4,4'-hexahydro-[2,6'-biquinolin]-2'(1'H)-one, 1'-methyl-1,2,3,3',4,4'-hexahydro-[2,6'-biquinolin]-2'(1'H)-one, N,N-diethyl-4-(1,2,3,4-tetrahydroquinolin-2-yl)benzamide, N-ethyl-4-(1,2,3,4-tetrahydroquinolin-2-yl)benzamide, 5-(1,2,3,4-tetrahydroquinolin-2-yl)isoindolin-1-one, (4-methylpiperazin-1-yl)(4-(1,2,3,4-tetrahydroquinolin-2-yl)phenyl)methanone, piperidin-1-yl(4-(1,2,3,4-tetrahydroquinolin-2-yl)phenyl)methanone, and morpholino(4-(1,2,3,4-tetrahydroquinolin-2-yl)phenyl)methanone, and pharmaceutically acceptable salts thereof.

[4] The tetrahydroquinoline derivative or a pharmaceutically acceptable salt thereof according to any of [1] to [3], wherein the tetrahydroquinoline derivative or the pharmaceutically acceptable salt thereof is selected from the group consisting of:

tert-butyl (2-phenyl-1,2,3,4-tetrahydroquinolin-6-yl)carbamate, (4-(1,2,3,4-tetrahydroquinolin-2-yl)phenyl)methanol, 4-(1,2,3,4-tetrahydroquinolin-2-yl)benzamide, 4-(1,2,3,4-tetrahydroquinolin-2-yl)benzenesulfonamide, 4-((2-phenyl-1,2,3,4-tetrahydroquinolin-6-yl)methyl)morpholine, 2-(2-phenyl-1,2,3,4-tetrahydroquinolin-6-yl)acetamide, N-(2-phenyl-1,2,3,4-tetrahydroquinolin-6-yl)acetamide, 1-(3-hydroxyazetidin-1-yl)-2-(2-phenyl-1,2,3,4-tetrahydroquinolin-6-yl)ethan-1-one, N-(2-phenyl-1,2,3,4-tetrahydroquinolin-6-yl)methanesulfonamide, 4-(6-(3-(tert-butyl)ureido)-1,2,3,4-tetrahydroquinolin-2-yl)benzamide, 3,3-dimethyl-N-(2-phenyl-1,2,3,4-tetrahydroquinolin-6-yl)butanamide, 1-(tert-butyl)-3-(2-phenyl-1,2,3,4-tetrahydroquinolin-6-yl)urea, N-(2-phenyl-1,2,3,4-tetrahydroquinolin-6-yl)pivalamide, 1-(2-phenyl-1,2,3,4-tetrahydroquinolin-6-yl)urea, and 5-(1,2,3,4-tetrahydroquinolin-2-yl)isoindolin-1-one, and pharmaceutically acceptable salts thereof.

[5] The tetrahydroquinoline derivative or a pharmaceutically acceptable salt thereof according to [1] or [2], wherein $R^{1x}$ is phenyl (the phenyl group is optionally substituted with a substituent as described below);

$R^{1y}$ is hydrogen;

for the combination of $R^2$, $R^4$, and $R^5$, all of $R^2$, $R^4$, and $R^5$ represent hydrogen; otherwise, one of $R^2$ and $R^4$ is fluorine, chlorine, or methyl, and both the other and $R^5$ represent hydrogen;

$R^v$ is hydrogen; and $R^w$ is hydrogen;

wherein, when $R^{1x}$ is phenyl (the hydrogen atom at the para-position of the phenyl group is optionally replaced by one substituent selected from the group consisting of fluorine, trifluoromethyl, cyano, and acetamide), $R^3$ is trifluoromethoxy, hydroxymethyl, or —$CH_2CONR^{13}R^{14}$ (wherein, when $R^2$ is methyl and both $R^4$ and $R^5$ represent hydrogen, $R^3$ is optionally hydrogen);

$R^{13}$ is hydrogen or methyl;

$R^{14}$ is tert-butyl, 2-hydroxyethyl, cyclopropyl, cyclobutyl, or oxetan-3-yl, or $R^{13}$ and $R^{14}$, together with the nitrogen atom which is bound to $R^{13}$ and $R^{14}$, optionally form a piperazine ring, a piperazin-2-one ring, an azetidine ring, a 3,3-difluoroazetidine ring, a 3,3-dimethylazetidine ring, a 3-hydroxyazetidine ring, or a 3-methoxyazetidine ring; or when $R^{1x}$ is phenyl (the hydrogen atom at the para-position of the phenyl group is replaced by a trifluoromethoxy, aminocarbonyl, aminosulfonyl, methylsulfonylamino, or methylsulfonyl group), $R^3$ is hydrogen, fluorine, chlorine, methyl, hydroxymethyl, trifluoromethoxy, or —$CH_2CONR^{13}R^{14}$;

$R^{13}$ is hydrogen or methyl;

$R^{14}$ is tert-butyl, 2-hydroxyethyl, cyclopropyl, cyclobutyl, or oxetan-3-yl, or $R^{13}$ and $R^{14}$, together with the nitrogen atom which is bound to $R^{13}$ and $R^{14}$, optionally form a piperazine ring, a piperazin-2-one ring, an azetidine ring, a 3,3-difluoroazetidine ring, a 3,3-dimethylazetidine ring, a 3-hydroxyazetidine ring, or a 3-methoxyazetidine ring.

[6] The tetrahydroquinoline derivative or a pharmaceutically acceptable salt thereof according to [1], wherein the tetrahydroquinoline derivative or the pharmaceutically acceptable salt thereof is selected from the group consisting of:

4-(1,2,3,4-tetrahydroquinolin-2-yl)benzenesulfonamide, 4-(1,2,3,4-tetrahydroquinolin-2-yl)benzamide, 1-(3-hydroxyazetidin-1-yl)-2-(2-phenyl-1,2,3,4-tetrahydroquinolin-6-yl)ethan-1-one, 4-(6-methyl-1,2,3,4-tetrahydroquinolin-2-yl)benzamide, 4-(6-methyl-1,2,3,4-tetrahydroquinolin-2-yl)benzenesulfonamide, 4-(7-methyl-1,2,3,4-tetrahydroquinolin-2-yl)benzenesulfonamide, 4-(7-methyl-1,2,3,4-tetrahydroquinolin-2-yl)benzamide, 4-(6-fluoro-1,2,3,4-tetrahydroquinolin-2-yl)benzenesulfonamide, 4-(5-methyl-1,2,3,4-tetrahydroquinolin-2-yl)benzenesulfonamide, 4-(6-chloro-1,2,3,4-tetrahydroquinolin-2-yl)benzenesulfonamide, 4-(7-fluoro-1,2,3,4-tetrahydroquinolin-2-yl)benzenesulfonamide, 4-(6-chloro-1,2,3,4-tetrahydroquinolin-2-yl)benzamide, 4-(6-fluoro-1,2,3,4-tetrahydroquinolin-2-yl)benzamide, 4-(5-chloro-1,2,3,4-tetrahydroquinolin-2-yl)benzenesulfonamide, 4-(5-fluoro-1,2,3,4-tetrahydroquinolin-2-yl)benzamide, 4-(5-chloro-1,2,3,4-tetrahydroquinolin-2-yl)benzamide, 1-(3-methoxyazetidin-1-yl)-2-(2-phenyl-1,2,3,4-tetrahydroquinolin-6-yl)ethan-1-one, N-(oxetan-3-yl)-2-(2-phenyl-1,2,3,4-tetrahydroquinolin-6-yl)acetamide, 1-(3,3-difluoroazetidin-1-yl)-2-(2-phenyl-1,2,3,4-tetrahydroquinolin-6-yl)ethan-1-one, N-(2-hydroxyethyl)-N-methyl-2-(2-phenyl-1,2,3,4-tetrahydroquinolin-6-yl)acetamide, 1-(azetidin-1-yl)-2-(2-phenyl-1,2,3,4-tetrahydroquinolin-6-yl)ethan-1-one, N-cyclopropyl-2-(2-phenyl-1,2,3,4-tetrahydroquinolin-6-yl)acetamide, N-cyclobutyl-2-(2-phenyl-1,2,3,4-tetrahydroquinolin-6-yl) acetamide, 2-(2-phenyl-1,2,3,4-tetrahydroquinolin-6-yl)-1-(piperazin-1-yl)ethan-1-one, and 4-(1,2,3,4-tetrahydroquinolin-3-yl)benzenesulfonamide, and pharmaceutically acceptable salts thereof.

[7] A drug containing a tetrahydroquinoline derivative represented by the general formula (I) below (hereinafter also referred to as "tetrahydroquinoline derivative (I)") or a pharmaceutically acceptable salt thereof as an active ingredient, (I)

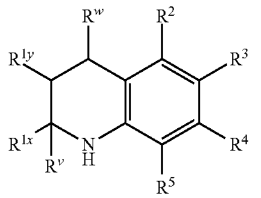

wherein $R^{1x}$ is hydrogen, aryl, or 5- or 6-membered heteroaryl having one or two heteroatoms selected from nitrogen, oxygen, and sulfur atoms (any one or two hydrogen atoms in the aryl or the 5- or 6-membered heteroaryl are each independently optionally replaced by a halogen atom(s), a $C_1$-$C_3$ alkyl in which any one to three hydrogen atoms are each independently optionally replaced by a hydroxy group(s) or a fluorine atom(s), $C_1$-$C_3$ alkoxy in which any one to three hydrogen atoms are optionally replaced by a fluorine atom(s), cyano, methoxycarbonyl, —$CONR^6R^7$, —$NHCOR^8$, aminosulfonyl, $C_1$-$C_3$ alkylsulfonylamino, aminosulfonylamino, or $C_1$-$C_3$ alkylsulfonyl group(s)), or when the aryl group is phenyl (the phenyl optionally forms a fused ring group as described below), $R^{1x}$ is optionally a fused ring group formed by fusing of the phenyl group and one ring selected from the group consisting of 5- or 6-membered lactam rings and 5- or 6-membered saturated heterocycles each containing one or two oxygen atoms as the atom constituting the ring (any one hydrogen atom in the fused ring group is optionally replaced by a methyl group);

$R^{1y}$ is hydrogen, phenyl, 4-hydroxymethylphenyl, 4-aminocarbonylphenyl, 4-acetamidophenyl, 4-aminosulfonylphenyl, 4-methylsulfonylphenyl, or 3-pyridyl (except that both $R^{1x}$ and $R^{1y}$ represent hydrogen);

for the combination of $R^2$, $R^4$, and $R^5$, all of $R^2$, $R^4$, and $R^5$ represent hydrogen, or one of $R^2$, $R^4$, and $R^5$ is halogen, methoxy, or methyl in which one hydrogen atom is optionally replaced by a hydroxy group, and the other two are hydrogen;

$R^3$ is hydrogen, halogen, $C_1$-$C_3$ alkyl in which any one to three hydrogen atoms are each independently optionally replaced by a hydroxy group(s) or a fluorine atom(s), 3-hydroxyoxetan-3-yl, hydroxy, $C_1$-$C_3$ alkoxy in which any one to three hydrogen atoms are optionally replaced by a fluorine atom(s), methoxycarbonyl, —$NR^9R^{10}$, —$CH_2NR^{11}R^{12}$, or —$CH_2CONR^{13}R^{14}$;

$R^6$ and $R^7$ each independently represent hydrogen or $C_1$-$C_3$ alkyl, or $R^6$ and $R^7$ together represent —$(CH_2)_h$—;

h is an integer of 3 to 5, wherein any one of the methylene groups is optionally replaced by an oxygen atom, —NH—, or —$N(CH_3)$—;

$R^8$ is hydrogen or $C_1$-$C_3$ alkyl;

$R^9$ and $R^{10}$ each independently represent hydrogen, —$COR^{15}$, or $C_1$-$C_3$ alkylsulfonyl, or $R^9$ and $R^{10}$ together represent —$(CH_2)_n$—;

n is an integer of 3 to 6;

$R^{11}$ and $R^{12}$ together represent —$(CH_2)_m$—;

m is an integer of 3 to 5, wherein any one of the methylene groups is optionally replaced by an oxygen atom;

$R^{13}$ and $R^{14}$ each independently represent hydrogen, $C_1$-$C_5$ alkyl group, 2-hydroxyethyl, $C_3$ or $C_4$ cycloalkyl in which any one carbon atom is optionally replaced by an oxygen atom, or methyl which is substituted with a $C_3$ or $C_4$ cycloalkyl group in which any one carbon atom is optionally replaced by a nitrogen or oxygen atom, or $R^{13}$ and $R^{14}$ together represent —$(CH_2)_k$— in which any one or two hydrogen atoms are optionally replaced by a fluorine atom(s), a methyl group(s), a hydroxy group(s), or a methoxy group(s) or in which any one $CH_2$ group is optionally replaced by an oxygen atom, a nitrogen atom, or —CONH—;

k is an integer of 3 to 5;

$R^{15}$ is $C_1$-$C_5$ alkyl, $C_1$-$C_5$ alkoxy, or —$NHR^{16}$;

$R^{16}$ is hydrogen or $C_1$-$C_5$ alkyl;

$R^v$ is hydrogen, methyl in which any one hydrogen atom is optionally replaced by a hydroxy or methoxycarbonyl group, or methoxycarbonyl; and $R^w$ is hydrogen, methyl, hydroxymethyl, or methoxycarbonyl (provided that 2-phenyl-1,2,3,4-tetrahydroquinoline and 3-phenyl-1,2,3,4-tetrahydroquinoline are excluded).

[8] The drug according to [7], containing the tetrahydroquinoline derivative or a pharmaceutically acceptable salt thereof as an active ingredient, wherein $R^{1x}$ is phenyl (any one hydrogen atom in the phenyl group is optionally replaced by a halogen atom or a $C_1$-$C_3$ alkyl in which any one to three hydrogen atoms are optionally replaced by a fluorine atom(s) or any one hydrogen atom is optionally replaced by a hydroxy group, $C_1$-$C_3$ alkoxy in which any one to three hydrogen atoms are optionally replaced by a fluorine atom(s), cyano, methoxycarbonyl, —$CONR^6R^7$, —$NHCOR^8$, aminosulfonyl, or $C_1$-$C_3$ alkylsulfonyl group) or 5- or 6-membered heteroaryl selected from the group consisting of furyl, thienyl, pyrrolyl, imidazolyl, pyrazolyl, thiazolyl, isothiazolyl, oxazolyl, isoxazolyl, and pyridyl (any one hydrogen atom in the 5- or 6-membered heteroaryl is optionally replaced by a $C_1$-$C_3$ alkyl or $C_1$-$C_3$ alkoxy group), or $R^{1x}$ is optionally a fused ring group formed by fusing of a phenyl group and one ring selected from the group consisting of pyrrolidin-2-one, piperidin-2-one, and 1,3-dioxolane (wherein any one hydrogen atom in the fused ring group is optionally replaced by a methyl group);

$R^{1y}$ is hydrogen;

for the combination of $R^2$, $R^4$, and $R^5$, all of $R^2$, $R^4$, and $R^5$ represent hydrogen; otherwise, one of $R^2$ and $R^4$ is fluorine, chlorine, methoxy, or methyl in which one hydrogen atom is optionally replaced by a hydroxy group, and both the other and $R^5$ represent hydrogen; otherwise, both $R^2$ and $R^4$ represent hydrogen, and $R^5$ is fluorine or chlorine;

$R^3$ is hydrogen, fluorine, chlorine, bromine, $C_1$-$C_3$ alkyl in which any one to three hydrogen atoms are optionally replaced by a fluorine atom(s) or any one hydrogen atom is optionally replaced by a hydroxy group, 3-hydroxyoxetan-3-yl, hydroxy, methoxy in which any one to three hydrogen atoms are optionally replaced by a fluorine atom(s), methoxycarbonyl, —$NR^9R^{10}$, —$CH_2NR^{11}R^{12}$, or —$CH_2CONR^{13}R^{14}$;

$R^6$ and $R^7$ each independently represent hydrogen or $C_1$-$C_3$ alkyl, or $R^6$ and $R^7$, together with the nitrogen atom which is bound to $R^6$ and $R^7$, optionally form a piperidine ring, a morpholine ring, a piperazine ring, or an N-methylpiperazine ring;

$R^8$ is hydrogen or $C_1$-$C_3$ alkyl;

$R^9$ is hydrogen;

$R^{10}$ is hydrogen, —$COR^{15}$, or $C_1$-$C_3$ alkylsulfonyl, or $R^9$ and $R^{10}$ together represent —$(CH_2)_n$—;

n is 4 or 5;

$R^{11}$ and $R^{12}$ together represent —$(CH_2)_m$—;

m is 4 or 5, wherein any one of the methylene groups is optionally replaced by an oxygen atom;

$R^{13}$ is hydrogen;

$R^{14}$ is hydrogen, methyl, ethyl, isopropyl, or tert-butyl, or $R^{13}$ and $R^{14}$, together with the nitrogen atom which is bound to $R^{13}$ and $R^{14}$, optionally form an azetidine ring in which any one hydrogen atom is optionally replaced by a hydroxy group;

$R^{15}$ is $C_1$-$C_5$ alkyl, $C_1$-$C_5$ alkoxy, or —$NHR^{16}$;

$R^{16}$ is hydrogen or $C_1$-$C_5$ alkyl;

$R^v$ is hydrogen; and $R^w$ is hydrogen (provided that 2-phenyl-1,2,3,4-tetrahydroquinoline is excluded).

[9] The drug according to [7] or [8], containing the tetrahydroquinoline derivative or a pharmaceutically acceptable salt thereof as an active ingredient, wherein $R^{1x}$ is phenyl (optionally, the phenyl group has a substituent as described below or forms a fused ring group as described below) or 5- or 6-membered heteroaryl selected from the group consisting of furyl, thienyl, pyrrolyl, imidazolyl, pyrazolyl, thiazolyl, isothiazolyl, oxazolyl, isoxazolyl, and pyridyl (the heteroaryl is optionally substituted with a substituent as described below);

$R^{1y}$ is hydrogen;

for the combination of $R^2$, $R^4$, and $R^5$, all of $R^2$, $R^4$, and $R^5$ represent hydrogen; otherwise, one of $R^2$ and $R^4$ is fluorine, chlorine, methoxy, or methyl in which one hydrogen atom is optionally replaced by a hydroxy group, and both the other and $R^5$ represent hydrogen; otherwise, both $R^2$ and $R^4$ represent hydrogen, and $R^5$ is fluorine or chlorine;

$R^v$ is hydrogen; and $R^w$ is hydrogen;

wherein, when $R^{1x}$ is phenyl (any one hydrogen atom in the phenyl group is optionally replaced by one substituent selected from the group consisting of halogen, $C_1$-$C_3$ alkyl in which any one to three hydrogen atoms are optionally replaced by a fluorine atom(s), $C_1$-$C_3$ alkoxy in which any one to three hydrogen atoms are optionally replaced by a fluorine atom(s), cyano, methoxycarbonyl, and —$NHCOR^8$, provided that m-cyanophenyl and p-(trifluoromethoxy)phenyl are excluded) or 5- or 6-membered heteroaryl (any one hydrogen atom in the 5- or 6-membered heteroaryl is optionally replaced by a $C_1$-$C_3$ alkyl or $C_1$-$C_3$ alkoxy group, provided that 1-methyl-1H-pyrazol-4-yl and 6-methoxypyridin-3-yl are excluded), $R^3$ is $C_1$-$C_3$ alkyl in which any one to three hydrogen atoms are replaced by a fluorine atom(s), $C_1$-$C_3$ alkyl in which any one hydrogen atom is replaced by a hydroxy group, ethyl, propyl, isopropyl, 3-hydroxyoxetan-3-yl, methoxy in which any one to three hydrogen atoms are replaced by a fluorine atom(s), methoxycarbonyl, —$NR^9R^{10}$, —$CH_2NR^{11}R^{12}$, or —$CH_2CONR^{13}R^{14}$ (wherein, when both $R^2$ and $R^4$ represent hydrogen and $R^5$ is fluorine or chlorine, $R^3$ is optionally hydrogen or fluorine, or when both $R^2$ and $R^5$ represent hydrogen and $R^4$ is fluorine or chlorine, $R^3$ is optionally fluorine, or when $R^2$ is methyl in which one hydrogen atom is optionally replaced by a hydroxy group, and both $R^4$ and $R^5$ represent hydrogen, $R^3$ is optionally hydrogen);

$R^8$ is hydrogen or $C_1$-$C_3$ alkyl;

$R^9$ is hydrogen;

$R^{10}$ is hydrogen, —$COR^{15}$, or $C_1$-$C_3$ alkylsulfonyl, or $R^9$ and $R^{10}$ together represent —$(CH_2)_n$—;

n is 4 or 5;

$R^{11}$ and $R^{12}$ together represent —$(CH_2)_m$—;

m is 4 or 5, wherein any one of the methylene groups is optionally replaced by an oxygen atom;

$R^{13}$ is hydrogen;

$R^{14}$ is hydrogen, methyl, ethyl, isopropyl, or tert-butyl, or $R^{13}$ and $R^{14}$, together with the nitrogen atom which is bound to $R^{13}$ and $R^{14}$, optionally form an azetidine ring in which any one hydrogen atom is optionally replaced by a hydroxy group;

$R^{15}$ is $C_1$-$C_5$ alkyl, $C_1$-$C_5$ alkoxy, or —$NHR^{16}$; and $R^{16}$ is hydrogen or $C_1$-$C_5$ alkyl; or when $R^{1x}$ is phenyl (any one hydrogen atom in the phenyl group is replaced by a $C_1$-$C_3$ alkyl in which any one hydrogen atom is replaced by a hydroxy group, —$CONR^6R^7$, aminosulfonyl, or $C_1$-$C_3$ alkylsulfonyl group; otherwise, the hydrogen atom at the meta-position of the phenyl group is replaced by a cyano group; otherwise, the hydrogen atom at the para-position of the phenyl group is replaced by a trifluoromethoxy group), 1-methyl-1H-pyrazol-4-yl, or 6-methoxypyridin-3-yl, or when $R^{1x}$ is a fused ring group formed by fusing of a phenyl group and one ring selected from the group consisting of pyrrolidin-2-one, piperidin-2-one, and 1,3-dioxolane (wherein any one hydrogen atom in the fused ring group is optionally replaced by a methyl group), $R^3$ is hydrogen, fluorine, chlorine, bromine, $C_1$-$C_3$ alkyl in which any one to three hydrogen atoms are optionally replaced by a fluorine atom(s) or any one hydrogen atom is optionally replaced by a hydroxy group, 3-hydroxyoxetan-3-yl, hydroxy, methoxy in which any one to three hydrogen atoms are optionally replaced by a fluorine atom(s), methoxycarbonyl, —$NR^9R^{10}$, —$CH_2NR^{11}R^{12}$, or —$CH_2CONR^{13}R^{14}$;

$R^6$ and $R^7$ each independently represent hydrogen or $C_1$-$C_3$ alkyl, or $R^6$ and $R^7$, together with the nitrogen atom which is bound to $R^6$ and $R^7$, optionally form a piperidine ring, a morpholine ring, a piperazine ring, or an N-methylpiperazine ring;

$R^9$ is hydrogen;

$R^{10}$ is hydrogen, —$COR^{15}$, or $C_1$-$C_3$ alkylsulfonyl, or $R^9$ and $R^{10}$ together represent —$(CH_2)_n$—;

n is 4 or 5;

$R^{11}$ and $R^{12}$ together represent —$(CH_2)_m$—;

m is 4 or 5, wherein any one of the methylene groups is optionally replaced by an oxygen atom;

$R^{13}$ is hydrogen;

$R^{14}$ is hydrogen, methyl, ethyl, isopropyl, or tert-butyl, or $R^{13}$ and $R^{14}$, together with the nitrogen atom which is bound to $R^{13}$ and $R^{14}$, optionally form an azetidine ring in which any one hydrogen atom is optionally replaced by a hydroxy group;

$R^{15}$ is $C_1$-$C_5$ alkyl, $C_1$-$C_5$ alkoxy, or —$NHR^{16}$; and $R^{16}$ is hydrogen or $C_1$-$C_5$ alkyl.

[10] The drug according to any of [7] to [9], wherein the tetrahydroquinoline derivative or the pharmaceutically acceptable salt thereof is selected from the group consisting of those as described in [3].

[11] The drug according to any of [7] to [10], wherein the tetrahydroquinoline derivative or the pharmaceutically acceptable salt thereof is selected from the group consisting of those as described in [4].

[12] The drug according to any of [7] to [9], containing the tetrahydroquinoline derivative or the pharmaceutically acceptable salt thereof as an active ingredient, wherein $R^{1x}$ is phenyl (the hydrogen atom at the para-position of the phenyl group is optionally replaced by a fluorine atom or a trifluoromethyl, trifluoromethoxy, cyano, aminocarbonyl, acetamide, aminosulfonyl, methylsulfonylamino, or methylsulfonyl group);

$R^{1y}$ is hydrogen;

for the combination of $R^2$, $R^4$, and $R^5$, all of $R^2$, $R^4$, and $R^5$ represent hydrogen; otherwise, one of $R^2$ and $R^4$ is fluorine, chlorine, or methyl, and both the other and $R^5$ represent hydrogen;

$R^3$ is hydrogen, fluorine, chlorine, methyl, hydroxymethyl, trifluoromethoxy, or —$CH_2CONR^{13}R^{14}$;

$R^{13}$ is hydrogen or methyl;

$R^{14}$ is tert-butyl, 2-hydroxyethyl, cyclopropyl, cyclobutyl, or oxetan-3-yl, or $R^{13}$ and $R^{14}$, together with the nitrogen atom which is bound to $R^{13}$ and $R^{14}$, optionally form a piperazine ring, a piperazin-2-one ring, an azetidine ring, a 3,3-difluoroazetidine ring, a 3,3-dimethylazetidine ring, a 3-hydroxyazetidine ring, or a 3-methoxyazetidine ring;

$R^v$ is hydrogen; and $R^w$ is hydrogen (provided that 2-phenyl-1,2,3,4-tetrahydroquinoline is excluded).

[13] The drug according to [7] or [8], wherein the tetrahydroquinoline derivative or the pharmaceutically acceptable salt thereof is selected from the group consisting of those as described in [6].

[14] The drug according to any of [7] to [13], for treating or preventing diseases, disorders or syndromes related to ferroptosis inhibition.

[15] The drug according to [14], wherein the diseases, disorders or syndromes is multiple sclerosis.

We also provide a ferroptosis inhibitor containing the tetrahydroquinoline derivative represented by the general formula (I) below or a pharmaceutically acceptable salt thereof as an active ingredient,

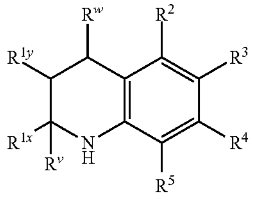

(I)

wherein $R^{1x}$ is hydrogen, aryl, or 5- or 6-membered heteroaryl having one or two heteroatoms selected from nitrogen, oxygen, and sulfur atoms (any one or two hydrogen atoms in the aryl or the 5- or 6-membered heteroaryl are each independently optionally replaced by a halogen atom(s), a $C_1$-$C_3$ alkyl in which any one to three hydrogen atoms are each independently optionally replaced by a hydroxy group(s) or a fluorine atom(s), $C_1$-$C_3$ alkoxy in which any one to three hydrogen atoms are optionally replaced by a fluorine atom(s), cyano, methoxycarbonyl, —$CONR^6R^7$, —$NHCOR^8$, aminosulfonyl, $C_1$-$C_3$ alkylsulfonylamino, aminosulfonylamino, or $C_1$-$C_3$ alkylsulfonyl group(s)), or when the aryl group is phenyl (the phenyl optionally forms a fused ring group as described below), $R^{1x}$ is optionally a fused ring group formed by fusing of the phenyl group and one ring selected from the group consisting of 5- or 6-membered lactam rings and 5- or 6-membered saturated heterocycles each containing one or two oxygen atoms as the atom constituting the ring (any one hydrogen atom in the fused ring group is optionally replaced by a methyl group);

$R^{1y}$ is hydrogen, phenyl, 4-hydroxymethylphenyl, 4-aminocarbonylphenyl, 4-acetamidophenyl, 4-aminosulfonylphenyl, 4-methylsulfonylphenyl, or 3-pyridyl (except that both $R^{1x}$ and $R^{1y}$ represent hydrogen);

for the combination of $R^2$, $R^4$, and $R^5$, all of $R^2$, $R^4$, and $R^5$ represent hydrogen, or one of $R^2$, $R^4$, and $R^5$ is halogen, methoxy, or methyl in which one hydrogen atom is optionally replaced by a hydroxy group, and the other two are hydrogen;

$R^3$ is hydrogen, halogen, $C_1$-$C_3$ alkyl in which any one to three hydrogen atoms are each independently optionally replaced by a hydroxy group(s) or a fluorine atom(s), 3-hydroxyoxetan-3-yl, hydroxy, $C_1$-$C_3$ alkoxy in which any one to three hydrogen atoms are optionally replaced by a fluorine atom(s), methoxycarbonyl, —$NR^9R^{10}$, —$CH_2NR^{11}R^{12}$, or —$CH_2CONR^{13}R^{14}$;

$R^6$ and $R^7$ each independently represent hydrogen or $C_1$-$C_3$ alkyl, or $R^6$ and $R^7$ together represent —$(CH_2)_h$—;

h is an integer of 3 to 5, wherein any one of the methylene groups is optionally replaced by an oxygen atom, —NH—, or —$N(CH_3)$—;

$R^8$ is hydrogen or $C_1$-$C_3$ alkyl;

$R^9$ and $R^{10}$ each independently represent hydrogen, —$COR^{15}$, or $C_1$-$C_3$ alkylsulfonyl, or $R^9$ and $R^{10}$ together represent —$(CH_2)_n$—;

n is an integer of 3 to 6;

$R^{11}$ and $R^{12}$ together represent —$(CH_2)_m$—;

m is an integer of 3 to 5, wherein any one of the methylene groups is optionally replaced by an oxygen atom;

$R^{13}$ and $R^{14}$ each independently represent hydrogen, $C_1$-$C_5$ alkyl group, 2-hydroxyethyl, $C_3$ or $C_4$ cycloalkyl in which any one carbon atom is optionally replaced by an oxygen atom, or methyl which is substituted with a $C_3$ or $C_4$ cycloalkyl group in which any one carbon atom is optionally replaced by a nitrogen or oxygen atom, or $R^{13}$ and $R^{14}$ together represent $—(CH_2)_k—$ in which any one or two hydrogen atoms are optionally replaced by a fluorine atom(s), a methyl group(s), a hydroxy group(s), or a methoxy group(s) or in which any one $CH_2$ group is optionally replaced by an oxygen atom, a nitrogen atom, or —CONH—;

k is an integer of 3 to 5;

$R^{15}$ is $C_1$-$C_5$ alkyl, $C_1$-$C_5$ alkoxy, or $—NHR^{16}$;

$R^{16}$ is hydrogen or $C_1$-$C_5$ alkyl;

$R^v$ is hydrogen, methyl in which any one hydrogen atom is optionally replaced by a hydroxy or methoxycarbonyl group, or methoxycarbonyl; and $R^w$ is hydrogen, methyl, hydroxymethyl, or methoxycarbonyl.

In another configuration, we include use of the tetrahydroquinoline derivative (I) as described above or a pharmaceutically acceptable salt thereof in the manufacture of a ferroptosis inhibitor.

In yet another configuration, we include use of the tetrahydroquinoline derivative (I) as described above or a pharmaceutically acceptable salt thereof in the manufacture of a drug, preferably use of the tetrahydroquinoline derivative (I) as described above or a pharmaceutically acceptable salt thereof in the manufacture of a drug for treating or preventing diseases, disorders or syndromes related to ferroptosis inhibition, more preferably use of the tetrahydroquinoline derivative (I) as described above or a pharmaceutically acceptable salt thereof in the manufacture of a drug for treating or preventing multiple sclerosis.

In yet another configuration, we include the tetrahydroquinoline derivative (I) as described above or a pharmaceutically acceptable salt thereof for use in treatment or prevention of diseases, disorders or syndromes related to ferroptosis inhibition, preferably the tetrahydroquinoline derivative (I) as described above or a pharmaceutically acceptable salt thereof for use in treatment or prevention of multiple sclerosis.

In yet another configuration, we include a method of treating or preventing diseases, disorders or syndromes related to ferroptosis inhibition, wherein the method comprises administering an effective amount of the tetrahydroquinoline derivative (I) as described above or a pharmaceutically acceptable salt thereof to a subject in need thereof, preferably a method of treating or preventing multiple sclerosis, wherein the method comprises administering an effective amount of the tetrahydroquinoline derivative (I) as described above or a pharmaceutically acceptable salt thereof to a subject in need thereof.

The tetrahydroquinoline derivative or a pharmaceutically acceptable salt thereof, each of which is an active ingredient in a drug of this disclosure, have inhibitory effect against ferroptosis and a pharmacological action based on the inhibitory effect. Therefore, the drug has a therapeutic or preventive effect on diseases, disorders or syndromes related to ferroptosis inhibition such as multiple sclerosis.

DETAILED DESCRIPTION

Figure 1:
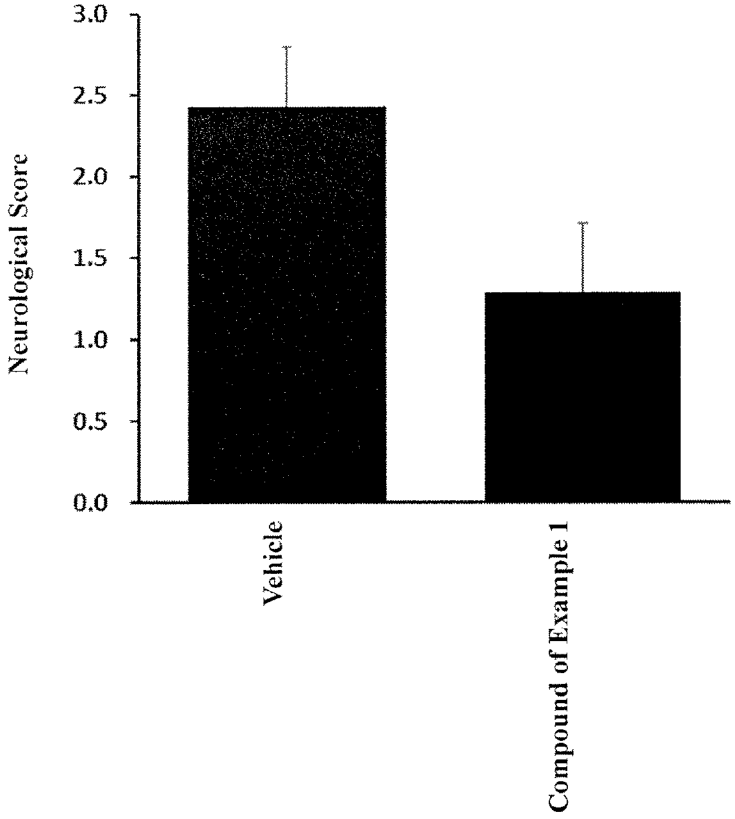
FIG. 1 shows the inhibitory effect of the compound of Example 1 on an increase in neurological score in a myelin oligodendrocyte glycoprotein-induced experimental autoimmune encephalomyelitis mouse model.

A tetrahydroquinoline derivative or a pharmaceutically acceptable salt thereof, which is an active ingredient in a drug of this disclosure, is characterized by the general formula (I) below:

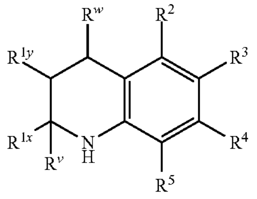

(I)

wherein $R^{1x}$ is hydrogen, aryl, or 5- or 6-membered heteroaryl having one or two heteroatoms selected from nitrogen, oxygen, and sulfur atoms (any one or two hydrogen atoms in the aryl or the 5- or 6-membered heteroaryl are each independently optionally replaced by a halogen atom(s), a $C_1$-$C_3$ alkyl in which any one to three hydrogen atoms are each independently optionally replaced by a hydroxy group(s) or a fluorine atom(s), $C_1$-$C_3$ alkoxy in which any one to three hydrogen atoms are optionally replaced by a fluorine atom(s), cyano, methoxycarbonyl, $—CONR^6R^7$, $—NHCOR^8$, aminosulfonyl, $C_1$-$C_3$ alkylsulfonylamino, aminosulfonylamino, or $C_1$-$C_3$ alkylsulfonyl group(s)), or when the aryl group is phenyl (the phenyl optionally forms a fused ring group as described below), $R^{1x}$ is optionally a fused ring group formed by fusing of the phenyl group and one ring selected from the group consisting of 5- or 6-membered lactam rings and 5- or 6-membered saturated heterocycles each containing one or two oxygen atoms as the atom constituting the ring (any one hydrogen atom in the fused ring group is optionally replaced by a methyl group);

$R^{1y}$ is hydrogen, phenyl, 4-hydroxymethylphenyl, 4-aminocarbonylphenyl, 4-acetamidophenyl, 4-aminosulfonylphenyl, 4-methylsulfonylphenyl, or 3-pyridyl (except that both $R^{1x}$ and $R^{1y}$ represent hydrogen);

for the combination of $R^2$, $R^4$, and $R^5$, all of $R^2$, $R^4$, and $R^5$ represent hydrogen, or one of $R^2$, $R^4$, and $R^5$ is halogen, methoxy, or methyl in which one hydrogen atom is optionally replaced by a hydroxy group, and the other two are hydrogen;

$R^3$ is hydrogen, halogen, $C_1$-$C_3$ alkyl in which any one to three hydrogen atoms are each independently optionally replaced by a hydroxy group(s) or a fluorine atom(s), 3-hydroxyoxetan-3-yl, hydroxy, $C_1$-$C_3$ alkoxy in which any one to three hydrogen atoms are optionally replaced by a fluorine atom(s), methoxycarbonyl, $—NR^9R^{10}$, $—CH_2NR^{11}R^{12}$, or $—CH_2CONR^{13}R^{14}$;

$R^6$ and $R^7$ each independently represent hydrogen or $C_1$-$C_3$ alkyl, or $R^6$ and $R^7$ together represent $—(CH_2)_h—$;

h is an integer of 3 to 5, wherein any one of the methylene groups is optionally replaced by an oxygen atom, —NH—, or $—N(CH_3)—$;

$R^8$ is hydrogen or $C_1$-$C_3$ alkyl;

$R^9$ and $R^{10}$ each independently represent hydrogen, $—COR^{15}$, or $C_1$-$C_3$ alkylsulfonyl, or $R^9$ and $R^{10}$ together represent $—(CH_2)_n—$;

n is an integer of 3 to 6;

$R^{11}$ and $R^{12}$ together represent $—(CH_2)_m—$;

m is an integer of 3 to 5, wherein any one of the methylene groups is optionally replaced by an oxygen atom;

$R^{13}$ and $R^{14}$ each independently represent hydrogen, $C_1$-$C_5$ alkyl, 2-hydroxyethyl, $C_3$ or $C_4$ cycloalkyl in which any one carbon atom is optionally replaced by an oxygen atom, or methyl which is substituted with a $C_3$ or $C_4$ cycloalkyl group in which any one carbon atom is optionally replaced by a nitrogen or oxygen atom, or $R^{13}$ and $R^{14}$ together represent $—(CH_2)_k—$ in which any one or two hydrogen atoms are optionally replaced by a fluorine atom(s), a methyl group(s), a hydroxy group(s), or a methoxy group(s) or in which any one $CH_2$ group is optionally replaced by an oxygen atom, a nitrogen atom, or —CONH—;

k is an integer of 3 to 5;

$R^{15}$ is $C_1$-$C_5$ alkyl, $C_1$-$C_5$ alkoxy, or $—NHR^{16}$;

$R^{16}$ is hydrogen or $C_1$-$C_5$ alkyl;

$R^v$ is hydrogen, methyl in which any one hydrogen atom is optionally replaced by a hydroxy or methoxycarbonyl group, or methoxycarbonyl; and $R^w$ is hydrogen, methyl, hydroxymethyl, or methoxycarbonyl (provided that 2-phenyl-1,2,3,4-tetrahydroquinoline and 3-phenyl-1,2,3,4-tetrahydroquinoline are excluded).

Among the tetrahydroquinoline derivative (I) or a pharmaceutically acceptable salt thereof, each of which is an active ingredient in the drug, the tetrahydroquinoline derivative or a pharmaceutically acceptable salt thereof according to [1] as described above are novel compounds. The tetrahydroquinoline derivative or a pharmaceutically acceptable salt thereof according to [1] are included in the tetrahydroquinoline derivative (I) as described above or a pharmaceutically acceptable salt thereof.

Unless otherwise specified, the following terms used in this description are defined as below.

The term "halogen" means fluorine, chlorine, bromine, or iodine.

The term "$C_1$-$C_3$ alkyl" means methyl, ethyl, propyl, or isopropyl.

The term "$C_1$-$C_5$ alkyl" means a linear or branched hydrocarbon group containing one to five carbon atoms, for example, methyl, ethyl, propyl, isopropyl, butyl, isobutyl, sec-butyl, tert-butyl, pentyl, isopentyl, sec-pentyl, tert-pentyl, or neopentyl.

The phrase "$C_1$-$C_3$ alkyl in which any one to three hydrogen atoms are each independently optionally replaced by a hydroxy group(s) or a fluorine atom(s)" means "$C_1$-$C_3$ alkyl" as described above in which any one to three hydrogen atoms are each independently optionally replaced by a hydroxy group(s) or a fluorine atom(s), for example, methyl, hydroxymethyl, ethyl, 1-hydroxyethyl, 2-hydroxyethyl, 1,2-dihydroxyethyl, propyl, 1-hydroxypropyl, 2-hydroxypropyl, 3-hydroxypropyl, 1,2-dihydroxypropyl, 1,3-dihydroxypropyl, 2,3-dihydroxypropyl, isopropyl, 2-hydroxypropan-2-yl, 1-hydroxypropan-2-yl, 1,2-dihydroxy-1-methylethyl, fluoromethyl, difluoromethyl, trifluoromethyl, 1,1-difluoroethyl, 2,2,2-trifluoroethyl, 1,1-difluoropropyl, 2,2-difluoropropyl, 3,3,3-trifluoropropyl, 2-fluoropropan-2-yl, or 1,1,1-trifluoropropan-2-yl.

The phrase "$C_1$-$C_3$ alkyl in which any one to three hydrogen atoms are optionally re-placed by a fluorine atom(s)" means "$C_1$-$C_3$ alkyl" as described above in which any one to three hydrogen atoms are optionally replaced by a fluorine atom(s), for example, methyl, fluoromethyl, difluoromethyl, trifluoromethyl, ethyl, 1,1-difluoroethyl, 2,2,2-trifluoroethyl, propyl, 1,1-difluoropropyl, 2,2-difluoropropyl, 3,3,3-trifluoropropyl, isopropyl, 2-fluoropropan-2-yl, or 1,1,1-trifluoropropan-2-yl.

The phrase "$C_1$-$C_3$ alkyl in which any one to three hydrogen atoms are replaced by a fluorine atom(s)" means "$C_1$-$C_3$ alkyl" as described above in which any one to three hydrogen atoms are replaced by a fluorine atom(s), for example, fluoromethyl, difluoromethyl, trifluoromethyl, 1,1-difluoroethyl, 2,2,2-trifluoroethyl, 1,1-difluoropropyl, 2,2-difluoropropyl, 3,3,3-trifluoropropyl, 2-fluoropropan-2-yl, or 1,1,1-trifluoropropan-2-yl.

The phrase "$C_1$-$C_3$ alkyl in which any one hydrogen atom is optionally replaced by a hydroxy group" means "$C_1$-$C_3$ alkyl" as described above in which any one hydrogen atom is optionally replaced by a hydroxy group, for example, methyl, hydroxymethyl, ethyl, 1-hydroxyethyl, 2-hydroxyethyl, propyl, 1-hydroxypropyl, 2-hydroxypropyl, 3-hydroxypropyl, isopropyl, 2-hydroxypropan-2-yl, or 1-hydroxypropan-2-yl.

The phrase "$C_1$-$C_3$ alkyl in which any one hydrogen atom is replaced by a hydroxy group" means "$C_1$-$C_3$ alkyl" as described above in which any one hydrogen atom is replaced by a hydroxy group, for example, hydroxymethyl, 1-hydroxyethyl, 2-hydroxyethyl, 1-hydroxypropyl, 2-hydroxypropyl, 3-hydroxypropyl, 2-hydroxypropan-2-yl, or 1-hydroxypropan-2-yl.

The phrase "$C_1$-$C_3$ alkyl in which any one to three hydrogen atoms are optionally replaced by a fluorine atom (s) or any one hydrogen atom is optionally replaced by a hydroxy group" means "$C_1$-$C_3$ alkyl in which any one to three hydrogen atoms are optionally replaced by a fluorine atom(s)" as described above or "$C_1$-$C_3$ alkyl in which any one hydrogen atom is optionally replaced by a hydroxy group" as described above.

The phrase "methyl in which one hydrogen atom is optionally replaced by a hydroxy group" means methyl or hydroxymethyl.

The term "$C_1$-$C_3$ alkoxy" means methoxy, ethoxy, propoxy, or isopropoxy.

The term "$C_1$-$C_5$ alkoxy" means a monovalent substituent in which a $C_1$-$C_5$ linear or branched hydrocarbon group is bound to an oxygen atom, for example, methoxy, ethoxy, propoxy, isopropoxy, butoxy, isobutoxy, sec-butoxy, tert-butoxy, pentyloxy, isopentyloxy, sec-pentyloxy, tert-pentyloxy, or neopentyloxy.

The phrase "$C_1$-$C_3$ alkoxy in which any one to three hydrogen atoms are optionally replaced by a fluorine atom(s)" means "$C_1$-$C_3$ alkoxy" as described above in which any one to three hydrogen atoms are optionally replaced by a fluorine atom(s), for example, methoxy, fluoromethoxy, difluoromethoxy, trifluoromethoxy, ethoxy, 1,1-difluoroethoxy, 2,2,2-trifluoroethoxy, propoxy, 1,1-difluoropropoxy, 2,2-difluoropropoxy, 3,3,3-trifluoropropoxy, isopropoxy, (2-fluoropropan-2-yl)oxy, or (1,1,1-trifluoropropan-2-yl)oxy.

The phrase "methoxy in which any one to three hydrogen atoms are replaced by a fluorine atom(s)" means fluoromethoxy, difluoromethoxy, or trifluoromethoxy.

The phrase "methoxy in which any one to three hydrogen atoms are optionally replaced by a fluorine atom(s)" means "methoxy in which any one to three hydrogen atoms are replaced by a fluorine atom(s)" as described above or methoxy.

The term "$C_1$-$C_3$ alkylsulfonyl" means methylsulfonyl, ethylsulfonyl, propylsulfonyl, or isopropylsulfonyl.

The term "aryl" means a monocyclic or bicyclic aromatic hydrocarbon group, for example, phenyl, or naphthyl (1-naphthyl, or 2-naphthyl).

The phrase "5- or 6-membered heteroaryl having one or two heteroatoms selected from nitrogen, oxygen, and sulfur atoms" means a 5- or 6-membered monocyclic aromatic heterocyclic group containing one or two heteroatoms selected from nitrogen, oxygen, and sulfur, other than carbon atoms, as the atom constituting the ring, for example, furyl (for example, 2-furyl, or 3-furyl), thienyl (for example, 2-thienyl, or 3-thienyl), pyrrolyl (for example, 1-pyrrolyl, 2-pyrrolyl, or 3-pyrrolyl), imidazolyl (for example, 1-imidazolyl, 2-imidazolyl, 4-imidazolyl, or 5-imidazolyl), pyrazolyl (for example, 1-pyrazolyl, 3-pyrazolyl, or 4-pyrazolyl), thiazolyl (for example, 2-thiazolyl, 4-thiazolyl, or 5-thiazolyl), isothiazolyl (for example, 3-isothiazolyl, 4-isothiazolyl, or 5-isothiazolyl), oxazolyl (for example, 2-oxazolyl, 4-oxazolyl, or 5-oxazolyl) or isoxazolyl (for example, 3-isoxazolyl, 4-isoxazolyl, or 5-isoxazolyl), pyridyl (for example, 2-pyridyl, 3-pyridyl, or 4-pyridyl), pyrimidinyl (for example, 2-pyrimidinyl, 4-pyrimidinyl, 5-pyrimidinyl, or 6-pyrimidinyl), pyridazinyl (for example, 3-pyridazinyl, or 4-pyridazinyl), or pyrazinyl (for example, 2-pyrazinyl).

The term "5- or 6-membered lactam rings" means a pyrrolidin-2-one ring and a piperidin-2-one ring.

The phrase "5- or 6-membered saturated heterocycles each containing one or two oxygen atoms as the atom constituting the ring" means 5- or 6-membered monocyclic saturated heterocycles each containing one or two oxygen atoms, other than carbon atoms, as the atom constituting the ring and includes, for example, a tetrahydrofuran ring, a 1,3-dioxolane ring, a tetrahydro-2H-pyran ring, a 1,2-dioxane ring, a 1,3-dioxane ring, and a 1,4-dioxane ring.

The phrase "a fused ring group formed by fusing of a phenyl group and one ring selected from the group consisting of 5- or 6-membered lactam rings and 5- or 6-membered saturated heterocycles each containing one or two oxygen atoms as the atom constituting the ring" means a bicyclic fused ring group formed by fusing of a phenyl group and one ring selected from the group consisting of "5- or 6-membered lactam rings" as described above and "5- or 6-membered saturated heterocycles each containing one or two oxygen atoms as the atom constituting the ring" as described above. Examples of the bicyclic fused ring group include 3-oxoisoindolin-4-yl, 3-oxoisoindolin-5-yl, 1-oxoisoindolin-5-yl, 1-oxoisoindolin-4-yl, 2-oxoindolin-4-yl, 2-oxoindolin-5-yl, 2-oxoindolin-6-yl, 2-oxoindolin-7-yl, 2,3-dihydrobenzofuran-4-yl, 2,3-dihydro-benzofuran-5-yl, 2,3-dihydrobenzofuran-6-yl, 2,3-dihydrobenzofuran-7-yl, benzo[d][1,3]dioxol-4-yl, benzo[d][1,3]dioxol-5-yl, 1-oxo-1,2,3,4-tetrahydroisoquinolin-5-yl, 1-oxo-1,2,3,4-tetrahydroisoquinolin-6-yl, 1-oxo-1,2,3,4-tetrahydroisoquinolin-7-yl, 1-oxo-1,2,3,4-tetrahydroisoquinolin-8-yl, 2-oxo-1,2,3,4-tetrahydroisoquinolin-5-yl, 2-oxo-1,2,3,4-tetrahydroisoquinolin-6-yl, 2-oxo-1,2,3,4-tetrahydroisoquinolin-7-yl, 2-oxo-1,2,3,4-tetrahydroisoquinolin-8-yl, 3-oxo-1,2,3,4-tetrahydroisoquinolin-5-yl, 3-oxo-1,2,3,4-tetrahydroisoquinolin-6-yl, 3-oxo-1,2,3,4-tetrahydroisoquinolin-7-yl, 3-oxo-1,2,3,4-tetrahydroisoquinolin-8-yl, chroman-5-yl, chroman-6-yl, chroman-7-yl, chroman-8-yl, isochroman-5-yl, isochroman-6-yl, 2,3-dihydrobenzo[b][1,4]dioxin-5-yl, 2,3-dihydrobenzo[b][1,4]dioxin-6-yl, 4H-benzo[d][1,3]dioxin-5-yl, 4H-benzo[d][1,3]dioxin-6-yl, 4H-benzo[d][1,3]dioxin-7-yl, 4H-benzo[d][1,3]dioxin-8-yl, 3,4-dihydrobenzo[c][1,2]dioxin-5-yl, 3,4-dihydrobenzo[c][1,2]dioxin-6-yl, 3,4-dihydrobenzo[c][1,2]dioxin-7-yl, 3,4-dihydrobenzo[c][1,2]dioxin-8-yl, 1,4-dihydrobenzo[d][1,2]dioxin-5-yl, and 1,4-dihydrobenzo[d][1,2]dioxin-6-yl.

The phrase "a fused ring group formed by fusing of a phenyl group and one ring selected from the group consisting of pyrrolidin-2-one, piperidin-2-one, and 1,3-dioxolane" refers to a bicyclic fused ring group such as 3-oxoisoindolin-4-yl, 3-oxoisoindolin-5-yl, 1-oxoisoindol-in-5-yl, 1-oxoisoindolin-4-yl, 2-oxoindolin-4-yl, 2-oxoindolin-5-yl, 2-oxoindolin-6-yl, 2-oxoin-dolin-7-yl, benzo[d][1,3]dioxol-4-yl, benzo[d][1,3]dioxol-5-yl, 1-oxo-1,2,3,4-tetrahydroisoquin-olin-5-yl, 1-oxo-1,2,3,4-tetrahydroisoquinolin-6-yl, 1-oxo-1,2,3,4-tetrahydroisoquinolin-7-yl, 1-oxo-1,2,3,4-tetrahydroisoquinolin-8-yl, 2-oxo-1,2,3,4-tetrahydroisoquinolin-5-yl, 2-oxo-1,2,3,4-tetrahydroisoquinolin-6-yl, 2-oxo-1,2,3,4-tetrahydroisoquinolin-7-yl, 2-oxo-1,2,3,4-tetrahydroisoquinolin-8-yl, 3-oxo-1,2,3,4-tetrahydroisoquinolin-5-yl, 3-oxo-1,2,3,4-tetrahydroisoquinolin-6-yl, 3-oxo-1,2,3,4-tetrahydroisoquinolin-7-yl, or 3-oxo-1,2,3,4-tetrahydroisoquinolin-8-yl.

The phrase "one of $R^2$, $R^4$, and $R^5$ is halogen, methoxy, or methyl in which one hydrogen atom is optionally replaced by a hydroxy group, and the other two are hydrogen" means that $R^2$ is halogen, methoxy, or methyl in which one hydrogen atom is optionally replaced by a hydroxy group, and both $R^4$ and $R^5$ represent hydrogen, or that $R^4$ is halogen, methoxy, or methyl in which one hydrogen atom is optionally replaced by a hydroxy group, and both $R^2$ and $R^5$ represent hydrogen, or that $R^5$ is halogen, methoxy, or methyl in which one hydrogen atom is optionally replaced by a hydroxy group, and both $R^2$ and $R^4$ represent hydrogen.

The phrase "one of $R^2$ and $R^4$ is fluorine, chlorine, methoxy, or methyl in which one hydrogen atom is optionally replaced by a hydroxy group, and both the other and $R^5$ represent hydrogen" means that $R^2$ is fluorine, chlorine, methoxy, or methyl in which one hydrogen atom is optionally replaced by a hydroxy group, and both $R^4$ and $R^5$ represent hydrogen, or that $R^4$ is fluorine, chlorine, methoxy, or methyl in which one hydrogen atom is optionally replaced by a hydroxy group, and both $R^2$ and $R^5$ represent hydrogen.

The phrase "$R^6$ and $R^7$ together represent $-(CH_2)_h-$; h is an integer of 3 to 5, wherein any one of the methylene groups is optionally replaced by an oxygen atom, —NH—, or $-N(CH_3)-$" means that $R^6$ and $R^7$, together with the nitrogen atom which is bound to $R^6$ and $R^7$, form an azetidine ring (h=3), a pyrrolidine ring (h=4), or a piperidine ring (h=5), in which any one of the methylene groups is optionally replaced by an oxygen atom, —NH—, or —N($CH_3$)—, and examples of the rings include an azetidine ring (h=3), a pyrrolidine ring (h=4), a piperidine ring (h=5), a morpholine ring (h=5), a piperazine ring (h=5), and a 1-methylpiperazine ring (h=5).

The phrase "$R^9$ and $R^{10}$ together represent —$(CH_2)_n$—; n is an integer of 3 to 6" means that $R^9$ and $R^{10}$, together with the nitrogen atom which is bound to $R^9$ and $R^{10}$, form an azetidine ring (n=3), a pyrrolidine ring (n=4), a piperidine ring (n=5), or an azepane ring (n=6).

The phrase "$R^{11}$ and $R^{12}$ together represent —$(CH_2)_m$—; m is an integer of 3 to 5, wherein any one of the methylene groups is optionally replaced by an oxygen atom" means that $R^{11}$ and $R^{12}$, together with the nitrogen atom which is bound to $R^{11}$ and $R^{12}$, form an azetidine ring (m=3), a pyrrolidine ring (m=4), or a piperidine ring (m=5), in which any one of the methylene groups is optionally replaced by an oxygen atom, and examples of the rings include an azetidine ring (m=3), a pyrrolidine ring (m=4), a piperidine ring (m=5), a morpholine ring (m=5), a piperazine ring (m=5), and a 1-methylpiperazine ring (m=5).

The phrase "$R^{13}$ and $R^{14}$ together represent —$(CH_2)_k$— in which any one hydrogen atom is optionally replaced by a hydroxy group; k is 3 or 4" means that $R^{13}$ and $R^{14}$, together with the nitrogen atom which is bound to $R^{13}$ and $R^{14}$, form an azetidine ring (k=3) or a pyrrolidine ring (k=4), in which any one hydrogen atom is optionally replaced by a hydroxy group, and examples of the rings include an azetidine ring (k=3), a 3-hydroxyazetidin ring (k=3), a pyrrolidine ring (k=4), and a 3-hydroxypyrrolidine ring (k=4).

The phrase "$R^{13}$ and $R^{14}$ together represent —$(CH_2)_k$— in which any one or two hydrogen atoms are optionally replaced by a fluorine atom(s), a methyl group(s), a hydroxy group(s), or a methoxy group(s) or in which any one $CH_2$ group is optionally replaced by an oxygen atom, a nitrogen atom, or —CONH—; k is an integer of 3 to 5" means that $R^{13}$ and $R^{14}$, together with the nitrogen atom which is bound to $R^{13}$ and $R^{14}$, form an azetidine ring (k=3), a pyrrolidine ring (k=4), or a piperidine ring (k=5), in which any one or two hydrogen atoms are optionally replaced by a fluorine atom(s), a methyl group(s), a hydroxy group(s), or a methoxy group(s) or in which any one $CH_2$ group is optionally replaced by an oxygen atom, a nitrogen atom, or —CONH—, and examples of the rings include an azetidine ring (k=3), a 3-fluoroazetidine ring (k=3), a 3,3-difluoroazetidine ring (k=3), a 2-methylazetidine ring (k=3), a 3-methylazetidine ring (k=3), a 4-methylazetidine ring (k=3), a 2,2-dimethylazetidine ring (k=3), a 2,3-dimethylazetidine ring (k=3), a 2,4-dimethylazetidine ring (k=3), a 3,3-dimethylazetidine ring (k=3), a 3-hydroxyazetidin ring (k=3), a 3-methoxyazetidine ring (k=3), a pyrrolidine ring (k=4), a 3-fluoropyrrolidine ring (k=4), a 3,3-difluoropyrrolidine ring (k=4), a 3,4-difluoropyrrolidine ring (k=4), a 2-methylpyrrolidine ring (k=4), a 3-methylpyrrolidine ring (k=4), a 2,2-dimethylpyrrolidine ring (k=4), a 2,3-dimethylpyrrolidine ring (k=4), a 2,4-dimethylpyrrolidine ring (k=4), a 2,5-dimethylpyrrolidine ring (k=4), a 3,3-dimethylpyrrolidine ring (k=4), a 3,4-dimethylpyrrolidine ring (k=4), a 3,5-dimethylpyrrolidine ring (k=4), a 3-hydroxypyrrolidine ring (k=4), a 3,4-dihydroxypyrrolidine ring (k=4), a 3-methoxypyrrolidine ring (k=4), a 3,4-dimethoxypyrrolidine ring (k=4), a tetrahydropyrimidin-2(1H)-one ring (k=4), a piperazin-2-one ring (k=4), a piperidine ring (k=5), a 3-fluoropiperidine ring (k=5), a 4-fluoropiperidine ring (k=5), a 3,3-difluoropiperidine ring (k=5), a 3,4-difluoropiperidine ring (k=5), a 3,5-difluoropiperidine ring (k=5), a 4,4-difluoropiperidine ring (k=5), a 4,5-difluoropiperidine ring (k=5), a 2-methylpiperidine ring (k=5), a 3-methylpiperidine ring (k=5), a 4-methylpiperidine ring (k=5), a 5-methylpiperidine ring (k=5), a 2,2-dimethylpiperidine ring (k=5), a 2,3-dimethylpiperidine ring (k=5), a 2,4-dimethylpiperidine ring (k=5), a 2,5-dimethylpiperidine ring (k=5), a 3,3-dimethylpiperidine ring (k=5), a 3,4-dimethylpiperidine ring (k=5), a 3,5-dimethylpiperidine ring (k=5), a 3-hydroxypiperidine ring (k=5), a 4-hydroxypiperidine ring (k=5), a 3,4-dihydroxypiperidine ring (k=5), a 3,5-dihydroxypiperidine ring (k=5), a morpholine ring (k=5), a piperazine ring (k=5), a 1,3-diazepan-2-one ring (k=5), a 1,4-diazepan-2-one ring (k=5), and a 1,4-diazepan-5-one ring (k=5).

The phrase "$R^{13}$ and $R^{14}$, together with the nitrogen atom which is bound to $R^{13}$ and $R^{14}$, forms an azetidine ring in which any one hydrogen atom is optionally replaced by a hydroxy group" refers to, for example, an azetidine ring or a 3-hydroxyazetidine ring.

The phrase "an azetidine ring in which any two hydrogen atoms are optionally re-placed by a methyl group(s) and/or a fluorine atom(s) or in which any one hydrogen atom is optionally replaced by a hydroxy or methoxy group" refers to an azetidine ring, a 2,2-dimethylazetidine ring, a 2,3-dimethylazetidine ring, a 2,4-dimethylazetidine ring, a 3,3-dimethylazetidine ring, a 3,3-difluoroazetidine ring, a 3-hydroxyazetidin ring, or a 3-methoxyazetidine ring.

The phrase "$C_3$ or $C_4$ cycloalkyl in which any one carbon atom is optionally replaced by an oxygen atom" refers to, for example, cyclopropyl, cyclobutyl, oxiran-2-yl, or oxetan-3-yl.

The phrase "methyl which is substituted with a $C_3$ or $C_4$ cycloalkyl group in which any one carbon atom is optionally replaced by a nitrogen or oxygen atom" refers to, for example, cyclopropylmethyl, cyclobutylmethyl, oxiran-2-ylmethyl, oxetan-2-ylmethyl, oxetan-3-ylmethyl, aziridin-2-ylmethyl, azetidin-2-ylmethyl, or azetidin-3-ylmethyl.

The phrase "methyl in which any one hydrogen atom is optionally replaced by a hydroxy or methoxycarbonyl group" refers to, for example, methyl, hydroxymethyl, or methoxycarbonylmethyl.

Preferably, $R^{1x}$ is phenyl (any one hydrogen atom in the phenyl group is optionally replaced by a fluorine or chlorine atom or $C_1$-$C_3$ alkyl in which any one to three hydrogen atoms are optionally replaced by a fluorine atom(s) or any one hydrogen atom is optionally replaced by a hydroxy group, $C_1$-$C_3$ alkoxy in which any one to three hydrogen atoms are optionally replaced by a fluorine atom(s), cyano, methoxycarbonyl, —$CONR^6R^7$, —$NHCOR^8$, aminosulfonyl, $C_1$-$C_3$ alkylsulfonylamino, aminosulfonylamino, or $C_1$-$C_3$ alkylsulfonyl group), pyrazolyl, 1-oxoisoindolin-5-yl, 2-oxo-1,2,3,4-tetrahydroquinolin-6-yl, or benzo[d][1,3]dioxol-5-yl, more preferably phenyl (any one hydrogen atom in the phenyl group is optionally replaced by a fluorine atom or a trifluoromethyl, hydroxymethyl, 2-hydroxypropan-2-yl, methoxy, trifluoromethoxy, cyano, methoxycarbonyl, —$CONR^6R^7$, —$NHCOR^8$, aminosulfonyl, methylsulfonylamino, aminosulfonylamino, or methylsulfonyl group), pyrazolyl, 1-oxoisoindolin-5-yl, 2-oxo-1,2,3,4-tetrahydroquinolin-6-yl, or benzo[d][1,3]dioxol-5-yl, still more preferably phenyl (any one hydrogen atom in the phenyl group is optionally replaced by a fluorine atom or a hydroxymethyl, trifluoromethoxy, cyano, aminocarbonyl, acetamide, aminosulfonyl, methylsulfonylamino, or methylsulfonyl group).

When $R^{1x}$ is a substituted phenyl group, the substitution of the hydrogen atom at the para-position is preferred.

In the tetrahydroquinoline derivative or a pharmaceutically acceptable salt thereof according to [1] as described above, which are novel compounds, $R^{1x}$ is preferably phenyl (any one hydrogen atom in the phenyl group is optionally replaced by one substituent selected from the group consisting of halogen, $C_1$-$C_3$ alkyl in which any one to three hydrogen atoms are optionally replaced by a fluorine atom(s), $C_1$-$C_3$ alkoxy in which any one to three hydrogen atoms are optionally replaced by a fluorine atom(s), cyano, methoxycarbonyl, and —$NHCOR^8$, provided that m-cyanophenyl and p-(trifluoromethoxy)phenyl are excluded) or 5- or 6-membered heteroaryl (any one hydrogen atom in the 5- or 6-membered heteroaryl is optionally replaced by a $C_1$-$C_3$ alkyl or $C_1$-$C_3$ alkoxy group, provided that 1-methyl-1H-pyrazol-4-yl and 6-methoxypyridin-3-yl are excluded).

Moreover, in the tetrahydroquinoline derivative or a pharmaceutically acceptable salt thereof according to [1] as described above, which are novel compounds, $R^{1x}$ is preferably hydrogen, phenyl (any one hydrogen atom in the phenyl group is replaced by a $C_1$-$C_3$ alkyl in which any one hydrogen atom is replaced by a hydroxy group, —$CONR^6R^7$, aminosulfonyl, methylsulfonylamino, aminosulfonylamino, or $C_1$-$C_3$ alkylsulfonyl group; otherwise, the hydrogen atom at the meta-position of the phenyl group is replaced by a cyano group; otherwise, the hydrogen atom at the para-position of the phenyl group is replaced by a trifluoromethoxy group), 1-methyl-1H-pyrazol-4-yl, or 6-methoxypyridin-3-yl or a fused ring group formed by fusing of a phenyl group and one ring selected from the group consisting of pyrrolidin-2-one, piperidin-2-one, and 1,3-dioxolane (wherein any one hydrogen atom in the fused ring group is optionally replaced by a methyl group).

Preferably, $R^{1y}$ is hydrogen, phenyl, 4-hydroxymethylphenyl, 4-aminocarbonylphenyl, 4-acetamidophenyl, 4-aminosulfonylphenyl, or 4-methylsulfonylphenyl, more preferably 4-hydroxymethylphenyl, 4-aminocarbonylphenyl, 4-acetamidophenyl, 4-aminosulfonylphenyl, or 4-methylsulfonylphenyl, still more preferably 4-aminocarbonylphenyl, 4-aminosulfonylphenyl, or 4-methylsulfonylphenyl.

However, in that instance both $R^{1x}$ and $R^{1y}$ representing hydrogen is excluded.

For the combination of $R^{1x}$ and $R^{1y}$, it is preferable that $R^{1x}$ is hydrogen and $R^{1y}$ is a substituent other than hydrogen, or that $R^{1x}$ is a substituent other than hydrogen and $R^{1y}$ is hydrogen; more preferably, $R^{1x}$ is a substituent other than hydrogen and $R^{1y}$ is hydrogen.

Preferably, $R^2$ is hydrogen, fluorine, chlorine, hydroxymethyl, or methyl, more preferably hydrogen.

Preferably, $R^3$ is hydrogen, fluorine, chlorine, $C_1$-$C_3$ alkyl in which any one hydrogen atom is optionally replaced by a hydroxy group, trifluoromethoxy, —$CH_2NR^{11}R^{12}$, or —$CH_2CONR^{13}R^{14}$, more preferably hydrogen, fluorine, chlorine, methyl, hydroxymethyl, trifluoromethoxy, or —$CH_2CONR^{13}R^{14}$, still more preferably hydrogen, fluorine, chlorine, or methyl.

Preferably, $R^4$ is hydrogen, fluorine, chlorine, or methyl, more preferably hydrogen.

Preferably, $R^5$ is hydrogen.

Preferably, $R^6$ and $R^7$ each independently represent hydrogen or $C_1$-$C_3$ alkyl, or $R^6$ and $R^7$, together with the nitrogen atom which is bound to $R^6$ and $R^7$, form a piperidine ring, a morpholine ring, a piperazine ring, or an N-methylpiperazine ring; more preferably, both $R^6$ and $R^7$ represent hydrogen.

Preferably, $R^8$ is hydrogen or $C_1$-$C_3$ alkyl, more preferably methyl.

Preferably, $R^9$ is hydrogen, and $R^{10}$ is hydrogen, —$COR^{15}$, or $C_1$-$C_3$ alkylsulfonyl, or $R^9$ and $R^{10}$ together represent —$(CH_2)_n$—, and n is 4 or 5; more preferably, $R^9$ is hydrogen, and $R^{10}$ is —$COR^{15}$.

Preferably, $R^{11}$ and $R^{12}$ together represent —$(CH_2)_m$—, and m is 4 or 5 (wherein any one of the methylene groups is optionally replaced by an oxygen atom).

It is preferable that $R^{13}$ is hydrogen or methyl, and $R^{14}$ is hydrogen, methyl, ethyl, isopropyl, tert-butyl, 2-hydroxyethyl, cyclopropyl, cyclobutyl, oxetan-3-yl, cyclopropylmethyl, cyclobutylmethyl, or oxetan-3-ylmethyl, or that $R^{13}$ and $R^{14}$, together with the nitrogen atom which is bound to $R^{13}$ and $R^{14}$, form a pyrrolidine ring, a piperidine ring, a piperazine ring, a morpholine ring, an azetidine ring, a 3,3-dimethylazetidine ring, a 3,3-difluoroazetidine ring, a 3-hydroxyazetidin ring, or a 3-methoxyazetidine ring.

Preferably, $R^{1s}$ is $C_1$-$C_5$ alkyl, $C_1$-$C_5$ alkoxy, or —$NHR^{16}$.

Preferably, $R^{16}$ is hydrogen or $C_1$-$C_5$ alkyl.

Preferably, $R^v$ is hydrogen.

Preferably, $R^w$ is hydrogen.

The tetrahydroquinoline derivative (I) as described above or a pharmaceutically acceptable salt thereof include not only single stereoisomers but also all of the mixtures of stereoisomers such as racemates or a diastereomeric mixtures, (for example, mixtures of enantiomers).

The term "stereoisomer" refers to compounds which have identical chemical structure but different three-dimensional configurations, and the term includes, for example, conformer, rotamer, tautomer, enantiomer, and diastereomer.

The tetrahydroquinoline derivative (I) may be represented by general formulae (I-1) to (I-8):

(I-1)

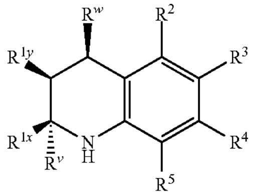

(I-2)

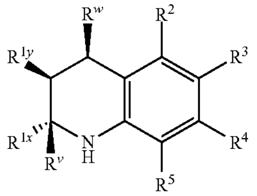

(I-3)

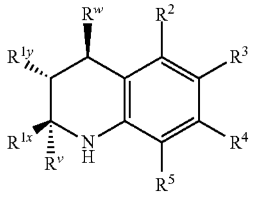

-continued (I-4)

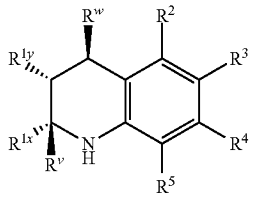

(I-5)

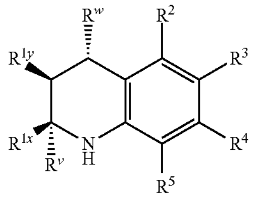

(I-6)

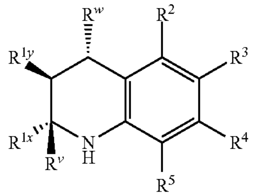

(I-7)

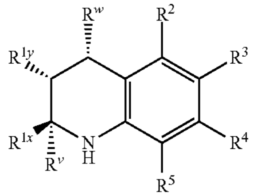

(I-8)

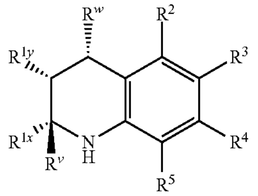

In the formulae, $R^{1x}$, $R^{1y}$, $R^2$, $R^3$, $R^4$, $R^5$, $R^v$, and $R^w$ have the same definitions as described above.

In the tetrahydroquinoline derivative (I), any configuration of preferable $R^{1x}$, $R^{1y}$, $R^2$ to $R^{16}$, $R^v$, and $R^w$ described above and preferable h, k, m, and n described above can be selected and combined together. The following combinations are shown as examples, but this disclosure is not limited to those examples.

For example, in the tetrahydroquinoline derivative (I) as described above, $R^{1x}$ is phenyl (any hydrogen atom in the phenyl group is optionally replaced by a fluorine or chlorine atom, $C_1$-$C_3$ alkyl in which any one to three hydrogen atoms are optionally replaced by a fluorine atom(s) or any one hydrogen atom is optionally replaced by a hydroxy group, $C_1$-$C_3$ alkoxy in which any one to three hydrogen atoms are optionally replaced by a fluorine atom(s), cyano, methoxycarbonyl, —$CONR^6R^7$, —$NHCOR^8$, aminosulfonyl, $C_1$-$C_3$ alkylsulfonylamino, aminosulfonylamino, or $C_1$-$C_3$ alkylsulfonyl group), pyrazolyl, 1-oxoisoindolin-5-yl, 2-oxo-1,2,3,4-tetrahydroquinolin-6-yl, or benzo[d][1,3]dioxol-5-yl;

$R^{1y}$ is hydrogen;

$R^2$ is hydrogen;

$R^3$ is hydrogen, fluorine, chlorine, $C_1$-$C_3$ alkyl in which any one hydrogen atom is optionally replaced by a hydroxy group, methoxy, —$NR^9R^{10}$, —$CH_2NR^{11}R^{12}$, or —$CH_2CONR^{13}R^{14}$;

$R^4$ is hydrogen or methoxy;

$R^5$ is hydrogen;

$R^6$ and $R^7$ each independently represent hydrogen or $C_1$-$C_3$ alkyl, or $R^6$ and $R^7$, together with the nitrogen atom which is bound to $R^6$ and $R^7$, optionally form a piperidine ring, a morpholine ring, a piperazine ring, or an N-methylpiperazine ring;

$R^8$ is hydrogen or $C_1$-$C_3$ alkyl;

$R^9$ is hydrogen, and $R^{10}$ is hydrogen, —$COR^{15}$, or $C_1$-$C_3$ alkylsulfonyl, or $R^9$ and $R^{10}$ together represent —$(CH_2)_n$—;

n is 4 or 5;

$R^{11}$ and $R^{12}$ together represent —$(CH_2)_m$—;

m is 4 or 5, wherein any one of the methylene groups is optionally replaced by an oxygen atom;

$R^{13}$ is hydrogen or methyl, and $R^{14}$ is hydrogen, methyl, ethyl, isopropyl, tert-butyl, 2-hydroxyethyl, cyclopropyl, cyclobutyl, oxetan-3-yl, cyclopropylmethyl, cyclobutylmethyl, or oxetan-3-ylmethyl, or $R^{13}$ and $R^{14}$, together with the nitrogen atom which is bound to $R^{13}$ and $R^{14}$, optionally form a pyrrolidine ring, a piperidine ring, a piperazine ring, a morpholine ring, an azetidine ring, a 3,3-dimethylazetidine ring, a 3,3-difluoroazetidine ring, a 3-hydroxyazetidin ring, or a 3-methoxyazetidine ring;

$R^{15}$ is $C_1$-$C_5$ alkyl, $C_1$-$C_5$ alkoxy, or —$NHR^{16}$;

$R^{16}$ is hydrogen or $C_1$-$C_5$ alkyl;

$R^v$ is hydrogen; and $R^w$ is hydrogen (provided that 2-phenyl-1,2,3,4-tetrahydroquinoline is excluded).

In one example, the tetrahydroquinoline derivative (I) are, for example, a tetrahydroquinoline derivative represented by the general formula (II-a) below or a pharmaceutically acceptable salt thereof, (II-a)

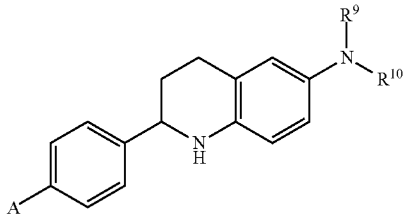

wherein A is hydrogen or —$CONH_2$, and $R^9$ and $R^{10}$ each independently represent hydrogen, —$COR^{15}$, or $C_1$-$C_3$ alkylsulfonyl, or $R^9$ and $R^{10}$ together represent —$(CH_2)_n$—, and n is an integer of 3 to 6, and $R^{15}$ is $C_1$-$C_5$ alkyl, $C_1$-$C_5$ alkoxy, or —$NHR^{16}$, and $R^{16}$ is hydrogen or $C_1$-$C_5$ alkyl.

Preferably, in the tetrahydroquinoline derivative represented by the general formula (II-a) (hereinafter also referred to as "tetrahydroquinoline derivative (II-a)"), $R^9$ is hydrogen, and $R^{10}$ is —$COR^{15}$, and $R^{15}$ is $C_1$-$C_5$ alkoxy; more preferably, A is hydrogen, and $R^9$ is hydrogen, and $R^{10}$ is —$COR^{15}$, and $R^{15}$ is $C_1$-$C_5$ alkoxy; still more preferably, A is hydrogen, and $R^9$ is hydrogen, and $R^{10}$ is —$COR^{15}$, and $R^{15}$ is tert-butoxy.

For the pharmaceutically acceptable salt of the tetrahydroquinoline derivative (II-a), reference may be made to the below-described description of the pharmaceutically acceptable salt of the tetrahydroquinoline derivative (I).

Moreover, each of the tetrahydroquinoline derivative (II-a) or a pharmaceutically acceptable salt thereof can be used as a drug that contains the tetrahydroquinoline derivative (II-a) or the pharmaceutically acceptable salt thereof as an active ingredient and more preferably be used as a drug for treating or preventing diseases, disorders or syndromes related to ferroptosis inhibition.

The diseases, disorders or syndromes related to ferroptosis inhibition will be described below.

Furthermore, each of the tetrahydroquinoline derivative (II-a) or a pharmaceutically acceptable salt thereof can be used as a ferroptosis inhibitor that contains the tetrahydroquinoline derivative (II-a) or the pharmaceutically acceptable salt thereof as an active ingredient.

The ferroptosis inhibitor will be described below.

In one example, the tetrahydroquinoline derivative (I) are, for example, a tetrahydroquinoline derivative represented by the general formula (II-b) below or a pharmaceutically acceptable salt thereof,

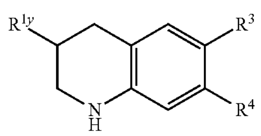

(II-b)

wherein $R^{1y}$ is phenyl, 4-hydroxymethylphenyl, 4-aminocarbonylphenyl, 4-acetamidophenyl, 4-aminosulfonylphenyl, 4-methylsulfonylphenyl, or 3-pyridyl, and $R^3$ is hydrogen or halogen, and $R^4$ is hydrogen or halogen (provided that 3-phenyl-1,2,3,4-tetrahydroquinoline is excluded).

Preferably, in the tetrahydroquinoline derivative represented by the general formula (II-b) (hereinafter also referred to as "tetrahydroquinoline derivative (II-b)"), $R^{1y}$ is 4-hydroxymethylphenyl, 4-aminocarbonylphenyl, 4-acetamidophenyl, 4-aminosulfonylphenyl, or 4-methylsulfonylphenyl, and $R^3$ is hydrogen, fluorine, or chlorine, and $R^4$ is hydrogen, fluorine, or chlorine; more preferably, $R^{1y}$ is 4-aminocarbonylphenyl, 4-aminosulfonylphenyl, or 4-methylsulfonylphenyl, and $R^3$ is hydrogen, and $R^4$ is hydrogen.

For the pharmaceutically acceptable salt of the tetrahydroquinoline derivative (II-b), reference may be made to the below-described description of the pharmaceutically acceptable salt of the tetrahydroquinoline derivative (I).

Moreover, each of the tetrahydroquinoline derivative (II-b) or a pharmaceutically acceptable salt thereof can be used as a drug that contains the tetrahydroquinoline derivative (II-b) or the pharmaceutically acceptable salt thereof as an active ingredient, and more preferably be used as a drug for treating or preventing diseases, disorders or syndromes related to ferroptosis inhibition.

The diseases, disorders or syndromes related to ferroptosis inhibition will be described below.

Furthermore, each of the tetrahydroquinoline derivative (II-b) or a pharmaceutically acceptable salt thereof can be used as a ferroptosis inhibitor that contains the tetrahydroquinoline derivative (II-b) or the pharmaceutically acceptable salt thereof as an active ingredient.

The ferroptosis inhibitor will be described below.

Specific examples of the tetrahydroquinoline derivative (I) are shown in Tables 1-1 to 1-7, but this disclosure is not limited to those compounds.

TABLE 1-1

| Structural formula |
|---|
| 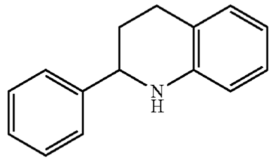 [SMILES: c1ccc(C2CCc3ccccc3N2)cc1] |
| 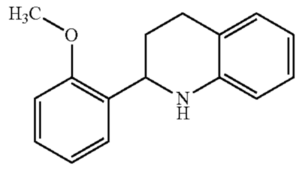 [SMILES: COc1ccccc1C1CCc2ccccc2N1] |
| 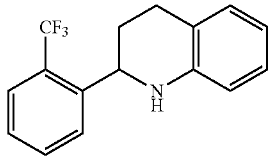 [SMILES: FC(F)(F)c1ccccc1C1CCc2ccccc2N1] |
| 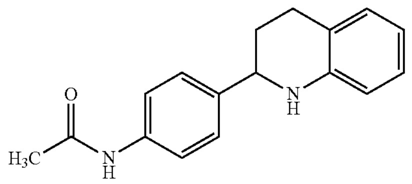 [SMILES: CC(=O)Nc1ccc(C2CCc3ccccc3N2)cc1] |
| 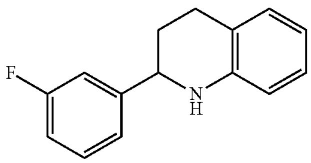 [SMILES: Fc1cccc(C2CCc3ccccc3N2)c1] |
| 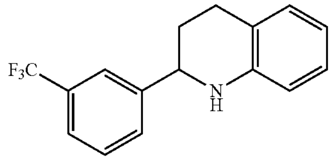 [SMILES: FC(F)(F)c1cccc(C2CCc3ccccc3N2)c1] |
| 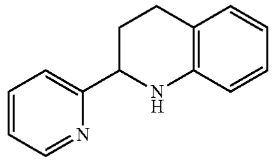 [SMILES: c1ccc(C2CCc3ccccc3N2)nc1] |
| 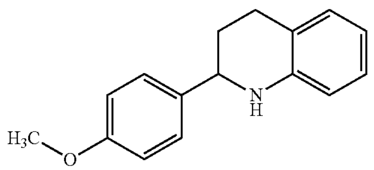 [SMILES: COc1ccc(C2CCc3ccccc3N2)cc1] |
| 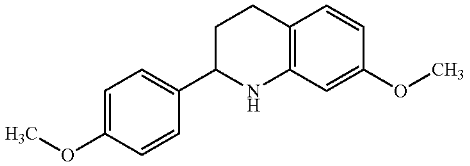 |

TABLE 1-1-continued
| Structural formula |
| --- |
| 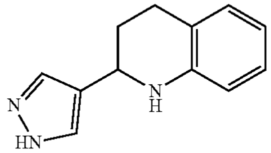 [SMILES: c1ccc2c(c1)CCC(c1cn[nH]c1)N2] |
| 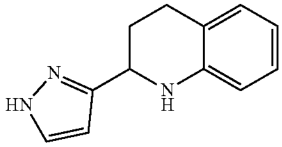 [SMILES: c1ccc2c(c1)CCC(c1cc[nH]n1)N2] |
| 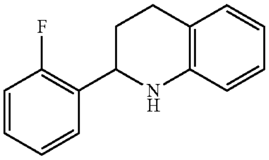 [SMILES: Fc1ccccc1C1CCc2ccccc2N1] |
| 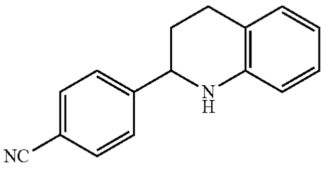 [SMILES: N#Cc1ccc(C2CCc3ccccc3N2)cc1] |
| 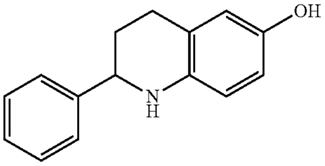 [SMILES: Oc1ccc2c(c1)CCC(c1ccccc1)N2] |
| 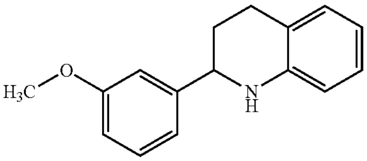 [SMILES: COc1cccc(C2CCc3ccccc3N2)c1] |
| 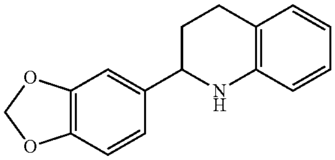 [SMILES: c1ccc2c(c1)CCC(c1ccc3c(c1)OCO3)N2] |
| 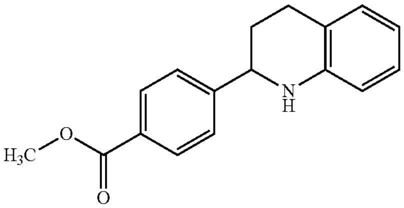 |
| 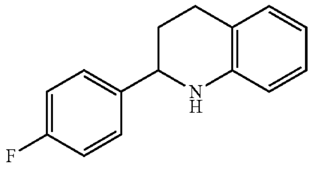 [SMILES: Fc1ccc(C2CCc3ccccc3N2)cc1] |
| 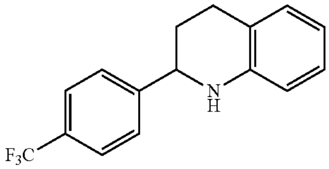 [SMILES: FC(F)(F)c1ccc(C2CCc3ccccc3N2)cc1] |
| 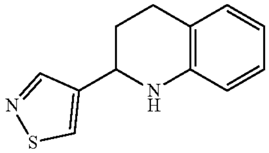 [SMILES: c1ccc2c(c1)CCC(c1cnsc1)N2] |
| 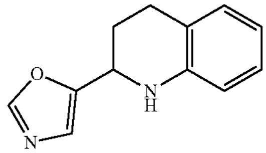 [SMILES: c1ccc2c(c1)CCC(c1cnco1)N2] |
TABLE 1-2
| Structural formula |
| --- |
| 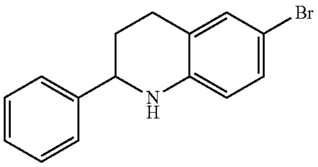 [SMILES: Brc1ccc2c(c1)CCC(c1ccccc1)N2] |
| 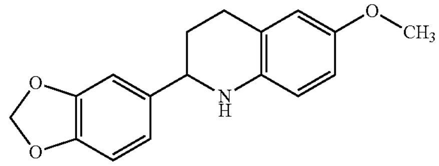 [SMILES: COc1ccc2c(c1)CCC(c1ccc3c(c1)OCO3)N2] |
| 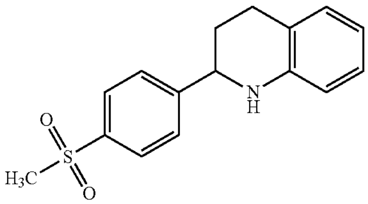 [SMILES: CS(=O)(=O)c1ccc(C2CCc3ccccc3N2)cc1] |
| 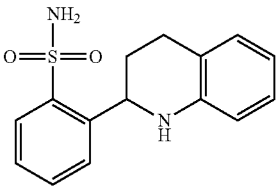 [SMILES: NS(=O)(=O)c1ccccc1C1CCc2ccccc2N1] |
| 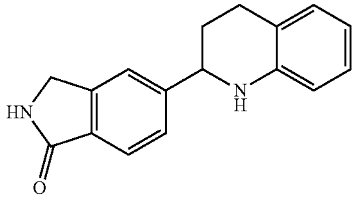 [SMILES: O=C1NCc2cc(C3CCc4ccccc4N3)ccc21] |

TABLE 1-2-continued
| Structural formula |
| --- |
| 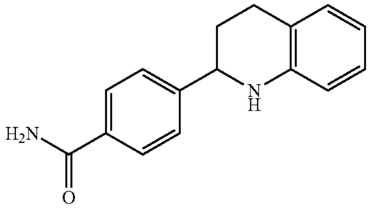 [SMILES: NC(=O)c1ccc(C2CCc3ccccc3N2)cc1] |
| 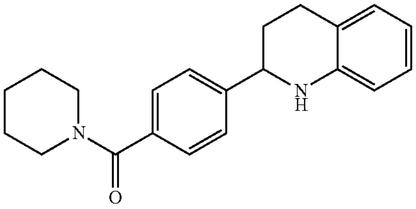 [SMILES: O=C(c1ccc(C2CCc3ccccc3N2)cc1)N1CCCCC1] |
| 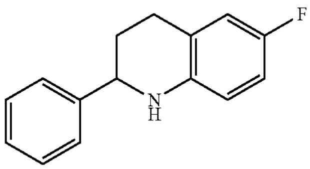 [SMILES: Fc1ccc2c(c1)CCC(c1ccccc1)N2] |
| 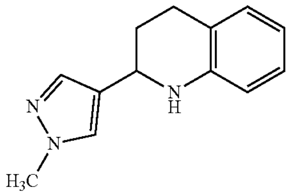 [SMILES: Cn1cc(C2CCc3ccccc3N2)cn1] |
| 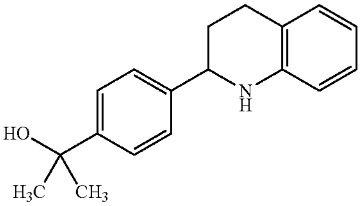 [SMILES: CC(C)(O)c1ccc(C2CCc3ccccc3N2)cc1] |
| 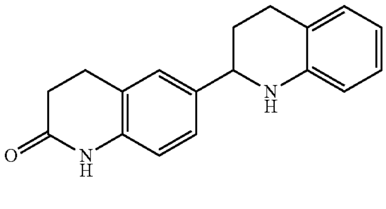 [SMILES: O=C1CCc2cc(C3CCc4ccccc4N3)ccc2N1] |
| 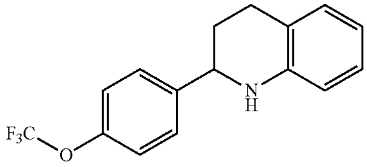 [SMILES: FC(F)(F)Oc1ccc(C2CCc3ccccc3N2)cc1] |
TABLE 1-2-continued
| Structural formula |
| --- |
| 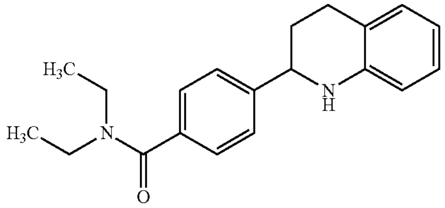 [SMILES: CCN(CC)C(=O)c1ccc(C2CCc3ccccc3N2)cc1] |
| 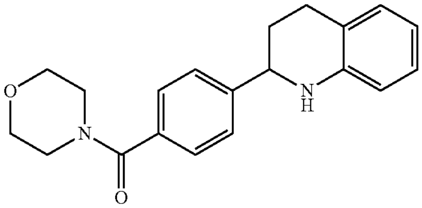 [SMILES: O=C(c1ccc(C2CCc3ccccc3N2)cc1)N1CCOCC1] |
| 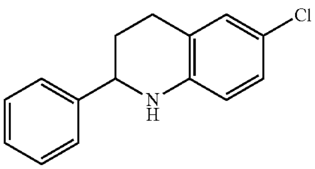 |
| 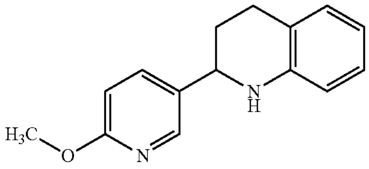 [SMILES: COc1ccc(C2CCc3ccccc3N2)cn1] |
| 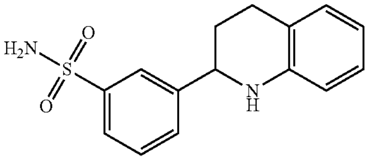 [SMILES: NS(=O)(=O)c1cccc(C2CCc3ccccc3N2)c1] |
| 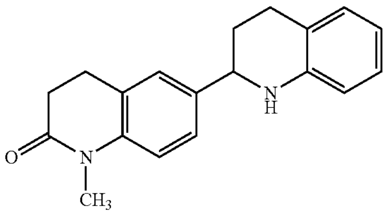 [SMILES: CN1C(=O)CCc2cc(C3CCc4ccccc4N3)ccc21] |
| 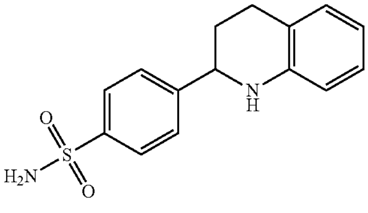 [SMILES: NS(=O)(=O)c1ccc(C2CCc3ccccc3N2)cc1] |

TABLE 1-2-continued
| Structural formula |
|---|
| 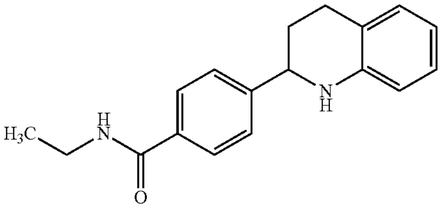 [SMILES: CCNC(=O)c1ccc(C2CCc3ccccc3N2)cc1] |
| 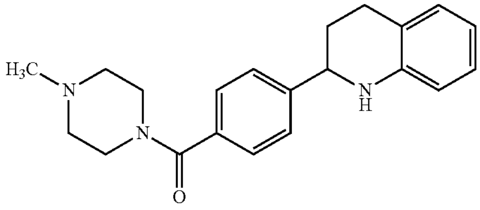 [SMILES: CN1CCN(C(=O)c2ccc(C3CCc4ccccc4N3)cc2)CC1] |
TABLE 1-3
| Structural formula |
|---|
| 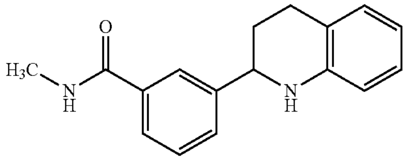 [SMILES: CNC(=O)c1cccc(C2CCc3ccccc3N2)c1] |
| 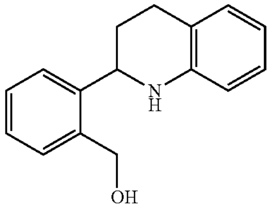 [SMILES: OCc1ccccc1C1CCc2ccccc2N1] |
| 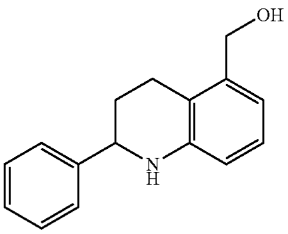 [SMILES: OCc1cccc2c1CCC(c1ccccc1)N2] |
| 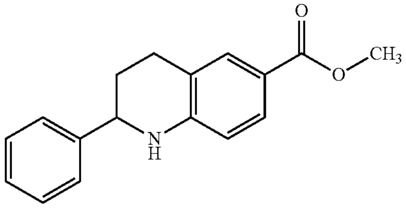 [SMILES: COC(=O)c1ccc2c(c1)CCC(c1ccccc1)N2] |
| 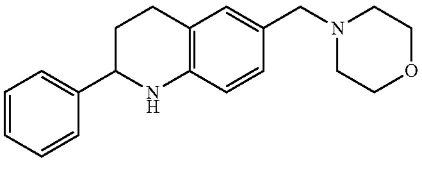 [SMILES: c1ccc(C2CCc3cc(CN4CCOCC4)ccc3N2)cc1] |
TABLE 1-3-continued
| Structural formula |
|---|
| 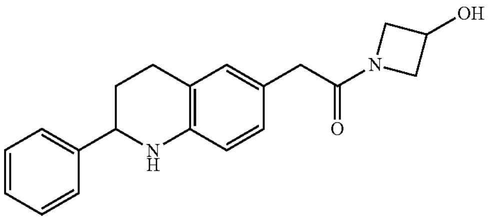 [SMILES: O=C(Cc1ccc2c(c1)CCC(c1ccccc1)N2)N1CC(O)C1] |
| 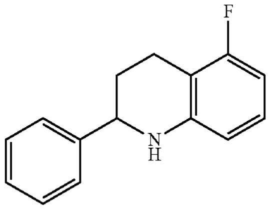 [SMILES: Fc1cccc2c1CCC(c1ccccc1)N2] |
| 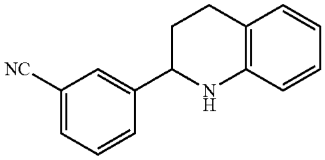 [SMILES: N#Cc1cccc(C2CCc3ccccc3N2)c1] |
| 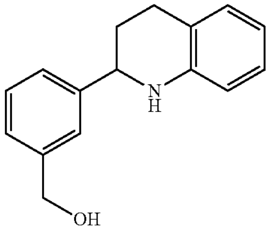 [SMILES: OCc1cccc(C2CCc3ccccc3N2)c1] |
| 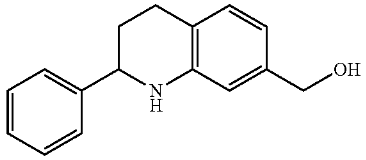 [SMILES: OCc1ccc2c(c1)NC(c1ccccc1)CC2] |
| 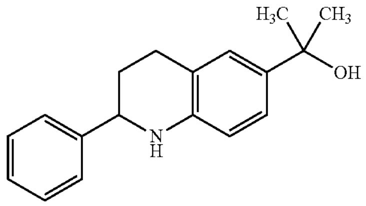 [SMILES: CC(C)(O)c1ccc2c(c1)CCC(c1ccccc1)N2] |
| 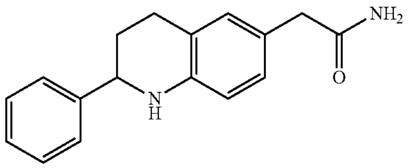 [SMILES: NC(=O)Cc1ccc2c(c1)CCC(c1ccccc1)N2] |
| 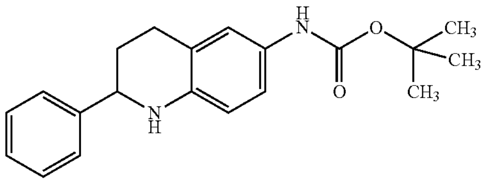 [SMILES: CC(C)(C)OC(=O)Nc1ccc2c(c1)CCC(c1ccccc1)N2] |

TABLE 1-3-continued
| Structural formula |
| --- |
| 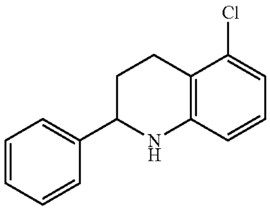 [SMILES: Clc1cccc2c1CCC(c1ccccc1)N2] |
| 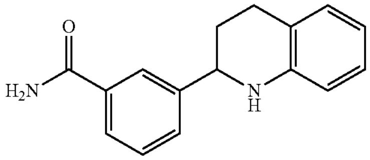 [SMILES: NC(=O)c1cccc(C2CCc3ccccc3N2)c1] |
| 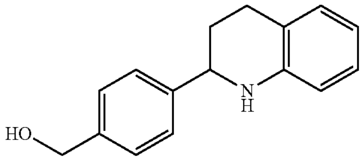 [SMILES: OCc1ccc(C2CCc3ccccc3N2)cc1] |
| 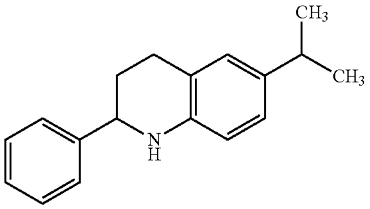 [SMILES: CC(C)c1ccc2c(c1)CCC(c1ccccc1)N2] |
| 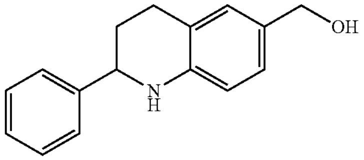 [SMILES: OCc1ccc2c(c1)CCC(c1ccccc1)N2] |
| 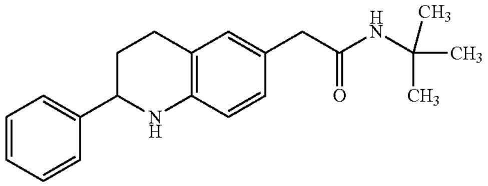 [SMILES: CC(C)(C)NC(=O)Cc1ccc2c(c1)CCC(c1ccccc1)N2] |
| 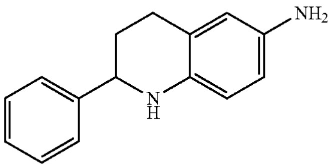 [SMILES: Nc1ccc2c(c1)CCC(c1ccccc1)N2] |
| 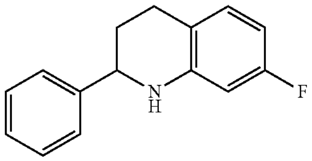 [SMILES: Fc1ccc2c(c1)NC(c1ccccc1)CC2] |
TABLE 1-4
| Structural formula |
| --- |
| 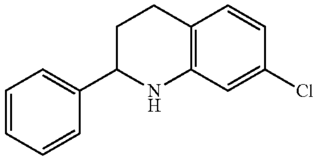 [SMILES: Clc1ccc2c(c1)NC(c1ccccc1)CC2] |
| 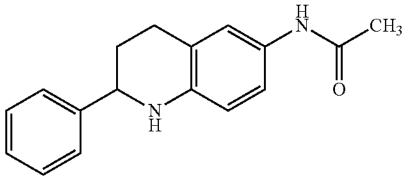 [SMILES: CC(=O)Nc1ccc2c(c1)CCC(c1ccccc1)N2] |
| 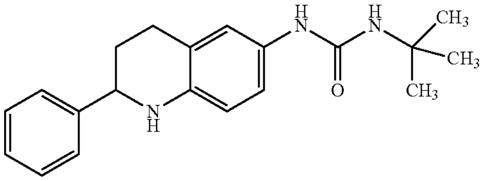 [SMILES: CC(C)(C)NC(=O)Nc1ccc2c(c1)CCC(c1ccccc1)N2] |
| 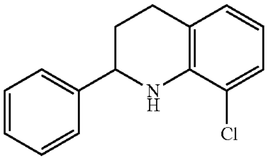 [SMILES: Clc1cccc2c1NC(c1ccccc1)CC2] |
| 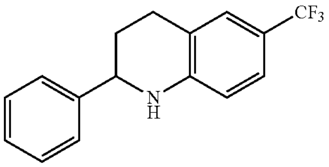 [SMILES: FC(F)(F)c1ccc2c(c1)CCC(c1ccccc1)N2] |
| 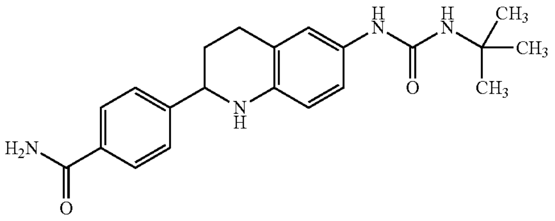 [SMILES: CC(C)(C)NC(=O)Nc1ccc2c(c1)CCC(c1ccc(C(N)=O)cc1)N2] |
| 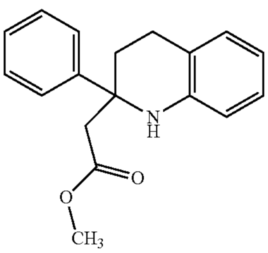 [SMILES: COC(=O)CC1(c2ccccc2)CCc2ccccc2N1] |

TABLE 1-4-continued
| Structural formula |
| --- |
| 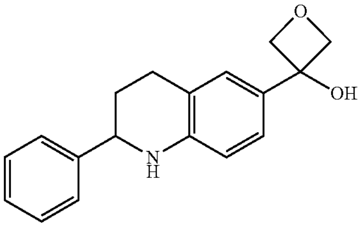 [SMILES: OC1(c2ccc3c(c2)CCC(c2ccccc2)N3)COC1] |
| 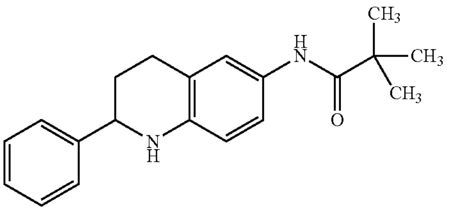 [SMILES: CC(C)(C)C(=O)Nc1ccc2c(c1)CCC(c1ccccc1)N2] |
| 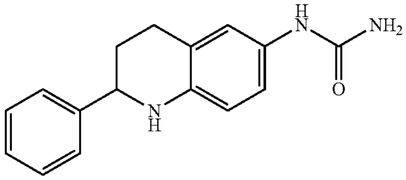 [SMILES: NC(=O)Nc1ccc2c(c1)CCC(c1ccccc1)N2] |
| 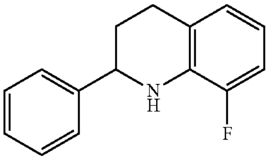 [SMILES: Fc1cccc2c1NC(c1ccccc1)CC2] |
| 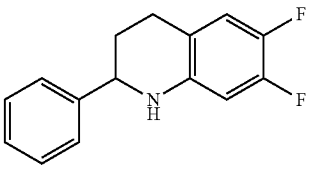 [SMILES: Fc1cc2c(cc1F)NC(c1ccccc1)CC2] |
| 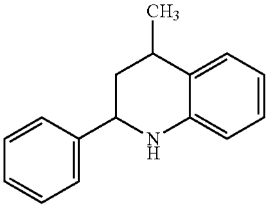 [SMILES: CC1CC(c2ccccc2)Nc2ccccc21] |
| 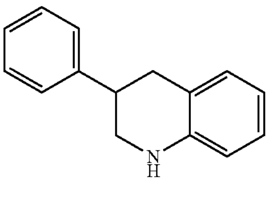 [SMILES: c1ccc(C2CNc3ccccc3C2)cc1] |
TABLE 1-4-continued
| Structural formula |
| --- |
| 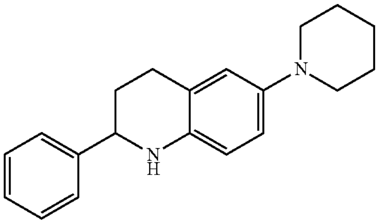 [SMILES: c1ccc(C2CCc3cc(N4CCCCC4)ccc3N2)cc1] |
| 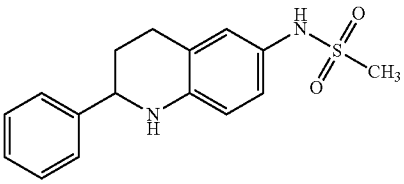 [SMILES: CS(=O)(=O)Nc1ccc2c(c1)CCC(c1ccccc1)N2] |
| 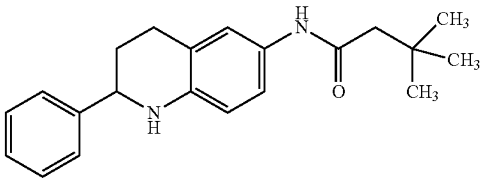 [SMILES: CC(C)(C)CC(=O)Nc1ccc2c(c1)CCC(c1ccccc1)N2] |
| 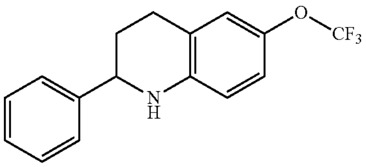 [SMILES: FC(F)(F)Oc1ccc2c(c1)CCC(c1ccccc1)N2] |
| 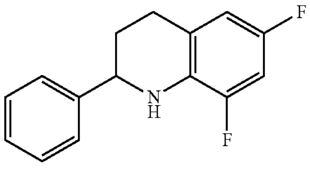 [SMILES: Fc1cc(F)c2c(c1)CCC(c1ccccc1)N2] |
| 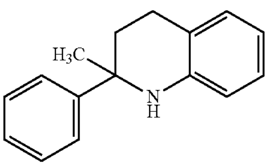 [SMILES: CC1(c2ccccc2)CCc2ccccc2N1] |
| 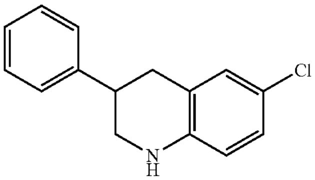 [SMILES: Clc1ccc2c(c1)CC(c1ccccc1)CN2] |

TABLE 1-5
| Structural formula |
|---|
| 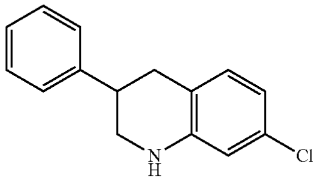 [SMILES: Clc1ccc2c(c1)NCC(c1ccccc1)C2] |
| 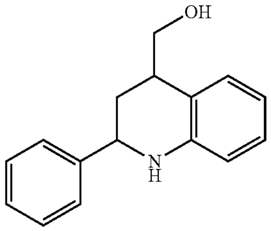 [SMILES: OCC1CC(c2ccccc2)Nc2ccccc21] |
| 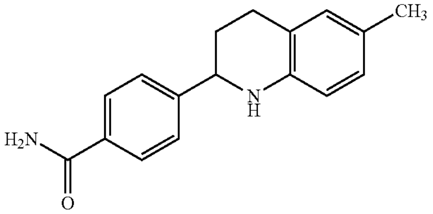 [SMILES: Cc1ccc2c(c1)CCC(c1ccc(C(N)=O)cc1)N2] |
| 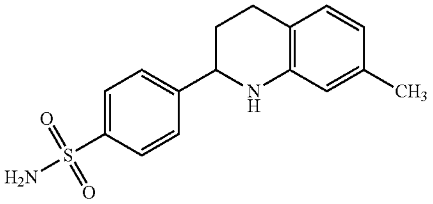 [SMILES: Cc1ccc2c(c1)NC(c1ccc(S(N)(=O)=O)cc1)CC2] |
| 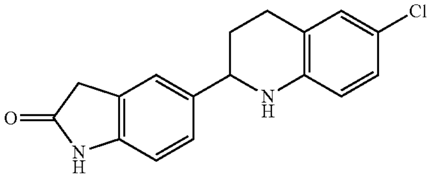 [SMILES: O=C1Cc2cc(C3CCc4cc(Cl)ccc4N3)ccc2N1] |
| 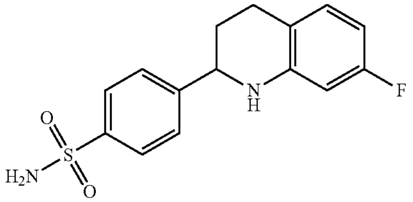 [SMILES: NS(=O)(=O)c1ccc(C2CCc3ccc(F)cc3N2)cc1] |
| 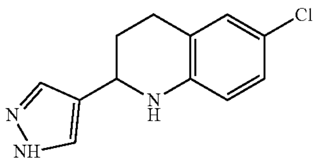 [SMILES: Clc1ccc2c(c1)CCC(c1cn[nH]c1)N2] |
TABLE 1-5-continued
| Structural formula |
|---|
| 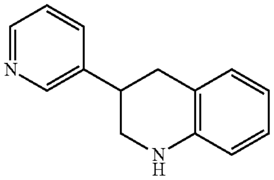 [SMILES: c1cncc(C2CNc3ccccc3C2)c1] |
| 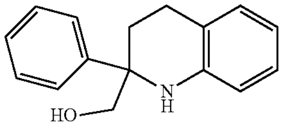 [SMILES: OCC1(c2ccccc2)CCc2ccccc2N1] |
| 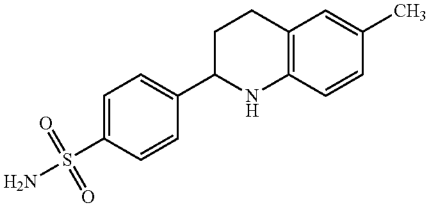 [SMILES: Cc1ccc2c(c1)CCC(c1ccc(S(N)(=O)=O)cc1)N2] |
| 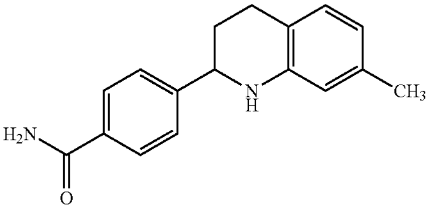 [SMILES: Cc1ccc2c(c1)NC(c1ccc(C(N)=O)cc1)CC2] |
| 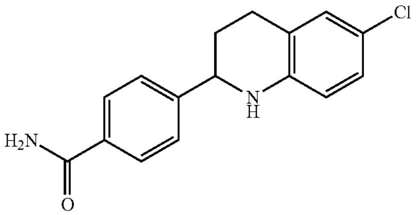 [SMILES: NC(=O)c1ccc(C2CCc3cc(Cl)ccc3N2)cc1] |
| 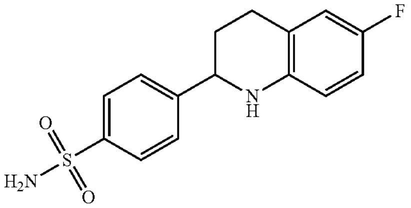 [SMILES: NS(=O)(=O)c1ccc(C2CCc3cc(F)ccc3N2)cc1] |
| 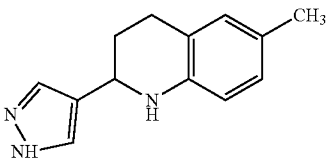 [SMILES: Cc1ccc2c(c1)CCC(c1cn[nH]c1)N2] |

TABLE 1-5-continued
| Structural formula |
|---|
| 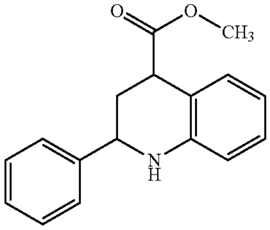 [SMILES: COC(=O)C1CC(c2ccccc2)Nc2ccccc21] |
| 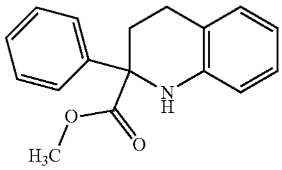 [SMILES: COC(=O)C1(c2ccccc2)CCc2ccccc2N1] |
| 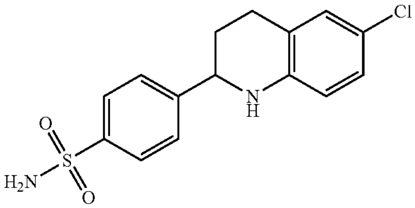 |
| 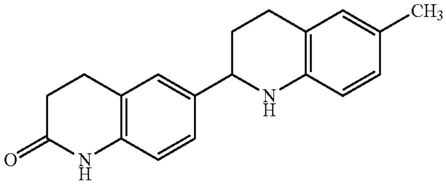 [SMILES: Cc1ccc2c(c1)CCC(c1ccc3c(c1)CCC(=O)N3)N2] |
| 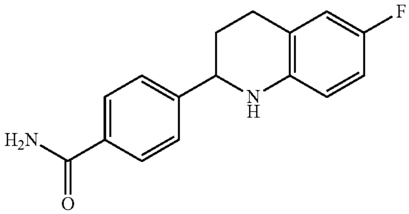 [SMILES: NC(=O)c1ccc(C2CCc3cc(F)ccc3N2)cc1] |
| 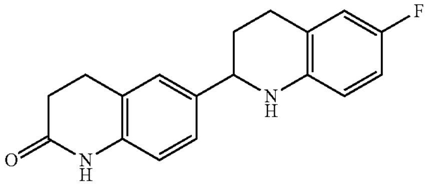 [SMILES: O=C1CCc2cc(C3CCc4cc(F)ccc4N3)ccc2N1] |
| 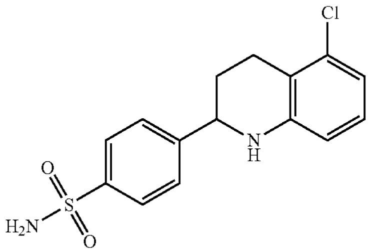 [SMILES: NS(=O)(=O)c1ccc(C2CCc3c(Cl)cccc3N2)cc1] |
TABLE 1-6
| Structural formula |
|---|
| 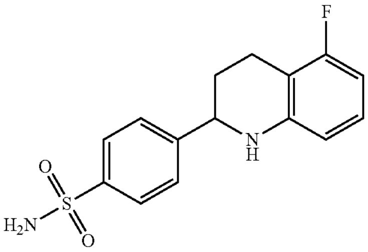 [SMILES: NS(=O)(=O)c1ccc(C2CCc3c(F)cccc3N2)cc1] |
| 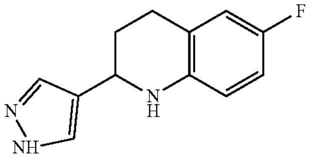 [SMILES: Fc1ccc2c(c1)CCC(c1cn[nH]c1)N2] |
| 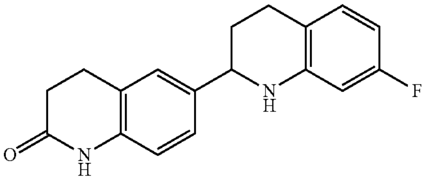 [SMILES: O=C1CCc2cc(C3CCc4ccc(F)cc4N3)ccc2N1] |
| 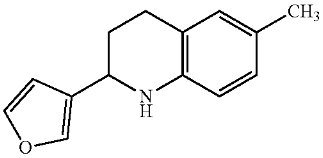 [SMILES: Cc1ccc2c(c1)CCC(c1ccoc1)N2] |
| 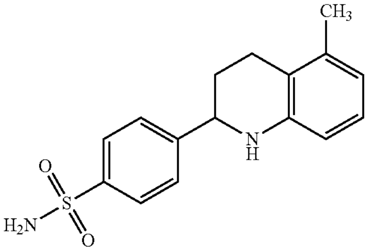 |
| 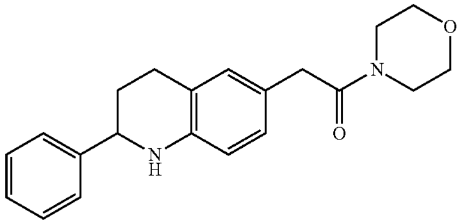 [SMILES: O=C(Cc1ccc2c(c1)CCC(c1ccccc1)N2)N1CCOCC1] |
| 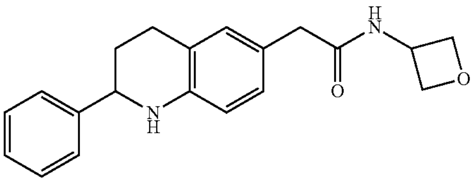 [SMILES: O=C(Cc1ccc2c(c1)CCC(c1ccccc1)N2)NC1COC1] |

TABLE 1-6-continued
| Structural formula |
|---|
| 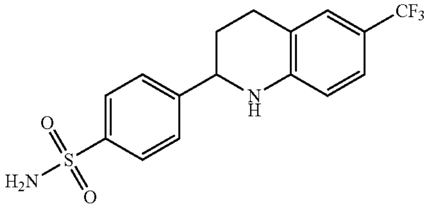 [SMILES: NS(=O)(=O)c1ccc(C2CCc3cc(C(F)(F)F)ccc3N2)cc1] |
| 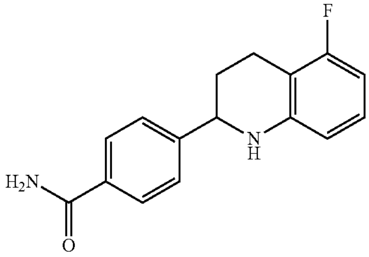 [SMILES: NC(=O)c1ccc(C2CCc3c(F)cccc3N2)cc1] |
| 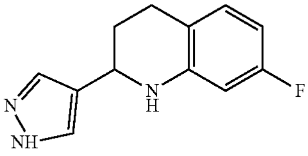 [SMILES: Fc1ccc2c(c1)NC(c1cn[nH]c1)CC2] |
| 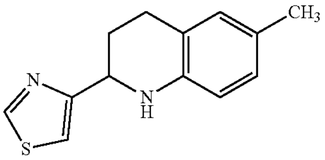 [SMILES: Cc1ccc2c(c1)CCC(c1cscn1)N2] |
| 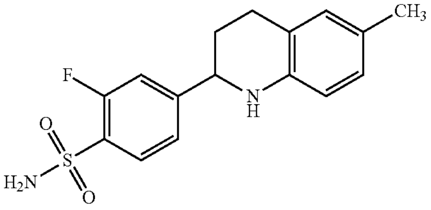 [SMILES: Cc1ccc2c(c1)CCC(c1ccc(S(N)(=O)=O)c(F)c1)N2] |
| 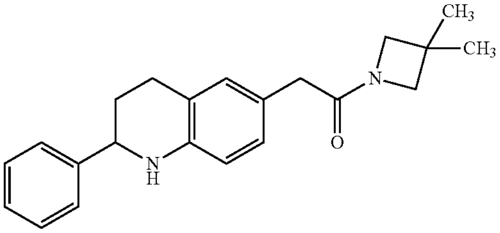 [SMILES: CC1(C)CN(C(=O)Cc2ccc3c(c2)CCC(c2ccccc2)N3)C1] |
| 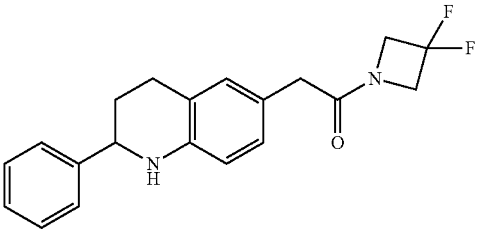 [SMILES: O=C(Cc1ccc2c(c1)CCC(c1ccccc1)N2)N1CC(F)(F)C1] |
TABLE 1-6-continued
| Structural formula |
|---|
| 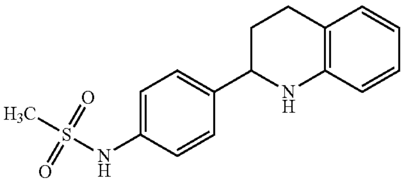 [SMILES: CS(=O)(=O)Nc1ccc(C2CCc3ccccc3N2)cc1] |
| 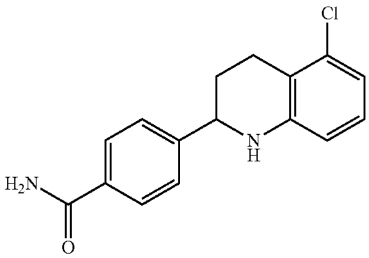 |
| 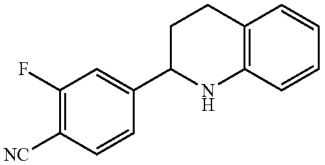 [SMILES: N#Cc1ccc(C2CCc3ccccc3N2)cc1F] |
| 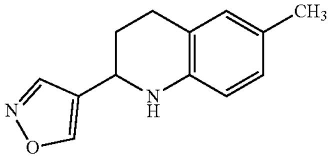 [SMILES: Cc1ccc2c(c1)CCC(c1cnoc1)N2] |
| 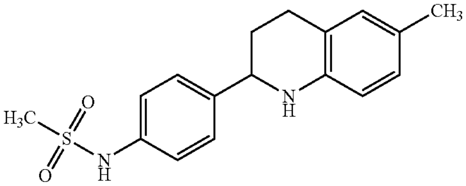 |
| 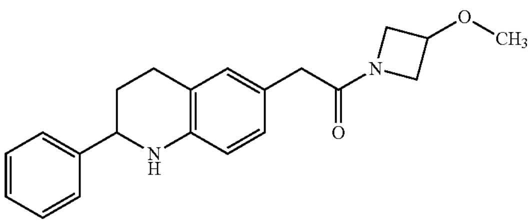 [SMILES: COC1CN(C(=O)Cc2ccc3c(c2)CCC(c2ccccc2)N3)C1] |
| 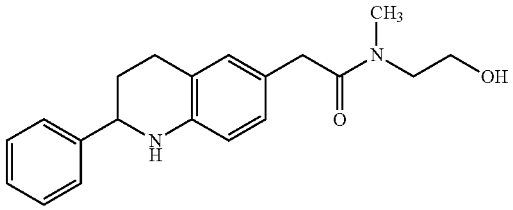 [SMILES: CN(CCO)C(=O)Cc1ccc2c(c1)CCC(c1ccccc1)N2] |

TABLE 1-7
| Structural formula |
| --- |
| 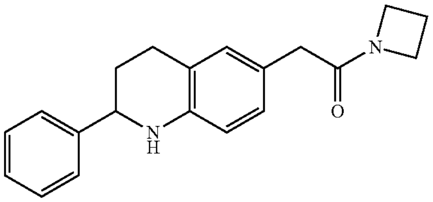 [SMILES: O=C(Cc1ccc2c(c1)CCC(c1ccccc1)N2)N1CCC1] |
| 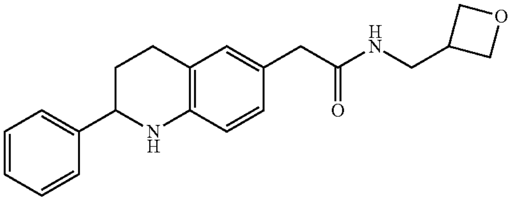 [SMILES: O=C(Cc1ccc2c(c1)CCC(c1ccccc1)N2)NCC1COC1] |
| 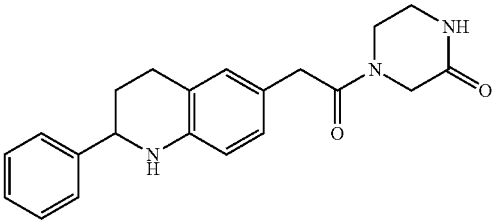 [SMILES: O=C1CN(C(=O)Cc2ccc3c(c2)CCC(c2ccccc2)N3)CCN1] |
| 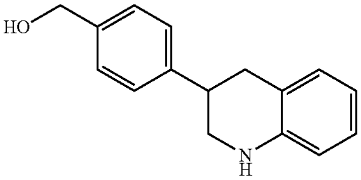 [SMILES: OCc1ccc(C2CNc3ccccc3C2)cc1] |
| 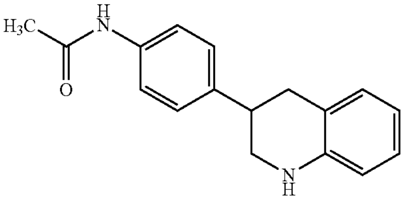 [SMILES: CC(=O)Nc1ccc(C2CNc3ccccc3C2)cc1] |
| 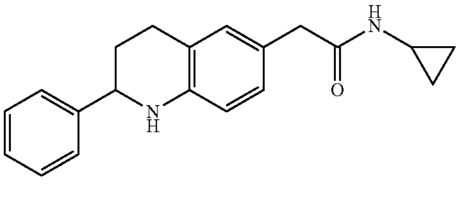 [SMILES: O=C(Cc1ccc2c(c1)CCC(c1ccccc1)N2)NC1CC1] |
| 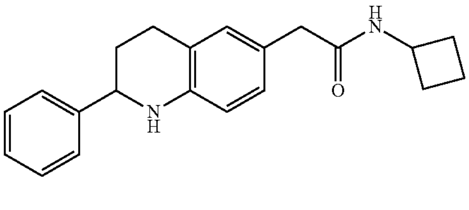 [SMILES: O=C(Cc1ccc2c(c1)CCC(c1ccccc1)N2)NC1CCC1] |
TABLE 1-7-continued
| Structural formula |
| --- |
| 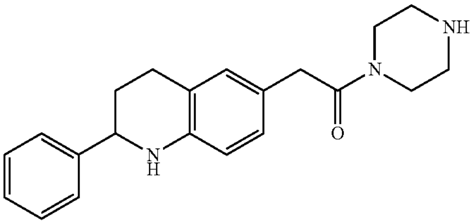 [SMILES: O=C(Cc1ccc2c(c1)CCC(c1ccccc1)N2)N1CCNCC1] |
| 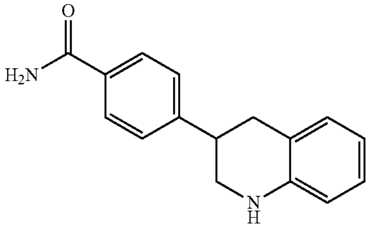 [SMILES: NC(=O)c1ccc(C2CNc3ccccc3C2)cc1] |
| 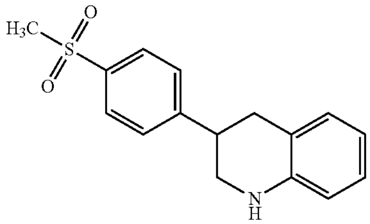 [SMILES: CS(=O)(=O)c1ccc(C2CNc3ccccc3C2)cc1] |
| 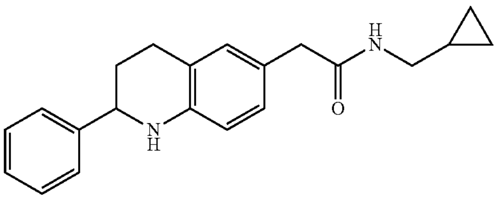 [SMILES: O=C(Cc1ccc2c(c1)CCC(c1ccccc1)N2)NCC1CC1] |
| 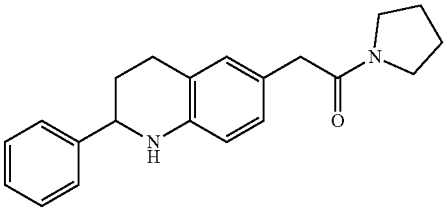 [SMILES: O=C(Cc1ccc2c(c1)CCC(c1ccccc1)N2)N1CCCC1] |
| 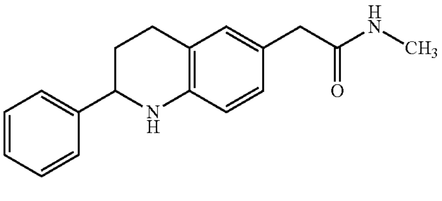 [SMILES: CNC(=O)Cc1ccc2c(c1)CCC(c1ccccc1)N2] |
| 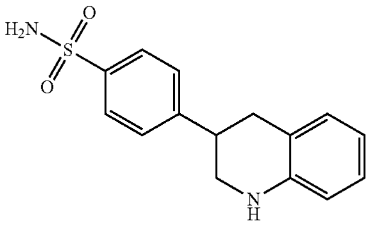 [SMILES: NS(=O)(=O)c1ccc(C2CNc3ccccc3C2)cc1] |

The compounds shown in Tables 1-1 to 1-7 include stereoisomers, solvates, and pharmaceutically acceptable salts of those compounds, and mixtures thereof.

Additionally, this disclosure includes prodrugs of the tetrahydro-quinoline derivative (I). A prodrug of the tetrahydroquinoline derivative (I) as described above is a compound that is enzymatically or chemically converted to the tetrahydroquinoline derivative (I) within the body. The active substance of the tetrahydroquinoline derivative (I) prodrug is the tetrahydroquinoline derivative (I), but the tetrahydroquinoline derivative (I) prodrug itself may have activity.

Groups used to produce a prodrug of the tetrahydroquinoline derivative (I) as described above include those described in published literatures (for example, "Development of Pharmaceutical Products," Hirokawa Shoten Co., 1990, vol. 7, p. 163-198 and Progress in Medicine, vol. 5, 1985, p. 2157-2161).

Examples of the "pharmaceutically acceptable salt" of the tetrahydroquinoline derivative (I) include inorganic acid salts such as hydrochloride, sulfate, nitrate, hydrobromide, hydroiodide, and phosphate; and organic acid salts such as oxalate, malonate, citrate, fumarate, lactate, malate, succinate, tartrate, acetate, trifluoroacetate, maleate, gluconate, benzoate, ascorbate, glutarate, mandelate, phthalate, methanesulfonate, ethanesulfonate, benzenesulfonate, p-toluenesulfonate, camphorsulfonate, aspartate, glutamate, and cinnamate.

The tetrahydroquinoline derivative (I) may be crystals, and these crystals are included in the tetrahydroquinoline derivative (I), whether those crystals are a single crystal form or a mixture of crystal forms.

The tetrahydroquinoline derivative (I) may be pharmaceutically acceptable co-crystals or co-crystalline salts thereof. The term "co-crystal" or "co-crystalline salt" as used herein means a crystalline material composed of two or more unique solids at room temperature and each have distinct physical properties (for example, structure, melting point, heat of fusion, hygroscopicity, solubility, and stability). The co-crystals or co-crystalline salts can be produced according to known co-crystallization methods.

The tetrahydroquinoline derivative (I) or a pharmaceutically acceptable salt thereof may be anhydrates or may form solvates such as hydrates.

The tetrahydroquinoline derivative (I) or a pharmaceutically acceptable salt thereof can be converted to solvates such as hydrates, by known methods. For example, in a known method, the tetrahydroquinoline derivative (I) as described above or a pharmaceutically acceptable salt thereof is treated with water or other solvent (for example, an alcoholic solvent such as methanol, ethanol, or n-propanol, N,N-dimethylformamide (hereinafter referred to as DMF), dimethyl sulfoxide (hereinafter referred to as DMSO)), or any combination thereof.

The tetrahydroquinoline derivative (I) may be labeled with one or more isotopes, and examples of the isotopes for labeling include $^{2}H$, $^{3}H$, $^{13}C$, $^{14}C$, $^{15}N$, $^{15}O$, $^{17}O$, $^{18}O$, and/or $^{125}I$.

The tetrahydroquinoline derivative (I) can be produced by an appropriate method based on the features derived from basic skeleton thereof and the types of the substituents. The starting materials and reagents used for the production of these compounds are commercially available or can be produced by known methods.

The tetrahydroquinoline derivative (I), as well as the intermediates and starting materials for use in the manufacture of the derivative, can be isolated and purified by known procedures. Examples of the known isolation and purification procedures include solvent extraction, recrystallization, and chromatography.

When the tetrahydroquinoline derivative (I) include optical isomers or stereoisomers, each isomer can be obtained as a single compound by known methods or methods similar thereto. Examples of the known methods include crystallization, enzymatic resolution, and chiral chromatography.

Examples of general production methods of the tetrahydroquinoline derivative (I) are shown below. Some of the compounds included in the following schemes are in the form of salts, and the salts similar to, for example, the salts of the tetrahydroquinoline derivative (I) are used. The production methods are not limited to the following examples.

Production Method 1

Among the tetrahydroquinoline derivative (I), a tetrahydroquinoline derivative (I-a) can be produced by a method shown in, for example, Scheme 1, in which all of $R^{1y}$, $R^{v}$, and $R^{w}$ are hydrogen, and $R^{3}$ is hydrogen, halogen, $C_1$-$C_3$ alkyl in which any one to three hydrogen atoms are each independently optionally replaced by a hydroxy group(s) or a fluorine atom(s), hydroxy, $C_1$-$C_3$ alkoxy in which any one to three hydrogen atoms are optionally replaced by a fluorine atom(s), or methoxycarbonyl.

Scheme 1

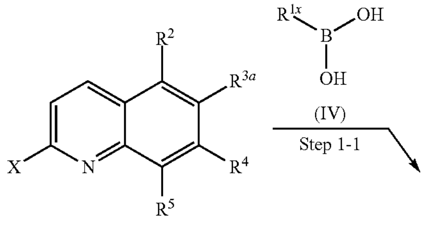

(III)

-continued

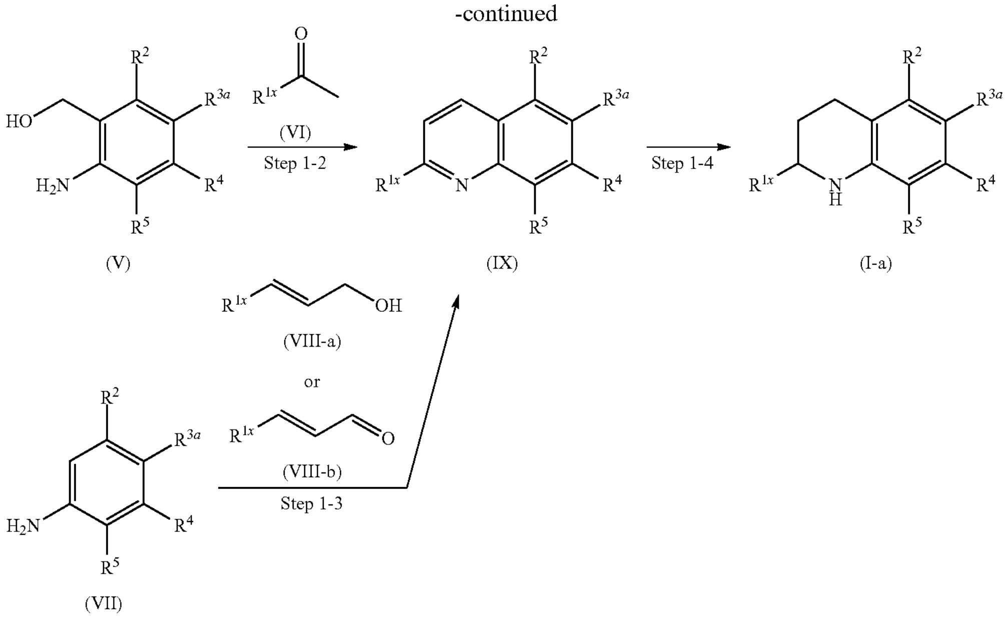

(V)
(IX)
(I-a)
(VIII-a)
or
(VIII-b)
(VII)

In the scheme, X is halogen, and $R^{3a}$ is hydrogen, halogen, $C_1$-$C_3$ alkyl in which any one to three hydrogen atoms are each independently optionally replaced by a hydroxy group (s) or a fluorine atom(s), hydroxy, $C_1$-$C_3$ alkoxy in which any one to three hydrogen atoms are optionally replaced by a fluorine atom(s), or methoxycarbonyl, and the symbols in the scheme have the same definitions as above.

Step 1-1

A Quinoline derivative (IX) can be produced by coupling reaction of a 2-haloquinoline derivative (III) and a boronic acid derivative (IV) in the presence of a metal catalyst and a base.

The boronic acid derivative (IV) used for the coupling reaction are preferably in an amount of 0.5 to 10 equivalents, more preferably in an amount of 0.8 to 4 equivalents, relative to the 2-haloquinoline derivative (III).

Examples of the metal catalyst used in the coupling reaction include [1,1'-bis(diphenylphosphino)ferrocene]dichloro-palladium(II) dichloromethane adduct, palladium(II) chloride, palladium(II) acetate, bis(dibenzylideneacetone) palladium(0), tetrakis(triphenylphosphine)palladium(0), and dichlorobis(triphenylphosphine)palladium(0); and tetrakis (triphenylphosphine)palladium(0) is preferable.

The metal catalyst used for the coupling reaction is preferably in an amount of 0.01 to 5 equivalents, more preferably in an amount of 0.025 to 1 equivalent, relative to the 2-haloquinoline derivative (III).

A ligand may further be used for the coupling reaction. Examples of the ligand used include triphenylphosphine, tert-butylphosphine, and 2,2'-bis(diphenylphosphino)-1,1'-binaphthyl.

Examples of the base used in the coupling reaction include organic bases such as triethylamine and N,N-diisopropylethylamine; inorganic bases such as sodium carbonate, potassium carbonate, and cesium carbonate, lithium amides such as lithium hexamethyldisilazide and lithium diisopropylamide; metal alkoxides such as sodium tert-butoxide and potassium tert-butoxide, and mixtures thereof; and an inorganic base such as sodium carbonate, potassium carbonate, or cesium carbonate, is preferable.

The base used for the coupling reaction is preferably in an amount of 0.5 to 10 equivalents, more preferably in an amount of 1 to 4 equivalents, relative to the 2-haloquinoline derivative (III).

The reaction solvent used in the coupling reaction is appropriately selected depending on the types of the reagents used and the like, and the reaction solvent is not limited to a specific solvent as long as the reaction is not inhibited by the solvent. Examples of the reaction solvent include ether solvents such as tetrahydrofuran (hereinafter referred to as THF), 1,4-dioxane, and 1,2-dimethoxyethane (hereinafter referred to as DME); nitrile solvents such as acetonitrile and propionitrile; aromatic hydrocarbon solvents such as benzene and toluene; polar aprotic solvent such as DMF, N,N-dimethylacetamide (hereinafter referred to as DMA), and DMSO; water, and mixtures thereof, and an ether solvent such as THF, 1,4-dioxane, or DME; a polar aprotic solvent such as DMF, DMA, or DMSO, or a mixture of water with any of the solvents is preferable.

The reaction temperature in the coupling reaction is preferably from 0° C. to 200° C., more preferably from 50° C. to 150° C.

The reaction time for the coupling reaction is appropriately selected depending on conditions such as reaction temperature, and a preferred reaction time is from 1 hour to 30 hours.

The 2-haloquinoline derivative (III) and the boronic acid derivative (IV) used in the coupling reaction can be purchased or produced according to known methods or methods similar thereto.

Step 1-2

The quinoline derivative (IX) can be produced by cycloaddition reaction of a 2-aminobenzyl alcohol derivative (V) and a ketone derivative (VI) in the presence of a base, for example, according to a method described in Tetrahedron Letters, 2008, 6893-6895 or methods similar thereto.

The ketone derivative (VI) used for the cycloaddition reaction are preferably in an amount of 0.5 to 10 equivalents, more preferably in an amount of 0.8 to 5 equivalents, relative to the 2-aminobenzyl alcohol derivative (V).

Examples of the base used in the cycloaddition reaction include inorganic bases such as sodium hydroxide, potassium hydroxide and cesium hydroxide; metal alkoxides such as sodium ethoxide, sodium tert-butoxide, and potassium tert-butoxide; metal hydride compounds such as sodium hydride, potassium hydride, and calcium hydride, and mixtures thereof, and a metal alkoxide such as sodium ethoxide, sodium tert-butoxide, or potassium tert-butoxide, is preferable.

The base used for the cycloaddition reaction is preferably in an amount of 0.5 to 10 equivalents, more preferably in an amount of 1 to 3 equivalents, relative to the 2-aminobenzyl alcohol derivative (V).

The reaction solvent used in the cycloaddition reaction is appropriately selected depending on the types of the reagents used and the like, and the reaction solvent is not limited as long as the reaction is not inhibited by the solvent. Examples of the reaction solvent include ether solvents such as THF, 1,4-dioxane, and DME; aromatic hydrocarbon solvents such as benzene and toluene; polar aprotic solvents such as DMF, DMA, and DMSO; and mixtures thereof; and an ether solvent such as THF, 1,4-dioxane, or DME, is preferable.

The reaction temperature in the cycloaddition reaction is preferably from 0° C. to 200° C., more preferably from 50° C. to 150° C.

The reaction time for the cycloaddition reaction is appropriately selected depending on conditions such as reaction temperature, and a preferred reaction time is from 1 hour to 24 hours.

The 2-aminobenzyl alcohol derivative (V) and the ketone derivative (VI) used in the cycloaddition reaction can be purchased or produced according to known methods or methods similar thereto.

Step 1-3

The quinoline derivative (IX) can be produced by oxidative cyclization reaction of an aniline derivative (VII) and an allyl alcohol derivative (VIII-a) or an α,β-unsaturated aldehyde derivative (VIII-b) in the presence of a metal catalyst under oxygen atmosphere, for example, according to a method described in RSC Advances, 2017, 36242-36245 or methods similar thereto.

The allyl alcohol derivative (VIII-a) or the α,β-unsaturated aldehyde derivative (VIII-b) used for the oxidative cyclization reaction are preferably in an amount of 0.5 to 10 equivalents, more preferably in an amount of 0.8 to 2 equivalents, relative to the aniline derivative (VII).

Examples of the metal catalyst used in the oxidative cyclization reaction include palladium(II) acetate, trifluoropalladium(II) acetate, palladium(II) chloride, and dichlorobis(acetonitrile)palladium(II); and palladium(II) acetate is preferable.

The metal catalyst used for the oxidative cyclization reaction is preferably in an amount of 0.01 to 5 equivalents, more preferably in an amount of 0.025 to 1 equivalent, relative to the aniline derivative (VII).

The oxygen atmosphere used in the oxidative cyclization reaction preferably has a pressure of about 1 to about 20 atmospheres, more preferably a pressure of about 1 to about 5 atmospheres.

The reaction solvent used in the oxidative cyclization reaction is appropriately selected depending on the types of the reagents used and the like, and the reaction solvent is not limited as long as the reaction is not inhibited by the solvent. Examples of the reaction solvent include ether solvents such as THF, 1,4-dioxane, and DME; aromatic hydrocarbon solvents such as benzene and toluene; polar aprotic solvents such as DMF, DMA, and DMSO; and mixtures thereof; and a polar aprotic solvent such as DMF, DMA, or DMSO, is preferable.

The reaction temperature in the oxidative cyclization reaction is preferably from 0 to 300° C., more preferably from 70 to 200° C.

The reaction time for the oxidative cyclization reaction is appropriately selected depending on conditions such as reaction temperature, and a preferred reaction time is from 1 to 24 hours.

The aniline derivative (VII), the allyl alcohol derivative (VIII-a), and the α,β-unsaturated aldehyde derivative (VIII-b) used in the oxidative cyclization reaction can be purchased or produced according to known methods or methods similar thereto.

Step 1-4

The tetrahydroquinoline derivative (I-a) can be produced by hydrogenation reaction of the quinoline derivative (IX) in the presence of a metal catalyst under hydrogen atmosphere or by transfer hydrogenation reaction between a 1,4-dihydro-2,6-dimethyl-3,5-pyridine dicarboxylate derivative and the quinoline derivative (IX).

Examples of the metal catalyst used in the hydrogenation reaction include palladium compounds such as palladium on carbon, palladium(II) hydroxide on carbon, and palladium (II) oxide; nickel compounds such as sponge nickel catalyst; platinum compounds such as platinum(IV) oxide and platinum on carbon; rhodium compounds such as rhodium on carbon, and the like; and platinum(IV) oxide is preferable.

The metal catalyst used for the hydrogenation reaction is preferably in an amount of 0.001 to 1 equivalent, more preferably in an amount of 0.01 to 0.5 equivalent, relative to the quinoline derivative (IX).

The hydrogen atmosphere used in the hydrogenation reaction preferably has a pressure of about 1 to about 30 atmospheres, more preferably a pressure of about 1 to about 10 atmospheres.

The reaction solvent used in the hydrogenation reaction is appropriately selected depending on the types of the reagents used and the like, and the reaction solvent is not limited as long as the reaction is not inhibited by the solvent. Examples of the reaction solvent include alcohol solvents such as methanol, ethanol, isopropyl alcohol, and tert-butyl alcohol; aromatic hydrocarbon solvents such as toluene and xylene; chlorinated solvents such as dichloromethane, chloroform, and 1,2-dichloroethane; ether solvents such as diethyl ether, THF, DME, and 1,4-dioxane; ester solvents such as ethyl acetate and propyl acetate; polar aprotic solvents such as DMF, DMA, and DMSO; carboxylic acid solvents such as formic acid and acetic acid; water, and mixtures thereof, and a mixture of an alcohol solvent such as methanol, ethanol, isopropyl alcohol, or tert-butyl alcohol, and a carboxylic acid solvent such as formic acid or acetic acid, is referable.

The reaction temperature in the hydrogenation reaction is preferably from 0 to 200° C., more preferably from 10 to 100° C.

The reaction time for the hydrogenation reaction is appropriately selected depending on conditions such as reaction temperature, and a preferred reaction time is from 0.5 to 40 hours.

Examples of the 1,4-dihydro-2,6-dimethyl-3,5-pyridine dicarboxylic acid ester derivative used in the transfer hydrogenation reaction include dimethyl 2,6-dimethyl-1,4-dihydropyridin-3,5-dicarboxylate, diethyl 2,6-dimethyl-1,4-dihydropyridin-3,5-dicarboxylate, di-tert-butyl 1,4-dihydro-2,6-dimethyl-3,5-pyridinedicarboxylate, didodecyl 1,4- dihydro-2,6-dimethyl-3,5-pyridinedicarboxylate and the like; and diethyl 2,6-dimethyl-1,4-dihydropyridin-3,5-dicarboxylate is preferable.

The 1,4-dihydro-2,6-dimethyl-3,5-pyridine dicarboxylic acid ester derivative used for the transfer hydrogenation reaction is preferably in an amount of 1 to 10 equivalents, more preferably in an amount of 1.7 to 3 equivalents, relative to the quinoline derivative (IX).

The reaction solvent used in the transfer hydrogenation reaction is appropriately selected depending on the types of the reagents used and the like, and the reaction solvent is not limited as long as the reaction is not inhibited by the solvent. Examples of the reaction solvent include alcohol solvents such as methanol, ethanol, isopropyl alcohol, and tert-butyl alcohol; aromatic hydrocarbon solvents such as toluene and xylene; chlorinated solvents such as dichloromethane, chloroform, and 1,2-dichloroethane; ether solvents such as diethyl ether, THF, DME, and 1,4-dioxane; ester solvents such as ethyl acetate and propyl acetate; polar aprotic solvents such as DMF, DMA, and DMSO; and mixtures thereof, and a chlorinated solvent such as dichloromethane, chloroform, or 1,2-dichloroethane, or an ether solvent such as diethyl ether, THF, DME, or 1,4-dioxane, is preferable.

The reaction temperature in the transfer hydrogenation reaction is preferably from 0 to 100° C., more preferably from 10 to 50° C.

The reaction time for the transfer hydrogenation reaction is appropriately selected depending on conditions such as reaction temperature, and a preferred reaction time is from 1 to 24 hours.

Production Method 2

Among the tetrahydroquinoline derivative (I), a tetrahydroquinoline derivative (I-b) can be produced by a method shown in, for example, Scheme 2, in which all of $R^{1y}$, $R^v$, and $R^w$ are hydrogen, and $R^3$ is $-NR^9R^{10}$, and $R^9$ and $R^{10}$ together represent $-(CH_2)_n-$.

Scheme 2

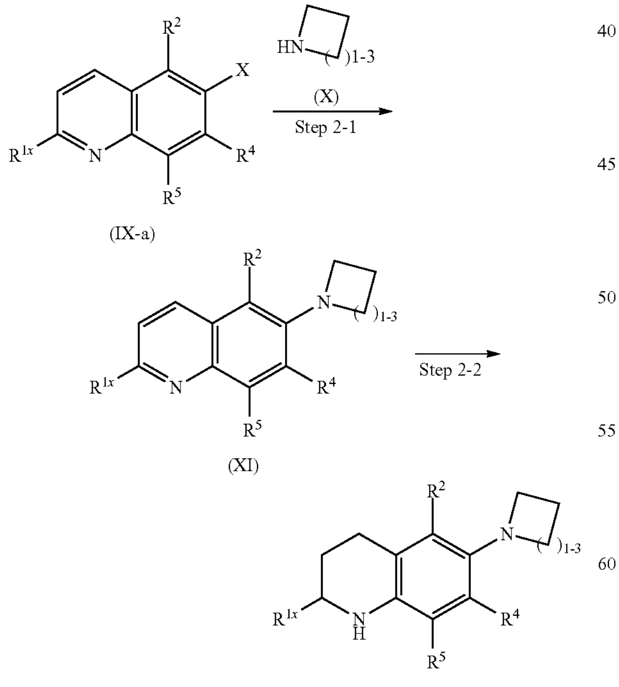

(IX-a)

(XI)

(I-b)

In the scheme, each symbol has the same definition as above.

Step 2-1

An aminoquinoline derivative (XI) can be produced by coupling reaction of a 6-haloquinoline derivative (IX-a) and a secondary amine derivative (X) in the presence of a metal catalyst and a base.

The secondary amine derivative (X) used for the coupling reaction are preferably in an amount of 0.5 to 20 equivalents, more preferably in an amount of 0.8 to 10 equivalents, relative to the 6-haloquinoline derivative (IX-a).

Examples of the metal catalyst used in the coupling reaction include [1,1'-bis(diphenylphosphino)ferrocene]dichloro-palladium(II) dichloromethane adduct, palladium(II) chloride, palladium(II) acetate, bis(dibenzylideneacetone) palladium(0), tris(dibenzylideneacetone)dipalladium(0), tetrakis(triphenylphosphine)palladium(0), and dichlorobis(triphenylphosphine)palladium(0); and palladium(II) acetate is preferable.

The metal catalyst used for the coupling reaction is preferably in an amount of 0.001 to 5 equivalents, more preferably in an amount of 0.02 to 0.5 equivalent, relative to the 6-haloquinoline derivative (IX-a).

A ligand may further be used for the coupling reaction. Examples of the ligand used include triphenylphosphine, tert-butylphosphine, 2,2'-bis(diphenylphosphino)-1,1'-binaphthyl, 2-(dicyclohexylphosphino)-2',4',6'-triisopropyl-1,1'-biphenyl, and 4,5-bis(diphenylphosphino)-9,9-dimethylxanthene.

When a ligand is used for the coupling reaction, the amount of the ligand is preferably from 0.001 to 5 equivalents, more preferably from 0.02 to 1 equivalent, relative to the 6-haloquinoline derivative (IX-a).

Examples of the base used in the coupling reaction include organic bases such as triethylamine and N,N-diisopropylethylamine; inorganic bases such as sodium carbonate, potassium carbonate, and cesium carbonate; lithium amides such as lithium hexamethyldisilazide and lithium diisopropylamide; metal alkoxides such as sodium tert-butoxide and potassium tert-butoxide; and mixtures thereof; and an inorganic base such as sodium carbonate, potassium carbonate, or cesium carbonate is preferable.

The base used for the coupling reaction is preferably in an amount of 0.8 to 10 equivalents, more preferably in an amount of 1 to 5 equivalents, relative to the 6-haloquinoline derivative (IX-a).

The reaction solvent used in the coupling reaction is appropriately selected depending on the types of the reagents used and the like, and the reaction solvent is not limited as long as the reaction is not inhibited by the solvent. Examples of the reaction solvent include alcohol solvents such as methanol, ethanol, isopropyl alcohol, and tert-butyl alcohol; ether solvents such as THF, 1,4-dioxane, and DME; aromatic hydrocarbon solvents such as benzene and toluene, nitrile solvents such as acetonitrile and propionitrile; polar aprotic solvents such as DMF, DMA, and DMSO; chlorinated solvents such as dichloromethane, chloroform, and 1,2-dichloroethane; and mixtures thereof; and an ether solvent such as THF, 1,4-dioxane, or DME is preferable.

The reaction temperature in the coupling reaction is preferably from 0 to 200° C., more preferably from 50 to 150° C.

The reaction time for the coupling reaction is appropriately selected depending on conditions such as reaction temperature, and a preferred reaction time is from 1 to 30 hours.

The 6-haloquinoline derivative (IX-a) used in the coupling reaction can be purchased or produced by the methods described in Steps 1-1 to 1-3, known methods, or methods similar thereto.

The secondary amine derivative (X) used in the coupling reaction can be purchased or produced according to known methods or methods similar thereto.

Step 2-2

The tetrahydroquinoline derivative (I-b) can be produced by hydrogenation reaction or transfer hydrogenation reaction of the aminoquinoline derivative (XI). The conditions selected for this step, including reagents, catalyst, hydrogen pressure, reaction solvent, and reaction temperature, are similar to those in the Step 1-4.

Production Method 3

Among the tetrahydroquinoline derivative (I), a tetrahydroquinoline derivative (I-c) can be produced by a method shown in, for example, Scheme 3, in which all of $R^{1y}$, $R^v$, and $R^w$ are hydrogen, and $R^3$ is $NR^9R^{10}$, and $R^9$ is hydrogen, and $R^{10}$ is —$COR^{15}$, and $R^{15}$ is $C_1$-$C_5$ alkoxy.

Scheme 3

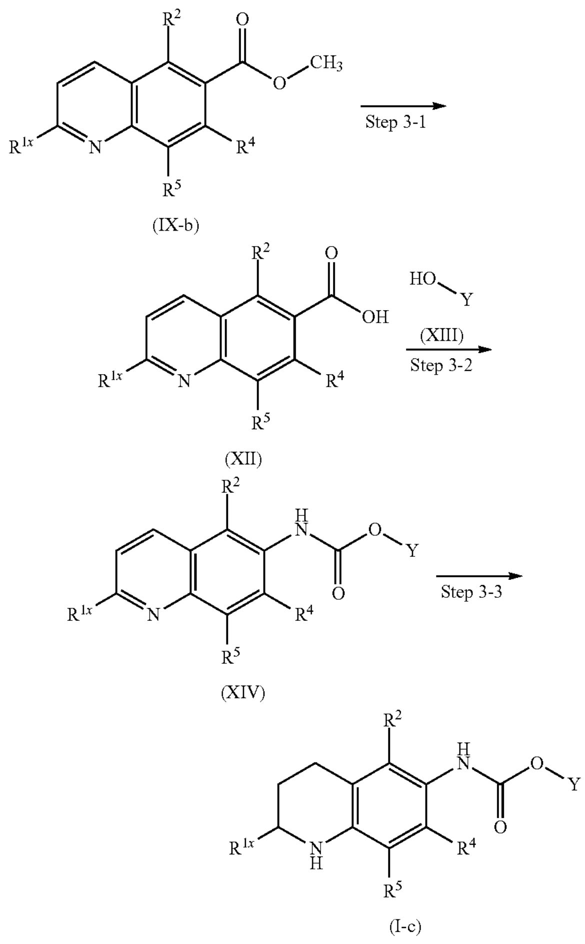

(IX-b)
(XII)
(XIV)
(I-c)

In the scheme, Y is $C_1$-$C_5$ alkyl, and the other symbols have the same definitions as above.

Step 3-1

A quinoline-6-carboxylic acid derivative (XII) can be produced by hydrolysis reaction of a quinoline-6-carboxylic acid ester derivative (IX-b) in the presence of a base.

Examples of the base used in the hydrolysis reaction include lithium hydroxide, potassium hydroxide, sodium hydroxide, and sodium tert-butoxide, and potassium hydroxide or sodium hydroxide is preferable.

The base used for the hydrolysis reaction is preferably in an amount of 0.5 to 100 equivalents, more preferably in an amount of 0.8 to 30 equivalents, relative to the quinoline-6-carboxylic acid ester derivative (IX-b).

The reaction solvent used in the hydrolysis reaction is appropriately selected depending on the types of the reagents used, and the reaction solvent is not limited as long as the reaction is not inhibited by the solvent. Examples of the reaction solvent include ether solvents such as THF, 1,4-dioxane, and DME; chlorinated solvents such as dichloromethane, chloroform, and 1,2-dichloroethane; aromatic hydrocarbon solvents such as benzene and toluene; polar aprotic solvents such as DMF, DMA, and DMSO; ketone solvents such as acetone and methyl ethyl ketone; alcohol solvents such as methanol, ethanol, and 2-propanol; water, and mixtures thereof; and a mixture of an alcohol solvent such as methanol, ethanol, or 2-propanol, and water is preferable.

The reaction temperature in the hydrolysis reaction is preferably from −50° C. to 150° C., more preferably from −20° C. to 100° C.

The reaction time for the hydrolysis reaction is appropriately selected depending on conditions such as reaction temperature, and a preferred reaction time is from 1 to 30 hours.

The quinoline-6-carboxylic acid ester derivative (IX-b) used in the hydrolysis reaction can be purchased or produced by the methods described in Steps 1-1 to 1-3, known methods, or equivalent methods.

Step 3-2

A quinoline-6-carbamic acid ester derivative (XIV) can be produced by reacting the quinoline-6-carboxylic acid derivative (XII) with diphenylphosphoryl azide to generate acyl azides, and then subjecting isocyanate derivative, which is generated by rearrangement reaction of the acyl azides, to alcoholysis reaction.

Diphenylphosphoryl azide used for the rearrangement reaction is preferably in an amount of 1 to 10 equivalents, more preferably in an amount of 1 to 3 equivalents, relative to the quinoline-6-carboxylic acid derivative (XII).

Examples of the base used in the rearrangement reaction include inorganic bases such as sodium carbonate, potassium carbonate, cesium carbonate, sodium hydroxide, potassium hydroxide, magnesium hydroxide, and calcium hydroxide; and organic bases such as triethylamine and N,N-diisopropylethylamine; and an organic base such as triethylamine or N,N-diisopropylethylamine is preferable.

The base used for the rearrangement reaction is preferably in an amount of 1 to 10 equivalents, more preferably in an amount of 1 to 3 equivalents, relative to the quinoline-6-carboxylic acid derivative (XII).

The reaction solvent used in the rearrangement reaction is appropriately selected depending on the types of the reagents used and the like, and the reaction solvent is not limited as long as the reaction is not inhibited by the solvent. Examples of the reaction solvent include ether solvents such as THF, 1,4-dioxane, and DME; ester solvents such as ethyl acetate and propyl acetate; chlorinated solvents such as dichloromethane, chloroform, and 1,2-dichloroethane; aromatic hydrocarbon solvents such as benzene and toluene; nitrile solvents such as acetonitrile and propionitrile; polar aprotic solvents such as DMF, DMA, and DMSO; and mixtures thereof.

Examples of alcohols (XIII) used for the alcoholysis reaction include methanol, ethanol, isopropyl alcohol, and tert-butyl alcohol.

The alcohols (XIII) used for the alcoholysis reaction may be in an amount of 1 to 20 equivalents relative to the quinoline-6-carboxylic acid derivative (XII) and may be used as the reaction solvent in place of the reaction solvent used in the rearrangement reaction.

The reaction temperature in the rearrangement reaction and alcoholysis reaction is preferably from 30 to 200° C., more preferably from 50 to 150° C.

The reaction time for the rearrangement reaction and alcoholysis reaction is appropriately selected depending on conditions such as reaction temperature, and a preferred reaction time is from 1 to 30 hours.

Moreover, the quinoline-6-carbamic acid ester derivative (XIV) can also be produced similarly by using acyl azides which are generated by converting the carboxyl group in the quinoline-6-carboxylic acid derivative (XII) to a reactive functional group and allowing the resulting derivative to react with a metal azide (for example, sodium azide).

Examples of the compounds with the reactive functional group include acid chlorides, mixed acid anhydrides with chlorocarbonate esters (for example, methyl chlorocarbonate, ethyl chlorocarbonate, or isobutyl chlorocarbonate), symmetrical acid anhydrides, and activated amides with imidazole.

Step 3-3

The tetrahydroquinoline derivative (I-c) can be produced by hydrogenation reaction or a transfer hydrogenation reaction of the quinoline-6-carbamic acid ester derivative (XIV). The conditions selected for this step, including reagents, catalyst, hydrogen pressure, reaction solvent, and reaction temperature, are similar to those in the step 1-4.

Production Method 4

Among the tetrahydroquinoline derivative (I), tetrahydroquinoline derivatives (I-d) to (I-f) can be produced by a method shown in, for example, Scheme 4, in which all of $R^{1y}$, $R^{v}$, and $R^{w}$ are hydrogen, and $R^3$ is —$NR^9R^{10}$, and $R^9$ is hydrogen, and $R^{10}$ is —$COR^{15}$ or $C_1$-$C_3$ alkylsulfonyl, and $R^{15}$ is $C_1$-$C_5$ alkyl or —$NHR^{16}$, and $R^{16}$ is hydrogen or $C_1$-$C_5$ alkyl.

Scheme 4

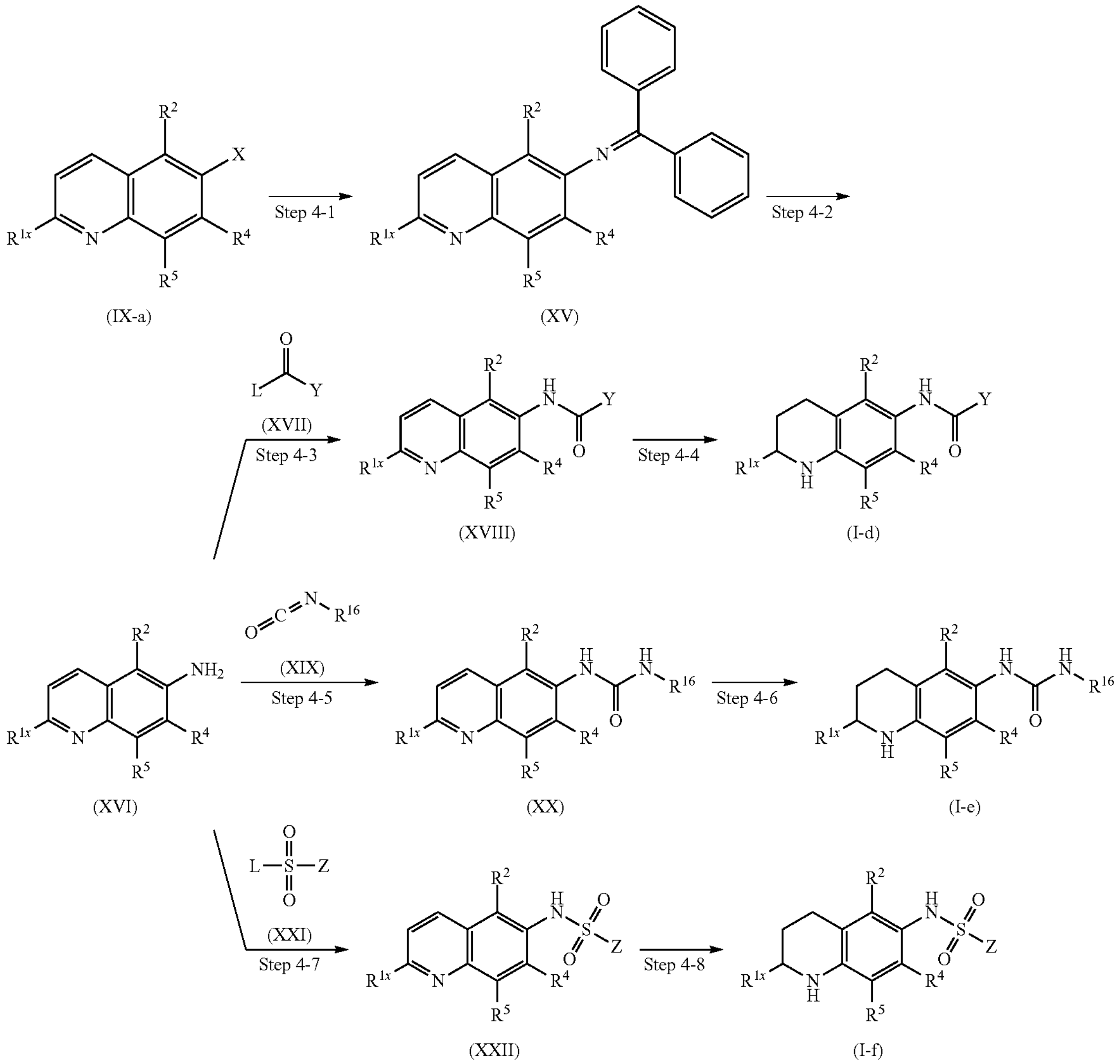

(IX-a)
(XV)
(XVII)
(XVIII)
(I-d)
(XIX)
(XVI)
(XX)
(I-e)
(XXI)
(XXII)
(I-f)

In the scheme, each L independently represents a leaving group, and Z is $C_1$-$C_3$ alkyl, and the other symbols have the same definitions as above.

Examples of the leaving group represented by L include halogen such as fluorine, chlorine, bromine, or iodine; $C_1$-$C_{12}$ alkylthio such as methylthio, ethylthio, or dodecylthio; aryloxy such as phenoxy; methanesulfonyloxy, ethanesulfonyloxy, or alkylsulfonyloxy in which a hydrogen atom(s) is(are) optionally replaced by a halogen atom(s) such as trifluoromethane-sulfonyloxy; alkylsulfonylamino such as trifluoromethanesulfonylamino; and azolyl such as imidazole-1-yl or pyrazol-1-yl.

Step 4-1

A diphenylmethanimine derivative (XV) can be produced by a coupling reaction of 6-haloquinoline derivative (IX-a) and diphenylmethanimine in the presence of a metal catalyst and a base. The conditions selected for this step, including reagents, catalyst, hydrogen pressure, reaction solvent, and reaction temperature, are similar to those in the step 2-1.

The 6-haloquinoline derivative (IX-a) used in the coupling reaction can be purchased or produced by the methods described in Steps 1-1 to 1-3, known methods, or methods similar thereto.

Step 4-2

An aminoquinoline derivative (XVI) can be produced by deprotection reaction of the diphenylmethanimine derivative (XV).

Examples of an acid used in the deprotection reaction include hydrochloric acid, 10% by weight hydrogen chloride-methanol solution, 4 mol/L hydrogen chloride-ethyl acetate solution, trifluoroacetic acid, and hydrofluoric acid; and hydrochloric acid is preferable.

The acid used for the deprotection reaction is preferably in an amount of 0.5 to 100 equivalents, more preferably in an amount of 1 to 10 equivalents relative to the diphenylmethanimine derivative (XV).

The reaction solvent used in the deprotection reaction is appropriately selected depending on the types of the reagents used and the like, and the reaction solvent is not limited as long as the reaction is not inhibited by the solvent. Examples of the reaction solvent include ether solvents such as diethyl ether, THF, DME, and 1,4-dioxane; ester solvents such as ethyl acetate and propyl acetate; chlorinated solvents such as dichloromethane, chloroform, and 1,2-dichloroethane; alcohol solvents such as methanol and ethanol; and mixtures thereof, and an ester solvent such as ethyl acetate or propyl acetate, or a chlorinated solvent such as dichloromethane, chloroform, or 1,2-dichloroethane, is preferable.

The reaction temperature in the deprotection reaction is preferably from 0 to 200° C., more preferably from 0 to 100° C.

The reaction time of the deprotection reaction varies depending on the reaction conditions, and a preferred reaction time is from 1 to 48 hours.

Step 4-3

An amidoquinoline derivative (XVIII) can be produced by acylation reaction of the aminoquinoline derivative (XVI) with an acylating agent (XVII).

The acylating agent (XVII) used for the acylation reaction is preferably in an amount of 0.5 to 10 equivalents, more preferably in an amount of 1 to 3 equivalents, relative to the aminoquinoline derivative (XVI).

A base may optionally be used for the acylation reaction. Examples of the base used include organic bases such as triethylamine, N,N-diisopropylethylamine, and pyridine; alkaline metal hydroxides such as sodium hydroxide, potassium hydroxide, and lithium hydroxide; alkaline metal hydrogencarbonates such as sodium hydrogencarbonate and potassium hydrogencarbonate; alkaline metal carbonates such as sodium carbonate and potassium carbonate; and mixtures thereof, and an alkaline metal hydroxide such as sodium hydroxide, potassium hydroxide, or lithium hydroxide, is preferable.

The reaction solvent used in the acylation reaction is appropriately selected depending on the types of the reagents used, and the reaction solvent is not limited as long as the reaction is not inhibited by the solvent. Examples of the reaction solvent include nitrile solvents such as acetonitrile and propionitrile; polar aprotic solvents such as DMF, DMA, and DMSO; ether solvents such as diethyl ether, THF, DME, and 1,4-dioxane; ester solvents such as ethyl acetate and propyl acetate; ketone solvents such as acetone and methyl ethyl ketone; water, and mixtures thereof, and a mixture of an ether solvent such as diethyl ether, THF, DME, or 1,4-dioxane, and water is preferable.

The reaction temperature in the acylation reaction is preferably from −78° C. to 100° C., more preferably from −20° C. to 50° C.

The reaction time of the acylation reaction varies depending on the reaction conditions, and a preferred reaction time is from 1 to 30 hours.

The acylating agent (XVII) used in the acylation reaction can be purchased or produced according to a known method or methods similar thereto.

Step 4-4

The tetrahydroquinoline derivative (I-d) can be produced by hydrogenation reaction or a transfer hydrogenation reaction of the amidoquinoline derivative (XVIII). The conditions selected for this step, including reagents, catalyst, hydrogen pressure, reaction solvent, and reaction temperature, are similar to those in the step 1-4.

Step 4-5

An urea-quinoline derivative (XX) can be produced by urea-forming reaction between the aminoquinoline derivative (XVI) and an urea-forming agent (XIX).

The urea-forming agent (XIX) used for the urea-forming reaction is preferably in an amount of 0.5 to 10 equivalents, more preferably in an amount of 1 to 3 equivalents, relative to the aminoquinoline derivative (XVI).

A base may optionally be used for the urea-forming reaction. Examples of the base used include, organic bases such as triethylamine, N,N-diisopropylethylamine, and pyridine; alkaline metal hydroxides such as sodium hydroxide, potassium hydroxide, and lithium hydroxide; alkaline metal hydrogencarbonates such as sodium hydrogencarbonate and potassium hydrogencarbonate; alkaline metal carbonates such as sodium carbonate and potassium carbonate; and mixtures thereof; and an organic base such as triethylamine, N,N-diisopropylethylamine, or pyridine, is preferable.

The reaction solvent used in the urea-forming reaction is appropriately selected depending on the types of the reagents used, and the reaction solvent is not limited as long as the reaction is not inhibited by the solvent. Examples of the reaction solvent include nitrile solvents such as acetonitrile and propionitrile, polar aprotic solvents such as DMF, DMA, and DMSO; ether solvents such as diethyl ether, THF, DME, and 1,4-dioxane; ester solvents such as ethyl acetate and propyl acetate; ketone solvents such as acetone and methyl ethyl ketone; water, and mixtures thereof; and an ether solvent such as diethyl ether, THF, DME, or 1,4-dioxane is preferable.

The reaction temperature in the urea-forming reaction is preferably from −78° C. to 100° C., more preferably from −20° C. to 50° C.

The reaction time of the urea-forming reaction varies depending on the reaction conditions, and a preferred reaction time is from 1 to 30 hours.

The urea-forming agent (XIX) used in the urea-forming reaction can be purchased or produced according to a known method or methods similar thereto.

Step 4-6

The tetrahydroquinoline derivative (I-e) can be produced by hydrogenation reaction or transfer hydrogenation reaction of the urea-quinoline derivative (XX). The conditions selected for this step, including reagents, catalyst, hydrogen pressure, reaction solvent, and reaction temperature, are similar to those in the step 1-4.

Step 4-7

A sulfonylamidoquinoline derivative (XXII) can be produced by sulfonylation of the aminoquinoline derivative (XVI) with a sulfonylating agent (XXI).

The sulfonylating agent (XXI) used for the sulfonylation reaction is preferably in an amount of 0.5 to 10 equivalents, more preferably in an amount of 1 to 3 equivalents, relative to the aminoquinoline derivative (XVI).

A base may optionally be used for the sulfonylation reaction. Examples of the base used include organic bases such as triethylamine, N,N-diisopropylethylamine, and pyridine; alkaline metal hydroxides such as sodium hydroxide, potassium hydroxide, and lithium hydroxide; alkaline metal hydrogencarbonate such as sodium hydrogencarbonate and potassium hydrogencarbonate; alkaline metal carbonates such as sodium carbonate and potassium carbonate; and mixtures thereof; and an organic base such as triethylamine, N,N-diisopropylethylamine, or pyridine, is preferable.

The reaction solvent used in the sulfonylation reaction is appropriately selected depending on the types of the reagents used, and the reaction solvent is not limited as long as the reaction is not inhibited by the solvent. Examples of the reaction solvent include nitrile solvents such as acetonitrile and propionitrile; polar aprotic solvents such as DMF, DMA, and DMSO; ether solvents such as diethyl ether, THF, DME, and 1,4-dioxane; ester solvents such as ethyl acetate and propyl acetate; ketone solvents such as acetone and methyl ethyl ketone; water, and mixtures thereof, and an ether solvent such as diethyl ether, THF, DME, or 1,4-dioxane, is preferable.

The reaction temperature in the sulfonylation reaction is preferably from −78° C. to 100° C., more preferably from −20° C. to 50° C.

The reaction time in the sulfonylation reaction varies depending on the reaction conditions, and a preferred reaction time is from 1 to 30 hours.

The sulfonylating agent (XXI) used in the sulfonylation reaction can be purchased or produced according to a known method or methods similar thereto.

Step 4-8

The tetrahydroquinoline derivative (I-f) can be produced by hydrogenation reaction or transfer hydrogenation reaction of the sulfonylamidoquinoline derivative (XXII). The conditions selected for this step, including reagents, catalyst, hydrogen pressure, reaction solvent, and reaction temperature, are similar to those in the step 1-4.

Production Method 5

Among the tetrahydroquinoline derivative (I), a tetrahydroquinoline derivative (I-g) can be produced by a method shown in, for example, Scheme 5, in which all of $R^{1y}$, $R^v$, and $R^w$ are hydrogen, and $R^3$ is $—CH_2NR^{11}R^{12}$.

Scheme 5

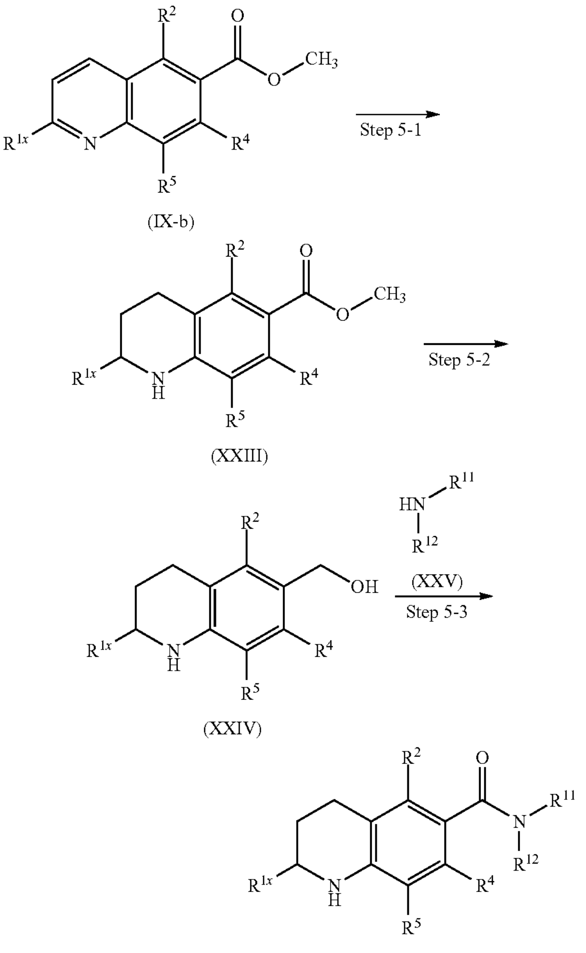

(IX-b)
(XXIII)
(XXIV)
(I-g)

In the scheme, the symbols have the same definitions as above.

Step 5-1

A (Methoxycarbonyl)tetrahydroquinoline derivative (XXIII) can be produced by hydrogenation reaction or transfer hydrogenation reaction of quinoline-6-carboxylic acid ester derivative (IX-b). The conditions selected for this step, including reagents, catalyst, hydrogen pressure, reaction solvent, and reaction temperature, are similar to those in the step 1-4.

The quinoline-6-carboxylic acid ester derivative (IX-b) used in the hydrogenation reaction or transfer hydrogenation reaction can be purchased or produced by the methods described in Steps 1-1 to 1-3, known methods, or methods similar thereto.

Step 5-2

A (Hydroxymethyl)tetrahydroquinoline derivative (XXIV) can be produced by reduction reaction of the (methoxycarbonyl)tetrahydroquinoline derivative (XXIII).

Examples of a reducing agent used in the reduction reaction include aluminum-based reducing agents such as lithium aluminum hydride and diisobutylaluminum hydride; and boron-based reducing agents such as sodium borohydride and lithium borohydride; and an aluminum-based reducing agent such as lithium aluminum hydride or diisobutylaluminum hydride, is preferable.

The reducing agent used in the reduction reaction is preferably in an amount of 0.3 to 100 equivalents, more preferably in an amount of 0.5 to 20 equivalents, relative to the (methoxycarbonyl)tetrahydroquinoline derivative (XXIII).

The reaction solvent used in the reduction reaction is appropriately selected depending on the types of the reagents used, and the reaction solvent is not limited as long as the reaction is not inhibited by the solvent. Examples of the reaction solvent include alcohol solvents such as methanol, ethanol, isopropyl alcohol, and tert-butyl alcohol; polar aprotic solvents such as DMF, DMA, and DMSO; ether solvents such as diethyl ether, THF, DME, and 1,4-dioxane; chlorinated solvents such as dichloromethane, chloroform, and 1,2-dichloroethane; aromatic hydrocarbon solvents such as toluene and xylene; and mixtures thereof, and an ether solvent such as diethyl ether, THF, DME, or 1,4-dioxane, or an aromatic hydrocarbon solvent such as toluene or xylene, is preferable.

The reaction temperature in the reduction reaction is preferably from −100° C. to 200° C., more preferably from −50° C. to 50° C.

The reaction time of the reduction reaction varies depending on the reaction conditions, and a preferred reaction time is from 1 to 30 hours.

Step 5-3

The tetrahydroquinoline derivative (I-g) can be produced by substitution reaction between the (hydroxymethyl)tetrahydroquinoline derivative (XXIV) and a secondary amine derivative (XXV) in the presence of a phosphine derivative and iodine.

The secondary amine derivative (XXV) used for the substitution reaction are preferably in an amount of 0.5 to 100 equivalents, more preferably in an amount of 1 to 20 equivalents, relative to the (hydroxymethyl)tetrahydroquinoline derivative (XXIV).

Examples of the phosphine derivative used in the substitution reaction include triphenylphosphine, trimethylphosphine, and tri-n-butylphosphine; and triphenylphosphine is preferable.

The phosphine derivative used for the substitution reaction is preferably in an amount of 0.5 to 20 equivalents, more preferably in an amount of 1 to 5 equivalents, relative to the (hydroxymethyl)tetrahydroquinoline derivative (XXIV).

Iodine used for the substitution reaction is preferably in an amount of 0.5 to 20 equivalents, more preferably in an amount of 1 to 5 equivalents, relative to the (hydroxymethyl) tetrahydroquinoline derivative (XXIV).

The reaction solvent used in the substitution reaction is not specifically limited as long as the reaction is not inhibited by the reaction solvent. Examples of the reaction solvent include polar aprotic solvents such as DMF, DMA, and DMSO; ketone solvents such as acetone and methyl ethyl ketone; ester solvents such as ethyl acetate and propyl acetate; ether solvents such as diethyl ether, THF, DME, and 1,4-dioxane; chlorinated solvents such as dichloromethane, chloroform, and 1,2-dichloroethane; aromatic hydrocarbon solvents such as toluene and xylene; and mixtures thereof, and a chlorinated solvent such as dichloromethane, chloroform, or 1,2-dichloroethane, is preferable.

The reaction temperature in the substitution reaction is preferably from 0 to 150° C., more preferably from 10 to 70° C.

The reaction time of the substitution reaction varies depending on the reaction conditions, and a preferred reaction time is from 1 to 24 hours.

Production Method 6

Among the tetrahydroquinoline derivative (I), tetrahydroquinoline derivatives (I-h) and (I-i) can be produced by a method shown in, for example, Scheme 6, in which all of $R^{1y}$, $R^v$, and $R^w$ are hydrogen, and $R^3$ is —$CH_2CONR^{13}R^{14}$.

Scheme 6

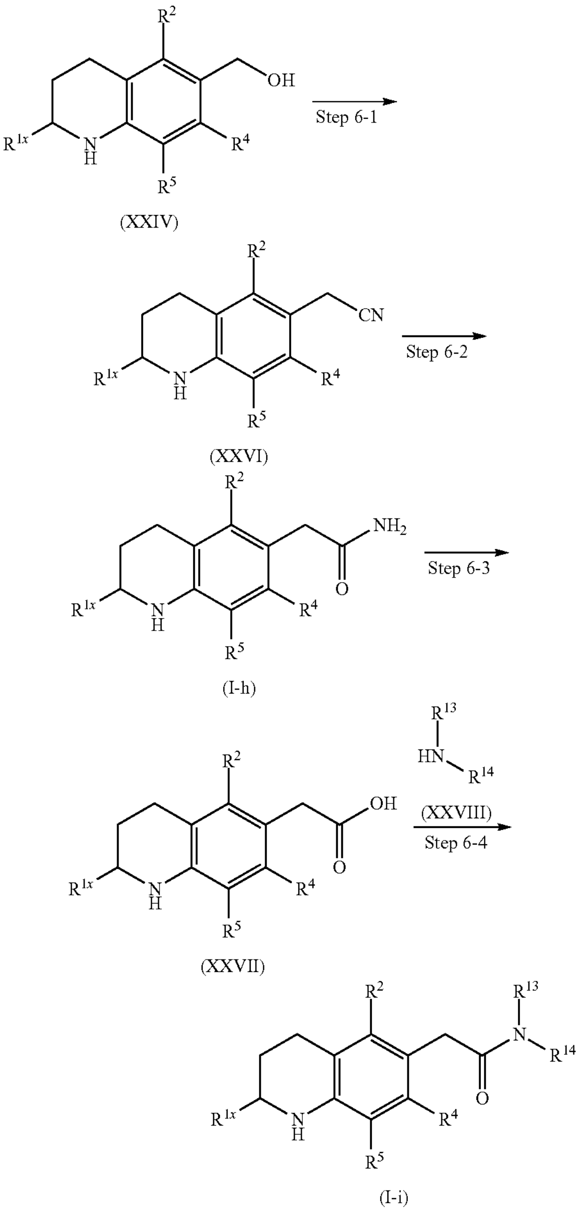

(XXIV)

(XXVI)

(I-h)

(XXVII)

(I-i)

In the scheme, the symbols have the same definitions as above.

Step 6-1

A nitrile derivative (XXVI) can be produced by a Mitsunobu reaction between the (hydroxymethyl)tetrahydroquinoline derivative (XXIV) and acetone cyanohydrin using an azodicarboxylic acid ester derivative in the presence of a phosphine derivative.

Examples of the azodicarboxylic acid ester derivative used in the Mitsunobu reaction include diethyl azodicarboxylate, diisopropyl azodicarboxylate, 1,1'-(azodicarbonyl)dipiperidine; and 1,1'-(azodicarbonyl)dipiperidine is preferable.

The azodicarboxylic acid ester derivative used for the Mitsunobu reaction is preferably in an amount of 0.5 to 30 equivalents, more preferably in an amount of 1 to 10 equivalents, relative to the (hydroxymethyl)tetrahydroquinoline derivative (XXIV).

Examples of the phosphine derivative used in the Mitsunobu reaction include triphenylphosphine, trimethylphosphine, and tri-n-butylphosphine; and tri-n-butylphosphine is preferable.

The phosphine derivative used for the Mitsunobu reaction is preferably in an amount of 0.5 to 30 equivalents, more preferably in an amount of 1 to 10 equivalents, relative to the (hydroxymethyl)tetrahydroquinoline derivative (XXIV).

The acetone cyanohydrin is preferably used for the Mitsunobu reaction in an amount of 0.5 to 50 equivalents, more preferably in an amount of 1 to 20 equivalents, relative to the (hydroxymethyl)tetrahydroquinoline derivative (XXIV).

The reaction solvent used in the Mitsunobu reaction is not specifically limited as long as the reaction is not inhibited by the reaction solvent. Examples of the reaction solvent include polar aprotic solvents such as DMF, DMA, and DMSO; ketone solvents such as acetone and methyl ethyl ketone; ester solvents such as ethyl acetate and propyl acetate; ether solvents such as diethyl ether, THF, DME, and 1,4-dioxane; chlorinated solvents such as dichloromethane, chloroform, and 1,2-dichloroethane; aromatic hydrocarbon solvents such as toluene and xylene; and mixtures thereof; and an ether solvent such as diethyl ether, THF, DME, or 1,4-dioxane, is preferable.

The reaction temperature in the Mitsunobu reaction is preferably from −20° C. to 200° C., more preferably from −10° C. to 100° C.

The reaction time of the Mitsunobu reaction varies depending on the reaction conditions, and a preferred reaction time is from 1 to 12 hours.

Step 6-2

The tetrahydroquinoline derivative (I-h) can be produced by hydrolysis reaction of the nitrile derivative (XXVI) in the presence of an aqueous solution of hydrogen peroxide and a base.

The aqueous solution of hydrogen peroxide used for the hydrolysis reaction is preferably in an amount of 0.5 to 100 equivalents, more preferably in an amount of 1 to 30 equivalents, relative to the nitrile derivative (XXVI).

Examples of the base used in the hydrolysis reaction include lithium hydroxide, potassium hydroxide, sodium hydroxide, and sodium tert-butoxide; and potassium hydroxide or sodium hydroxide is preferable.

The base used for the hydrolysis reaction is preferably in an amount of 0.5 to 100 equivalents, more preferably in an amount of 0.8 to 20 equivalents, relative to the nitrile derivative (XXVI).

The reaction solvent used in the hydrolysis reaction is appropriately selected depending on the types of the reagents used, and the reaction solvent is not limited as long as the reaction is not inhibited by the solvent. Examples of the reaction solvent include ether solvents such as THF, 1,4-dioxane, and DME; chlorinated solvents such as dichloromethane, chloroform, and 1,2-dichloroethane; aromatic hydrocarbon solvents such as benzene and toluene; polar aprotic solvents such as DMF, DMA, and DMSO, ketone solvents such as acetone and methyl ethyl ketone, alcohol solvents such as methanol, ethanol, and 2-propanol, and mixtures thereof, and a mixture of a polar aprotic solvent such as DMF, DMA, or DMSO; and an ether solvent such as THF, 1,4-dioxane, or DME, is preferable.

The reaction temperature in the hydrolysis reaction is preferably from −50° C. to 150° C., more preferably from −20° C. to 100° C.

The reaction time for the hydrolysis reaction is appropriately selected depending on conditions such as reaction temperature, and a preferred reaction time is from 1 to 30 hours.

Step 6-3

A carboxylic acid derivative (XXVII) can be produced by hydrolysis reaction of the tetrahydroquinoline derivative (I-h) in the presence of a base.

Examples of the base used in the hydrolysis reaction include lithium hydroxide, potassium hydroxide, sodium hydroxide, and sodium tert-butoxide; and potassium hydroxide or sodium hydroxide is preferable.

The base used for the hydrolysis reaction is preferably in an amount of 0.5 to 100 equivalents, more preferably in an amount of 0.8 to 30 equivalents, relative to the tetrahydroquinoline derivative (I-h).

The reaction solvent used in the hydrolysis reaction is appropriately selected depending on the types of the reagents used, and the reaction solvent is not limited as long as the reaction is not inhibited by the solvent. Examples of the reaction solvent include ether solvents such as THF, 1,4-dioxane, and DME; chlorinated solvents such as dichloromethane, chloroform, and 1,2-dichloroethane; aromatic hydrocarbon solvents such as benzene and toluene; polar aprotic solvents such as DMF, DMA, and DMSO; ketone solvents such as acetone and methyl ethyl ketone; alcohol solvents such as methanol, ethanol, and 2-propanol; water, and mixtures thereof; and a mixture of an alcohol solvent such as methanol, ethanol, or 2-propanol, and water is preferable.

The reaction temperature in the hydrolysis reaction is preferably from 0 to 200° C., more preferably from 20° C. to 100° C.

The reaction time for the hydrolysis reaction is selected appropriately depending on conditions such as reaction temperature, and a preferred reaction time is from 1 to 30 hours.

Step 6-4

The tetrahydroquinoline derivative (I-i) can be produced by condensation reaction between the carboxylic acid derivative (XXVII) and an amine derivative (XXVIII) in the presence of a condensing agent.

The amine derivative (XXVIII) used for the condensation reaction are preferably in an amount of 0.1 to 10 equivalents, more preferably in an amount of 0.5 to 5 equivalents, relative to the carboxylic acid derivative (XXVII).

Examples of the condensing agent used in the condensation reaction include N,N'-di-cyclohexylcarbodiimide, N-ethyl-N'-3-dimethylaminopropylcarbodiimide hydrochloride, N,N'-carbodiimidazole, {{[(1-cyano-2-ethoxy-2-oxoethylidene)amino]oxy}-4-morpholinomethylene}dimethylammonium hexafluorophosphate, O-(7-azabenzotriazol-1-yl)-1,1,3,3-tetramethyluronium hexafluorophosphate and O-(benzotriazol-1-yl)-N,N,N',N'-tetramethyluronium hexafluorophosphate; and O-(7-azabenzotriazol-1-yl)-1,1,3,3-tetramethyluronium hexafluorophosphate is preferable.

The condensing agent used for the condensation reaction is preferably in an amount of 0.5 to 10 equivalents, more preferably in an amount of 1 to 3 equivalents, relative to the carboxylic acid derivative (XXVII).

Examples of the base used in the condensation reaction include organic bases such as triethylamine and diisopropylethylamine; inorganic bases such as sodium hydrogencarbonate and potassium carbonate; metal hydride compounds such as sodium hydride, potassium hydride, and calcium hydride; alkyl lithium compounds such as methyl lithium and butyl lithium; lithium amides such as lithium hexamethyldisilazide and lithium diisopropylamide; and mixtures thereof; and an organic base such as triethylamine or diisopropylethylamine, is preferable.

The base used for the condensation reaction is preferably in an amount of 0.5 to 10 equivalents, more preferably in an amount of 1 to 5 equivalents, relative to the carboxylic acid derivative (XXVII).

The amine derivative (XXVIII) may each be used as a base for use in the condensation reaction. When the amine derivative (XXVIII) is used as a base for use in the condensation reaction, the amine derivative (XXVIII) used is preferably in an amount of 0.6 to 20 equivalents, more preferably in an amount of 1 to 10 equivalents, relative to the carboxylic acid derivative (XXVII).

The reaction solvent used in the condensation reaction is appropriately selected depending on the types of the reagents used and the like, and the reaction solvent is not limited as long as the reaction is not inhibited by the solvent. Examples of the reaction solvent include ether solvents such as THF, 1,4-dioxane, and DME; chlorinated solvents such as dichloromethane, chloroform, and 1,2-dichloroethane; polar aprotic solvents such as DMF and DMSO; and nitrile solvents such as acetonitrile and propionitrile; and a chlorinated solvent such as dichloromethane, chloroform, or 1,2-dichloroethane; or a polar aprotic solvent such as DMF or DMSO, is preferable.

The reaction temperature in the condensation reaction is preferably from 0 to 200° C., more preferably from 20 to 100° C.

The reaction time for the condensation reaction is appropriately selected depending on conditions such as reaction temperature, and a preferred reaction time is from 1 to 30 hours.

The amine derivative (XXVIII) used in the condensation reaction may be in free form or in the salt form such as hydrochloride.

The amine derivative (XXVIII) used in the condensation reaction can be purchased or produced according to known methods or methods similar thereto.

Production Method 7

Among the tetrahydroquinoline derivative (I), optical isomers of tetrahydroquinoline derivatives (I-j') and (I-j") can be produced by a method shown in, for example, Scheme 7, in which all of $R^{1y}$, $R^v$, and $R^w$ are hydrogen.

Scheme 7

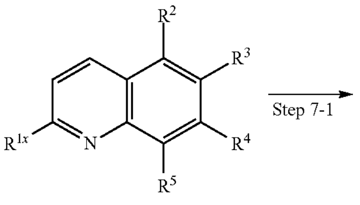

(XXIX)

-continued

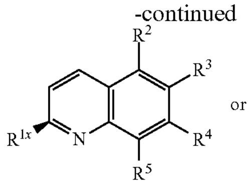

(I-j')

or

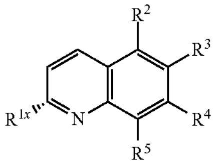

(I-j")

In the scheme, the symbols have the same definitions as above.

Step 7-1

The optical isomers (I-j') and (I-j") of the tetrahydroquinoline derivative (I) can be produced by asymmetric transfer hydrogenation reaction of a quinoline derivative (XXIX) with a 1,4-dihydro-2,6-dimethyl-3,5-pyridine dicarboxylic acid ester derivative in the presence of a chiral phosphate catalyst, for example, according to a method described in Tetrahedron: Asymmetry, 2015, p. 1174-1179 or methods similar thereto.

The quinoline derivative (XXIX) used in the asymmetric transfer hydrogenation reaction can be purchased or produced by the methods described in Steps 1-1 to 1-3, 2-1, 3-1, 3-2, 4-1 to 4-3, 4-5, and 4-7, known methods, or methods similar thereto.

Examples of the chiral phosphate catalyst used in the asymmetric transfer hydrogenation reaction include (S)-1,1'-binaphthalene-2,2'-diyl hydrogen phosphate, (R)-1,1'-binaphthalene-2,2'-diyl hydrogen phosphate, (S)-3,3'-bis(3,5-bis(trifluoromethyl)phenyl)-1,1'-binaphthyl-2,2'-diyl hydrogen phosphate, (R)-3,3'-bis(3,5-bis(trifluoromethyl)phenyl)-1,1'-binaphthyl-2,2'-diyl hydrogen phosphate, (S)-3,3'-bis(triphenylsilyl)-1,1'-binaphthyl-2,2'-diyl hydrogen phosphate, (R)-3,3'-bis(triphenylsilyl)-1,1'-binaphthyl-2,2'-diyl hydrogen phosphate, (S)-3,3'-bis(9-phenanthryl)-1,1'-binaphthalene-2,2'-diyl hydrogen phosphate, (R)-3,3'-bis(9-phenanthryl)-1,1'-binaphthalene-2,2'-diyl hydrogen phosphate, (S)-3,3'-bis(2,4,6-triisopropylphenyl)-1,1'-binaphthyl-2,2'-diyl hydrogen phosphate; and (R)-3,3'-bis(2,4,6-triisopropylphenyl)-1,1'-binaphthyl-2,2'-diyl hydrogen phosphate, and (S)-3,3'-bis(2,4,6-triisopropylphenyl)-1,1'-binaphthyl-2,2'-diyl hydrogen phosphate or (R)-3,3'-bis(2,4,6-triisopropylphenyl)-1,1'-binaphthyl-2,2'-diyl hydrogen phosphate is preferable.

Production Method 8

Among the tetrahydroquinoline derivative (I), a tetrahydroquinoline derivative (I-k) can be produced by a method shown in, for example, Scheme 8, in which all of $R^{1x}$, $R^v$, and $R^w$ are hydrogen.

Scheme 8

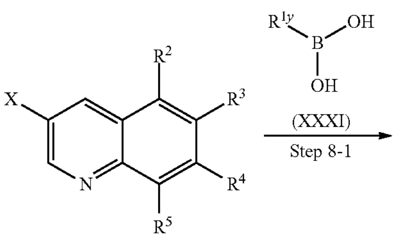

(XXX)

-continued

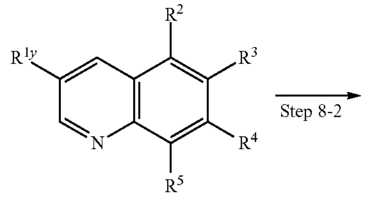

(XXXII)

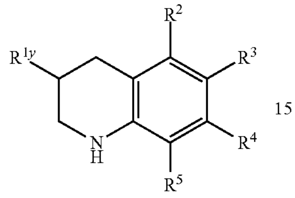

(I-k)

In the scheme, X is halogen, and the other symbols have the same definitions as above.

Step 8-1

A quinoline derivative (XXXII) can be produced by coupling reaction of a 3-haloquinoline derivative (XXX) and a boronic acid derivative (XXXI) in the presence of a metal catalyst and a base. The conditions selected for this step, including reagents, catalyst, hydrogen pressure, reaction solvent, and reaction temperature, are similar to those in the Step 1-1.

The 3-haloquinoline derivative (XXX) and the boronic acid derivative (XXXI) used in the coupling reaction can be purchased or produced according to known methods or methods similar thereto.

Step 8-2

The tetrahydroquinoline derivative (I-k) can be produced by hydrogenation reaction or transfer hydrogenation reaction of the quinoline derivative (XXXII). The conditions selected for this step, including reagents, catalyst, hydrogen pressure, reaction solvent, and reaction temperature, are similar to those in the Step 1-4.

Production Method 9

Among the tetrahydroquinoline derivative (I), optical isomers (I-k') and (I-k") of the tetrahydroquinoline derivative (I-k) can be produced by a method shown in, for example, Scheme 9, in which all of $R^{1x}$, $R^v$, and $R^w$ are hydrogen.

Scheme 9

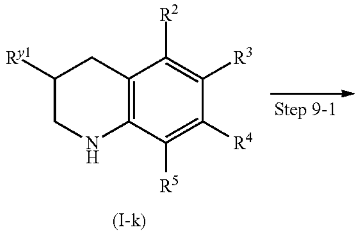

(I-k)

-continued

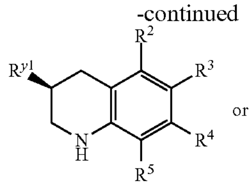

or

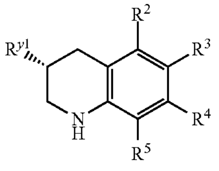

(I-k')

(I-k")

In the scheme, the symbols have the same definitions as above.

Step 9-1

The optical isomers (I-k') and (I-k") of the tetrahydroquinoline derivative (I-k) can be obtained by preparative HPLC using a chiral column.

In an example, each drug can be used as a drug for treating or preventing diseases, disorders or syndromes related to ferroptosis inhibition.

The term “ferroptosis inhibition” means inhibiting ferroptosis (ferrous iron-dependent controlled cell death). The ferroptosis inhibitors can be used against diseases, disorders or syndromes for which amelioration of clinical conditions or remission of symptoms can be expected by inhibiting ferroptosis.

The phrase “diseases, disorders or syndromes related to ferroptosis inhibition” means the diseases, disorders or syndromes for which amelioration of clinical conditions or remission of symptoms can be expected by the above-described ferroptosis inhibition. Examples of the diseases, disorders or syndromes related to the ferroptosis inhibition include kidney disease, Parkinson’s disease, Alzheimer’s disease, Huntington’s disease, non-alcoholic steatohepatitis, chronic obstructive pulmonary disease, Friedreich’s ataxia, and multiple sclerosis; and multiple sclerosis is preferable.

“Multiple sclerosis” is characterized by demyelination, in which the myelin sheath surrounding nerve fibers of the brain, spinal cord, optic nerve and the like is damaged, and is a disease in which the condition is deteriorated while repeating relapse and remission. Multiple sclerosis shows different pathologies depending on the sites of lesion, including various neurological symptoms such as vision disturbances, quadriplegia, sensory disturbances, and gait disturbances. Types of multiple sclerosis include, for example, relapsing remitting multiple sclerosis, primary progressive multiple sclerosis, and secondary progressive multiple sclerosis.

Each of the tetrahydroquinoline derivative (I), a pharmaceutically acceptable salt thereof, or a drug can be used as a ferroptosis inhibitor that contains the tetrahydroquinoline derivative (I) or a pharmaceutically acceptable salt thereof as an active ingredient. In this respect, the tetrahydroquinoline derivative (I) or a pharmaceutically acceptable salt thereof, or 2-phenyl-1,2,3,4-tetrahydroquinoline or a pharmaceutically acceptable salt thereof, can be used as a ferroptosis inhibitor.

The term “ferroptosis inhibitor” means a compound that has action to inhibit ferroptosis, thereby increasing cell survival and enhancing and preserving cellular functions, or composition that contains the compound as an active ingredient.

It is reported that the presence of radical scavenging action is important to exert inhibitory action against ferroptosis, as described in Jennifer Yinus Cao et al. Additionally, CN ’614 and Yu-Zhen Li et al. disclose that tetrahydroquinoxaline derivatives have strong radical scavenging action.

In contrast, Yu-Zhen Li et al. reports tetrahydroquinoline derivative with very low radical scavenging action. However, the tetrahydroquinoline derivative (I) or a pharmaceutically acceptable salt thereof exerts inhibitory action against ferroptosis, and therefore can be used as a novel drug for treating or preventing diseases, disorders or syndromes related to ferroptosis inhibition.

The inhibitory action against ferroptosis of the tetrahydroquinoline derivative (I) or a pharmaceutically acceptable salt thereof can be evaluated using an in vitro test. For example, the inhibitory action can be evaluated using, as an index, the inhibitory action against the cell death induced by treatment of established cells such as human fibrosarcoma cells (HT-1080 cells), primary cultured cells, iPS cells, or the like with a ferroptosis inducer such as Erastin, RSL3, FIN56, or buthionine sulfoximine.

The radical scavenging action of a test compound can be evaluated using an in vitro test and, for example, by a method (Antioxidants, 2019, vol. 258) using a stable radical, 1,1-diphenyl-2-picryl hydrazil (DPPH).

The effectiveness of the tetrahydroquinoline derivative (I) or a pharmaceutically acceptable salt thereof on the treatment or prevention of diseases, disorders or syndromes related to ferroptosis inhibition can be evaluated using a pathological model. Examples of the pathological model include experimental autoimmune encephalomyelitis model (Journal of Neuroscience Research, 2006, vol. 84, p. 1225-1234; International Immunology, 1997, vol. 9, p. 1243-1251). The experimental autoimmune encephalomyelitis model is an animal model generated by immunizing laboratory animals with myelin oligodendrocyte glycoprotein (hereinafter referred to as MOG) or with proteolipid protein or its partial peptide to induce neurological disorders such as hind limb paralysis, due to demyelination in the central nervous system. The pathological model is widely used to evaluate the efficacy of therapeutic or preventive agents for multiple sclerosis because the conditions and pathological findings in the pathological model are similar to those in human patients with multiple sclerosis. The effectiveness on the treatment or prevention of multiple sclerosis can be evaluated using the experimental autoimmune encephalomyelitis model and, for example, can be evaluated using, as an index, the reduction of neurological score, which is a characteristic index of multiple sclerosis.

Each of the tetrahydroquinoline derivative (I) or a pharmaceutically acceptable salt thereof has inhibitory action against ferroptosis and therefore can be used as a useful drug (particularly, for treating or preventing diseases, disorders or syndromes related to ferroptosis inhibition such as multiple sclerosis) for mammals (for example, mouse, rat, hamster, rabbit, cat, dog, cow, sheep, monkey, and human).

When the tetrahydroquinoline derivative (I) or a pharmaceutically acceptable salt thereof is used as a drug in clinical settings, the tetrahydroquinoline derivative (I) or the pharmaceutically acceptable salt thereof can be orally, parenterally, or topically administered directly or in combination with a pharmaceutically acceptable carrier(s). In the drug, additives such as an excipient, a binder, a lubricant, a disintegrating agent, a sweetening agent, a stabilizing agent, a taste masking agent, a flavoring agent, a coloring agent, a fluidizing agent, a preservative agent, a buffering agent, a solubilizing agent, an emulsifying agent, a surfactant, a suspending agent, a diluent, and a tonicity agent, may be appropriately mixed, if necessary. Examples of the pharmaceutically acceptable carrier(s) include these additives. Moreover, the above-described drug can be produced by a conventional method using those pharmaceutically acceptable carriers as appropriate. The dosage forms of the drug include, for example, oral forms such as tablets, pills, capsules, granules, powders, syrups, emulsions, and suspensions; parenteral forms such as inhalants, injections, suppositories, and liquids; and forms for topical administration such as ointments, creams, and patches. Also, an appropriate base (for example, polybutyric acid, polyglycolic acid, poly (butyric acid-co-glycolic acid), a mixture of polybutyric acid and polyglycolic acid, or a polyglycerol fatty acid ester) is effectively combined to provide a sustained-release preparation.

The preparation containing the tetrahydroquinoline derivative (I) as described above or a pharmaceutically acceptable salt thereof can be prepared according to a production method commonly used and known in the field of pharmaceutical preparation. Tablets can be prepared in admixture with, for example, an excipient, a binder, a disintegrating agent, a lubricant, and the like; pills and granules can be prepared in admixture with, for example, an excipient, a binder, a disintegrating agent, and the like; capsules and powders can be prepared in admixture with, for example, an excipient and the like; syrups can be prepared in admixture with, for example, a sweetening agent and the like; and emulsions and suspensions can be prepared in admixture with, for example, a surfactant, a suspending agent, an emulsifying agent, and the like.

Examples of the excipient include lactose, dextrose, starch, sucrose, microcrystalline cellulose, powdered glycyrrhiza, mannitol, sodium hydrogencarbonate, calcium phosphate, and calcium sulfate.

Examples of the binder include starch paste solution, gum arabic solution, gelatin solution, gum tragacanth solution, carboxymethylcellulose solution, sodium alginate solution, and glycerol.

Examples of the disintegrating agent include starch and calcium carbonate.

Examples of the lubricant include magnesium stearate, calcium stearate, polyethylene glycol, purified talc, and silica.

Examples of the sweetening agent include dextrose, fructose, invert sugar, sorbitol, xylitol, glycerol, and simple syrup.

Examples of the surfactant include sodium lauryl sulfate, polysorbate 80, sorbitan monofatty acid esters, and polyoxyl stearate 40.

Examples of the suspending agent include gum arabic, sodium alginate, sodium carboxymethylcellulose, methylcellulose, and bentonite.

Examples of the emulsifying agent include gum arabic, gum tragacanth, gelatin, and polysorbate 80.

Furthermore, when a drug containing the tetrahydroquinoline derivative (I) or a pharmaceutically acceptable salt thereof is formulated into any of the above-described dosage forms, agents commonly used in the field of pharmaceutical preparation such as a coloring agent, a preservative agent, a flavoring agent, a taste masking agent, a stabilizing agent, and a thickening agent, can be appropriately added thereto.

The drug preferably contains from 0.00001 to 90% by weight, more preferably from 0.01 to 70% by weight, of the tetrahydroquinoline derivative (I) or a pharmaceutically acceptable salt thereof. A daily dosage of the drug is appropriately selected depending on the condition, body weight, and age of a patient, route of administration, and the like. The amount of the active ingredient administered, for example, to adults (with a body weight of about 60 kg) is preferably from 1 mg to 1000 mg for oral agents and from 0.01 mg to 100 mg for injections, and can be administered as a single dose or divided doses.

The drug may be mixed or used together with an appropriate amount of another drug to complement or enhance the therapeutic or preventive effects or to reduce the dosage. The drug and another drug may be administered simultaneously or sequentially in any order. The drug can be used in combination with other agents such as, but not limited to, the following therapeutic agents for multiple sclerosis and agents for treating symptoms of patients with multiple sclerosis such as spasms and stiffness.

Other therapeutic agents for multiple sclerosis include, for example, adrenocorticosteroids (for example, prednisolone and methylprednisolone), interferon preparations (for example, interferonα, interferonβ-1b, interferonβ-1a, and PEG-interferonβ-1a), glatiramer acetate, fumarate compounds (dimethyl fumarate, diroximel fumarate, monomethyl fumarate), teriflunomide, S1P receptor agonists (fingorimodo, siponimod, ozanimod, ponesimod), anti-α4 integrin antibody (natalizumab), anti-CD20 antibodies (ocrelizumab, ofatumumab), anti-CD52 antibody (alemtuzumab), cladribine, mitoxantrone, Bruton's tyrosine kinase inhibitor, immunomodulators (for example, methotrexate, azathioprine, cyclophosphamide, cyclosporine A, tacrolimus, mizoribine, and leflunomide), copolymer I, immunoglobulin, T-cell receptor vaccine, adhesion inhibitor, analgesics (for example, indometacin and diclofenac), and muscle relaxants (for example, tizanidine, eperisone, afloqualone, baclofen, diazepam, and sodium dantrolene).

Examples of the agents for treating symptoms of patients with multiple sclerosis such as spasms and stiffness include anticonvulsants (for example, carbamazepine, phenytoin, clonazepam, and amitriptyline).

EXAMPLES

This disclosure will be described blow in detail with reference to Reference Examples and Examples, but this disclosure is not limited thereto.

For any compounds which were used for the synthesis of compounds of Reference Examples and Examples, but whose synthesis methods are not described, commercially available compounds were used. The "room temperature" used in Examples and Reference Examples below generally refers to a temperature from about 10° C. to about 35° C. The names of solvents indicated in the NMR data represent the solvents used for measurement. Moreover, 400 MHz NMR spectrum was measured using the JNM-ECS400 nuclear magnetic resonance spectrometer or the JNM-ECZ400S nuclear magnetic resonance spectrometer (JEOL Ltd.). Chemical shifts were expressed in δ (unit: ppm) as a reference to tetramethylsilane, while the multiplicity of each signal was expressed as s (singlet), d (doublet), t (triplet), q (quartet), quint (quintet), sept (septet), m (multiplet), br (broad), dd (double-doublet), dt (double-triplet), ddd (double-double-doublet), dq (double-quartet), td (triple-doublet), or tt (triple-triplet). In $^1$H-NMR, protons such as hydroxyl groups, amino groups, and carboxy groups, which give very broad peaks are not listed. ESI-MS spectrum was measured using the Agilent Technologies 1200 Series, G6130A (Agilent Technologies, Inc.). The silica gel 60 (Merck Co.) was used as a silica gel, and an amino-silica gel from Fuji Silysia Chemical Ltd. was used as an amino-silica gel, and the YFLCW-prep2XY (Yamazen Co.) was used for flash chromatography. The silica gel 60 (Merck Co.) was used for preparative thin-layer chromatography (hereinafter referred to as preparative TLC).

Example 1: Synthesis of 2-phenyl-1,2,3,4-tetrahydroquinoline hydrochloride

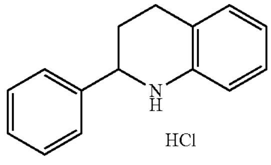 [SMILES: c1ccc(C2CCc3ccccc3N2)cc1 ; Cl]

HCl

2-Phenyl-1,2,3,4-tetrahydroquinoline (7.48 g, 35.7 mmol) was dissolved in ethyl acetate (100 mL), and a 4 mol/L hydrogen chloride-ethyl acetate solution (17.8 mL, 71.5 mmol) was added to the resulting solution, and the resulting mixture was stirred at room temperature for 16 hours under argon atmosphere. After the reaction was completed, the resulting precipitated solid was filtered and washed with ethyl acetate to obtain the title compound (hereinafter referred to as the compound of Example 1) as a white solid (8.07 g, 32.9 mmol, yield: 92%).

$^1$H-NMR (DMSO-$d_6$) δ: 7.40-7.34 (4H, m), 7.28 (1H, t, J=6.8 Hz), 6.94 (2H, t, J=7.9 Hz), 6.67 (1H, d, J=6.8 Hz), 6.56 (1H, s), 4.44 (1H, dd, J=8.6, 3.2 Hz), 2.81 (1H, dt, J=17.8, 6.1 Hz), 2.55 (1H, ddd, J=25.0, 12.3, 8.7 Hz), 2.03-1.99 (1H, m), 1.91 (1H, s). MS(ESI) $[M+H]^+$: 210.

Example 2: Synthesis of (R)-2-phenyl-1,2,3,4-tetrahydroquinoline

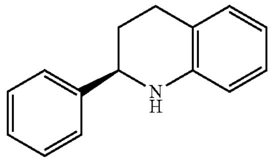 [SMILES: c1ccc([C@H]2CCc3ccccc3N2)cc1]

2-Phenylquinoline (0.100 g, 0.487 mmol) and (S)-3,3'-bis(2,4,6-triisopropylphenyl)-1,1'-binaphthyl-2,2'-diyl hydrogen phosphate (7.3 mg, 0.0097 mmol) were suspended in diethyl carbonate (5 mL), and diethyl 1,4-dihydro-2,6-dimethyl-3,5-pyridinedicarboxylate (0.296 g, 1.17 mmol) was added to the suspension, and the resulting mixture was stirred at −10° C. for 24 hours under argon atmosphere. After the reaction was completed, the reaction mixture was concentrated under reduced pressure. The obtained crude product was purified by column chromatography (silica gel, hexane/ethyl acetate) to obtain the title compound (hereinafter referred to as the compound of Example 2) as a colorless clear oily substance (95.0 mg, 0.457 mmol, yield: 95%, enantiomeric excess: 98.5% ee).

$^1$H-NMR ($CDCl_3$) δ: 7.37 (4H, ddt, J=16.0, 8.9, 2.8 Hz), 7.28 (1H, tt, J=7.0, 2.2 Hz), 7.01 (2H, t, J=7.2 Hz), 6.65 (1H, td, J=7.4, 1.1 Hz), 6.54 (1H, dd, J=8.4, 1.1 Hz), 4.44 (1H, dd, J=9.3, 3.4 Hz), 4.04 (1H, s), 2.97-2.89 (1H, m), 2.74 (1H, dt, J=16.3, 4.8 Hz), 2.16-2.09 (1H, m), 2.05-1.94 (1H, m).

MS(ESI) $[M+H]^+$: 210.

Retention time (hereinafter referred to as Rt): 18.40 min

HPLC analysis conditions:

Column: Daicel Chiralcel OD-H chiral column (inner diameter: 4.6 mm, length: 250 mm, particle size: 5 μm)

Column temperature: 40° C.

Mobile phase: propan-2-ol:hexane=5:95

Flow rate: 0.6 mL/min

Detection: UV (254 nm)

Example 3: Synthesis of (S)-2-phenyl-1,2,3,4-tetrahydroquinoline

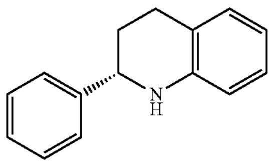 [SMILES: c1ccc([C@@H]2CCc3ccccc3N2)cc1]

2-Phenylquinoline (50.0 mg, 0.243 mmol) and (R)-3,3'-bis(2,4,6-triisopropylphenyl)-1,1'-binaphthyl-2,2'-diyl hydrogen phosphate (3.7 mg, 0.0048 mmol) were used in the same manner as in Example 2 to obtain the title compound (hereinafter referred to as the compound of Example 3) as a colorless clear oily substance (49.0 mg, 0.236 mmol, yield: 97%, enantiomeric excess: 97.2% ee).

$^1$H-NMR ($CDCl_3$) δ: 7.41-7.32 (4H, m), 7.31-7.25 (1H, m), 7.01 (2H, t, J=7.2 Hz), 6.65 (1H, td, J=7.4, 1.2 Hz), 6.55 (1H, dd, J=7.2, 1.4 Hz), 4.44 (1H, dd, J=9.3, 3.4 Hz), 4.04 (1H, s), 2.97-2.89 (1H, m), 2.74 (1H, dt, J=16.5, 4.9 Hz), 2.16-2.09 (1H, m), 2.04-1.94 (1H, m).

MS(ESI) $[M+H]^+$: 210.

Rt: 14.28 min

HPLC analysis conditions:

Column: Daicel Chiralcel OD-H chiral column (inner diameter: 4.6 mm, length: 250 mm, particle size: 5 μm)

Column temperature: 40° C.

Mobile phase: propan-2-ol:hexane=5:95

Flow rate: 0.6 mL/min

Detection: UV (254 nm)

Example 4: Synthesis of 2-(4-methoxyphenyl)-1,2,3,4-tetrahydroquinoline

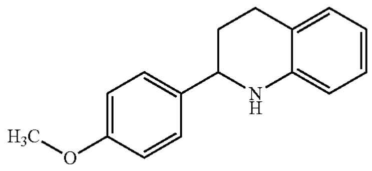 [SMILES: COc1ccc(C2CCc3ccccc3N2)cc1]

2-(4-Methoxyphenyl)quinoline (40.0 mg, 0.170 mmol) was dissolved in THF/methanol (1/1, v/v, 3.0 mL), and acetic acid (0.029 mL, 0.51 mmol) and platinum(IV) oxide (3.8 mg, 0.017 mmol) were added to the resulting solution, and the resulting mixture was stirred at room temperature and normal pressure for 6 hours under hydrogen atmosphere. After the reaction was completed, the hydrogen was replaced with nitrogen, and the reaction mixture was filtered using celite. The residue was washed with chloroform, and the filtrate was concentrated under reduced pressure. The obtained crude product was purified by column chromatography (silica gel, hexane/ethyl acetate) to obtain the title compound (hereinafter referred to as the compound of Example 4) as a white solid (26.9 mg, 0.113 mmol, yield: 66%).

$^1$H-NMR ($CDCl_3$) δ: 7.31 (2H, dt, J=9.2, 2.5 Hz), 7.00 (2H, dd, J=7.2, 6.3 Hz), 6.89 (2H, td, J=5.8, 3.5 Hz), 6.64 (1H, td, J=7.4, 1.2 Hz), 6.54-6.51 (1H, m), 4.38 (1H, dd, J=9.5, 3.2 Hz), 3.99 (1H, s), 3.81 (3H, s), 2.97-2.89 (1H, m), 2.74 (1H, dt, J=16.3, 4.5 Hz), 2.11-2.05 (1H, m), 2.01-1.91 (1H, m).

MS(ESI) $[M+H]^+$: 240.

Reference Example 1: Synthesis of 2-(3-methoxyphenyl)quinoline

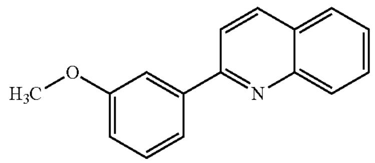 [SMILES: COc1cccc(-c2ccc3ccccc3n2)c1]

2-Chloroquinoline (0.120 g, 0.734 mmol) and 3-methoxyphenylboronic acid (0.111 g, 0.734 mmol) were dissolved in DME (4.0 mL), a 1 mol/L aqueous solution of sodium carbonate (1.5 mL), and tetrakis(triphenylphosphine)palladium(0) (8.5 mg, 0.0073 mmol) were added to the resulting solution, and the resulting mixture was stirred at 100° C. for 4 hours under argon atmosphere. After the reaction was completed, water was added to the reaction mixture, and the resulting mixture was extracted with hexane/ethyl acetate. The organic layers were combined, washed with saturated brine, and dried over anhydrous sodium sulfate, and the filtrate was then concentrated under reduced pressure. The obtained crude product was purified by column chromatography (silica gel, hexane/ethyl acetate) to obtain the title compound as a white solid (0.165 g, 0.702 mmol, yield: 95%).

$^1$H-NMR ($CDCl_3$) δ: 8.23 (1H, d, J=8.6 Hz), 8.18 (1H, t, J=4.8 Hz), 7.85 (2H, dt, J=12.5, 5.5 Hz), 7.77-7.69 (3H, m), 7.56-7.51 (1H, m), 7.44 (1H, t, J=7.9 Hz), 7.02 (1H, tt, J=5.4, 2.4 Hz), 3.94 (3H, s).

MS(ESI) $[M+H]^+$: 236.

Example 5: Synthesis of 2-(3-methoxyphenyl)-1,2,3,4-tetrahydroquinoline

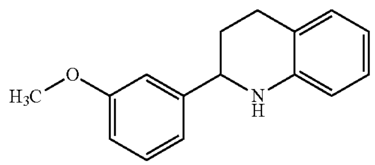 [SMILES: COc1cccc(C2CCc3ccccc3N2)c1]

The 2-(3-methoxyphenyl)quinoline synthesized in Reference Example 1 (60.0 mg, 0.255 mmol) was used in the same manner as in Example 4 to obtain the title compound (hereinafter referred to as the compound of Example 5) as a white solid (23.7 mg, 0.0991 mmol, yield: 39%).

$^1$H-NMR ($CDCl_3$) δ: 7.27 (1H, dd, J=8.8, 7.0 Hz), 7.03-6.96 (4H, m), 6.83 (1H, dq, J=8.2, 1.2 Hz), 6.65 (1H, td, J=7.4, 1.1 Hz), 6.54 (1H, d, J=7.7 Hz), 4.42 (1H, dd, J=9.3, 3.4 Hz), 4.01 (1H, brs), 3.81 (3H, s), 2.97-2.88 (1H, m), 2.74 (1H, dt, J=16.3, 4.8 Hz), 2.15-2.09 (1H, m), 2.05-1.94 (1H, m).

MS(ESI) $[M+H]^+$: 240.

Reference Example 2: Synthesis of 2-(2-methoxyphenyl)quinoline

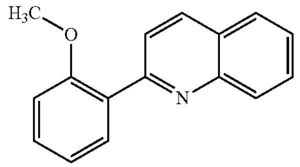 [SMILES: COc1ccccc1-c1ccc2ccccc2n1]

2-Chloroquinoline (0.100 g, 0.611 mmol) and 2-methoxyphenylboronic acid (92.8 mg, 0.611 mmol) were used in the same manner as in Reference Example 1 to obtain the title compound as a white solid (0.157 g, 0.668 mmol, yield: 99%).

$^1$H-NMR ($CDCl_3$) δ: 8.16 (2H, t, J=8.8 Hz), 7.89 (1H, d, J=8.2 Hz), 7.84 (2H, dq, J=7.7, 1.8 Hz), 7.73-7.69 (1H, m), 7.55-7.51 (1H, m), 7.43 (1H, td, J=7.9, 1.5 Hz), 7.13 (1H, td, J=7.5, 1.1 Hz), 7.04 (1H, t, J=4.3 Hz), 3.87 (3H, s).

MS(ESI) $[M+H]^+$: 236 . . .

Example 6: Synthesis of 2-(2-methoxyphenyl)-1,2,3,4-tetrahydroquinoline

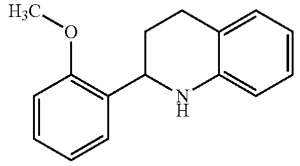 [SMILES: COc1ccccc1C1CCc2ccccc2N1]

The 2-(2-methoxyphenyl)quinoline synthesized in Reference Example 2 (60.0 mg, 0.255 mmol) was used in the same manner as in Example 4 to obtain the title compound (hereinafter referred to as the compound of Example 6) as a white solid (35.5 mg, 0.148 mmol, yield: 58%).

$^1$H-NMR ($CDCl_3$) δ: 7.43 (1H, dd, J=7.7, 1.8 Hz), 7.28-7.22 (1H, m), 7.05-6.85 (4H, m), 6.63 (1H, td, J=7.4, 1.2 Hz), 6.56 (1H, d, J=7.7 Hz), 4.87 (1H, dd, J=8.2, 3.6 Hz), 4.04 (1H, s), 3.85 (3H, s), 2.92-2.84 (1H, m), 2.69 (1H, td, J=10.8, 5.4 Hz), 2.14 (1H, dtd, J=13.4, 5.0, 2.9 Hz), 2.01-1.92 (1H, m).

MS(ESI) $[M+H]^+$: 240.

Reference Example 3: Synthesis of 2-(benzo[d][1,3]dioxol-5-yl)-6-methoxyquinoline

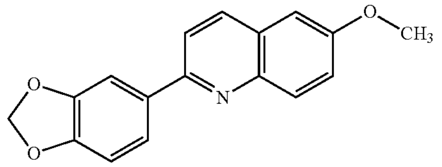 [SMILES: COc1ccc2nc(-c3ccc4c(c3)OCO4)ccc2c1]

2-Chloro-6-methoxyquinoline (0.130 g, 0.671 mmol) and benzo[d][1,3]dioxol-5-yl-phenylboronic acid (0.111 g, 0.671 mmol) were used in the same manner as in Reference Example 1 to obtain the title compound as a pale yellow solid (0.128 g, 0.459 mmol, yield: 68%).

$^1$H-NMR ($CDCl_3$) δ: 8.08 (1H, d, J=8.6 Hz), 8.02 (1H, d, J=8.6 Hz), 7.75 (1H, d, J=8.6 Hz), 7.70 (1H, d, J=1.8 Hz), 7.62 (1H, dd, J=8.2, 1.8 Hz), 7.37 (1H, dd, J=9.1, 2.7 Hz), 7.08 (1H, d, J=2.7 Hz), 6.94 (1H, d, J=4.1 Hz), 6.04 (2H, d, J=5.0 Hz), 3.95 (3H, s).

MS(ESI) $[M+H]^+$: 280.

Example 7: Synthesis of 2-(benzo[d][1,3]dioxol-5-yl)-6-methoxy-1,2,3,4-tetrahydro-quinoline (a Novel Compound)

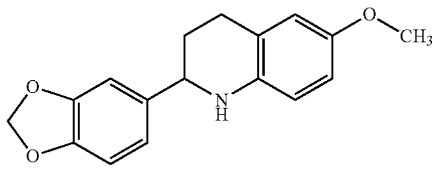 [SMILES: COc1ccc2c(c1)CCC(c1ccc3c(c1)OCO3)N2]

The 2-(benzo[d][1,3]dioxol-5-yl)-6-methoxyquinoline synthesized in Reference Example 3 (60.0 mg, 0.215 mmol) was used in the same manner as in Example 4 to obtain the title compound (hereinafter referred to as the compound of Example 7) as a white solid (24.3 mg, 0.0859 mmol, yield: 99%).

$^1$H-NMR ($CDCl_3$) δ: 6.91 (1H, d, J=1.8 Hz), 6.84 (1H, dd, J=8.2, 1.8 Hz), 6.77 (1H, d, J=7.7 Hz), 6.62 (2H, td, J=7.4, 2.7 Hz), 6.49 (1H, d, J=8.6 Hz), 5.95 (2H, s), 4.28 (1H, dd, J=9.7, 2.9 Hz), 3.74 (3H, s), 2.97-2.88 (1H, m), 2.72 (1H, dt, J=16.5, 4.5 Hz), 2.09-2.03 (1H, m), 1.98-1.88 (1H, m).

MS(ESI) $[M+H]^+$: 284.

Reference Example 4: Synthesis of 7-methoxy-2-(4-methoxyphenyl)quinoline

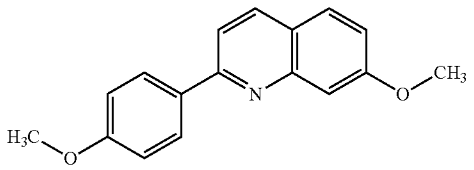

2-Chloro-7-methoxyquinoline (0.130 g, 0.671 mmol) and 4-methoxyphenylboronic acid (0.102 g, 0.671 mmol) were used in the same manner as in Reference Example 1 to obtain the title compound as a white solid (0.155 g, 0.585 mmol, yield: 87%).

$^1$H-NMR ($CDCl_3$) δ: 8.13-8.09 (3H, m), 7.69 (2H, dd, J=8.6, 5.0 Hz), 7.47 (1H, d, J=2.7 Hz), 7.16 (1H, dd, J=8.8, 2.5 Hz), 7.04 (2H, td, J=6.0, 3.5 Hz), 3.98 (3H, s), 3.89 (3H, s).

MS(ESI) $[M+H]^+$: 266.

Example 8: Synthesis of 7-methoxy-2-(4-methoxyphenyl)-1,2,3,4-tetrahydroquinoline

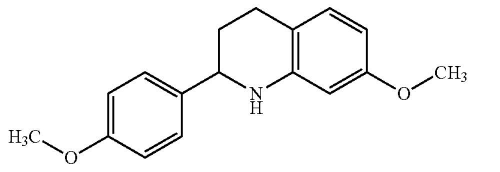

The 7-methoxy-2-(4-methoxyphenyl)quinoline synthesized in Reference Example 4 (62.0 mg, 0.234 mmol) was used in the same manner as in Example 4 to obtain the title compound (hereinafter referred to as the compound of Example 8) as a white solid (62.3 mg, 0.234 mmol, yield: 99%).

$^1$H-NMR ($CDCl_3$) δ: 7.30 (2H, td, J=5.8, 3.5 Hz), 6.91-6.87 (3H, m), 6.24 (1H, dd, J=8.4, 2.5 Hz), 6.10 (1H, d, J=2.3 Hz), 4.36 (1H, dd, J=9.5, 3.2 Hz), 4.00 (1H, s), 3.81 (3H, s), 3.75 (3H, s), 2.89-2.81 (1H, m), 2.67 (1H, dt, J=16.2, 4.6 Hz), 2.10-2.03 (1H, m), 1.99-1.89 (1H, m).

MS(ESI) $[M+H]^+$: 270.

Reference Example 5: Synthesis of 2-(benzo[d][1,3]dioxol-5-yl)quinoline

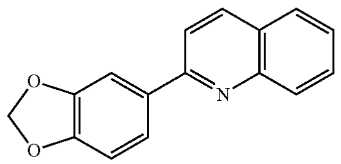 [SMILES: c1ccc2nc(-c3ccc4c(c3)OCO4)ccc2c1]

2-Chloro-quinoline (0.150 g, 0.917 mmol) and benzo[d][1,3]dioxol-5-ylphenylboronic acid (0.167 g, 1.01 mmol) were used in the same manner as in Reference Example 1 to obtain the title compound as a yellow solid (0.218 g, 0.876 mmol, yield: 87%).

$^1$H-NMR ($CDCl_3$) δ: 8.19 (1H, d, J=8.6 Hz), 8.13 (1H, t, J=4.8 Hz), 7.82-7.79 (2H, m), 7.72 (2H, tt, J=8.8, 2.9 Hz), 7.66 (1H, dd, J=8.2, 1.8 Hz), 7.53-7.49 (1H, m), 6.96 (1H, d, J=8.2 Hz), 6.05 (2H, s).

MS(ESI) $[M+H]^+$: 250.

Example 9: Synthesis of 2-(benzo[d][1,3]dioxol-5-yl)-1,2,3,4-tetrahydroquinoline

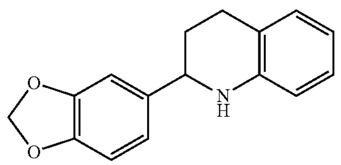 [SMILES: c1ccc2c(c1)CCC(c1ccc3c(c1)OCO3)N2]

The 2-(benzo[d][1,3]dioxol-5-yl)-quinoline synthesized in Reference Example 5 (60.0 mg, 0.241 mmol) was used in the same manner as in Example 4 to obtain the title compound (hereinafter referred to as the compound of Example 9) as a colorless clear oily substance (37.7 mg, 0.149 mmol, yield: 62%).

$^1$H-NMR ($CDCl_3$) δ: 7.00 (2H, t, J=7.2 Hz), 6.90 (1H, d, J=1.8 Hz), 6.84 (1H, dd, J=8.4, 1.6 Hz), 6.77 (1H, d, J=7.7 Hz), 6.64 (1H, td, J=7.4, 1.1 Hz), 6.53 (1H, d, J=7.2 Hz), 5.95 (2H, t, J=1.6 Hz), 4.35 (1H, dd, J=9.5, 3.2 Hz), 3.98 (1H, s), 2.95-2.87 (1H, m), 2.73 (1H, dt, J=16.3, 4.8 Hz), 2.08 (1H, tdd, J=8.4, 4.4, 2.7 Hz), 1.99-1.89 (1H, m).

MS(ESI) $[M+H]^+$: 254.

Reference Example 6: Synthesis of 2-(2-(trifluoromethyl)phenyl)quinoline

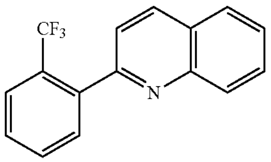 [SMILES: FC(F)(F)c1ccccc1-c1ccc2ccccc2n1]

2-Chloroquinoline (50.0 mg, 0.306 mmol), (2-(trifluoromethyl)phenyl)boronic acid (87.1 mg, 0.458 mmol), tetrakis(triphenylphosphine)palladium(0) (7.1 mg, 0.0061 mmol), and potassium carbonate (127 mg, 0.917 mmol) were dissolved in 1,4-dioxane/water (5/1, v/v, 3 mL), and the resulting solution was then stirred with heating at 100° C. for 16 hours. After the reaction mixture was cooled down to room temperature, water was poured into the reaction mixture, and the resulting mixture was extracted with ethyl acetate. The organic layer was dried over anhydrous sodium sulfate and then concentrated under reduced pressure. The obtained crude product was purified by column chromatography (silica gel, hexane-ethyl acetate) to obtain the title compound as a colorless clear oily substance (81.5 mg, 0.298 mmol, yield: 98%).

$^1$H-NMR ($CDCl_3$) δ: 8.23 (1H, d, J=8.2 Hz), 8.16 (1H, d, J=8.7 Hz), 7.89 (1H, d, J=7.8 Hz), 7.81 (1H, d, J=7.8 Hz), 7.77 (1H, t, J=8.2 Hz), 7.67 (1H, t, J=7.5 Hz), 7.62-7.54 (4H, m).

MS(ESI) $[M+H]^+$: 274.

Example 10: Synthesis of 2-(2-(trifluoromethyl)phenyl)-1,2,3,4-tetrahydroquinoline

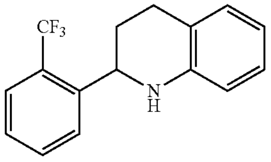

The 2-(2-(trifluoromethyl)phenyl)quinoline synthesized in Reference Example 6 (62.0 mg, 0.227 mmol) was used in the same manner as in Example 4 to obtain the title compound (hereinafter referred to as the compound of Example 10) as a colorless clear oily substance (52.2 mg, 0.188 mmol, yield: 83%).

$^1$H-NMR ($CDCl_3$) δ: 7.82 (1H, d, J=8.2 Hz), 7.65 (1H, d, J=7.8 Hz), 7.56 (1H, t, J=7.5 Hz), 7.38 (1H, t, J=7.5 Hz), 7.04-7.01 (2H, m), 6.69 (1H, t, J=7.5 Hz), 6.55 (1H, d, J=7.8 Hz), 4.82 (1H, d, J=9.6 Hz), 3.97 (1H, brs), 3.03-2.94 (1H, m), 2.81-2.75 (1H, m), 2.17-2.12 (1H, m), 1.97-1.91 (1H, m).

MS(ESI) $[M+H]^+$: 278.

Reference Example 7: Synthesis of 2-(1H-pyrazol-4-yl)quinoline

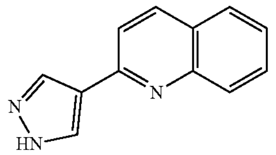 [SMILES: c1ccc2nc(-c3cn[nH]c3)ccc2c1]

2-Chloroquinoline (100 mg, 0.611 mmol) and (1H-pyrazol-4-yl)boronic acid (137 mg, 1.22 mmol) were used in the same manner as in Reference Example 6 to obtain the title compound as a white solid (63.7 mg, 0.326 mmol, yield: 53%).

$^1$H-NMR ($CDCl_3$) δ: 8.29 (2H, s), 8.16 (1H, d, J=8.7 Hz), 8.07 (1H, d, J=8.7 Hz), 7.79 (1H, d, J=8.2 Hz), 7.70 (1H, t, J=7.5 Hz), 7.66 (1H, d, J=8.2 Hz), 7.49 (1H, t, J=7.5 Hz).

MS(ESI) $[M+H]^+$: 196.

Example 11: Synthesis of 2-(1H-pyrazol-4-yl)-1,2,3,4-tetrahydroquinoline

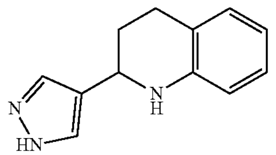 [SMILES: c1ccc2c(c1)CCC(c1cn[nH]c1)N2]

The 2-(1H-pyrazol-4-yl)quinoline synthesized in Reference Example 7 (30.0 mg, 0.154 mmol) was used in the same manner as in Example 4 to obtain the title compound (hereinafter referred to as the compound of Example 11) as a white solid (28.8 mg, 0.145 mmol, yield: 94%).

$^1$H-NMR ($CDCl_3$) δ: 7.58 (2H, s), 7.02-6.98 (2H, m), 6.66 (1H, t, J=7.1 Hz), 6.52 (1H, d, J=7.8 Hz), 4.50 (1H, dd, J=9.1, 3.2 Hz), 2.96-2.88 (1H, m), 2.80-2.74 (1H, m), 2.17-2.11 (1H, m), 2.04-1.95 (1H, m).

MS(ESI) $[M+H]^+$: 200.

Example 12: Synthesis of One of the Optical Isomers of 2-(1H-pyrazol-4-yl)-1,2,3,4-tetrahydroquinoline

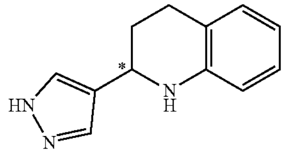 [SMILES: c1ccc2c(c1)CCC(c1cn[nH]c1)N2]

In the formula, the carbon atom marked with an asterisk (*) is an asymmetric center.

The 2-(1H-pyrazol-4-yl)quinoline synthesized in Reference Example 7 (50.0 mg, 0.256 mmol) and (R)-3,3'-bis(2,4,6-triisopropylphenyl)-1,1'-binaphthyl-2,2'-diyl hydrogen phosphate (3.8 mg, 0.0051 mmol) were suspended in 1,4-dioxane (2 mL), and diethyl 1,4-dihydro-2,6-dimethyl-3,5-pyridinedicarboxylate (0.155 g, 0.614 mmol) was added to the resulting suspension, and the resulting mixture was stirred at room temperature for 24 hours under argon atmosphere. After the reaction was completed, the reaction mixture was concentrated under reduced pressure. The obtained crude product was purified by column chromatography (silica gel, hexane/ethyl acetate), and the resulting solid was subjected to recrystallization with hexane/ethyl acetate to obtain the title compound (hereinafter referred to as the compound of Example 12) as a white solid (9.0 mg, 0.045 mmol, yield: 18%, enantiomeric excess: 98.1% ee).

$^1$H-NMR ($CDCl_3$) δ: 7.58 (2H, s), 6.98 (2H, d, J=8.8 Hz), 6.65 (1H, t, J=7.2 Hz), 6.52 (1H, d, J=8.2 Hz), 4.50 (1H, dd, J=9.3, 2.9 Hz), 3.96 (1H, s), 2.96-2.88 (1H, m), 2.76 (1H, dt, J=16.3, 4.8 Hz), 2.17-2.11 (1H, m), 2.05-1.95 (1H, m).

MS(ESI) $[M+H]^+$: 200.

Rt: 17.78 min

HPLC analysis conditions:

Column: Daicel Chiralcel OZ-3 chiral column (inner diameter: 4.6 mm, length: 150 mm, particle size: 3 μm)

Column temperature: 40° C.

Mobile phase: propan-2-ol:hexane=10:90

Flow rate: 0.6 mL/min

Detection: UV (254 nm)

Example 13: Synthesis of the Other of the Optical Isomers of 2-(1H-pyrazol-4-yl)-1,2,3,4-tetrahydroquinoline

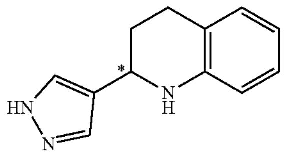 [SMILES: c1ccc2c(c1)CCC(c1cn[nH]c1)N2]

In the formula, the carbon atom marked with an asterisk (*) is an asymmetric center.

The 2-(1H-pyrazol-4-yl)quinoline synthesized in Reference Example 7 (70.0 mg, 0.359 mmol) and (S)-3,3'-bis(2,4,6-triisopropylphenyl)-1,1'-binaphthyl-2,2'-diyl hydrogen phosphate (5.40 mg, 7.17 μmol) were used in the same manner as in Example 12 to obtain the title compound (hereinafter referred to as the compound of Example 13) as a white solid (30.0 mg, 0.151 mmol, yield: 42%, enantiomeric excess: 96.9% ee).

$^1$H-NMR ($CDCl_3$) δ: 7.58 (2H, s), 7.01-6.98 (2H, m), 6.67-6.63 (1H, m), 6.53-6.50 (1H, m), 4.49 (1H, dd, J=9.3, 2.9 Hz), 3.97 (1H, brs), 2.96-2.88 (1H, m), 2.79-2.73 (1H, m), 2.17-2.10 (1H, m), 2.05-1.94 (1H, m).

MS(ESI) $[M+H]^+$: 200.

Rt: 13.11 min

HPLC analysis conditions:

Column: Daicel Chiralcel OZ-3 chiral column (inner diameter: 4.6 mm, length: 150 mm, particle size: 3 μm)

Column temperature: 40° C.

Mobile phase: propan-2-ol:hexane=10:90

Flow rate: 0.6 mL/min

Detection: UV (254 nm)

Example 14: Synthesis of 2-(1-methyl-1H-pyrazol-4-yl)-1,2,3,4-tetrahydroquinoline (a Novel Compound)

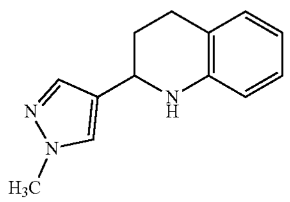 [SMILES: Cn1cc(C2CCc3ccccc3N2)cn1]

The 2-(1H-pyrazol-4-yl)-1,2,3,4-tetrahydroquinoline synthesized in Example 11 (25.0 mg, 0.125 mmol) was dissolved in DMF (1.2 mL), and potassium carbonate (34.7 mg, 0.251 mmol) and methyl iodide (7.8 μL, 0.125 mmol) were added to the resulting solution, and the resulting mixture was stirred at 50° C. for 2 hours. After the reaction mixture was cooled down to room temperature, water was added to the reaction mixture, and the resulting mixture was extracted with ethyl acetate. The organic layer was washed with saturated brine, dried over anhydrous sodium sulfate, and then concentrated under reduced pressure. The obtained crude product was purified by column chromatography (silica gel, chloroform/methanol) and column chromatography (amino-silica gel, hexane/ethyl acetate) to obtain the title compound above (hereinafter referred to as the compound of Example 14) as a colorless clear oily substance (4.1 mg, 0.019 mmol, yield: 15%).

$^1$H-NMR ($CDCl_3$) δ: 7.46 (1H, s), 7.32 (1H, s), 7.01-6.97 (2H, m), 6.64 (1H, t, J=7.1 Hz), 6.50 (1H, d, J=8.2 Hz), 4.43 (1H, dd, J=9.4, 3.0 Hz), 3.95 (1H, brs), 3.88 (3H, s), 2.94-2.86 (1H, m), 2.79-2.72 (1H, m), 2.14-2.08 (1H, m), 1.99-1.93 (1H, m).

MS(ESI) $[M+H]^+$: 214.

Reference Example 8: Synthesis of 2-(6-methoxypyridin-3-yl)quinoline

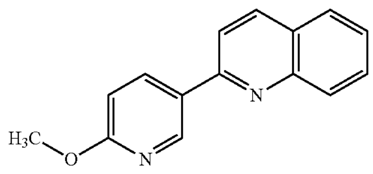 [SMILES: COc1ccc(-c2ccc3ccccc3n2)cn1]

2-Chloroquinoline (100 mg, 0.611 mmol) and (6-methoxypyridin-3-yl)boronic acid (140 mg, 0.917 mmol) were used in the same manner as in Reference Example 6 to obtain the title compound as a white solid (134 mg, 0.568 mmol, yield: 93%).

$^1$H-NMR ($CDCl_3$) δ: 8.91 (1H, d, J=2.3 Hz), 8.48 (1H, dd, J=8.7, 2.3 Hz), 8.22 (1H, d, J=8.2 Hz), 8.13 (1H, d, J=8.7 Hz), 7.83 (2H, d, J=8.7 Hz), 7.73 (1H, t, J=7.1 Hz), 7.53 (1H, t, J=7.1 Hz), 6.90 (1H, d, J=8.7 Hz), 4.03 (3H, s).

MS(ESI) $[M+H]^+$: 237.

Example 15: Synthesis of 2-(6-methoxypyridin-3-yl)-1,2,3,4-tetrahydroquinoline (a Novel Compound)

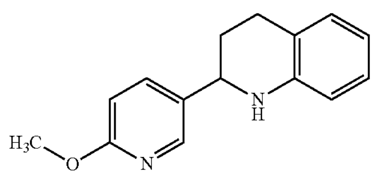 [SMILES: COc1ccc(C2CCc3ccccc3N2)cn1]

The 2-(6-methoxypyridin-3-yl)quinoline synthesized in Reference Example 8 (50.0 mg, 0.212 mmol) was used in the same manner as in Example 4 to obtain the title compound (hereinafter referred to as the compound of Example 15) as a colorless clear oily substance (11.0 mg, 0.0458 mmol, yield: 22%).

$^1$H-NMR ($CDCl_3$) δ: 8.14 (1H, d, J=2.3 Hz), 7.63 (1H, dd, J=8.7, 2.3 Hz), 7.03-6.99 (2H, m), 6.74 (1H, d, J=8.0 Hz), 6.66 (1H, t, J=7.3 Hz), 6.53 (1H, d, J=8.0 Hz), 4.40 (1H, dd, J=9.6, 3.2 Hz), 3.94 (3H, s), 3.94 (1H, brs), 2.99-2.91 (1H, m), 2.78-2.72 (1H, m), 2.09-1.93 (2H, m).

MS(ESI) $[M+H]^+$: 241.

Reference Example 9: Synthesis of 2-(4-(methylsulfonyl)phenyl)quinoline

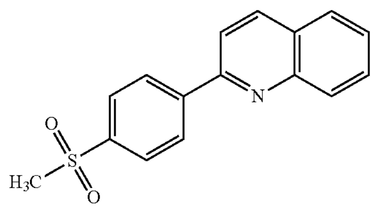 [SMILES: CS(=O)(=O)c1ccc(-c2ccc3ccccc3n2)cc1]

2-Chloroquinoline (200 mg, 1.22 mmol) and (4-(methylsulfonyl)phenyl)boronic acid (489 mg, 2.45 mmol) were used in the same manner as in Reference Example 6 to obtain a mixture of the title compound and impurities as a white solid (296 mg).

MS(ESI) $[M+H]^+$: 284.

Example 16: Synthesis of 2-(4-(methylsulfonyl)phenyl)-1,2,3,4-tetrahydroquinoline (a Novel Compound)

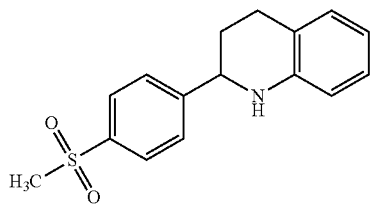

The 2-(4-(methylsulfonyl)phenyl)quinoline synthesized in Reference Example 9 (100 mg, 0.353 mmol) was used in the same manner as in Example 4 to obtain the title compound (hereinafter referred to as the compound of Example 16) as a white solid (65.6 mg, 0.228 mmol, yield: 65%).

$^1$H-NMR ($CDCl_3$) δ: 7.92 (2H, dt, J=8.7, 1.8 Hz), 7.60 (2H, dt, J=8.7, 1.8 Hz), 7.06-7.00 (2H, m), 6.69 (1H, td, J=7.3, 0.9 Hz), 6.59 (1H, dd, J=7.8, 0.9 Hz), 4.57 (1H, dd, J=8.7, 3.2 Hz), 4.09 (1H, brs), 3.06 (3H, s), 2.95-2.87 (1H, m), 2.70 (1H, td, J=10.9, 5.5 Hz), 2.19-2.12 (1H, m), 2.01-1.97 (1H, m).

MS(ESI) $[M+H]^+$: 288.

Reference Example 10: Synthesis of methyl 4-(quinolin-2-yl)benzoate

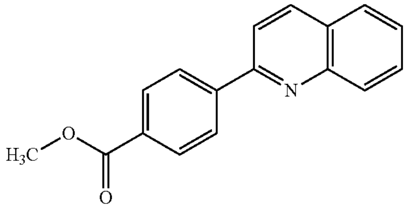 [SMILES: COC(=O)c1ccc(-c2ccc3ccccc3n2)cc1]

2-Chloroquinoline (1.50 g, 9.17 mmol) and (4-(methoxycarbonyl)phenyl)boronic acid (1.98 g, 11.0 mmol) were used in the same manner as in Reference Example 6 to obtain the title compound as a white solid (1.95 g, 7.40 mmol, yield: 81%).

$^1$H-NMR ($CDCl_3$) δ: 8.28-8.24 (3H, m), 8.21-8.18 (3H, m), 7.93 (1H, d, J=8.7 Hz), 7.86 (1H, d, J=8.2 Hz), 7.78-7.74 (1H, m), 7.59-7.55 (1H, m), 3.97 (3H, s).

MS(ESI) $[M+H]^+$: 264.

Example 17: Synthesis of methyl 4-(1,2,3,4-tetrahydroquinolin-2-yl)benzoate

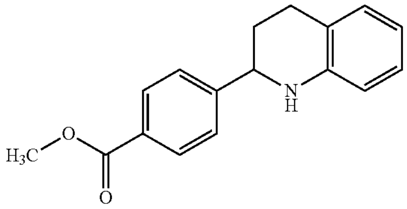 [SMILES: COC(=O)c1ccc(C2CCc3ccccc3N2)cc1]

The methyl 4-(quinolin-2-yl)benzoate synthesized in Reference Example 10 (600 mg, 2.28 mmol) was used in the same manner as in Example 4 to obtain the title compound (hereinafter referred to as the compound of Example 17) as a colorless clear oily substance (267 mg, 0.998 mmol, yield: 44%).

$^1$H-NMR ($CDCl_3$) δ: 8.02 (2H, dt, J=8.2, 1.8 Hz), 7.46 (2H, dt, J=8.2, 1.8 Hz), 7.05-6.99 (2H, m), 6.67 (1H, td, J=7.3, 0.9 Hz), 6.57 (1H, dd, J=7.8, 0.9 Hz), 4.52 (1H, dd, J=9.1, 3.2 Hz), 4.07 (1H, brs), 3.92 (3H, s), 2.95-2.87 (1H, m), 2.71 (1H, td, J=10.7, 5.5 Hz), 2.16-2.12 (1H, m), 2.03-1.94 (1H, m).

MS(ESI) $[M+H]^+$: 268.

Example 18: Synthesis of 2-(4-(1,2,3,4-tetrahydroquinolin-2-yl)phenyl)propan-2-ol (a Novel Compound)

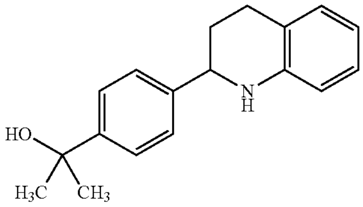 [SMILES: CC(C)(O)c1ccc(C2CCc3ccccc3N2)cc1]

The methyl 4-(1,2,3,4-tetrahydroquinolin-2-yl)benzoate synthesized in Example 17 (50.0 mg, 0.187 mmol) was dissolved in THE (1.9 mL), and a THE solution of methyl lithium (0.56 mL, 0.65 mmol) was then added dropwise to the resulting solution under ice cooling, and the resulting mixture was stirred for 2 hours under ice cooling. After the reaction was completed, water was added to the reaction mixture, and the reaction mixture was extracted with ethyl acetate. The organic layer was dried over anhydrous sodium sulfate and then concentrated under reduced pressure. The obtained crude product was purified by column chromatography (silica gel, hexane/ethyl acetate) to obtain the title compound (hereinafter referred to as the compound of Example 18) as a colorless clear oily substance (13.1 mg, 0.0490 mmol, yield: 26%).

$^1$H-NMR ($CDCl_3$) δ: 7.48 (2H, d, J=8.2 Hz), 7.37 (2H, d, J=8.2 Hz), 7.02-7.00 (2H, m), 6.65 (1H, t, J=7.5 Hz), 6.54 (1H, d, J=7.7 Hz), 4.44 (1H, dd, J=9.5, 3.2 Hz), 4.02 (1H, brs), 2.97-2.89 (1H, m), 2.74 (1H, dt, J=16.3, 4.5 Hz), 2.14-2.10 (1H, m), 2.02-1.96 (1H, m), 1.73 (1H, s), 1.59 (6H, s).

MS(ESI) $[M+H]^+$: 268.

Reference Example 11: Synthesis of 3-(quinolin-2-yl)benzenesulfonamide

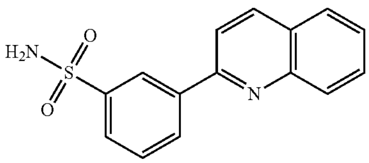 [SMILES: NS(=O)(=O)c1cccc(-c2ccc3ccccc3n2)c1]

2-Chloroquinoline (100 mg, 0.611 mmol), (3-sulfamoylphenyl)boronic acid (184 mg, 0.917 mmol), tetrakis (triphenylphosphine)palladium(0) (21.2 mg, 0.0183 mmol), and potassium carbonate (169 mg, 1.22 mmol) were dissolved in DMF/water (5/1, v/v, 3 mL), and the resulting solution was then stirred with heating at 100° C. for 17 hours. After the reaction mixture was cooled down to room temperature, water was poured into the reaction mixture, and the resulting mixture was extracted with ethyl acetate. The organic layer was washed with water and saturated brine, dried over anhydrous sodium sulfate, and then concentrated under reduced pressure. The obtained crude product was purified by column chromatography (silica gel, hexane/ethyl acetate) to obtain the title compound as a white solid (135 mg, 0.474 mmol, yield: 78%).

$^1$H-NMR ($CDCl_3$) δ: 8.78 (1H, t, J=1.6 Hz), 8.41 (1H, d, J=7.8 Hz), 8.29 (1H, d, J=8.5 Hz), 8.18 (1H, d, J=7.8 Hz), 8.03 (1H, d, J=7.8 Hz), 7.92 (1H, d, J=8.5 Hz), 7.87 (1H, d, J=7.8 Hz), 7.77 (1H, t, J=7.8 Hz), 7.70 (1H, t, J=7.8 Hz), 7.58 (1H, t, J=7.8 Hz), 4.87 (2H, brs).

MS(ESI) $[M+H]^+$: 285.

Example 19: Synthesis of 3-(1,2,3,4-tetrahydroquinolin-2-yl)benzenesulfonamide (a Novel Compound)

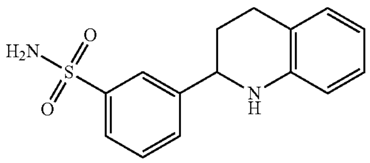 [SMILES: NS(=O)(=O)c1cccc(C2CCc3ccccc3N2)c1]

The 3-(quinolin-2-yl)benzenesulfonamide synthesized in Reference Example 11 (131 mg, 0.461 mmol) was used in the same manner as in Example 4 to obtain the title compound (hereinafter referred to as the compound of Example 19) as a colorless clear oily substance (118 mg, 0.409 mmol, yield: 89%).

$^1$H-NMR ($CDCl_3$) δ: 7.98 (1H, s), 7.85 (1H, d, J=7.8 Hz), 7.63 (1H, d, J=7.8 Hz), 7.51 (1H, t, J=7.8 Hz), 7.04-7.01 (2H, m), 6.69 (1H, t, J=7.1 Hz), 6.58 (1H, d, J=7.8 Hz), 4.80 (2H, brs), 4.54 (1H, dd, J=9.1, 3.2 Hz), 2.97-2.89 (1H, m), 2.74-2.69 (1H, m), 2.16-2.12 (1H, m), 2.02-1.97 (1H, m).

MS(ESI) $[M+H]^+$: 289.

Reference Example 12: Synthesis of 2-(quinolin-2-yl)benzenesulfonamide

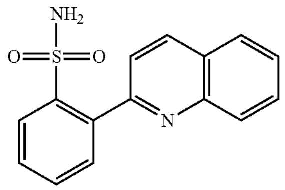 [SMILES: NS(=O)(=O)c1ccccc1-c1ccc2ccccc2n1]

2-Chloroquinoline (100 mg, 0.611 mmol) and (2-sulfamoylphenyl)boronic acid (184 mg, 0.917 mmol) were used in the same manner as in Reference Example 11 to obtain the title compound as a white solid (153 mg, 0.540 mmol, yield: 88%).

$^1$H-NMR (DMSO-$d_6$) δ: 8.54 (1H, d, J=8.7 Hz), 8.10-8.06 (3H, m), 7.86-7.67 (6H, m), 7.61 (2H, brs).

MS(ESI) $[M+H]^+$: 285.

Example 20: Synthesis of 2-(1,2,3,4-tetrahydroquinolin-2-yl)benzenesulfonamide (a Novel Compound)

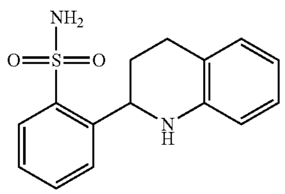 [SMILES: NS(=O)(=O)c1ccccc1C1CCc2ccccc2N1]

The 2-(quinolin-2-yl)benzenesulfonamide synthesized in Reference Example 12 (150 mg, 0.528 mmol) was used in the same manner as in Example 4 to obtain the title compound (hereinafter referred to as the compound of Example 20) as a white solid (28.8 mg, 0.0999 mmol, yield: 19%).

$^1$H-NMR ($CDCl_3$) δ: 8.06 (1H, d, J=7.8 Hz), 7.83 (1H, d, J=7.4 Hz), 7.60 (1H, t, J=7.8 Hz), 7.41 (1H, t, J=7.4 Hz), 7.05-7.01 (2H, m), 6.71 (1H, t, J=7.4 Hz), 6.56 (1H, d, J=7.8 Hz), 5.25 (1H, dd, J=9.6, 2.3 Hz), 4.96 (2H, brs), 4.00 (1H, brs), 3.04-2.96 (1H, m), 2.82-2.78 (1H, m), 2.32-2.29 (1H, m), 2.05-1.95 (1H, m).

MS(ESI) $[M+H]^+$: 289.

Reference Example 13: Synthesis of N-(4-(quinolin-2-yl)phenyl)acetamide

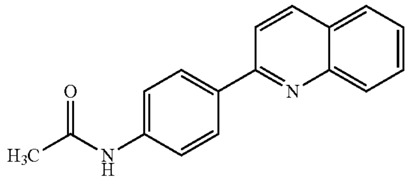 [SMILES: CC(=O)Nc1ccc(-c2ccc3ccccc3n2)cc1]

2-Chloroquinoline (100 mg, 0.611 mmol), potassium carbonate (211 mg, 1.53 mmol), palladium(II) acetate (13.7 mg, 61.1 μmol), tri-tert-butylphosphonium tetrafluoroborate (17.7 mg, 61.1 μmol), and 4-acetoxyphenylboronic acid (164 mg, 0.917 mmol) were suspended in acetonitrile/water (2.3 mL/0.70 mL), and the resulting suspension was stirred at 100° C. for 1 hour under microwave irradiation. After the reaction was completed, water was added to the reaction mixture, and the resulting mixture was extracted with chloroform. The organic layers were combined and dried over anhydrous sodium sulfate, and the filtrate was then concentrated under reduced pressure. The obtained crude product was purified by column chromatography (silica gel, hexane/ethyl acetate) to obtain the title compound as a white solid (48.8 mg, 0.186 mmol, yield: 30%).

$^1$H-NMR ($CDCl_3$) δ: 8.21 (1H, d, J=8.6 Hz), 8.17-8.13 (3H, m), 7.86 (1H, d, J=8.8 Hz), 7.82 (1H, d, J=8.2 Hz), 7.74-7.67 (3H, m), 7.54-7.50 (1H, m), 7.39 (1H, brs), 2.22 (3H, s).

MS(ESI) $[M+H]^+$: 263.

Example 21: Synthesis of N-(4-(1,2,3,4-tetrahydroquinolin-2-yl)phenyl)acetamide

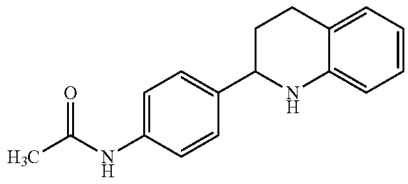 [SMILES: CC(=O)Nc1ccc(C2CCc3ccccc3N2)cc1]

The N-(4-(quinolin-2-yl)phenyl)acetamide synthesized in Reference Example 13 (40.0 mg, 0.152 mmol) was used in the same manner as in Example 4 to obtain the title compound (hereinafter referred to as the compound of Example 21) as a white amorphous (6.60 mg, 24.8 μmol, yield: 16%).

$^1$H-NMR ($CDCl_3$) δ: 7.46 (2H, d, J=8.6 Hz), 7.34 (2H, d, J=8.6 Hz), 7.15 (1H, brs), 7.03-6.99 (2H, m), 6.65 (1H, dd, J=6.8, 8.4 Hz), 6.54 (1H, d, J=7.7 Hz), 4.41 (1H, dd, J=9.5, 3.2 Hz), 4.01 (1H, brs), 2.95-2.87 (1H, m), 2.76-2.69 (1H, m), 2.19 (3H, s), 2.12-2.06 (1H, m), 2.01-1.91 (1H, m).

MS(ESI) $[M+H]^+$: 267.

Reference Example 14: Synthesis of 2-(1H-pyrazol-3-yl)quinoline

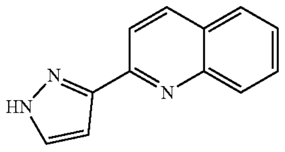 [SMILES: c1ccc2nc(-c3cc[nH]n3)ccc2c1]

2-Chloroquinoline (100 mg, 0.611 mmol) and 1H-pyrazole-3-boronic acid (164 mg, 0.917 mmol) were used in the same manner as in Reference Example 11 to obtain the title compound as a white solid (56.0 mg, 0.287 mmol, yield: 47%).

$^1$H-NMR ($CDCl_3$) δ: 8.21 (1H, d, J=8.6 Hz), 8.10 (1H, d, J=8.6 Hz), 7.86 (1H, d, J=8.6 Hz), 7.82 (1H, d, J=8.2 Hz), 7.75-7.71 (2H, m), 7.56-7.52 (1H, m), 6.96 (1H, s).

MS(ESI) $[M+H]^+$: 196.

Example 22: Synthesis of 2-(1H-pyrazol-3-yl)-1,2,3,4-tetrahydroquinoline

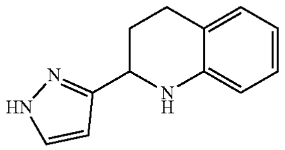 [SMILES: c1ccc2c(c1)CCC(c1cc[nH]n1)N2]

The 2-(1H-pyrazol-3-yl)quinoline synthesized in Reference Example 14 (56.0 mg, 0.287 mmol) was used in the same manner as in Example 4 to obtain the title compound (hereinafter referred to as the compound of Example 22) as a white amorphous (33.7 mg, 0.169 mmol, yield: 59%).

$^1$H-NMR ($CDCl_3$) δ: 7.52 (1H, s), 7.02-6.98 (2H, m), 6.67 (1H, ddd, J=7.6, 7.6, 1.2 Hz), 6.56 (1H, d, J=7.7 Hz), 6.27 (1H, s), 4.64 (1H, dd, J=9.1, 3.6 Hz), 4.23 (1H, brs), 2.96-2.86 (1H, m), 2.80-2.72 (1H, m), 2.24-2.17 (1H, m), 2.12-2.02 (1H, m).

MS(ESI) $[M+H]^+$: 200.

Reference Example 15: Synthesis of 3',4'-dihydro-[2,6'-biquinolin]-2'(1'H)-one

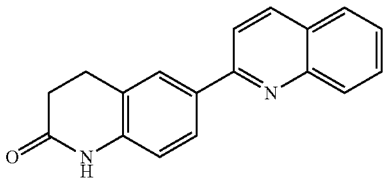 [SMILES: O=C1CCc2cc(-c3ccc4ccccc4n3)ccc2N1]

2-Chloroquinoline (100 mg, 0.611 mmol) and 6-(4,4,5,5-tetramethyl-1,3,2-dioxaborolan-2-yl)-3,4-dihydroquinolin-2(1H)-one (250 mg, 0.917 mmol) were used in the same manner as in Reference Example 11 to obtain the title compound as a white solid (118 mg, 0.431 mmol, yield: 71%).

$^1$H-NMR (DMSO-$d_6$) δ: 10.31 (1H, s), 8.41 (1H, d, J=8.6 Hz), 8.15 (1H, s), 8.12-8.08 (2H, m), 8.03 (1H, d, J=8.2 Hz), 7.97 (1H, d, J=7.2 Hz), 7.78-7.74 (1H, m), 7.59-7.55 (1H, m), 7.01 (1H, d, J=8.2 Hz), 3.02 (2H, t, J=7.5 Hz), 2.55-2.51 (2H, m).

MS(ESI) $[M+H]^+$: 275.

Example 23: Synthesis of 1,2,3,3',4,4'-hexahydro-[2,6'-biquinolin]-2'(1'H)-one (a Novel Compound)

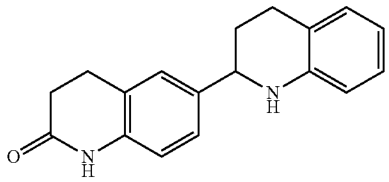 [SMILES: O=C1CCc2cc(C3CCc4ccccc4N3)ccc2N1]

The 3',4'-dihydro-[2,6'-biquinolin]-2'(1'H)-one synthesized in Reference Example 15 (118 mg, 0.431 mmol) was used in the same manner as in Example 4 to obtain the title compound (hereinafter referred to as the compound of Example 23) as a white solid (80.6 mg, 0.290 mmol, yield: 67%).

$^1$H-NMR ($CDCl_3$) δ: 8.30 (1H, brs), 7.21-7.18 (2H, m), 7.03-6.99 (2H, m), 6.77-6.74 (1H, m), 6.66 (1H, ddd, J=7.6, 7.2, 1.2 Hz), 6.54 (1H, d, J=7.2 Hz), 4.38 (1H, dd, J=9.5, 3.2 Hz), 3.99 (1H, brs), 2.99-2.89 (3H, m), 2.77-2.71 (1H, m), 2.66-2.62 (2H, m), 2.12-2.05 (1H, m), 2.01-1.91 (1H, m).

MS(ESI) $[M+H]^+$: 279.

Reference Example 16: Synthesis of 1'-methyl-3',4'-dihydro-[2,6'-biquinolin]-2'(1'H)-one

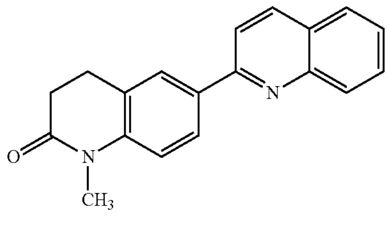 [SMILES: CN1C(=O)CCc2cc(-c3ccc4ccccc4n3)ccc21]

2-Chloroquinoline (100 mg, 0.611 mmol), 1-methyl-6-(4,4,5,5-tetramethyl-1,3,2-dioxaborolan-2-yl)-3,4-dihydroquinolin-2(1H)-one (263 mg, 0.917 mmol), and DMF/water (2.4 mL/0.60 mL) were used in the same manner as in Reference Example 11 to obtain the title compound as a white solid (171 mg, 0.593 mmol, yield: 97%).

$^1$H-NMR ($CDCl_3$) δ: 8.22 (1H, d, J=8.6 Hz), 8.15 (1H, d, J=8.6 Hz), 8.08-8.07 (1H, m), 8.03 (1H, dd, J=8.6, 2.3 Hz), 7.88-7.82 (2H, m), 7.76-7.71 (1H, m), 7.55-7.51 (1H, m), 7.13 (1H, d, J=8.6 Hz), 3.43 (3H, s), 3.06 (2H, t, J=7.5 Hz), 2.74-2.71 (2H, m).

MS(ESI) $[M+H]^+$: 289.

Example 24: Synthesis of 1'-methyl-1,2,3,3',4,4'-hexahydro-[2,6'-biquinolin]-2'(1'H)-one (a Novel Compound)

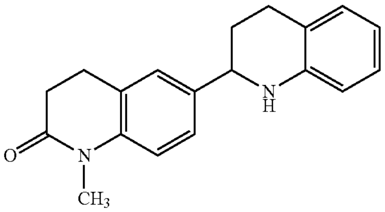 [SMILES: CN1C(=O)CCc2cc(C3CCc4ccccc4N3)ccc21]

The 1'-methyl-3',4'-dihydro-[2,6'-biquinolin]-2'(1'H)-one synthesized in Reference Example 16 (171 mg, 0.593 mmol) was used in the same manner as in Example 4 to obtain the title compound (hereinafter referred to as the compound of Example 24) as a white solid (54.3 mg, 0.186 mmol, yield: 31%).

$^1$H-NMR ($CDCl_3$) δ: 7.28-7.25 (1H, m), 7.21 (1H, s), 7.03-7.00 (2H, m), 6.95 (1H, d, J=8.6 Hz), 6.68-6.64 (1H, m), 6.55 (1H, d, J=7.2 Hz), 4.40 (1H, dd, J=9.5, 3.2 Hz), 4.00 (1H, brs), 3.36 (3H, s), 3.00-2.88 (3H, m), 2.78-2.71 (1H, m), 2.67-2.63 (2H, m), 2.13-2.06 (1H, m), 2.02-1.93 (1H, m).

MS(ESI) $[M+H]^+$: 293.

Reference Example 17: Synthesis of 5-(quinolin-2-yl)isoindolin-1-one

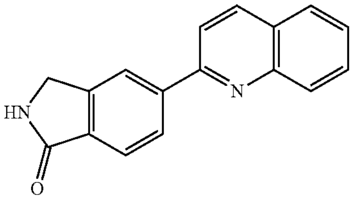 [SMILES: O=C1NCc2cc(-c3ccc4ccccc4n3)ccc21]

2-Chloroquinoline (100 mg, 0.611 mmol) and 5-(4,4,5,5-tetramethyl-1,3,2-dioxaborolan-2-yl)isoindolin-1-one (104 mg, 0.917 mmol) were used in the same manner as in Reference Example 11 to obtain the title compound as a gray solid (61.6 mg, 0.237 mmol, yield: 39%).

$^1$H-NMR (DMSO-$d_6$) δ: 8.69 (1H, brs), 8.54-8.49 (2H, m), 8.40 (1H, d, J=8.2 Hz), 8.24 (1H, d, J=8.6 Hz), 8.11 (1H, d, J=8.6 Hz), 8.04 (1H, d, J=7.2 Hz), 7.85-7.80 (2H, m), 7.66-7.62 (1H, m), 4.51 (2H, s).

MS(ESI) $[M+H]^+$: 261.

Example 25: Synthesis of 5-(1,2,3,4-tetrahydroquinolin-2-yl)isoindolin-1-one (a Novel Compound)

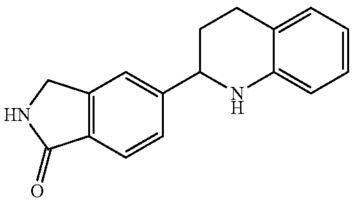 [SMILES: O=C1NCc2cc(C3CCc4ccccc4N3)ccc21]

The 5-(quinolin-2-yl)isoindolin-1-one synthesized in Reference Example 17 (61.6 mg, 0.237 mmol) was used in the same manner as in Example 4 to obtain the title compound (hereinafter referred to as the compound of Example 25) as a white solid (35.7 mg, 0.135 mmol, yield: 57%).

$^1$H-NMR ($CDCl_3$) δ: 7.85 (1H, d, J=7.7 Hz), 7.53 (1H, s), 7.49 (1H, d, J=7.7 Hz), 7.06-7.00 (2H, m), 6.70-6.67 (1H, m), 6.58 (1H, d, J=7.7 Hz), 6.15 (1H, brs), 4.58 (1H, d, J=9.1 Hz), 4.44 (2H, s), 4.10 (1H, brs), 2.95-2.88 (1H, m), 2.75-2.68 (1H, m), 2.18-2.14 (1H, m), 2.06-1.99 (1H, m).

MS(ESI) $[M+H]^+$: 265.

Reference Example 18: Synthesis of 2-(4-fluorophenyl)quinoline

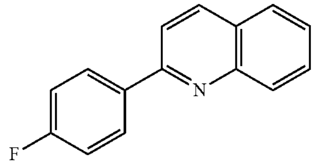 [SMILES: Fc1ccc(-c2ccc3ccccc3n2)cc1]

2-Chloroquinoline (50.0 mg, 0.306 mmol) and (4-fluorophenyl)boronic acid (64.1 mg, 0.458 mmol) were used in the same manner as in Reference Example 6 to obtain the title compound as a white solid (65.3 mg, 0.293 mmol, yield: 96%).

$^1$H-NMR ($CDCl_3$) δ: 8.23 (1H, d, J=8.7 Hz), 8.19-8.14 (3H, m), 7.85-7.82 (2H, m), 7.74 (1H, t, J=7.1 Hz), 7.54 (1H, t, J=7.1 Hz), 7.24-7.19 (2H, m).

MS(ESI) $[M+H]^+$: 224.

Example 26: Synthesis of 2-(4-fluorophenyl)-1,2,3,4-tetrahydroquinoline

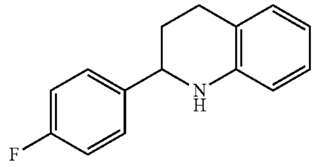 [SMILES: Fc1ccc(C2CCc3ccccc3N2)cc1]

The 2-(4-fluorophenyl)quinoline synthesized in Reference Example 18 (62.0 mg, 0.278 mmol) was dissolved in dichloromethane (2.8 mL), and diethyl 1,4-dihydro-2,6-dimethyl-3,5-pyridinedicarboxylate (148 mg, 0.583 mmol) and iodine (7.0 mg, 0.028 mmol) were then added to the resulting solution, and the resulting mixture was stirred at room temperature for 3 hours. After the reaction was completed, the reaction mixture was concentrated under reduced pressure. The obtained crude product was purified by column chromatography (silica gel, hexane/ethyl acetate) to obtain the title compound (hereinafter referred to as the compound of Example 26) as a colorless clear oily substance (60.2 mg, 0.264 mmol, yield: 95%).

$^1$H-NMR ($CDCl_3$) δ: 7.37-7.33 (2H, m), 7.05-6.99 (4H, m), 6.66 (1H, t, J=7.3 Hz), 6.54 (1H, d, J=7.8 Hz), 4.42 (1H, dd, J=9.4, 3.0 Hz), 4.00 (1H, brs), 2.96-2.88 (1H, m), 2.76-2.69 (1H, m), 2.12-2.06 (1H, m), 2.00-1.90 (1H, m).

MS(ESI) $[M+H]^+$: 228.

Reference Example 19: Synthesis of 2-(3-fluorophenyl)quinoline

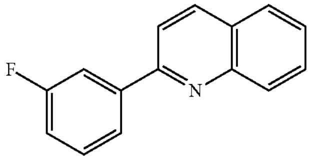 [SMILES: Fc1cccc(-c2ccc3ccccc3n2)c1]

2-Chloroquinoline (50.0 mg, 0.306 mmol) and (3-fluorophenyl)boronic acid (64.1 mg, 0.458 mmol) were used in the same manner as in Reference Example 6 to obtain the title compound as a white solid (68.5 mg, 0.307 mmol, yield: quant.).

$^1$H-NMR ($CDCl_3$) δ: 8.25 (1H, d, J=8.2 Hz), 8.17 (1H, d, J=8.2 Hz), 7.94-7.92 (2H, m), 7.87-7.85 (2H, m), 7.75 (1H, td, J=7.5, 1.4 Hz), 7.56 (1H, td, J=7.5, 1.4 Hz), 7.52-7.47 (1H, m), 7.19-7.14 (1H, m).

MS(ESI) $[M+H]^+$: 224.

Example 27: Synthesis of 2-(3-fluorophenyl)-1,2,3,4-tetrahydroquinoline

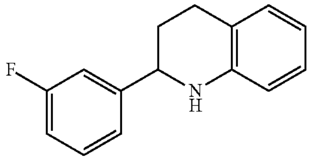 [SMILES: Fc1cccc(C2CCc3ccccc3N2)c1]

The 2-(3-fluorophenyl)quinoline synthesized in Reference Example 19 (65.0 mg, 0.291 mmol) was used in the same manner as in Example 26 to obtain the title compound (hereinafter referred to as the compound of Example 27) as a colorless clear oily substance (66.3 mg, 0.291 mmol, yield: 99%).

$^1$H-NMR ($CDCl_3$) δ: 7.32-7.28 (1H, m), 7.16-7.09 (2H, m), 7.03-6.95 (3H, m), 6.66 (1H, t, J=7.3 Hz), 6.55 (1H, d, J=7.8 Hz), 4.44 (1H, dd, J=9.1, 2.7 Hz), 4.04 (1H, brs), 2.94-2.86 (1H, m), 2.74-2.68 (1H, m), 2.15-2.08 (1H, m), 2.01-1.92 (1H, m).

MS(ESI) $[M+H]^+$: 228.

Reference Example 20: Synthesis of 2-(2-fluorophenyl)quinoline

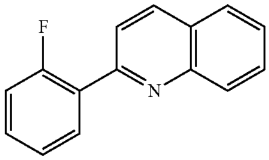 [SMILES: Fc1ccccc1-c1ccc2ccccc2n1]

2-Chloroquinoline (50.0 mg, 0.306 mmol) and (2-fluorophenyl)boronic acid (64.1 mg, 0.458 mmol) were used in the same manner as in Reference Example 6 to obtain the title compound as a white solid (69.9 mg, 0.309 mmol, yield: quant.).

$^1$H-NMR ($CDCl_3$) δ: 8.23 (1H, d, J=8.7 Hz), 8.18 (1H, d, J=8.2 Hz), 8.10 (1H, td, J=7.8, 1.8 Hz), 7.91-7.85 (2H, m), 7.75 (1H, td, J=7.8, 1.8 Hz), 7.57 (1H, t, J=7.3 Hz), 7.46-7.42 (1H, m), 7.33 (1H, t, J=7.3 Hz), 7.21 (1H, dd, J=10.5, 8.7 Hz).

MS(ESI) $[M+H]^+$: 224.

Example 28: Synthesis of 2-(2-fluorophenyl)-1,2,3,4-tetrahydroquinoline

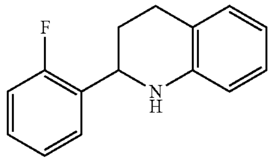 [SMILES: Fc1ccccc1C1CCc2ccccc2N1]

The 2-(3-fluorophenyl)quinoline synthesized in Reference Example 20 (65.0 mg, 0.291 mmol) was used in the same manner as in Example 26 to obtain the title compound (hereinafter referred to as the compound of Example 28) as a colorless clear oily substance (65.2 mg, 0.287 mmol, yield: 99%).

$^1$H-NMR ($CDCl_3$) δ: 7.47 (1H, t, J=7.5 Hz), 7.27-7.22 (1H, m), 7.12 (1H, t, J=7.5 Hz), 7.07-6.99 (3H, m), 6.66 (1H, t, J=7.2 Hz), 6.57 (1H, d, J=7.7 Hz), 4.85 (1H, d, J=6.8 Hz), 4.00 (1H, brs), 2.93-2.85 (1H, m), 2.72-2.66 (1H, m), 2.20-2.13 (1H, m), 2.04-1.97 (1H, m).

MS(ESI) $[M+H]^+$: 228.

Reference Example 21: Synthesis of 2-(4-(trifluoromethyl)phenyl)quinoline

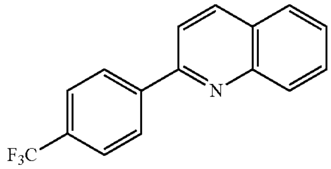 [SMILES: FC(F)(F)c1ccc(-c2ccc3ccccc3n2)cc1]

2-Chloroquinoline (50.0 mg, 0.306 mmol) and (4-(trifluoromethyl)phenyl)boronic acid (87.1 mg, 0.458 mmol) were used in the same manner as in Reference Example 6 to obtain the title compound as a white solid (80.7 mg, 0.295 mmol, yield: 97%).

$^1$H-NMR ($CDCl_3$) δ: 8.30-8.28 (3H, m), 8.19 (1H, d, J=8.2 Hz), 7.90 (1H, d, J=8.7 Hz), 7.87 (1H, d, J=8.2 Hz), 7.79-7.76 (3H, m), 7.58 (1H, t, J=8.2 Hz).

MS(ESI) $[M+H]^+$: 274.

Example 29: Synthesis of 2-(4-(trifluoromethyl)phenyl)-1,2,3,4-tetrahydroquinoline

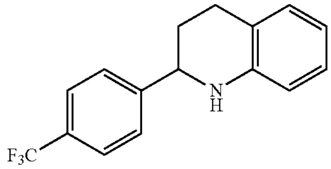 [SMILES: FC(F)(F)c1ccc(C2CCc3ccccc3N2)cc1]

The 2-(4-(trifluoromethyl)phenyl)quinoline synthesized in Reference Example 21 (80.0 mg, 0.293 mmol) was used in the same manner as in Example 26 to obtain the title compound (hereinafter referred to as the compound of Example 29) as a colorless clear oily substance (77.0 mg, 0.278 mmol, yield: 95%).

$^{1}$H-NMR ($CDCl_3$) δ: 7.60 (2H, d, J=8.2 Hz), 7.50 (2H, d, J=8.2 Hz), 7.04-7.00 (2H, m), 6.68 (1H, t, J=7.1 Hz), 6.57 (1H, d, J=7.8 Hz), 4.52 (1H, dd, J=8.7, 1.8 Hz), 4.05 (1H, brs), 2.95-2.87 (1H, m), 2.74-2.67 (1H, m), 2.17-2.10 (1H, m), 2.02-1.94 (1H, m).

MS(ESI) $[M+H]^+$: 278.

Reference Example 22: Synthesis of 2-(3-(trifluoromethyl)phenyl)quinoline

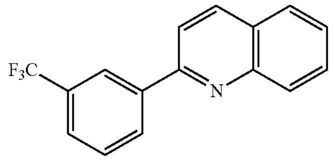 [SMILES: FC(F)(F)c1cccc(-c2ccc3ccccc3n2)c1]

2-Chloroquinoline (24.0 mg, 0.147 mmol) and (3-(trifluoromethyl)phenyl)boronic acid (30.6 mg, 0.161 mmol) were used in the same manner as in Reference Example 6 to obtain the title compound as a white solid (40.1 mg, 0.147 mmol, yield: quant.).

$^{1}$H-NMR ($CDCl_3$) δ: 8.47 (1H, brs), 8.36 (1H, d, J=7.8 Hz), 8.27 (1H, d, J=8.2 Hz), 8.19 (1H, d, J=8.7 Hz), 7.90 (1H, d, J=8.7 Hz), 7.86 (1H, d, J=8.2 Hz), 7.78-7.74 (1H, m), 7.72 (1H, d, J=7.8 Hz), 7.65 (1H, t, J=7.8 Hz), 7.59-7.55 (1H, m).

MS(ESI) $[M+H]^+$: 274.

Example 30: Synthesis of 2-(3-(trifluoromethyl)phenyl)-1,2,3,4-tetrahydroquinoline

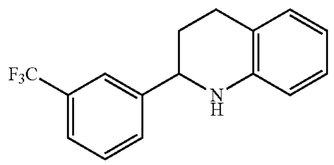 [SMILES: FC(F)(F)c1cccc(C2CCc3ccccc3N2)c1]

The 2-(3-(trifluoromethyl)phenyl)quinoline synthesized in Reference Example 22 (40.0 mg, 0.146 mmol) was used in the same manner as in Example 26 to obtain the title compound (hereinafter referred to as the compound of Example 30) as a colorless clear oily substance (39.1 mg, 0.141 mmol, yield: 96%).

$^{1}$H-NMR ($CDCl_3$) δ: 7.66 (1H, s), 7.59 (1H, d, J=7.8 Hz), 7.55 (1H, d, J=7.8 Hz), 7.46 (1H, t, J=7.5 Hz), 7.05-6.99 (2H, m), 6.68 (1H, td, J=7.4, 1.0 Hz), 6.58 (1H, dd, J=7.8, 1.0 Hz), 4.51 (1H, dd, J=9.1, 2.3 Hz), 4.04 (1H, brs), 2.98-2.90 (1H, m), 2.74 (1H, dt, J=16.5, 4.8 Hz), 2.16-2.10 (1H, m), 2.04-1.94 (1H, m).

MS(ESI) $[M+H]^+$: 278.

Reference Example 23: Synthesis of 2-(4-(trifluoromethoxy)phenyl)quinoline

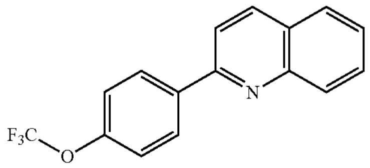 [SMILES: FC(F)(F)Oc1ccc(-c2ccc3ccccc3n2)cc1]

(4-(Trifluoromethoxy)phenyl)boronic acid (138 mg, 0.672 mmol) was used in the same manner as in Reference Example 6 to obtain the title compound as a white solid (158 mg, 0.547 mmol, yield: 90%).

$^{1}$H-NMR ($CDCl_3$) δ: 8.25 (1H, d, J=8.7 Hz), 8.22-8.20 (2H, m), 8.16 (1H, d, J=8.7 Hz), 7.86-7.84 (2H, m), 7.75 (1H, ddd, J=8.7, 6.9, 1.4 Hz), 7.56 (1H, ddd, J=7.8, 6.9, 0.9 Hz), 7.40-7.38 (2H, m).

MS(ESI) $[M+H]^+$: 290.

Example 31: Synthesis of 2-(4-(trifluoromethoxy)phenyl)-1,2,3,4-tetrahydroquinoline (a Novel Compound)

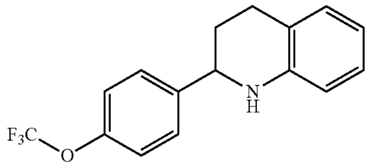 [SMILES: FC(F)(F)Oc1ccc(C2CCc3ccccc3N2)cc1]

The 2-(4-(trifluoromethoxy)phenyl)quinoline synthesized in Reference Example 23 (158 mg, 0.547 mmol) was used in the same manner as in Example 26 to obtain the title compound (hereinafter referred to as the compound of Example 31) as a pale yellow oily substance (160 mg, 0.544 mmol, yield: 99%).

$^{1}$H-NMR ($CDCl_3$) δ: 7.43-7.39 (2H, m), 7.19 (2H, d, J=8.2 Hz), 7.02-7.01 (2H, m), 6.67 (1H, ddd, J=7.8, 7.8, 1.4 Hz), 6.55 (1H, d, J=7.8 Hz), 4.46 (1H, dd, J=9.1, 3.2 Hz), 4.03 (1H, brs), 2.92 (1H, ddd, J=16.5, 10.5, 5.5 Hz), 2.72 (1H, ddd, J=16.5, 5.0, 5.0 Hz), 2.15-2.08 (1H, m), 2.01-1.92 (1H, m).

MS(ESI) $[M+H]^+$: 294.

Reference Example 24: Synthesis of 4-(quinolin-2-yl)benzenesulfonamide

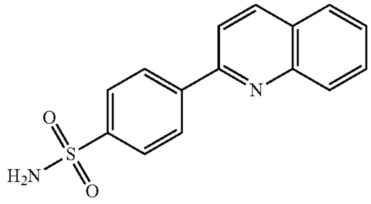 [SMILES: NS(=O)(=O)c1ccc(-c2ccc3ccccc3n2)cc1]

2-Chloroquinoline (50.0 mg, 0.306 mmol) and (4-sulfamoylphenyl)boronic acid (92.1 mg, 0.458 mmol) were used in the same manner as in Reference Example 11 to obtain the title compound as a pale yellow solid (66.1 mg, 0.232 mmol, yield: 76%).

$^1$H-NMR (DMSO-$d_6$) δ: 8.54 (1H, d, J=8.2 Hz), 8.48 (2H, d, J=8.2 Hz), 8.25 (1H, d, J=8.2 Hz), 8.12 (1H, d, J=8.2 Hz), 8.05 (1H, d, J=8.2 Hz), 8.00 (2H, d, J=8.2 Hz), 7.83 (1H, t, J=7.2 Hz), 7.65 (1H, t, J=7.2 Hz), 7.51 (2H, brs).

MS(ESI) $[M+H]^+$: 285.

Example 32: Synthesis of 4-(1,2,3,4-tetrahydroquinolin-2-yl)benzenesulfonamide (a Novel Compound)

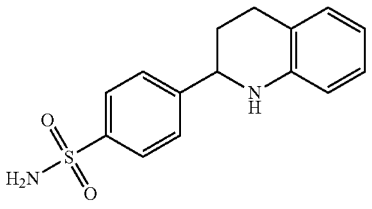

The 4-(quinolin-2-yl)benzenesulfonamide synthesized in Reference Example 24 (70.0 mg, 0.246 mmol) was used in the same manner as in Example 26 to obtain the title compound (hereinafter referred to as the compound of Example 32) as a white solid (36.1 mg, 0.125 mmol, yield: 51%).

$^1$H-NMR ($CDCl_3$) δ: 7.91 (2H, d, J=8.2 Hz), 7.55 (2H, d, J=8.2 Hz), 7.06-7.00 (2H, m), 6.69 (1H, t, J=7.1 Hz), 6.59 (1H, d, J=8.2 Hz), 4.83 (2H, brs), 4.55 (1H, dd, J=8.7, 3.2 Hz), 4.08 (1H, brs), 2.92-2.87 (1H, m), 2.72-2.67 (1H, m), 2.17-2.11 (1H, m), 2.01-1.95 (1H, m).

MS(ESI) $[M+H]^+$: 289.

Example 33: Synthesis of One of the Optical Isomers of 4-(1,2,3,4-tetrahydroquinolin-2-yl)benzenesulfonamide (a Novel Compound)

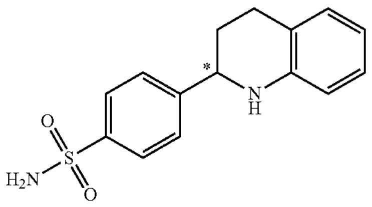 [SMILES: NS(=O)(=O)c1ccc(C2CCc3ccccc3N2)cc1]

In the formula, the carbon atom marked with an asterisk (*) is an asymmetric center.

The 4-(quinolin-2-yl)benzenesulfonamide synthesized in Reference Example 24 (50.0 mg, 0.176 mmol) and (R)-3,3'-bis(2,4,6-triisopropylphenyl)-1,1'-binaphthyl-2,2'-diyl hydrogen phosphate (2.6 mg, 0.0035 mmol) were suspended in 1,4-dioxane (1.75 mL), and diethyl 1,4-dihydro-2,6-dimethyl-3,5-pyridinedicarboxylate (106 mg, 0.422 mmol) was then added to the resulting suspension, and the resulting mixture was stirred at 60° C. for 6 hours. Diethyl 1,4-dihydro-2,6-dimethyl-3,5-pyridinedicarboxylate (106 mg, 0.422 mmol) was further added, and the resulting mixture was stirred at 60° C. for 18 hours. The reaction mixture was concentrated under reduced pressure, and the obtained crude product was purified by column chromatography (silica gel, chloroform/methanol) to obtain the title compound (hereinafter referred to as the compound of Example 33) as a pale yellow solid (22.4 mg, 0.0774 mmol, yield: 44%, enantiomeric excess: 98.1% ee).

$^1$H-NMR ($CDCl_3$) δ: 7.91 (2H, d, J=8.2 Hz), 7.55 (2H, d, J=8.2 Hz), 7.06-7.00 (2H, m), 6.69 (1H, t, J=7.1 Hz), 6.59 (1H, d, J=8.2 Hz), 4.83 (2H, brs), 4.55 (1H, dd, J=8.7, 3.2 Hz), 4.08 (1H, brs), 2.92-2.87 (1H, m), 2.72-2.67 (1H, m), 2.17-2.11 (1H, m), 2.01-1.95 (1H, m).

MS(ESI) $[M+H]^+$: 289.

Rt: 20.76 min

HPLC analysis conditions:

Column: Daicel Chiralcel OD-H chiral column (inner diameter: 4.6 mm, length: 250 mm, particle size: 5 μm)

Column temperature: 40° C.

Mobile phase: propan-2-ol:hexane=60:40

Flow rate: 0.6 mL/min

Detection: UV (254 nm)

Example 34: Synthesis of the Other of the Optical Isomers of 4-(1,2,3,4-tetrahydroquinolin-2-yl)benzenesulfonamide (a Novel Compound)

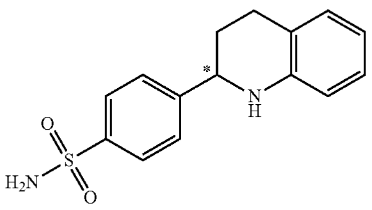 [SMILES: NS(=O)(=O)c1ccc(C2CCc3ccccc3N2)cc1]

In the formula, the carbon atom marked with an asterisk (*) is an asymmetric center.

The 4-(quinolin-2-yl)benzenesulfonamide synthesized in Reference Example 24 (50.0 mg, 0.176 mmol) and (S)-3,3'-bis(2,4,6-triisopropylphenyl)-1,1'-binaphthyl-2,2'-diyl hydrogen phosphate (2.6 mg, 0.0035 mmol) were used in the same manner as in Example 33 to obtain the title compound (hereinafter referred to as the compound of Example 34) as a white solid (37.7 mg, 0.131 mmol, yield: 74%, enantiomeric excess: 99.0% ee).

$^1$H-NMR ($CDCl_3$) δ: 7.91 (2H, d, J=8.2 Hz), 7.55 (2H, d, J=8.2 Hz), 7.06-7.00 (2H, m), 6.69 (1H, t, J=7.1 Hz), 6.59 (1H, d, J=8.2 Hz), 4.83 (2H, brs), 4.55 (1H, dd, J=8.7, 3.2 Hz), 4.08 (1H, brs), 2.92-2.87 (1H, m), 2.72-2.67 (1H, m), 2.17-2.11 (1H, m), 2.01-1.95 (1H, m).

MS(ESI) $[M+H]^+$: 289.

Rt: 17.40 min

HPLC analysis conditions:

Column: Daicel Chiralcel OD-H chiral column (inner diameter: 4.6 mm, length: 250 mm, particle size: 5 μm)

Column temperature: 40° C.

Mobile phase: propan-2-ol:hexane=60:40

Flow rate: 0.6 mL/min

Detection: UV (254 nm)

Reference Example 25: Synthesis of 4-(quinolin-2-yl)benzonitrile

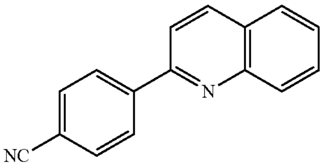 [SMILES: N#Cc1ccc(-c2ccc3ccccc3n2)cc1]

2-Chloroquinoline (150 mg, 0.917 mmol) and (4-cyanophenyl)boronic acid (269 mg, 1.83 mmol) were used in the same manner as in Reference Example 6 to obtain the title compound as a white solid (100 mg, 0.917 mmol, yield: 47%).

$^1$H-NMR ($CDCl_3$) δ: 8.32-8.29 (3H, m), 8.18 (1H, d, J=8.2 Hz), 7.92-7.86 (2H, m), 7.84-7.82 (2H, m), 7.78 (1H, t, J=7.1 Hz), 7.59 (1H, t, J=7.1 Hz).

MS(ESI) $[M+H]^+$: 231.

Example 35: Synthesis of 4-(1,2,3,4-tetrahydroquinolin-2-yl)benzonitrile

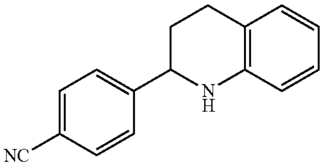 [SMILES: N#Cc1ccc(C2CCc3ccccc3N2)cc1]

The 4-(quinolin-2-yl)benzonitrile synthesized in Reference Example 25 (95.0 mg, 0.413 mmol) was used in the same manner as in Example 26 to obtain the title compound (hereinafter referred to as the compound of Example 35) as a white solid (94.9 mg, 0.405 mmol, yield: 98%).

$^1$H-NMR ($CDCl_3$) δ: 7.64 (2H, d, J=8.2 Hz), 7.50 (2H, d, J=8.2 Hz), 7.06-7.00 (2H, m), 6.69 (1H, t, J=7.3 Hz), 6.58 (1H, d, J=7.8 Hz), 4.53 (1H, d, J=7.3 Hz), 4.07 (1H, brs), 2.93-2.86 (1H, m), 2.72-2.64 (1H, m), 2.17-2.10 (1H, m), 2.00-1.93 (1H, m).

MS(ESI) $[M+H]^+$: 235.

Example 36: Synthesis of 4-(1,2,3,4-tetrahydroquinolin-2-yl)benzamide (a Novel Compound)

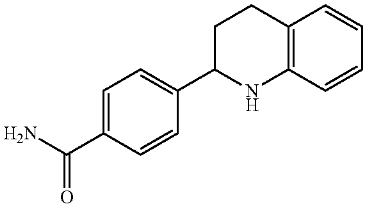 [SMILES: NC(=O)c1ccc(C2CCc3ccccc3N2)cc1]

The 4-(1,2,3,4-tetrahydroquinolin-2-yl)benzonitrile synthesized in Example 35 (32.0 mg, 0.137 mmol) was dissolved in DMSO/THF (1/4, v/v, 1.4 mL), and a 1 mol/L aqueous solution of sodium hydroxide (300 μL, 0.300 mmol) and a 30% aqueous solution of hydrogen peroxide (23 μL, 0.300 mmol) was then added to the resulting solution, and the resulting mixture was stirred at room temperature for 2 hours. A 10% aqueous solution of sodium thiosulfate was added to the reaction mixture, and the resulting mixture was extracted with ethyl acetate. The organic layer was dried over anhydrous sodium sulfate and then concentrated under reduced pressure. The obtained crude product was purified by column chromatography (silica gel, hexane/ethyl acetate) to obtain the title compound (hereinafter referred to as the compound of Example 36) as a pale yellow solid (29.9 mg, 0.119 mmol, yield: 87%).

$^1$H-NMR ($CDCl_3$) δ: 7.80 (2H, d, J=8.2 Hz), 7.48 (2H, d, J=7.8 Hz), 7.05-7.00 (2H, m), 6.68 (1H, t, J=7.1 Hz), 6.58 (1H, d, J=8.2 Hz), 6.08 (1H, brs), 5.67 (1H, brs), 4.52 (1H, dd, J=8.9, 3.4 Hz), 4.08 (1H, brs), 2.96-2.87 (1H, m), 2.72-2.68 (1H, m), 2.17-2.10 (1H, m), 2.02-1.95 (1H, m).

MS(ESI) $[M+H]^+$: 253.

Reference Example 26: Synthesis of 4-(chloroquinolin-2-yl)-benzamide

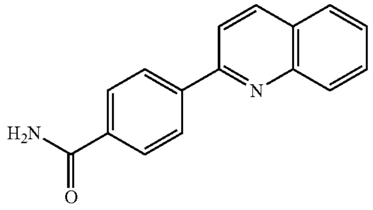 [SMILES: NC(=O)c1ccc(-c2ccc3ccccc3n2)cc1]

2-Chloroquinoline (400 mg, 2.45 mmol) and (4-carbamoylphenyl)boronic acid (605 mg, 3.67 mmol) were used in the same manner as in Reference Example 6 to obtain the title compound as a pale yellow solid (329.0 mg, 1.32 mmol, yield: 54%).

$^1$H-NMR (DMSO-$d_6$) δ: 8.51 (1H, d, J=8.6 Hz), 8.37 (2H, d, J=8.6 Hz), 8.24 (1H, d, J=8.6 Hz), 8.12-8.02 (5H, m), 7.81 (1H, t, J=7.7 Hz), 7.63 (1H, t, J=7.0 Hz), 7.48 (1H, s).

MS(ESI) $[M+H]^+$: 249.

Example 37: Synthesis of One of the Optical Isomers of 4-(1,2,3,4-tetrahydroquinolin-2-yl)benzamide (a Novel Compound)

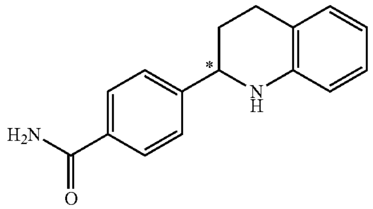 [SMILES: NC(=O)c1ccc(C2CCc3ccccc3N2)cc1]

In the formula, the carbon atom marked with an asterisk (*) is an asymmetric center.

The 4-(quinolin-2-yl)benzamide synthesized in Reference Example 26 (50.0 mg, 0.201 mmol) and (R)-3,3'-bis(2,4,6-triisopropylphenyl)-1,1'-binaphthyl-2,2'-diyl hydrogen phosphate (3.0 mg, 0.0040 mmol) were suspended in 1,4- dioxane (2 mL), and diethyl 1,4-dihydro-2,6-dimethyl-3,5-pyridinedicarboxylate (0.122 g, 0.483 mmol) was added to the resulting suspension, and the resulting mixture was stirred at room temperature for 24 hours under argon atmosphere. After the reaction was completed, the reaction mixture was concentrated under reduced pressure. The obtained crude product was purified by column chromatography (silica gel, hexane/ethyl acetate) and recrystallization (ethyl acetate/methanol) to obtain the title compound (hereinafter referred to as the compound of Example 37) as a white solid (11.0 mg, 0.0436 mmol, yield: 22%, enantiomeric excess: 98.2% ee).

$^1$H-NMR ($CDCl_3$) δ: 7.80 (2H, d, J=8.2 Hz), 7.49 (2H, t, J=11.3 Hz), 7.02 (2H, d, J=6.9 Hz), 6.67 (1H, t, J=7.2 Hz), 6.58 (1H, d, J=7.7 Hz), 6.05 (1H, s), 5.58 (1H, s), 4.52 (1H, d, J=6.8 Hz), 4.07 (1H, s), 2.95-2.87 (1H, m), 2.71 (1H, dt, J=16.6, 5.1 Hz), 2.16-2.11 (1H, m), 2.05-1.94 (1H, m).

MS(ESI) $[M+H]^+$: 253.

Rt: 14.28 min

HPLC analysis conditions:

Column: Daicel Chiralcel OD-H chiral column (inner diameter: 4.6 mm, length: 250 mm, particle size: 5 μm)

Column temperature: 40° C.

Mobile phase: propan-2-ol:hexane=40:60

Flow rate: 0.6 mL/min

Detection: UV (254 nm)

Example 38: Synthesis of the Other of the Optical Isomers of 4-(1,2,3,4-tetrahydroquinolin-2-yl)benzamide (a Novel Compound)

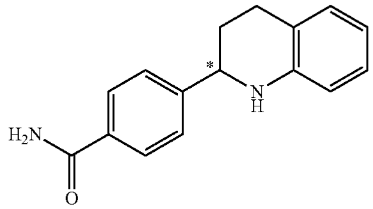 [SMILES: NC(=O)c1ccc(C2CCc3ccccc3N2)cc1]

In the formula, the carbon atom marked with an asterisk (*) is an asymmetric center.

The 4-(quinolin-2-yl)benzamide synthesized in Reference Example 26 (50.0 mg, 0.201 mmol) and (S)-3,3'-bis(2,4,6-triisopropylphenyl)-1,1'-binaphthyl-2,2'-diyl hydrogen phosphate (3.0 mg, 0.0040 mmol) were used in the same manner as in Example 37 to obtain the title compound (hereinafter referred to as the compound of Example 38) as a white solid (13.7 mg, 0.0543 mmol, yield: 46%, enantiomeric excess: 97.6% ee).

$^1$H-NMR ($CDCl_3$) δ: 7.80 (2H, d, J=8.2 Hz), 7.49 (2H, t, J=11.3 Hz), 7.02 (2H, d, J=6.9 Hz), 6.67 (1H, t, J=7.2 Hz), 6.58 (1H, d, J=7.7 Hz), 6.05 (1H, s), 5.58 (1H, s), 4.52 (1H, d, J=6.8 Hz), 4.07 (1H, s), 2.95-2.87 (1H, m), 2.71 (1H, dt, J=16.6, 5.1 Hz), 2.16-2.11 (1H, m), 2.05-1.94 (1H, m).

MS(ESI) $[M+H]^+$: 253.

Rt: 24.14 min

HPLC analysis conditions:

Column: Daicel Chiralcel OD-H chiral column (inner diameter: 4.6 mm, length: 250 mm, particle size: 5 μm)

Column temperature: 40° C.

Mobile phase: propan-2-ol:hexane=40:60

Flow rate: 0.6 mL/min

Detection: UV (254 nm)

Reference Example 27: Synthesis of 4-(1,2,3,4-tetrahydroquinolin-2-yl)benzoic acid

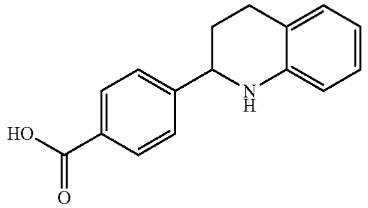 [SMILES: O=C(O)c1ccc(C2CCc3ccccc3N2)cc1]

The methyl 4-(1,2,3,4-tetrahydroquinolin-2-yl)benzoate synthesized in Example 17 (545 mg, 2.04 mmol) was dissolved in THF/methanol (5.0 mL/5.0 mL), and an 8 mol/L aqueous solution of sodium hydroxide (0.764 mL, 6.11 mmol) was added to the resulting solution, and the resulting mixture was stirred at room temperature for 20 hours under argon atmosphere. After the reaction was completed, a saturated aqueous solution of ammonium chloride was added to the reaction mixture, and the resulting mixture was concentrated under reduced pressure, followed by extraction with ethyl acetate. The obtained crude product was purified by column chromatography (silica gel, hexane/ethyl acetate) to obtain the title compound as a cream-colored solid (497 mg, 1.96 mmol, yield: 96%).

$^1$H-NMR ($CD_3OD$) δ: 7.97 (2H, d, J=8.4 Hz), 7.46 (2H, d, J=8.2 Hz), 6.94-6.89 (2H, m), 6.61-6.52 (2H, m), 4.52-4.49 (1H, m), 2.88-2.80 (1H, m), 2.65-2.58 (1H, m), 2.14-2.07 (1H, m), 2.01-1.91 (1H, m).

MS(ESI) $[M+H]^+$: 254.

Example 39: Synthesis of N,N-diethyl-4-(1,2,3,4-tetrahydroquinolin-2-yl)benzamide (a Novel Compound)

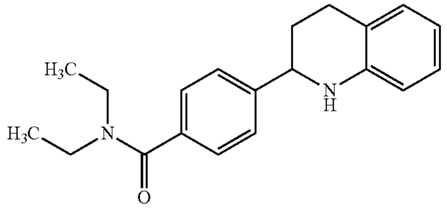 [SMILES: CCN(CC)C(=O)c1ccc(C2CCc3ccccc3N2)cc1]

The 4-(1,2,3,4-tetrahydroquinolin-2-yl)benzoic acid synthesized in Reference Example 27 (37.9 mg, 0.150 mmol), 1-[bis(dimethylamino)methylene]-1H-1,2,3-triazolo[4,5-b]pyridinium 3-oxide hexafluorophosphate (68.3 mg, 0.180 mmol), diethylamine (17.0 μL, 0.165 mmol), and N,N-diisopropylethylamine (39.1 μL, 0.224 mmol) were dissolved in DMF (1.2 mL), and the resulting mixture was stirred at room temperature for 16 hours. After the reaction was completed, water was added to the reaction mixture, and the resulting mixture was extracted with ethyl acetate. The organic layers were combined, washed with saturated brine, and dried over anhydrous sodium sulfate, and the filtrate was then concentrated under reduced pressure. The obtained crude product was purified by column chromatography (silica gel, hexane/ethyl acetate) to obtain the title compound (hereinafter referred to as the compound of Example 39) as a colorless clear oily substance (14.5 mg, 47.0 μmol, yield: 31%).

$^1$H-NMR ($CDCl_3$) δ: 7.41 (2H, d, J=8.4 Hz), 7.35 (2H, d, J=8.4 Hz), 7.04-6.99 (2H, m), 6.68-6.64 (1H, m), 6.56 (1H, d, J=8.4 Hz), 4.47 (1H, dd, J=9.1, 3.6 Hz), 4.05 (1H, brs), 3.60-3.22 (2H, m), 3.33-3.22 (2H, m), 2.95-2.87 (1H, m), 2.76-2.69 (1H, m), 2.15-2.09 (1H, m), 2.03-1.93 (1H, m), 1.28-1.08 (6H, m).

MS(ESI) $[M+H]^+$: 309.

Example 40: Synthesis of N-ethyl-4-(1,2,3,4-tetrahydroquinolin-2-yl)benzamide (a Novel Compound)

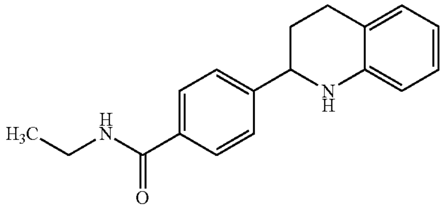 [SMILES: CCNC(=O)c1ccc(C2CCc3ccccc3N2)cc1]

The 4-(1,2,3,4-tetrahydroquinolin-2-yl)benzoic acid synthesized in Reference Example 27 (30.0 mg, 0.118 mmol), 1-[bis(dimethylamino)methylene]-1H-1,2,3-triazolo[4,5-b] pyridinium 3-oxide hexafluorophosphate (54.0 mg, 0.142 mmol), a 2 mol/L methanol solution of ethylamine (65.1 μL, 0.130 mmol), and N,N-diisopropylethylamine (30.9 μL, 0.178 mmol) were dissolved in DMF (1.2 mL), and the resulting mixture was stirred at room temperature for 16 hours. After the reaction was completed, water was added to the reaction mixture, and the resulting mixture was extracted with ethyl acetate. The organic layers were combined, washed with saturated brine, and dried over anhydrous sodium sulfate, and the filtrate was then concentrated under reduced pressure. The obtained crude product was purified by column chromatography (silica gel, hexane/ethyl acetate) to obtain the title compound (hereinafter referred to as the compound of Example 40) as a white solid (24.5 mg, 47.0 μmol, yield: 74%).

$^1$H-NMR ($CDCl_3$) δ: 7.75-7.72 (2H, m), 7.44 (2H, d, J=8.2 Hz), 7.04-6.99 (2H, m), 6.68-6.66 (1H, ddd, J=7.6, 7.6, 0.8 Hz), 6.57 (1H, dd, J=7.7, 0.9 Hz), 6.09 (1H, brs), 4.50 (1H, dd, J=9.1, 3.6 Hz), 4.06 (1H, brs), 3.54-3.47 (2H, m), 2.95-2.87 (1H, m), 2.74-2.67 (1H, m), 2.16-2.09 (1H, m), 2.02-1.93 (1H, m).

MS(ESI) $[M+H]^+$: 281.

Example 41: Synthesis of piperidin-1-yl(4-(1,2,3,4-tetrahydroquinolin-2-yl)phen-yl)methanone (a Novel Compound)

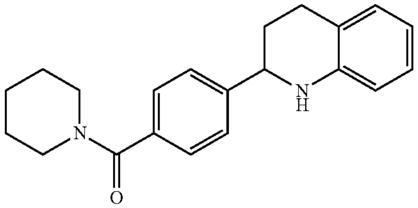 [SMILES: O=C(c1ccc(C2CCc3ccccc3N2)cc1)N1CCCCC1]

The 4-(1,2,3,4-tetrahydroquinolin-2-yl)benzoic acid synthesized in Reference Example 27 (30.0 mg, 0.118 mmol) and 1-[bis(dimethylamino)methylene]-1H-1,2,3-triazolo[4,5-b]pyridinium 3-oxide hexafluorophosphate (54.0 mg, 0.142 mmol) were dissolved in DMF (1.2 mL), and piperidine (12.9 μL, 0.130 mmol) and N,N-diisopropylethylamine (30.9 μL, 0.178 mmol) were added to the resulting solution, and the resulting mixture was stirred at room temperature for 14 hours under argon atmosphere. After the reaction was completed, water was added to the reaction mixture, and the resulting mixture was extracted with ethyl acetate. The organic layers were combined, washed with an aqueous solution of sodium bicarbonate and saturated brine, and dried over anhydrous sodium sulfate, and the filtrate was then concentrated under reduced pressure. The obtained crude product was purified by column chromatography (silica gel, hexane/ethyl acetate) to obtain the title compound (hereinafter referred to as the compound of Example 41) as a white amorphous (28.6 mg, 89.3 μmol, yield: 75%).

$^1$H-NMR ($CDCl_3$) δ: 7.42-7.36 (4H, m), 7.04-7.00 (2H, m), 6.66 (1H, ddd, J=7.6, 7.6, 1.2 Hz), 6.56 (1H, d, J=7.7 Hz), 4.47 (1H, dd, J=9.1, 3.6 Hz), 4.05 (1H, brs), 3.71 (2H, brs), 3.36 (2H, brs), 2.95-2.87 (1H, m), 2.76-2.69 (1H, m), 2.16-2.09 (1H, m), 2.03-1.93 (1H, m), 1.68 (4H, brs), 1.53 (2H, brs).

MS(ESI) $[M+H]^+$: 321.

Example 42: Synthesis of morpholino(4-(1,2,3,4-tetrahydroquinolin-2-yl)phenyl)methanone (a Novel Compound)

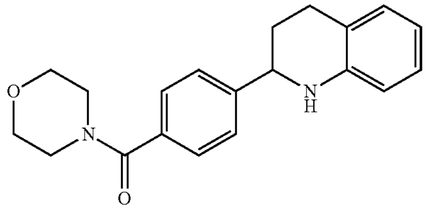 [SMILES: O=C(c1ccc(C2CCc3ccccc3N2)cc1)N1CCOCC1]

The 4-(1,2,3,4-tetrahydroquinolin-2-yl)benzoic acid synthesized in Reference Example 27 (30.0 mg, 0.118 mmol) and 1-[bis(dimethylamino)methylene]-1H-1,2,3-triazolo[4,5-b]pyridinium 3-oxide hexafluorophosphate (54.0 mg, 0.142 mmol) were dissolved in DMF (1.2 mL), and morpholine (11.2 μL, 0.130 mmol) and N,N-diisopropylethylamine (30.9 μL, 0.178 mmol) were added to the resulting solution, and the resulting mixture was stirred at room temperature for 16 hours under argon atmosphere. After the reaction was completed, water was added to the reaction mixture, and the resulting mixture was extracted with ethyl acetate. The organic layers were combined, washed with an aqueous solution of sodium bicarbonate and saturated brine, and dried over anhydrous sodium sulfate, and the filtrate was then concentrated under reduced pressure. The obtained crude product was purified by column chromatography (silica gel, hexane/ethyl acetate) to obtain the title compound (hereinafter referred to as the compound of Example 42) as a white solid (33.4 mg, 0.104 mmol, yield: 88%).

$^1$H-NMR ($CDCl_3$) δ: 7.45-7.38 (4H, m), 7.04-6.98 (2H, m), 6.69-6.64 (1H, m), 6.56 (1H, d, J=7.7 Hz), 4.48 (1H, dd, J=9.1, 3.2 Hz), 4.05 (1H, brs), 3.77-3.48 (8H, m), 2.95-2.87 (1H, m), 2.75-2.68 (1H, m), 2.21-2.09 (1H, m), 2.02-1.93 (1H, m).

MS(ESI) $[M+H]^+$: 323.

Example 43: Synthesis of (4-methylpiperazin-1-yl)(4-(1,2,3,4-tetrahydroquinolin-2-yl)phenyl)methanone (a Novel Compound)

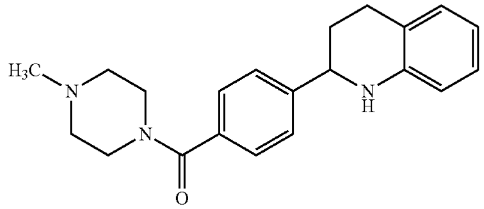 [SMILES: CN1CCN(C(=O)c2ccc(C3CCc4ccccc4N3)cc2)CC1]

The 4-(1,2,3,4-tetrahydroquinolin-2-yl)benzoic acid synthesized in Reference Example 27 (30.0 mg, 0.118 mmol) and 1-[bis(dimethylamino)methylene]-1H-1,2,3-triazolo[4,5-b]pyridinium 3-oxide hexafluorophosphate (54.0 mg, 0.142 mmol) were dissolved in DMF (1.2 mL), and 1-methylpiperazine (14.3 μL, 0.130 mmol) and N,N-diisopropylethylamine (30.9 μL, 0.178 mmol) were added to the resulting solution, and the resulting mixture was stirred at room temperature for 14 hours under argon atmosphere. After the reaction was completed, water was added to the reaction mixture, and the resulting mixture was extracted with ethyl acetate. The organic layers were combined, washed with an aqueous solution of sodium bicarbonate and saturated brine, and dried over anhydrous sodium sulfate, and the filtrate was then concentrated under reduced pressure. The obtained crude product was purified by column chromatography (silica gel, hexane/ethyl acetate) to obtain the title compound (hereinafter referred to as the compound of Example 43) as a white amorphous (32.8 mg, 97.8 μmol, yield: 83%).

$^1$H-NMR ($CDCl_3$) δ: 7.44-7.37 (4H, m), 7.04-7.00 (2H, m), 6.67 (1H, ddd, J=7.5, 1.1, 0.5 Hz), 6.56 (1H, d, J=8.4 Hz), 4.48 (1H, dd, J=8.8, 3.4 Hz), 4.04 (1H, brs), 3.80 (2H, brs), 3.46 (2H, brs), 2.96-2.87 (1H, m), 2.75-2.69 (1H, m), 2.49-2.33 (7H, m), 2.16-2.09 (1H, m), 2.03-1.93 (1H, m).

MS(ESI) [M+H]$^+$: 336.

Reference Example 28: Synthesis of N-methyl-3-(quinolin-2-yl)benzamide

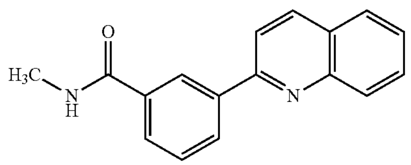 [SMILES: CNC(=O)c1cccc(-c2ccc3ccccc3n2)c1]

2-Chloroquinoline (100 mg, 0.611 mmol), (4-(methylcarbamoyl)phenyl)boronic acid (164 mg, 0.917 mmol), tetrakis(triphenylphosphine)palladium(0) (14.1 mg, 0.0122 mmol), and potassium carbonate (253 mg, 1.83 mmol) were suspended in 1,4-dioxane (2 mL), and the resulting suspension was stirred with heating at 100° C. for 15 hours. After the reaction mixture was cooled down to room temperature, water was added to the reaction mixture, and the resulting mixture was extracted with ethyl acetate. The organic layer was dried over anhydrous sodium sulfate and then concentrated under reduced pressure. The obtained crude product was purified by column chromatography (silica gel, hexane/ethyl acetate) to obtain the title compound as a colorless clear oily substance (156 mg, 0.593 mmol, yield: 97%).

$^1$H-NMR ($CDCl_3$) δ: 8.58 (1H, s), 8.29-8.25 (2H, m), 8.17 (1H, d, J=8.7 Hz), 7.94-7.84 (3H, m), 7.76 (1H, t, J=7.3 Hz), 7.62-7.54 (2H, m), 6.44 (1H, brs), 3.07 (3H, d, J=5.0 Hz).

MS(ESI) [M+H]$^+$: 263.

Example 44: Synthesis of N-methyl-3-(1,2,3,4-tetrahydroquinolin-2-yl)benzamide (a Novel Compound)

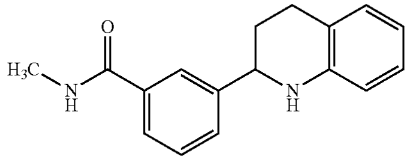 [SMILES: CNC(=O)c1cccc(C2CCc3ccccc3N2)c1]

The N-methyl-3-(quinolin-2-yl)benzamide synthesized in Reference Example 28 (155 mg, 0.591 mmol) was used in the same manner as in Example 26 to obtain the title compound (hereinafter referred to as the compound of Example 44) as a colorless clear oily substance (132 mg, 0.496 mmol, yield: 84%).

$^1$H-NMR ($CDCl_3$) δ: 7.80 (1H, s), 7.68 (1H, d, J=7.8 Hz), 7.53 (1H, d, J=7.3 Hz), 7.41 (1H, t, J=7.8 Hz), 7.04-7.00 (2H, m), 6.67 (1H, t, J=7.1 Hz), 6.57 (1H, d, J=7.8 Hz), 6.16 (1H, brs), 4.50 (1H, dd, J=9.4, 3.0 Hz), 4.06 (1H, brs), 3.02 (3H, d, J=5.0 Hz), 2.97-2.89 (1H, m), 2.75-2.71 (1H, m), 2.16-2.09 (1H, m), 2.04-1.94 (1H, m).

MS(ESI) [M+H]$^+$: 267.

Reference Example 29: Synthesis of 3-(quinolin-2-yl)benzonitrile

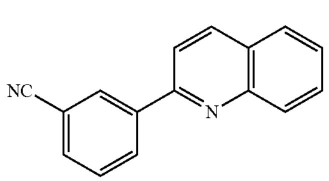 [SMILES: N#Cc1cccc(-c2ccc3ccccc3n2)c1]

2-Chloroquinoline (150 mg, 0.917 mmol) and (3-cyanophenyl)boronic acid (269 mg, 1.83 mmol) were used in the same manner as in Reference Example 6 to obtain the title compound as a white solid (211 mg, 0.917 mmol, yield: quant.).

$^1$H-NMR ($CDCl_3$) δ: 8.23 (1H, d, J=8.7 Hz), 8.19-8.14 (3H, m), 7.85-7.82 (2H, m), 7.74 (1H, t, J=7.1 Hz), 7.54 (1H, t, J=7.1 Hz), 7.24-7.19 (2H, m).

MS(ESI) [M+H]$^+$: 224.

Example 45: Synthesis of 3-(1,2,3,4-tetrahydroquinolin-2-yl)benzonitrile (a Novel Compound)

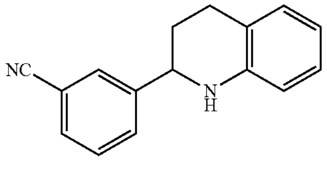 [SMILES: N#Cc1cccc(C2CCc3ccccc3N2)c1]

The 3-(quinolin-2-yl)benzonitrile synthesized in Reference Example 29 (210 mg, 0.912 mmol) was used in the same manner as in Example 4 to obtain the title compound (hereinafter referred to as the compound of Example 45) as a colorless clear oily substance (191 mg, 0.812 mmol, yield: 89%).

$^1$H-NMR ($CDCl_3$) δ: 7.70 (1H, s), 7.63 (1H, d, J=7.8 Hz), 7.58 (1H, d, J=7.8 Hz), 7.46 (1H, t, J=7.8 Hz), 7.05-7.01 (2H, m), 6.69 (1H, t, J=7.3 Hz), 6.58 (1H, d, J=7.8 Hz), 4.50 (1H, d, J=6.9 Hz), 4.05 (1H, brs), 2.95-2.87 (1H, m), 2.73-2.67 (1H, m), 2.17-2.10 (1H, m), 2.01-1.94 (1H, m).

MS(ESI) $[M+H]^+$: 235.

Example 46: Synthesis of 3-(1,2,3,4-tetrahydroquinolin-2-yl)benzamide (a Novel Compound)

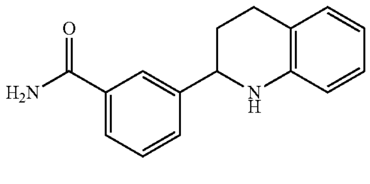 [SMILES: NC(=O)c1cccc(C2CCc3ccccc3N2)c1]

The 3-(1,2,3,4-tetrahydroquinolin-2-yl)benzonitrile synthesized in Example 45 (140 mg, 0.598 mmol) was dissolved in DMSO/THF (1/4, v/v, 6 mL), and an 8 mol/L aqueous solution of sodium hydroxide (164 μL, 1.31 mmol) and a 30% aqueous solution of hydrogen peroxide (103 μL, 1.31 mmol) were then added to the resulting solution, and the resulting mixture was stirred at room temperature for 2 hours. A 10% aqueous solution of sodium thiosulfate was added to the reaction mixture, and the resulting mixture was extracted with ethyl acetate. The organic layer was dried over anhydrous sodium sulfate and then concentrated under reduced pressure. The obtained crude product was purified by column chromatography (silica gel, hexane/ethyl acetate) to obtain the title compound (hereinafter referred to as the compound of Example 46) as a white solid (115 mg, 0.454 mmol, yield: 76%).

$^1$H-NMR ($CDCl_3$) δ: 7.86 (1H, s), 7.73 (1H, d, J=7.8 Hz), 7.57 (1H, d, J=7.8 Hz), 7.44 (1H, t, J=7.5 Hz), 7.04-6.99 (2H, m), 6.68 (1H, t, J=7.5 Hz), 6.57 (1H, d, J=7.8 Hz), 6.11 (1H, brs), 5.62 (1H, brs), 4.51 (1H, dd, J=9.4, 3.0 Hz), 4.06 (1H, brs), 2.98-2.90 (1H, m), 2.76-2.70 (1H, m), 2.16-2.10 (1H, m), 2.05-1.95 (1H, m).

MS(ESI) $[M+H]^+$: 253.

Reference Example 30: Synthesis of (2-(quinolin-2-yl)phenyl)methanol

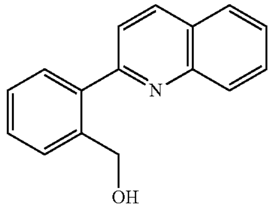 [SMILES: OCc1ccccc1-c1ccc2ccccc2n1]

2-Chloroquinoline (100 mg, 0.611 mmol) and (2-(hydroxymethyl)phenyl)boronic acid (102 mg, 0.672 mmol) were used in the same manner as in Reference Example 28 to obtain the title compound as a white solid (139 mg, 0.592 mmol, yield: 97%).

$^1$H-NMR ($CDCl_3$) δ: 8.33 (1H, d, J=8.7 Hz), 8.12 (1H, d, J=7.8 Hz), 7.89 (1H, dd, J=8.0, 1.1 Hz), 7.78-7.76 (2H, m), 7.72-7.69 (1H, m), 7.60 (1H, ddd, J=8.2, 6.9, 0.9 Hz), 7.57-7.53 (1H, m), 7.49-7.46 (2H, m), 6.81 (1H, dd, J=6.9, 6.9 Hz), 4.56 (2H, d, J=6.9 Hz).

MS(ESI) $[M+H]^+$: 236.

Example 47: Synthesis of (2-(1,2,3,4-tetrahydroquinolin-2-yl)phenyl)methanol (a Novel Compound)

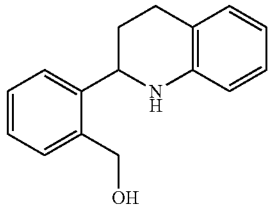 [SMILES: OCc1ccccc1C1CCc2ccccc2N1]

The (2-(quinolin-2-yl)phenyl)methanol synthesized in Reference Example 30 (139 mg, 0.592 mmol) was used in the same manner as in Example 26 to obtain the title compound (hereinafter referred to as the compound of Example 47) as a pale yellow oily substance (56.6 mg, 0.237 mmol, yield: 40%).

$^1$H-NMR ($CDCl_3$) δ: 7.57 (1H, dd, J=7.3, 1.4 Hz), 7.41-7.27 (4H, m), 7.04-7.00 (2H, m), 6.69 (1H, ddd, J=7.3, 7.3, 1.4 Hz), 6.56 (1H, d, J=8.2 Hz), 4.79 (2H, dd, J=19.7, 12.3 Hz), 4.73 (1H, dd, J=9.6, 3.2 Hz), 2.99 (1H, ddd, J=16.9, 11.4, 5.5 Hz), 2.81 (1H, ddd, J=16.5, 4.1, 4.1 Hz), 2.19-2.05 (2H, m).

MS(ESI) $[M+H]^+$: 240.

Reference Example 31: Synthesis of (3-(quinolin-2-yl)phenyl)methanol

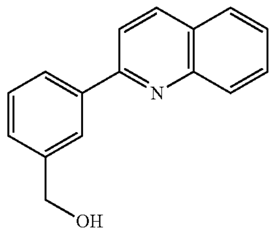 [SMILES: OCc1cccc(-c2ccc3ccccc3n2)c1]

2-Chloroquinoline (100 mg, 0.611 mmol) and (3-(hydroxymethyl)phenyl)boronic acid (102 mg, 0.672 mmol) were used in the same manner as in Reference Example 28 to obtain the title compound as a colorless amorphous (143 mg, 0.607 mmol, yield: 99%).

$^1$H-NMR ($CDCl_3$) δ: 8.24 (1H, d, J=8.7 Hz), 8.18-8.17 (2H, m), 8.06 (1H, ddd, J=7.8, 1.4, 1.4 Hz), 7.89 (1H, d, J=8.2 Hz), 7.85-7.83 (1H, m), 7.74 (1H, ddd, J=8.2, 6.9, 1.4 Hz), 7.56-7.46 (3H, m), 4.83 (2H, d, J=5.9 Hz), 1.95 (1H, dd, J=5.9, 5.9 Hz).

MS(ESI) $[M+H]^+$: 236.

Example 48: Synthesis of (3-(1,2,3,4-tetrahydroquinolin-2-yl)phenyl)methanol (a Novel Compound)

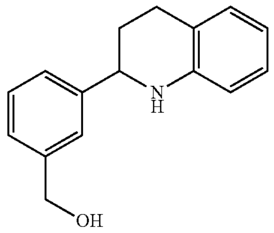 [SMILES: OCc1cccc(C2CCc3ccccc3N2)c1]

The (3-(quinolin-2-yl)phenyl)methanol synthesized in Reference Example 31 (143 mg, 0.607 mmol) was used in the same manner as in Example 26 to obtain the title compound (hereinafter referred to as the compound of Example 48) as a pale yellow oily substance (133 mg, 0.554 mmol, yield: 94%).

$^1$H-NMR ($CDCl_3$) δ: 7.37-7.33 (4H, m), 7.02-7.00 (2H, m), 6.66 (1H, dd, J=7.3, 7.3 Hz), 6.55 (1H, d, J=8.2 Hz), 4.71 (2H, d, J=4.6 Hz), 4.45 (1H, dd, J=9.1, 3.2 Hz), 4.03 (1H, brs), 2.93 (1H, ddd, J=16.5, 11.0, 5.9 Hz), 2.74 (1H, ddd, J=16.0, 4.6, 4.6 Hz), 2.14-2.10 (1H, m), 2.05-1.95 (1H, m), 1.67 (1H, t, J=5.5 Hz).

MS(ESI) $[M+H]^+$: 240.

Reference Example 32: Synthesis of (4-(quinolin-2-yl)phenyl)methanol

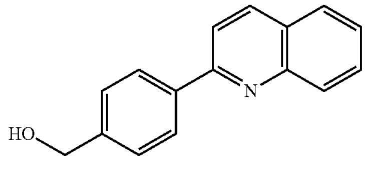 [SMILES: OCc1ccc(-c2ccc3ccccc3n2)cc1]

2-Chloroquinoline (100 mg, 0.611 mmol) and (4-(hydroxymethyl)phenyl)boronic acid (102 mg, 0.672 mmol) were used in the same manner as in Reference Example 28 to obtain the title compound as a white solid (136 mg, 0.576 mmol, yield: 94%).

$^1$H-NMR ($CDCl_3$) δ: 8.23 (1H, d, J=8.7 Hz), 8.18-8.17 (3H, m), 7.89 (1H, d, J=8.7 Hz), 7.84 (1H, dd, J=8.0, 1.1 Hz), 7.74 (1H, ddd, J=8.2, 6.9, 12.8 Hz), 7.56-7.52 (3H, m), 4.80 (2H, d, J=5.9 Hz), 1.81 (1H, t, J=5.9 Hz).

MS(ESI) $[M+H]^+$: 236.

Example 49: Synthesis of (4-(1,2,3,4-tetrahydroquinolin-2-yl)phenyl)methanol (a Novel Compound)

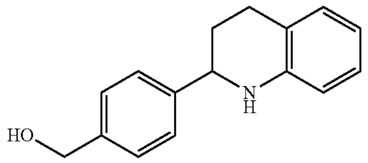 [SMILES: OCc1ccc(C2CCc3ccccc3N2)cc1]

The (4-(quinolin-2-yl)phenyl)methanol synthesized in Reference Example 32 (136 mg, 0.576 mmol) was used in the same manner as in Example 26 to obtain the title compound (hereinafter referred to as the compound of Example 49) as a pale yellow oily substance (77.3 mg, 0.323 mmol, yield: 56%).

$^1$H-NMR ($CDCl_3$) δ: 7.40 (2H, d, J=8.2 Hz), 7.36 (2H, d, J=8.2 Hz), 7.02-7.00 (2H, m), 6.66 (1H, ddd, J=7.2, 7.2, 1.4 Hz), 6.55 (1H, d, J=7.7 Hz), 4.70 (2H, d, J=5.9 Hz), 4.45 (1H, dd, J=9.3, 3.4 Hz), 4.03 (1H, brs), 2.92 (1H, ddd, J=16.3, 10.4, 5.4 Hz), 2.73 (1H, ddd, J=16.3, 4.5, 4.5 Hz), 2.15-2.08 (1H, m), 2.03-1.93 (1H, m), 1.64 (1H, t, J=5.9 Hz).

MS(ESI) $[M+H]^+$: 240.

Reference Example 33: Synthesis of 4-(quinolin-2-yl)isothiazole

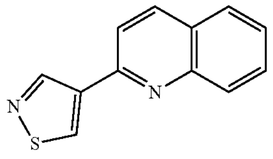 [SMILES: c1ccc2nc(-c3cnsc3)ccc2c1]

2-Chloroquinoline (100 mg, 0.611 mmol) and isothiazol-4-ylboronic acid (118 mg, 0.917 mmol) were used in the same manner as in Reference Example 6 to obtain the title compound as a yellow solid (122 mg, 0.574 mmol, yield: 94%).

$^1$H-NMR ($CDCl_3$) δ: 9.28 (1H, s), 9.25 (1H, s), 8.23 (1H, d, J=8.7 Hz), 8.13 (1H, d, J=8.2 Hz), 7.83 (1H, d, J=8.2 Hz), 7.78-7.73 (2H, m), 7.55 (1H, t, J=7.5 Hz).

MS(ESI) $[M+H]^+$: 213.

Example 50: Synthesis of 4-(1,2,3,4-tetrahydroquinolin-2-yl)isothiazole

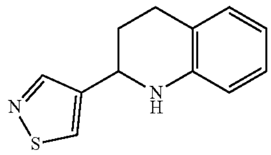 [SMILES: c1ccc2c(c1)CCC(c1cnsc1)N2]

The 4-(quinolin-2-yl)isothiazole synthesized in Reference Example 33 (110 mg, 0.518 mmol) was used in the same manner as in Example 26 to obtain the title compound (hereinafter referred to as the compound of Example 50) as a yellow oily substance (77.5 mg, 0.357 mmol, yield: 69%).

$^1$H-NMR ($CDCl_3$) δ: 8.51 (1H, s), 8.50 (1H, s), 7.04-6.99 (2H, m), 6.68 (1H, t, J=7.1 Hz), 6.55 (1H, d, J=7.8 Hz), 4.71 (1H, dd, J=8.7, 2.7 Hz), 4.09 (1H, brs), 2.95-2.87 (1H, m), 2.75-2.70 (1H, m), 2.22-2.15 (1H, m), 2.07-2.01 (1H, m).

MS(ESI) [M+H]$^+$: 217.

Reference Example 34: Synthesis of (2-phenylquinolin-5-yl)methanol

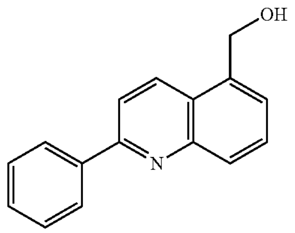 [SMILES: OCc1cccc2nc(-c3ccccc3)ccc12]

Methyl 2-phenylquinoline-5-carboxylate (60.0 mg, 0.228 mmol) was dissolved in toluene (1 mL) under argon atmosphere, and a 1.0 mol/L hexane solution of diisobutylaluminum hydride (0.912 mL, 0.912 mmol) was added at −78° C. to the resulting solution, and the resulting mixture was stirred at −78° C. for 1.5 hours. After the reaction was completed, the reaction mixture was allowed to warm to 0° C., and a saturated aqueous solution of potassium sodium tartrate was added to the reaction mixture, and the resulting mixture was stirred at room temperature for 16 hours, and the aqueous layer was extracted with ethyl acetate. The organic layers were combined, washed with saturated brine, and dried over anhydrous sodium sulfate, and the filtrate was then concentrated under reduced pressure. The obtained crude product was purified by column chromatography (silica gel, hexane/ethyl acetate) to obtain the title compound as a white solid (51.7 mg, 0.220 mmol, yield: 96%).

$^1$H-NMR ($CDCl_3$) δ: 8.59 (1H, d, J=9.1 Hz), 8.19-8.14 (3H, m), 7.94 (1H, d, J=8.7 Hz), 7.69 (1H, dd, J=8.5, 7.1 Hz), 7.57-7.52 (3H, m), 7.50-7.46 (1H, m), 5.17 (2H, d, J=5.9 Hz), 5.12 (1H, brs).

MS(ESI) [M+H]$^+$: 236.

Example 51: Synthesis of (2-phenyl-1,2,3,4-tetrahydroquinolin-5-yl)methanol (a Novel Compound)

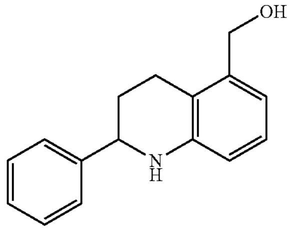 [SMILES: OCc1cccc2c1CCC(c1ccccc1)N2]

The (2-phenylquinolin-5-yl)methanol synthesized in Reference Example 34 (51.7 mg, 0.220 mmol) was used in the same manner as in Example 26 to obtain the title compound (hereinafter referred to as the compound of Example 51) as a pale yellow solid (47.2 mg, 0.197 mmol, yield: 90%).

$^1$H-NMR ($CDCl_3$) δ: 7.39-7.36 (5H, m), 7.03 (1H, dd, J=7.8, 7.8 Hz), 6.74 (1H, d, J=7.3 Hz), 6.54 (1H, d, J=7.8 Hz), 5.09 (1H, brs), 4.65 (2H, d, J=5.9 Hz), 4.42 (1H, dd, J=9.8, 3.0 Hz), 4.10 (1H, brs), 2.93-2.80 (2H, m), 2.17-2.15 (1H, m), 2.02-1.99 (1H, m).

MS(ESI) [M+H]$^+$: 240.

Example 52: Synthesis of (2-phenyl-1,2,3,4-tetrahydroquinolin-7-yl)methanol (a Novel Compound)

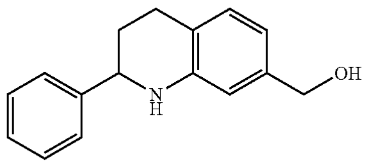 [SMILES: OCc1ccc2c(c1)NC(c1ccccc1)CC2]

(2-Phenylquinolin-7-yl)methanol (40.0 mg, 0.170 mol) was used in the same manner as in Example 26 to obtain the title compound (hereinafter referred to as the compound of Example 52) as a colorless amorphous (38.8 mg, 0.162 mmol, yield: 95%).

$^1$H-NMR ($CDCl_3$) δ: 7.41-7.28 (5H, m), 7.00-6.99 (1H, m), 6.64 (1H, d, J=7.8 Hz), 6.57 (1H, s), 4.58 (2H, d, J=5.9 Hz), 4.45 (1H, dd, J=9.1, 3.2 Hz), 4.10 (1H, brs), 2.90 (1H, ddd, J=16.0, 10.5, 5.5 Hz), 2.73 (1H, ddd, J=16.5, 5.0, 5.0 Hz), 2.16-2.09 (1H, m), 2.05-1.93 (1H, m).

MS(ESI) [M+H]$^+$: 240.

Example 53: Synthesis of 2-(pyridin-2-yl)-1,2,3,4-tetrahydroquinoline

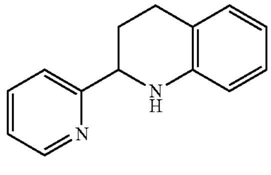

2-(Pyridin-2-yl)quinoline (30.0 mg, 0.145 mmol) was used in the same manner as in Example 26 to obtain the title compound (hereinafter referred to as the compound of Example 53) as a pale yellow amorphous (25.3 mg, 0.120 mmol, yield: 83%).

$^1$H-NMR ($CDCl_3$) δ: 8.59-8.58 (1H, m), 7.68 (1H, ddd, J=7.8, 7.8, 1.4 Hz), 7.43 (1H, d, J=8.2 Hz), 7.20 (1H, dd, J=7.5, 4.8 Hz), 7.05-6.99 (2H, m), 6.67 (1H, d, J=7.3 Hz), 6.64 (1H, d, J=7.8 Hz), 4.60 (1H, dd, J=8.5, 3.4 Hz), 4.52 (1H, brs), 2.92 (1H, ddd, J=15.6, 10.1, 5.0 Hz), 2.70 (1H, ddd, J=16.0, 4.6, 4.6 Hz), 2.31-2.24 (1H, m), 2.05-2.02 (1H, m).

MS(ESI) [M+H]$^+$: 211.

Reference Example 35: Synthesis of 2-(2-chloroquinolin-6-yl)propan-2-ol

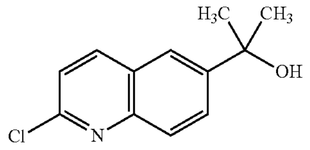

Methyl 2-chloroquinoline-6-carboxylate (100 mg, 0.451 mmol) was dissolved in THF (2 mL), and a 1 mol/L THE solution of methyl magnesium bromide (1.35 mL, 1.35 mmol) was added at −78° C. to the resulting solution under argon atmosphere, and the resulting mixture was stirred at room temperature for 3 hours. After the reaction was completed, a saturated aqueous solution of ammonium chloride was added to the reaction mixture until the reaction mixture reached a pH of 6 to 7, and the aqueous layer was extracted with ethyl acetate. The organic layers were combined, washed with saturated brine, and dried over anhydrous sodium sulfate, and the filtrate was then concentrated under reduced pressure. The obtained crude product was purified by column chromatography (silica gel, hexane/ethyl acetate) to obtain the title compound as a white solid (75.5 mg, 0.341 mmol, yield: 75%).

$^1$H-NMR ($CDCl_3$) δ: 8.11 (1H, d, J=8.7 Hz), 8.00 (1H, d, J=9.1 Hz), 7.95 (1H, d, J=2.3 Hz), 7.85 (1H, dd, J=8.9, 2.1 Hz), 7.39 (1H, d, J=8.2 Hz), 1.88 (1H, s), 1.68 (6H, s).

MS(ESI) [M+H]$^+$: 222.

Reference Example 36: Synthesis of 2-(2-phenylquinolin-6-yl)propan-2-ol

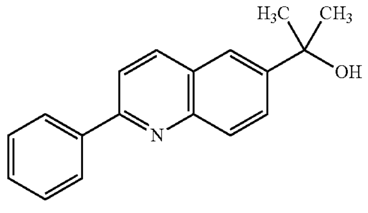 [SMILES: CC(C)(O)c1ccc2nc(-c3ccccc3)ccc2c1]

The 2-(2-chloroquinolin-6-yl)propan-2-ol synthesized in Reference Example 35 (75.5 mg, 0.341 mmol) and phenylboronic acid (45.7 mg, 0.375 mmol) were used in the same manner as in Reference Example 28 to obtain the title compound as a white solid (89.2 mg, 0.339 mmol, yield: 99%).

$^1$H-NMR ($CDCl_3$) δ: 8.22 (1H, d, J=8.6 Hz), 8.16-8.14 (3H, m), 7.94 (1H, d, J=1.8 Hz), 7.88 (1H, d, J=8.6 Hz), 7.85 (1H, dd, J=9.1, 2.3 Hz), 7.53-7.47 (3H, m), 1.90 (1H, s), 1.71 (6H, s).

MS(ESI) [M+H]$^+$: 264.

Example 54: Synthesis of 6-isopropyl-2-phenyl-1,2,3,4-tetrahydroquinoline (a Novel Compound)

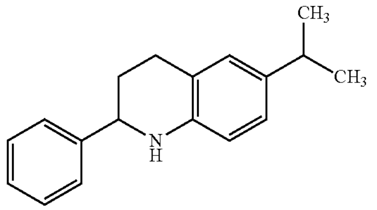 [SMILES: CC(C)c1ccc2c(c1)CCC(c1ccccc1)N2]

The 2-(2-phenylquinolin-6-yl)propan-2-ol synthesized in Reference Example 36 (40.0 mg, 0.152 mmol) was used in the same manner as in Example 4 to obtain the title compound (hereinafter referred to as the compound of Example 54) as a colorless amorphous (21.4 mg, 85.1 μmol, yield: 56%).

$^1$H-NMR ($CDCl_3$) δ: 7.40-7.33 (4H, m), 7.30-7.26 (1H, m), 6.90-6.88 (2H, m), 6.50 (1H, d, J=7.7 Hz), 4.40 (1H, dd, J=9.5, 3.2 Hz), 3.93 (1H, brs), 2.94 (1H, ddd, J=16.8, 11.3, 5.9 Hz), 2.84-2.70 (2H, m), 2.12-2.09 (1H, m), 2.01-1.97 (1H, m), 1.22 (3H, s), 1.21 (3H, s).

MS(ESI) [M+H]$^+$: 252.

Reference Example 37: Synthesis of 2-phenylquinolin-6-ol

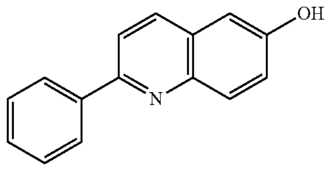 [SMILES: Oc1ccc2nc(-c3ccccc3)ccc2c1]

2-Chloroquinolin-6-ol (50.0 mg, 0.278 mmol) was used in the same manner as in Reference Example 28 to obtain the title compound as a white solid (47.0 mg, 0.212 mmol, yield: 76%).

$^1$H-NMR ($CDCl_3$) δ: 8.13-8.11 (2H, m), 8.08 (2H, dd, J=8.8, 4.3 Hz), 7.83 (1H, d, J=8.6 Hz), 7.53-7.51 (2H, m), 7.46-7.42 (1H, m), 7.33 (1H, dd, J=9.1, 2.7 Hz), 7.12 (1H, d, J=2.7 Hz), 5.32 (1H, s).

MS(ESI) [M+H]$^+$: 222.

Example 55: Synthesis of 2-phenyl-1,2,3,4-tetrahydroquinolin-6-ol

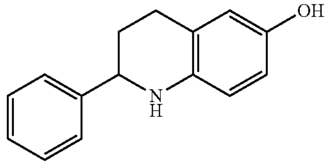 [SMILES: Oc1ccc2c(c1)CCC(c1ccccc1)N2]

The 2-phenylquinolin-6-ol synthesized in Reference Example 37 (20.0 mg, 90.4 μmol) was used in the same manner as in Example 4 to obtain the title compound (hereinafter referred to as the compound of Example 55) as a colorless amorphous (20.3 mg, 90.1 μmol, yield: >99%).

$^1$H-NMR ($CDCl_3$) δ: 7.41-7.24 (5H, m), 6.57-6.38 (3H, m), 4.36 (1H, dd, J=9.5, 2.7 Hz), 4.20 (1H, brs), 2.91 (1H, ddd, J=16.8, 10.9, 5.9 Hz), 2.70 (1H, ddd, J=16.8, 4.5, 4.5 Hz), 2.11-2.09 (1H, m), 2.00-1.96 (1H, m), 1.79 (1H, brs).

MS(ESI) $[M+H]^+$: 226.

Reference Example 38: Synthesis of methyl 2-phenylquinoline-6-carboxylate

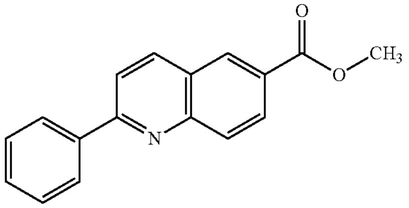 [SMILES: COC(=O)c1ccc2nc(-c3ccccc3)ccc2c1]

Methyl 2-chlorophenylquinoline-6-carboxylate (100 mg, 0.451 mmol) was used in the same manner as in Reference Example 28 to obtain the title compound as a white solid (91.0 mg, 0.346 mmol, yield: 77%).

$^1$H-NMR ($CDCl_3$) δ: 8.61 (1H, d, J=1.8 Hz), 8.33-8.31 (2H, m), 8.21-8.19 (3H, m), 7.96 (1H, d, J=8.6 Hz), 7.52-7.47 (3H, m), 4.01 (3H, s).

MS(ESI) $[M+H]^+$: 264.

Example 56: Synthesis of methyl 2-phenyl-1,2,3,4-tetrahydroquinoline-6-carboxylate (a Novel Compound)

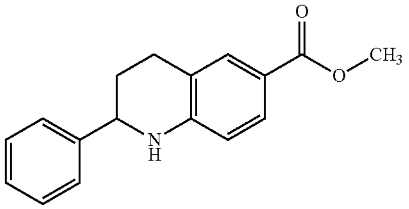 [SMILES: COC(=O)c1ccc2c(c1)CCC(c1ccccc1)N2]

The methyl 2-phenylquinoline-6-carboxylate synthesized in Reference Example 38 (120 mg, 0.456 mmol) was used in the same manner as in Example 26 to obtain the title compound (hereinafter referred to as the compound of Example 56) as a pale yellow oily substance (112 mg, 0.420 mmol, yield: 92%).

$^1$H-NMR ($CDCl_3$) δ: 7.71-7.70 (2H, m), 7.39-7.28 (5H, m), 6.50 (1H, d, J=8.6 Hz), 4.55-4.50 (2H, m), 3.85 (3H, s), 2.89 (1H, ddd, J=16.3, 10.9, 5.4 Hz), 2.75 (1H, ddd, J=16.3, 5.0, 5.0 Hz), 2.16-2.13 (1H, m), 2.02-1.93 (1H, m).

MS(ESI) $[M+H]^+$: 268.

Example 57: Synthesis of 2-(2-phenyl-1,2,3,4-tetrahydroquinolin-6-yl)propan-2-ol (a Novel Compound)

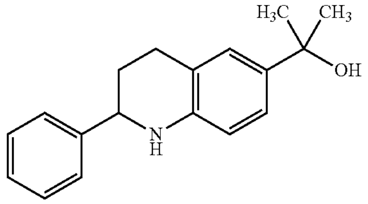 [SMILES: CC(C)(O)c1ccc2c(c1)CCC(c1ccccc1)N2]

The methyl 2-phenyl-1,2,3,4-tetrahydroquinoline-6-carboxylate synthesized in Example 56 (25.0 mg, 93.5 μmol) was dissolved in THE (1 mL), and a 1 mol/L THE solution of methyl magnesium bromide (0.374 mL, 0.374 mmol) was added at 0° C. to the resulting solution under argon atmosphere, and the resulting mixture was stirred at room temperature for 16 hours. After the reaction was completed, water was added to the reaction mixture, and the resulting mixture was extracted with ethyl acetate. The organic layers were combined, washed with saturated brine, and dried over anhydrous sodium sulfate, and the filtrate was then concentrated under reduced pressure. The obtained crude product was purified by preparative thin-layer chromatography (hexane/ethyl acetate) to obtain the title compound (hereinafter referred to as the compound of Example 57) as a pale yellow amorphous (3.70 mg, 13.8 μmol, yield: 15%).

$^1$H-NMR ($CDCl_3$) δ: 7.38-7.31 (5H, m), 7.14-7.13 (2H, m), 6.53 (1H, d, J=8.2 Hz), 4.43 (1H, dd, J=9.5, 3.2 Hz), 4.05 (1H, brs), 2.94 (1H, ddd, J=16.8, 10.9, 6.3 Hz), 2.75 (1H, ddd, J=16.8, 5.0, 5.0 Hz), 2.18-2.10 (1H, m), 2.01-1.98 (1H, m), 1.63 (1H, s), 1.57 (6H, s).

MS(ESI) $[M+H]^+$: 268.

Example 58: Synthesis of (2-phenyl-1,2,3,4-tetrahydroquinolin-6-yl)methanol (a Novel Compound)

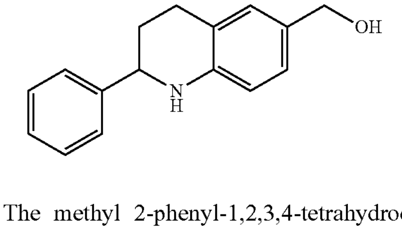

The methyl 2-phenyl-1,2,3,4-tetrahydroquinoline-6-carboxylate synthesized in Example 56 (38.0 mg, 0.142 mmol) was dissolved in toluene (2.0 mL), and a 1.01 mol/L toluene solution of diisobutylaluminum hydride (0.426 mL, 0.426 mmol) was then slowly added dropwise at −78° C. to the resulting solution under argon atmosphere. Then, the reaction mixture was allowed to warm slowly to room temperature and was stirred for 6 hours. After the reaction was completed, an aqueous solution of sodium potassium tartrate (8 mL) was added to the reaction mixture, and the resulting mixture was stirred overnight at room temperature. The aqueous layer was extracted with ethyl acetate. The organic layers were combined, washed with saturated brine, and dried over anhydrous sodium sulfate, and the filtrate was then concentrated under reduced pressure. The obtained crude product was purified by column chromatography (silica gel, hexane/ethyl acetate) to obtain the title compound (hereinafter referred to as the compound of Example 58) as a colorless clear oily substance (25.6 mg, 0.107 mmol, yield: 75%).

$^1$H-NMR ($CDCl_3$) δ: 7.40-7.33 (4H, m), 7.31-7.25 (1H, m), 7.05-7.00 (2H, m), 6.54 (1H, dd, J=6.3, 2.3 Hz), 4.54 (2H, d, J=4.5 Hz), 4.45 (1H, dd, J=9.1, 3.2 Hz), 4.12 (1H, q, J=7.1 Hz), 2.95-2.87 (1H, m), 2.73 (1H, td, J=10.6, 5.6 Hz), 2.16-2.10 (1H, m), 2.05-1.94 (1H, m), 1.44 (1H, t, J=5.4 Hz).

MS(ESI) $[M+H]^+$: 240.

Example 59: Synthesis of 4-((2-phenyl-1,2,3,4-tetrahydroquinolin-6-yl)methyl)morph-oline (a Novel Compound)

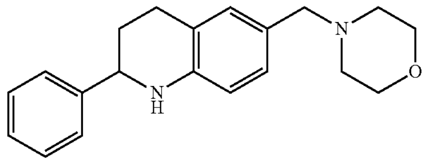 [SMILES: c1ccc(C2CCc3cc(CN4CCOCC4)ccc3N2)cc1]

The (2-phenyl-1,2,3,4-tetrahydroquinolin-6-yl)methanol synthesized in Example 58 (30.0 mg, 0.125 mmol) was dissolved in dichloromethane (1.3 mL), and morpholine (55 μL, 0.63 mmol), triphenylphosphine (39.5 mg, 0.150 mmol), and iodine (38.2 mg, 0.150 mmol) were then added to the resulting solution, and the resulting mixture was stirred at room temperature for 2 hours. The reaction mixture was concentrated under reduced pressure, and the obtained crude product was purified by amino-column chromatography (silica gel, hexane/ethyl acetate) to obtain the title compound (hereinafter referred to as the compound of Example 59) as a colorless clear oily substance (21.0 mg, 0.0675 mmol, yield: 54%).

$^1$H-NMR ($CDCl_3$) δ: 7.40-7.33 (4H, m), 7.30-7.27 (1H, m), 6.95-6.93 (2H, m), 6.50 (1H, d, J=8.7 Hz), 4.42 (1H, dd, J=9.4, 3.0 Hz), 4.03 (1H, brs), 3.71 (4H, t, J=4.6 Hz), 3.37 (2H, s), 2.96-2.88 (1H, m), 2.76-2.70 (1H, m), 2.44 (4H, brs), 2.15-2.08 (1H, m), 2.03-1.93 (1H, m).

MS(ESI)[M-morpholine]+: 222.

Reference Example 39: Synthesis of 2-(2-phenyl-1,2,3,4-tetrahydroquinolin-6-yl)acetonitrile

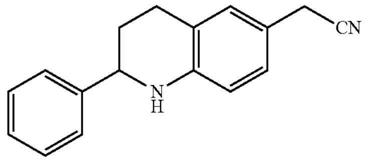 [SMILES: N#CCc1ccc2c(c1)CCC(c1ccccc1)N2]

The (2-phenyl-1,2,3,4-tetrahydroquinolin-6-yl)methanol synthesized in Example 58 (100 mg, 0.418 mmol) was dissolved in THF (4.2 mL), and acetone cyanohydrin (114 μL, 1.25 mmol) and tri-n-butylphosphine (207 μL, 0.836 mmol) were added to the resulting solution. 1,1'-(Azodicarbonyl)dipiperidine (211 mg, 0.836 mmol) was added to the solution under ice cooling, and the resulting mixture was stirred at room temperature for 1 hour. Water was added to the reaction mixture, and the resulting mixture was extracted with ethyl acetate. The organic layer was dried over anhydrous sodium sulfate and then concentrated under reduced pressure. The obtained crude product was purified by column chromatography (silica gel, hexane/ethyl acetate) to obtain the title compound as a colorless clear oily substance (64.2 mg, 0.259 mmol, yield: 62%).

$^1$H-NMR ($CDCl_3$) δ: 7.37-7.27 (5H, m), 6.96-6.92 (2H, m), 6.52 (1H, d, J=7.8 Hz), 4.45 (1H, ddd, J=9.1, 3.2, 1.4 Hz), 4.12 (1H, brs), 3.62 (2H, s), 2.94-2.86 (1H, m), 2.72 (1H, dt, J=16.5, 4.8 Hz), 2.15-2.10 (1H, m), 2.02-1.93 (1H, m).

MS(ESI) $[M+H]^+$: 249.

Example 60: Synthesis of 2-(2-phenyl-1,2,3,4-tetrahydroquinolin-6-yl)acetamide (a Novel Compound)

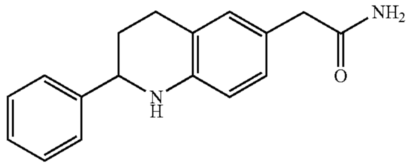 [SMILES: NC(=O)Cc1ccc2c(c1)CCC(c1ccccc1)N2]

The 2-(2-phenyl-1,2,3,4-tetrahydroquinolin-6-yl)acetonitrile synthesized in Reference Example 39 (62.0 mg, 0.250 mmol) was dissolved in DMSO/THF/ethanol (1/1/2, v/v/v, 5 mL), and an 8 mol/L aqueous solution of sodium hydroxide (69 μL, 0.55 mmol) and a 30% aqueous solution of hydrogen peroxide (43 μL, 0.55 mmol) were then added to the resulting solution, and the resulting mixture was stirred at room temperature for 1 hour. A 30% aqueous solution of hydrogen peroxide (43 μL, 0.55 mmol) was further added to the solution, and the resulting mixture was stirred at room temperature for 1 hour. A 10% aqueous solution of sodium thiosulfate was added to the reaction mixture, and the resulting mixture was extracted with ethyl acetate. The organic layer was dried over anhydrous sodium sulfate and then concentrated under reduced pressure. The obtained crude product was purified by column chromatography (silica gel, hexane/ethyl acetate) to obtain the title compound (hereinafter referred to as the compound of Example 60) as a white solid (59.0 mg, 0.223 mmol, yield: 89%).

$^1$H-NMR ($CDCl_3$) δ: 7.38-7.28 (5H, m), 6.91-6.89 (2H, m), 6.53 (1H, d, J=8.7 Hz), 5.48 (1H, brs), 5.41 (1H, brs), 4.44 (1H, dd, J=9.4, 3.0 Hz), 4.09 (1H, brs), 3.46 (2H, s), 2.94-2.86 (1H, m), 2.72 (1H, dt, J=16.5, 4.8 Hz), 2.14-2.10 (1H, m), 2.02-1.95 (1H, m).

MS(ESI) $[M+H]^+$: 267.

Reference Example 40: Synthesis of 2-(2-phenyl-1,2,3,4-tetrahydroquinolin-6-yl)acetic acid

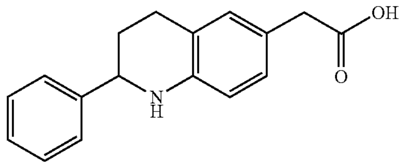 [SMILES: O=C(O)Cc1ccc2c(c1)CCC(c1ccccc1)N2]

The 2-(2-phenyl-1,2,3,4-tetrahydroquinolin-6-yl)acetamide synthesized in Example 60 (57.0 mg, 0.214 mmol) was suspended in ethanol (1.05 mL)/water (1.05 mL), and potassium hydroxide (240 mg, 4.28 mmol) was then added to the resulting suspension, and the resulting mixture was heated to reflux for 4 hours. After the reaction mixture was cooled down to room temperature, the reaction mixture was concentrated under reduced pressure. After the pH was adjusted to 5 by adding 6 mol/L hydrochloric acid to the obtained crude product, the crude product was extracted with ethyl acetate. The organic layer was dried over anhydrous sodium sulfate, and then concentrated under reduced pressure to obtain the title compound as a pale yellow oily substance (40.9 mg, 0.152 mmol, yield: 71%).

$^1$H-NMR ($CDCl_3$) δ: 7.39-7.29 (5H, m), 6.94-6.91 (2H, m), 6.51 (1H, d, J=8.7 Hz), 4.43 (1H, dd, J=9.1, 3.2 Hz), 3.52 (2H, s), 2.95-2.87 (1H, m), 2.72 (1H, dt, J=16.3, 4.7 Hz), 2.14-2.07 (1H, m), 2.02-1.93 (1H, m).

MS(ESI) $[M+H]^+$: 268.

Example 61: Synthesis of N-(tert-butyl)-2-(2-phenyl-1,2,3,4-tetrahydroquinolin-6-yl)acetamide (a Novel Compound)

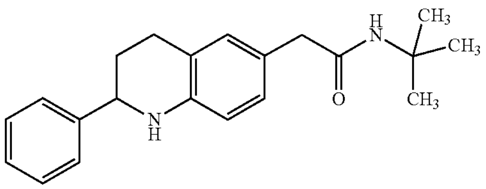 [SMILES: CC(C)(C)NC(=O)Cc1ccc2c(c1)CCC(c1ccccc1)N2]

The 2-(2-phenyl-1,2,3,4-tetrahydroquinolin-6-yl)acetic acid synthesized in Reference Example 40 (20.0 mg, 0.0748 mmol) was dissolved in DMF (0.75 mL), and N,N-diisopropylethylamine (39 μL, 0.22 mmol), tert-butylamine (79 μL, 0.75 mmol), and 1-[bis(dimeth-ylamino)methylene]-1H-1,2,3-triazolo[4,5-b]pyridinium 3-oxide hexafluorophosphate (42.7 mg, 0.112 mmol) were then added to the resulting solution, and the resulting mixture was stirred at room temperature for 19 hours. Water was added to the reaction mixture, and the resulting mixture was extracted with ethyl acetate. The organic layer was washed with water and saturated brine, dried over anhydrous sodium sulfate, and then concentrated under reduced pressure. The obtained crude product was purified by column chromatography (silica gel, hexane/ethyl acetate) to obtain the title compound (hereinafter referred to as the compound of Example 61) as a colorless clear oily substance (9.7 mg, 0.030 mmol, yield: 40%).

$^1$H-NMR ($CDCl_3$) δ: 7.40-7.27 (5H, m), 6.87-6.84 (2H, m), 6.51 (1H, dd, J=6.2, 2.5 Hz), 5.29 (1H, brs), 4.44 (1H, dd, J=9.1, 3.2 Hz), 4.05 (1H, brs), 3.35 (2H, s), 2.95-2.87 (1H, m), 2.72 (1H, dt, J=16.5, 4.8 Hz), 2.16-2.09 (1H, m), 2.05-1.94 (1H, m), 1.29 (9H, s).

MS(ESI) $[M+H]^+$: 323.

Example 62: Synthesis of 1-(3-hydroxyazetidin-1-yl)-2-(2-phenyl-1,2,3,4-tetrahydroquinolin-6-yl)ethan-1-one (a Novel Compound)

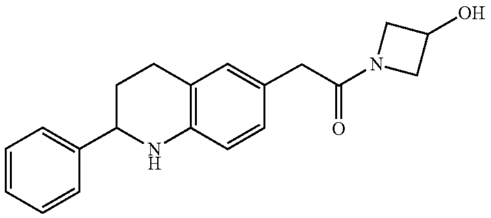 [SMILES: O=C(Cc1ccc2c(c1)CCC(c1ccccc1)N2)N1CC(O)C1]

The 2-(2-phenyl-1,2,3,4-tetrahydroquinolin-6-yl)acetic acid synthesized in Reference Example 40 (20.0 mg, 0.0748 mmol) was dissolved in DMF (0.75 mL), and N,N-diisopropylethylamine (104 μL, 0.599 mmol), azetidin-3-ol (41.0 mg, 0.374 mmol), and 1-[bis(dimethyl-amino)methylene]-1H-1,2,3-triazolo[4,5-b]pyridinium 3-oxide hexafluorophosphate (42.7 mg, 0.112 mmol) were then added to the resulting solution, and the resulting mixture was stirred at room temperature for 16 hours. Water was added to the reaction mixture, and the resulting mixture was extracted with ethyl acetate. The organic layer was washed with water and saturated brine, dried over anhydrous sodium sulfate, and then concentrated under reduced pressure. The obtained crude product was purified by column chromatography (silica gel, chloroform/methanol) to obtain the title compound (hereinafter referred to as the compound of Example 62) as a colorless clear oily substance (9.4 mg, 0.029 mmol, yield: 39%).

$^1$H-NMR ($CDCl_3$) δ: 7.38-7.28 (5H, m), 6.90-6.87 (2H, m), 6.48 (1H, d, J=8.2 Hz), 4.58 (1H, brs), 4.41 (1H, dd, J=9.4, 3.0 Hz), 4.30 (1H, t, J=8.2 Hz), 4.21 (1H, dd, J=10.4, 7.1 Hz), 4.02 (1H, brs), 3.97 (1H, dd, J=9.4, 3.9 Hz), 3.83 (1H, dd, J=10.4, 4.1 Hz), 3.33 (2H, s), 2.92-2.86 (2H, m), 2.70 (1H, dt, J=16.3, 4.7 Hz), 2.13-2.07 (1H, m), 2.01-1.92 (1H, m).

MS(ESI) $[M+H]^+$: 323.

Reference Example 41: Synthesis of 2-phenylquinoline-6-carboxylic acid

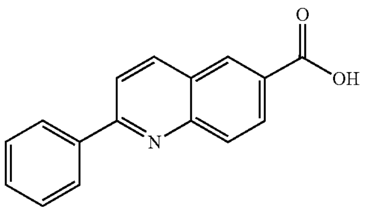 [SMILES: O=C(O)c1ccc2nc(-c3ccccc3)ccc2c1]

The methyl 2-phenylquinoline-6-carboxylate synthesized in Reference Example 38 (0.279 g, 1.06 mmol) was dissolved in a THF/methanol solution (10 mL), and a 1 mol/L aqueous solution of sodium hydroxide (2.12 mL, 2.12 mmol) was added to the resulting solution, and the resulting mixture was stirred at room temperature for 17 hours. After the reaction was completed, the reaction mixture was concentrated under reduced pressure. To the obtained crude product, 1 mol/L hydrochloric acid (4 mL) was added, and the resulting precipitated solid was filtered. The solid was washed with water and dried under vacuum to obtain the title compound as a white solid (0.246 g, 0.988 mmol, yield: 93%).

$^1$H-NMR (DMSO-$d_6$) δ: 8.67 (2H, dd, J=10.4, 5.0 Hz), 8.32 (2H, td, J=4.2, 2.1 Hz), 8.27-8.22 (2H, m), 8.13 (1H, d, J=9.1 Hz), 7.61-7.52 (3H, m).

MS(ESI) $[M+H]^+$: 250.

Reference Example 42: Synthesis of tert-butyl (2-phenylquinolin-6-yl)carbamate

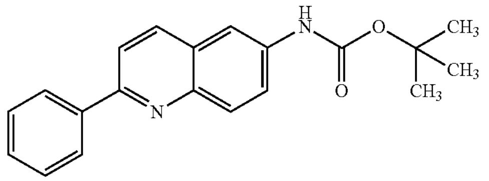 [SMILES: CC(C)(C)OC(=O)Nc1ccc2nc(-c3ccccc3)ccc2c1]

The 2-phenylquinoline-6-carboxylic acid synthesized in Reference Example 41 (0.224 g, 0.898 mmol) was dissolved in tert-butanol (4.0 mL), and triethylamine (0.189 mL, 1.35 mmol) and diphenylphosphoryl azide (0.254 mL, 1.17 mmol) were added to the resulting solution, and the resulting mixture was stirred at 80° C. for 5 hours. After the reaction was completed, the reaction mixture was concentrated under reduced pressure. The obtained crude product was purified by column chromatography (silica gel, hexane/ethyl acetate) to obtain the title compound as a white solid (0.269 g, 0.840 mmol, yield: 94%).

$^1$H-NMR ($CDCl_3$) δ: 8.16-8.07 (4H, m), 7.84 (1H, d, J=8.6 Hz), 7.54-7.35 (4H, m), 7.27-7.24 (1H, m), 6.72 (1H, s), 1.57 (9H, s).

MS(ESI) $[M+H]^+$: 321.

Example 63: Synthesis of tert-butyl (2-phenyl-1,2,3,4-tetrahydroquinolin-6-yl)carbamate (a Novel Compound)

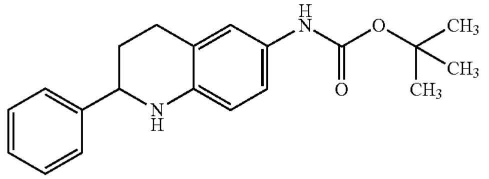 [SMILES: CC(C)(C)OC(=O)Nc1ccc2c(c1)CCC(c1ccccc1)N2]

The tert-butyl (2-phenylquinolin-6-yl)carbamate synthesized in Reference Example 42 (72.0 mg, 0.225 mmol) was used in the same manner as in Example 4 to obtain the title compound (hereinafter referred to as the compound of Example 63) as a white solid (29.0 mg, 0.0895 mmol, yield: 40%).

$^1$H-NMR ($CDCl_3$) δ: 7.39-7.32 (4H, m), 7.30-7.20 (1H, m), 7.10 (1H, brs), 6.90 (1H, dd, J=8.4, 2.5 Hz), 6.48 (1H, d, J=8.6 Hz), 4.40 (1H, dd, J=9.1, 3.2 Hz), 3.95 (1H, s), 2.94-2.86 (1H, m), 2.71 (1H, dt, J=16.5, 4.8 Hz), 2.12-2.07 (1H, m), 1.97 (1H, ddt, J=16.8, 10.6, 3.6 Hz), 1.50 (9H, s).

MS(ESI) $[M+H]^+$: 325.

Example 64: Synthesis of 2-phenyl-1,2,3,4-tetrahydroquinoline-6-amine dihydrochloride (a Novel Compound)

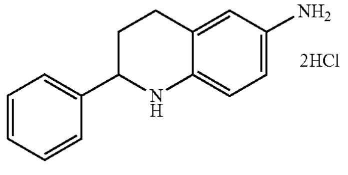 [SMILES: Nc1ccc2c(c1)CCC(c1ccccc1)N2 ; "2HCl"]

The tert-butyl (2-phenyl-1,2,3,4-tetrahydroquinolin-6-yl) carbamate synthesized in Example 63 (25.0 mg, 0.0771 mmol) was dissolved in ethyl acetate (1.0 mL), and a 4 mol/L hydrogen chloride-ethyl acetate solution (0.50 mL, 1.54 mmol) was added to the resulting solution, and the resulting mixture was stirred at room temperature for 16 hours under argon atmosphere. After the reaction was completed, the resulting precipitated solid was filtered and washed with ethyl acetate to obtain the title compound (hereinafter referred to as the compound of Example 64) as a white solid (20.4 mg, 0.0784 mmol, yield: 99%).

$^1$H-NMR (DMSO-$d_6$) δ: 9.69 (2H, brs), 7.38-7.33 (4H, m), 7.28 (1H, dq, J=11.7, 3.1 Hz), 6.89 (2H, dt, J=15.1, 5.3 Hz), 6.66 (1H, d, J=8.2 Hz), 4.44 (1H, dd, J=7.9, 3.4 Hz), 2.82-2.75 (1H, m), 2.60-2.50 (1H, m), 1.99 (1H, dd, J=9.7, 7.0 Hz), 1.85 (1H, dt, J=14.6, 5.3 Hz).

MS(ESI) $[M+H]^+$: 225.

Reference Example 43: Synthesis of 5-(quinolin-2-yl)oxazole

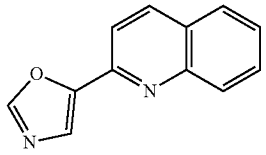 [SMILES: c1ccc2nc(-c3cnco3)ccc2c1]

Quinoline-2-carbaldehyde (200 mg, 1.27 mmol) and potassium carbonate (352 mg, 2.55 mmol) were suspended in methanol (6.3 mL), and toluenesulfonylmethyl isocyanide (273 mg, 1.40 mmol) was then added to the resulting suspension, and the resulting mixture was heated to reflux for 1 hour. The reaction mixture was cooled to room temperature, and water was added to the reaction mixture. The reaction mixture was concentrated under reduced pressure, and the obtained solution was extracted with ethyl acetate. The organic layer was dried over anhydrous sodium sulfate and then concentrated under reduced pressure. The obtained crude product was purified by column chromatography (silica gel, hexane/ethyl acetate) to obtain the title compound as an orange solid (205 mg, 1.04 mmol, yield: 82%).

$^1$H-NMR ($CDCl_3$) δ: 8.23 (1H, d, J=8.5 Hz), 8.14 (1H, dd, J=8.4, 0.9 Hz), 8.06 (1H, s), 7.86 (1H, s), 7.82 (1H, dd, J=8.4, 1.4 Hz), 7.79 (1H, d, J=8.5 Hz), 7.77-7.73 (1H, m), 7.58-7.54 (1H, m).

MS(ESI) $[M+H]^+$: 197.

Example 65: Synthesis of 5-(1,2,3,4-tetrahydroquinolin-2-yl)oxazole

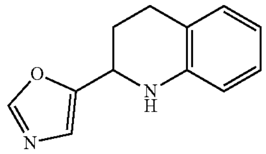 [SMILES: c1ccc2c(c1)CCC(c1cnco1)N2]

The 5-(quinolin-2-yl)oxazole synthesized in Reference Example 43 (70.0 mg, 0.357 mmol) was used in the same manner as in Example 26 to obtain the title compound (hereinafter referred to as the compound of Example 65) as a colorless clear oily substance (52.1 mg, 0.261 mmol, yield: 73%).

$^1$H-NMR ($CDCl_3$) δ: 7.83 (1H, s), 7.04-6.96 (3H, m), 6.68 (1H, t, J=7.1 Hz), 6.57 (1H, d, J=7.8 Hz), 4.63 (1H, brs), 4.11 (1H, brs), 2.90-2.84 (1H, m), 2.77-2.73 (1H, m), 2.27-2.12 (2H, m).

MS(ESI) $[M+H]^+$: 201.

Reference Example 44: Synthesis of 5-fluoro-2-phenylquinoline

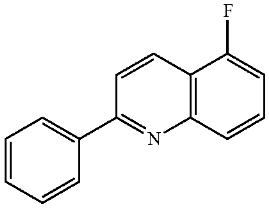 [SMILES: Fc1cccc2nc(-c3ccccc3)ccc12]

Acetophenone (0.165 mL, 1.42 mmol) and potassium tert-butoxide (119 mg, 1.06 mmol) were added to a 1,4-dioxane solution (2 mL) of (2-amino-6-fluorophenyl)methanol (100 mg, 0.709 mmol), and the resulting mixture was stirred at 80° C. for 1 hour. After the reaction was completed, the reaction mixture was filtered using celite, and the filtrate was concentrated under reduced pressure. The obtained crude product was purified by column chromatography (silica gel, hexane/ethyl acetate) to obtain the title compound as a pale yellow solid (74.4 mg, 0.333 mmol, yield: 47%).

$^1$H-NMR ($CDCl_3$) δ: 8.50 (1H, d, J=9.1 Hz), 8.18-8.17 (2H, m), 7.98 (1H, d, J=8.6 Hz), 7.95 (1H, d, J=9.1 Hz), 7.66 (1H, ddd, J=8.2, 8.2, 5.9 Hz), 7.57-7.47 (3H, m), 7.22-7.18 (1H, m).

MS(ESI) $[M+H]^+$: 224.

Example 66: Synthesis of 5-fluoro-2-phenyl-1,2,3,4-tetrahydroquinoline (a Novel Compound)

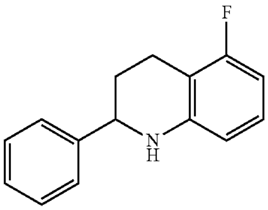 [SMILES: Fc1cccc2c1CCC(c1ccccc1)N2]

The 5-fluoro-2-phenylquinoline synthesized in Reference Example 44 (74.4 mg, 0.333 mmol) was used in the same manner as in Example 26 to obtain the title compound (hereinafter referred to as the compound of Example 66) as a pale yellow oily substance (69.3 mg, 0.305 mmol, yield: 91%).

$^1$H-NMR ($CDCl_3$) δ: 7.34-7.32 (5H, m), 6.99-6.92 (1H, m), 6.38 (1H, dd, J=8.6, 8.6 Hz), 6.32 (1H, d, J=8.2 Hz), 4.40 (1H, dd, J=9.5, 2.7 Hz), 4.17 (1H, brs), 2.86-2.72 (2H, m), 2.17-2.11 (1H, m), 2.00-1.90 (1H, m).

MS(ESI) $[M+H]^+$: 228.

Reference Example 45: Synthesis of 5-chloro-2-phenylquinoline

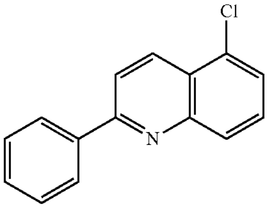 [SMILES: Clc1cccc2nc(-c3ccccc3)ccc12]

(2-Amino-6-chlorophenyl)methanol (100 mg, 0.635 mmol) was used in the same manner as in Reference Example 44 to obtain the title compound as a pale yellow solid (86.3 mg, 0.360 mmol, yield: 57%).

$^1$H-NMR ($CDCl_3$) δ: 8.64 (1H, d, J=9.1 Hz), 8.19-8.17 (2H, m), 8.10 (1H, dd, J=8.2, 0.9 Hz), 7.99 (1H, d, J=8.6 Hz), 7.67-7.47 (5H, m).

MS(ESI) $[M+H]^+$: 240.

Example 67: Synthesis of 5-chloro-2-phenyl-1,2,3,4-tetrahydroquinoline

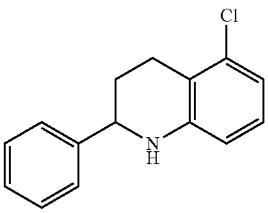 [SMILES: Clc1cccc2c1CCC(c1ccccc1)N2]

The 5-chloro-2-phenylquinoline synthesized in Reference Example 45 (86.3 mg, 0.360 mmol) was used in the same manner as in Example 26 to obtain the title compound (hereinafter referred to as the compound of Example 67) as a pale yellow oily substance (71.1 mg, 0.292 mmol, yield: 81%).

$^1$H-NMR ($CDCl_3$) δ: 7.38-7.27 (5H, m), 6.93 (1H, dd, J=8.2, 8.2 Hz), 6.72 (1H, dd, J=7.9, 1.1 Hz), 6.45 (1H, dd, J=7.9, 1.1 Hz), 4.39 (1H, dd, J=9.1, 2.7 Hz), 4.15 (1H, brs), 2.93-2.78 (2H, m), 2.20-2.14 (1H, m), 2.03-1.94 (1H, m).

MS(ESI) [M+H]$^+$: 244.

Reference Example 46: Synthesis of 7-fluoro-2-phenylquinoline

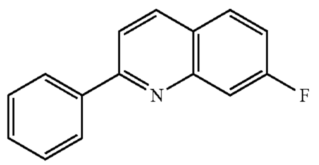 [SMILES: Fc1ccc2ccc(-c3ccccc3)nc2c1]

(2-Amino-4-fluorophenyl)methanol (100 mg, 0.709 mmol) was used in the same manner as in Reference Example 44 to obtain the title compound as a yellow solid (107 mg, 0.478 mmol, yield: 68%).

$^1$H-NMR ($CDCl_3$) δ: 8.22 (1H, d, J=8.7 Hz), 8.17-8.14 (2H, m), 7.86 (1H, d, J=8.7 Hz), 7.83-7.81 (1H, m), 7.60-7.43 (4H, m), 7.35-7.30 (1H, m).

MS(ESI) [M+H]$^+$: 224.

Example 68: Synthesis of 7-fluoro-2-phenyl-1,2,3,4-tetrahydroquinoline

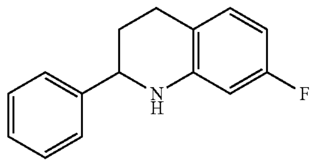 [SMILES: Fc1ccc2c(c1)NC(c1ccccc1)CC2]

The 7-fluoro-2-phenylquinoline synthesized in Reference Example 46 (107 mg, 0.478 mmol) was used in the same manner as in Example 26 to obtain the title compound (hereinafter referred to as the compound of Example 68) as a pale yellow oily substance (95.6 mg, 0.421 mmol, yield: 88%).

$^1$H-NMR ($CDCl_3$) δ: 7.38-7.27 (5H, m), 6.91 (1H, dd, J=6.8, 6.8 Hz), 6.33 (1H, ddd, J=8.6, 8.6, 2.7 Hz), 6.24 (1H, dd, J=10.6, 2.5 Hz), 4.44 (1H, ddd, J=9.1, 3.2, 1.4 Hz), 4.13 (1H, brs), 2.84 (1H, ddd, J=15.9, 10.4, 5.0 Hz), 2.68 (1H, ddd, J=16.3, 5.0, 5.0 Hz), 2.15-2.07 (1H, m), 2.01-1.92 (1H, m).

MS(ESI) [M+H]$^+$: 228.

Reference Example 47: Synthesis of 7-chloro-2-phenylquinoline

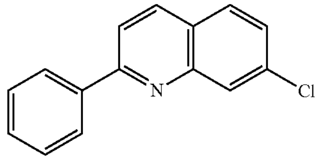 [SMILES: Clc1ccc2ccc(-c3ccccc3)nc2c1]

(2-Amino-4-chlorophenyl)methanol (100 mg, 0.635 mmol) was used in the same manner as in Reference Example 44 to obtain the title compound as a yellow solid (110 mg, 0.457 mmol, yield: 72%).

$^1$H-NMR ($CDCl_3$) δ: 8.21 (1H, d, J=8.7 Hz), 8.17-8.16 (3H, m), 7.89 (1H, d, J=8.7 Hz), 7.77 (1H, d, J=8.7 Hz), 7.59-7.45 (5H, m).

MS(ESI) [M+H]$^+$: 240.

Example 69: Synthesis of 7-chloro-2-phenyl-1,2,3,4-tetrahydroquinoline

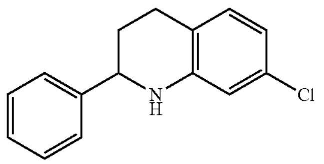 [SMILES: Clc1ccc2c(c1)NC(c1ccccc1)CC2]

The 7-chloro-2-phenylquinoline synthesized in Reference Example 47 (110 mg, 0.457 mmol) was used in the same manner as in Example 26 to obtain the title compound (hereinafter referred to as the compound of Example 69) as a pale yellow oily substance (107 mg, 0.438 mmol, yield: 96%).

$^1$H-NMR ($CDCl_3$) δ: 7.35-7.31 (5H, m), 6.89 (1H, d, J=8.2 Hz), 6.59 (1H, dd, J=8.2, 1.8 Hz), 6.52 (1H, d, J=2.3 Hz), 4.44 (1H, dd, J=9.1, 2.7 Hz), 4.11 (1H, brs), 2.84 (1H, ddd, J=15.9, 10.4, 5.4 Hz), 2.68 (1H, ddd, J=16.3, 5.0, 5.0 Hz), 2.15-2.08 (1H, m), 1.97-1.94 (1H, m).

MS(ESI) [M+H]$^+$: 244.

Reference Example 48: Synthesis of (2-amino-5-bromophenyl)methanol

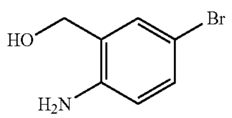

(2-Aminophenyl)methanol (2.80 g, 22.7 mmol) was dissolved in DMF (11.3 mL), and N-bromosuccinimide (4.05 g, 22.7 mmol) was then added in three portions to the resulting solution every 5 minutes under ice cooling, and the resulting mixture was stirred for 2 hours under ice cooling. After the reaction was completed, the reaction mixture was poured into ice-cold water (56 mL). The resulting solid was filtered. The obtained brown solid was dissolved in ethyl acetate, and the resulting solution was dried over anhydrous sodium sulfate, and the filtrate was then concentrated under reduced pressure to obtain the title compound as a brown solid (3.52 g, 17.5 mmol, yield: 77%).

$^1$H-NMR ($CDCl_3$) δ: 7.22-7.20 (2H, m), 6.58 (1H, d, J=8.2 Hz), 4.63 (2H, d, J=4.1 Hz), 4.19 (2H, s), 1.60 (1H, brs).

MS(ESI) [M+H]$^+$: 202.

Reference Example 49: Synthesis of 6-bromo-2-phenylquinoline

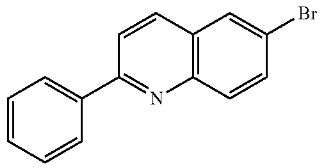 [SMILES: Brc1ccc2nc(-c3ccccc3)ccc2c1]

The (2-amino-5-bromophenyl)methanol synthesized in Reference Example 48 (2.46 g, 12.2 mmol) was dissolved in 1,4-dioxane (36 mL), and acetophenone (2.91 mL, 25.0 mmol) and potassium tert-butoxide (2.05 g, 18.3 mmol) were then added to the resulting solution, and the resulting mixture was stirred at 80° C. for 4 hours. Ice and a saturated aqueous solution of ammonium chloride were added to the reaction mixture, and the resulting mixture was extracted with ethyl acetate. The organic layer was dried over anhydrous sodium sulfate and then concentrated under reduced pressure. The obtained crude product was purified by column chromatography (silica gel, hexane/chloroform) and slurry washing (hexane) to obtain the title compound as a white solid (1.49 g, 5.25 mmol, yield: 43%).

$^1$H-NMR ($CDCl_3$) δ: 8.17-8.13 (3H, m), 8.04 (1H, d, J=9.1 Hz), 8.00 (1H, d, J=2.3 Hz), 7.91 (1H, d, J=8.7 Hz), 7.79 (1H, dd, J=9.1, 2.3 Hz), 7.56-7.46 (3H, m).

MS(ESI) $[M+H]^+$: 284.

Example 70: Synthesis of 6-bromo-2-phenyl-1,2,3,4-tetrahydroquinoline

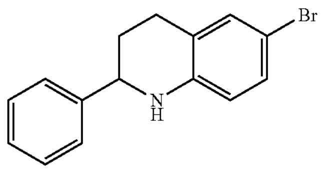 [SMILES: Brc1ccc2c(c1)CCC(c1ccccc1)N2]

The 6-bromo-2-phenylquinoline synthesized in Reference Example 49 (50.0 mg, 0.176 mmol) was used in the same manner as in Example 26 to obtain the title compound (hereinafter referred to as the compound of Example 70) as a yellow oil (47.0 mg, 0.163 mmol, yield: 93%).

$^1$H-NMR ($CDCl_3$) δ: 7.36-7.27 (5H, m), 7.11-7.07 (2H, m), 6.42 (1H, d, J=8.4 Hz), 4.44-4.41 (1H, m), 4.07 (1H, brs), 2.91-2.83 (1H, m), 2.73-2.66 (1H, m), 2.14-2.07 (1H, m), 2.00-1.91 (1H, m).

MS(ESI) $[M+H]^+$: 288.

Reference Example 50: Synthesis of 3-(2-phenylquinolin-6-yl)oxetan-3-ol

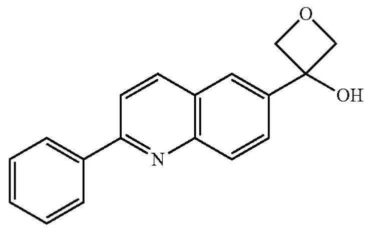 [SMILES: OC1(c2ccc3nc(-c4ccccc4)ccc3c2)COC1]

The 6-bromo-2-phenylquinoline synthesized in Reference Example 49 (100 mg, 0.352 mmol) was dissolved in THF (without addition of a stabilizing agent, 3.5 mL), and a 1.67 mol/L hexane solution of n-butyl lithium (0.25 mL, 0.42 mmol) was then added dropwise at −78° C. to the resulting solution over 3 minutes. Oxetan-3-one (26 μL, 0.026 mmol) was added to the solution, and the resulting mixture was warmed from −78° C. to room temperature over 15 minutes and further stirred at room temperature for 15 minutes. A saturated aqueous solution of ammonium chloride was added to the reaction mixture under ice cooling, and the resulting mixture was extracted with ethyl acetate. The organic layer was dried over anhydrous sodium sulfate and then concentrated under reduced pressure. The obtained crude product was purified by column chromatography (silica gel, hexane/ethyl acetate) to obtain the title compound as a white solid (73.7 mg, 0.268 mmol, yield: 76%).

$^1$H-NMR ($CDCl_3$) δ: 8.25-8.23 (2H, m), 8.18-8.16 (2H, m), 8.02-8.01 (2H, m), 7.92 (1H, d, J=8.7 Hz), 7.55-7.54 (2H, m), 7.48 (1H, t, J=7.1 Hz), 5.04 (2H, d, J=6.9 Hz), 5.01 (2H, d, J=6.9 Hz).

MS(ESI) $[M+H]^+$: 278.

Example 71: Synthesis of 3-(2-phenyl-1,2,3,4-tetrahydroquinolin-6-yl)oxetan-3-ol (a Novel Compound)

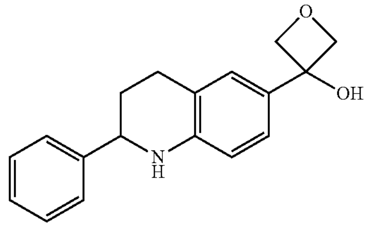 [SMILES: OC1(c2ccc3c(c2)CCC(c2ccccc2)N3)COC1]

The 3-(2-phenylquinolin-6-yl)oxetan-3-ol synthesized in Reference Example 50 (70.0 mg, 0.252 mmol) was dissolved in THF/ethanol (1/1, v/v, 2.5 mL), and acetic acid (44 μL, 0.76 mmol) and platinum(IV) oxide (7.0 mg, 0.031 mmol) were added to the resulting solution. The resulting mixture was vigorously stirred under hydrogen atmosphere, at room temperature for 16 hours. The reaction mixture was filtered using celite, and the filtrate was concentrated under reduced pressure. The obtained crude product was purified by column chromatography (silica gel, hexane/ethyl acetate) to obtain the title compound (hereinafter referred to as the compound of Example 71) as a colorless clear oily substance (49.2 mg, 0.174 mmol, yield: 69%).

$^1$H-NMR ($CDCl_3$) δ: 7.39-7.27 (5H, m), 7.18-7.16 (2H, m), 6.58 (1H, d, J=8.9 Hz), 4.94 (2H, d, J=7.1 Hz), 4.87 (2H, d, J=7.1 Hz), 4.46 (1H, dd, J=9.1, 3.2 Hz), 4.16 (1H, brs), 2.97-2.89 (1H, m), 2.75 (1H, dt, J=16.3, 4.9 Hz), 2.43 (1H, brs), 2.18-2.11 (1H, m), 2.04-1.95 (1H, m).

MS(ESI) $[M+H]^+$: 282.

Reference Example 51: Synthesis of 2-phenyl-6-(piperidin-1-yl)quinoline

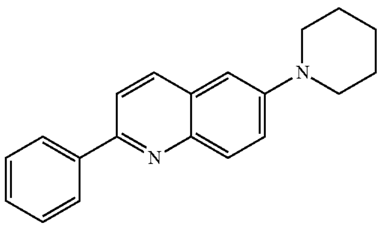 [SMILES: c1ccc(-c2ccc3cc(N4CCCCC4)ccc3n2)cc1]

The 6-bromo-2-phenylquinoline synthesized in Reference Example 49 (60.0 mg, 0.211 mmol), cesium carbonate (241 mg, 0.739 mmol), palladium(II) acetate (4.74 mg, 21.1 μmol), and 2,2'-bis(diphenylphosphino)-1,1'-binaphthyl (26.3 mg, 42.2 μmol) were suspended in 1,4-dioxane (2.10 mL), and piperidine (69.7 μL, 0.633 mmol) was added to the resulting suspension, and the resulting mixture was stirred at 100° C. for 15 hours under argon atmosphere. After the reaction was completed, water was added to the reaction mixture, and the resulting mixture was extracted with chloroform. The organic layers were combined and dried over anhydrous sodium sulfate, and the filtrate was then concentrated under reduced pressure. The obtained crude product was purified by column chromatography (silica gel, hexane/ethyl acetate) to obtain the title compound as a yellow solid (27.3 mg, 94.7 μmol, yield: 45%).

$^1$H-NMR ($CDCl_3$) δ: 8.12-8.10 (2H, m), 8.03 (2H, dd, J=8.8, 8.0 Hz), 7.78 (1H, d, J=8.6 Hz), 7.54-7.48 (3H, m), 7.44-7.40 (1H, m), 7.04 (1H, d, J=2.7 Hz), 3.31 (4H, t, J=7.2 Hz), 1.80-1.75 (4H, m), 1.67-1.61 (2H, m).

MS(ESI) $[M+H]^+$: 289.

Example 72: Synthesis of 2-phenyl-6-(piperidin-1-yl)-1,2,3,4-tetrahydroquinoline (a Novel Compound)

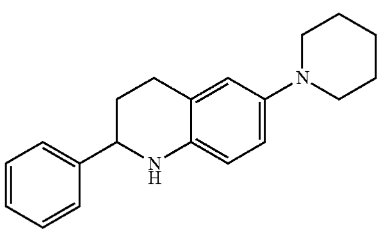 [SMILES: c1ccc(C2CCc3cc(N4CCCCC4)ccc3N2)cc1]

The 2-phenyl-6-(piperidin-1-yl)quinoline synthesized in Reference Example 51 (27.3 mg, 94.7 μmol) was dissolved in dioxane (1.4 mL), and iodine (2.40 mg, 9.46 μmol) and diethyl 1,4-dihydro-2,6-dimethyl-3,5-pyridinedicarboxylate (50.4 mg, 0.199 mmol) were added to the resulting solution, and the resulting mixture was stirred at room temperature for 17 hours under argon atmosphere. Diethyl 1,4-dihydro-2,6-dimethyl-3,5-pyridinedicarboxylate (50.4 mg, 0.199 mmol) was then added to the mixture, and the resulting mixture was stirred at room temperature for 3 hours under argon atmosphere. Iodine (2.40 mg, 9.46 μmol) and diethyl 1,4-dihydro-2,6-dimethyl-3,5-pyridinedicarboxylate (50.4 mg, 0.199 mmol) were further added to the mixture, and the resulting mixture was stirred at 40° C. for 19 hours. After the reaction was completed, the reaction mixture was concentrated under reduced pressure. The obtained crude product was purified by column chromatography (silica gel, hexane/ethyl acetate) to obtain the title compound (hereinafter referred to as the compound of Example 72) as a brown solid (6.00 mg, 20.5 μmol, yield: 22%).

$^1$H-NMR ($CDCl_3$) δ: 7.41-7.39 (2H, m), 7.36-7.32 (2H, m), 7.30-7.26 (1H, m), 6.73-6.70 (2H, m), 6.50 (1H, d, J=8.2 Hz), 4.37 (1H, dd, J=9.5, 3.2 Hz), 2.99-2.89 (5H, m), 2.72 (1H, ddd, J=12.0, 4.8, 4.4 Hz), 2.13-1.93 (2H, m), 1.75-1.69 (4H, m), 1.56-1.50 (2H, m).

MS(ESI) $[M+H]^+$: 293.

Reference Example 52: Synthesis of 1,1-diphenyl-N-(2-phenylquinolin-6-yl)methanimine

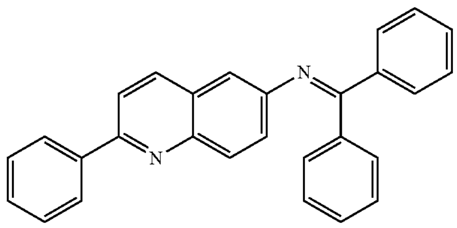 [SMILES: c1ccc(C(=Nc2ccc3nc(-c4ccccc4)ccc3c2)c2ccccc2)cc1]

Cesium carbonate (161 mg, 0.493 mmol), palladium(II) acetate (1.58 mg, 7.04 μmol), and 4,5-bis(diphenylphosphino)-9,9-dimethylxanthene (6.11 mg, 10.6 μmol) were suspended in dioxane (0.50 mL), and the resulting suspension was stirred at room temperature for 10 minutes under argon atmosphere. Triethylamine (1.47 μL, 10.6 μmol) was then added to the mixture, and the resulting mixture was stirred at room temperature for 10 minutes under argon atmosphere. The 6-bromo-2-phenyl-1,2,3,4-tetrahydroquinoline synthesized in Reference Example 49 (100 mg, 0.352 mmol) and a dioxane solution (0.50 mL) of diphenylmethanimine (76.5 mg, 0.422 mmol) were further added to the mixture, and the resulting mixture was stirred at 100° C. for 17 hours under argon atmosphere. After the reaction was completed, water was added to the reaction mixture, and the resulting mixture was extracted with ethyl acetate. The organic layers were combined and dried over anhydrous sodium sulfate, and the filtrate was then concentrated under reduced pressure. The obtained crude product was purified by column chromatography (silica gel, hexane/ethyl acetate) to obtain the title compound as a yellow amorphous (108 mg, 0.280 mmol, yield: 80%).

$^1$H-NMR ($CDCl_3$) δ: 8.12-8.09 (2H, m), 8.01 (1H, d, J=8.6 Hz), 7.93 (1H, d, J=9.1 Hz), 7.82-7.77 (3H, m), 7.53-7.41 (6H, m), 7.25-7.21 (3H, m), 7.19-7.14 (3H, m), 7.11 (1H, d, J=2.3 Hz).

MS(ESI) $[M+H]^+$: 365.

Reference Example 53: Synthesis of 2-phenylquinoline-6-amine

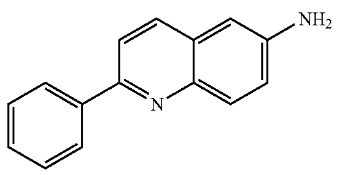 [SMILES: Nc1ccc2nc(-c3ccccc3)ccc2c1]

The 1,1-diphenyl-N-(2-phenylquinolin-6-yl)methanimine synthesized in Reference Example 52 (108 mg, 0.280 mmol) was dissolved in THE (1.0 mL), and 2 mol/L hydrochloric acid (0.420 mL, 0.840 mmol) was added to the resulting solution, and the resulting mixture was stirred at room temperature for 1 hour. After the reaction was completed, a saturated aqueous solution of sodium bicarbonate was added to the reaction mixture, and the resulting mixture was extracted with chloroform. The organic layers were combined and dried over anhydrous sodium sulfate, and the filtrate was then concentrated under reduced pressure. The obtained crude product was purified by column chromatography (silica gel, hexane/ethyl acetate) to obtain the title compound as a pale orange solid (47.3 mg, 0.215 mmol, yield: 77%).

$^1$H-NMR ($CDCl_3$) δ: 8.12-8.09 (2H, m), 7.98 (2H, dd, J=8.6, 2.7 Hz), 7.77 (1H, d, J=8.8 Hz), 7.52-7.48 (2H, m), 7.44-7.40 (1H, m), 7.18 (1H, dd, J=8.8, 2.5 Hz), 6.93 (1H, d, J=2.7 Hz), 3.96 (2H, brs).

MS(ESI) $[M+H]^+$: 221.

Reference Example 54: Synthesis of N-(2-phenylquinolin-6-yl)acetamide

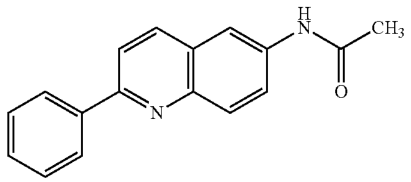 [SMILES: CC(=O)Nc1ccc2nc(-c3ccccc3)ccc2c1]

The 2-phenylquinoline-6-amine synthesized in Reference Example 53 (13.5 mg, 61.3 μmol) was dissolved in pyridine (0.5 mL), and acetic anhydride (6.36 μL, 67.4 μmol) was added to the resulting solution, and the resulting mixture was stirred at room temperature for 30 minutes. After the reaction was completed, the reaction mixture was concentrated under reduced pressure to obtain the title compound as a pale yellow solid (15.5 mg, 59.1 μmol, yield: 96%).

$^1$H-NMR ($CDCl_3$) δ: 8.37 (1H, d, J=1.8 Hz), 8.20 (1H, d, J=8.6 Hz), 8.14-8.12 (3H, m), 7.87 (1H, d, J=8.6 Hz), 7.55-7.52 (3H, m), 7.47-7.45 (1H, m), 7.36 (1H, s), 2.27 (3H, s).

MS(ESI) $[M+H]^+$: 263.

Example 73: Synthesis of N-(2-phenyl-1,2,3,4-tetrahydroquinolin-6-yl)acetamide (a Novel Compound)

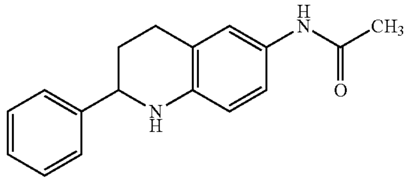 [SMILES: CC(=O)Nc1ccc2c(c1)CCC(c1ccccc1)N2]

The N-(2-phenylquinolin-6-yl)acetamide synthesized in Reference Example 54 (15.5 mg, 59.1 μmol) was used in the same manner as in Example 4 to obtain the title compound (hereinafter referred to as the compound of Example 73) as a colorless amorphous (12.1 mg, 45.4 μmol, yield: 77%).

$^1$H-NMR ($CDCl_3$) δ: 7.39-7.28 (5H, m), 7.16 (1H, d, J=2.7 Hz), 7.02 (1H, dd, J=8.7, 2.3 Hz), 6.93 (1H, brs), 6.50 (1H, d, J=8.7 Hz), 4.42 (1H, dd, J=9.1, 3.2 Hz), 4.02 (1H, brs), 2.91 (1H, ddd, J=16.0, 10.5, 5.5 Hz), 2.72 (1H, ddd, J=16.5, 4.6, 4.6 Hz), 2.14 (3H, s), 2.12-2.08 (1H, m), 2.02-1.92 (1H, m).

MS(ESI) $[M+H]^+$: 267.

Reference Example 55: Synthesis of N-(2-phenylquinolin-6-yl)pivalamide

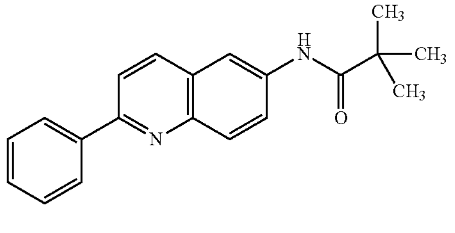 [SMILES: CC(C)(C)C(=O)Nc1ccc2nc(-c3ccccc3)ccc2c1]

The 2-phenylquinoline-6-amine synthesized in Reference Example 53 (50.0 mg, 0.226 mmol) was dissolved in THF (1.0 mL), and pivaloyl chloride (30.4 μL, 0.250 mmol) and triethylamine (35.0 μL, 0.250 mmol) were added to the resulting solution, and the resulting mixture was stirred at room temperature for 2 hours under argon atmosphere. After the reaction was completed, the reaction mixture was concentrated under reduced pressure. The obtained crude product was purified by column chromatography (silica gel, hexane/ethyl acetate) to obtain the title compound as a white solid (64.8 mg, 0.213 mmol, yield: 94%).

$^1$H-NMR ($CDCl_3$) δ: 8.44 (1H, d, J=2.3 Hz), 8.18 (1H, d, J=8.7 Hz), 8.15-8.14 (2H, m), 8.11 (1H, d, J=9.1 Hz), 7.87 (1H, d, J=8.2 Hz), 7.57-7.50 (4H, m), 7.46-7.44 (1H, m), 1.38 (9H, s).

MS(ESI) $[M+H]^+$: 305.

Example 74: Synthesis of N-(2-phenyl-1,2,3,4-tetrahydroquinolin-6-yl)pivalamide (a Novel Compound)

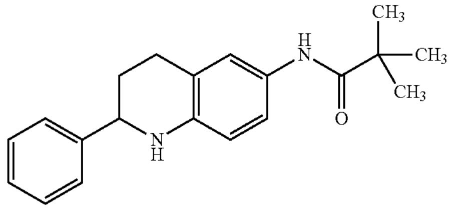 [SMILES: CC(C)(C)C(=O)Nc1ccc2c(c1)CCC(c1ccccc1)N2]

The N-(2-phenylquinolin-6-yl)pivalamide synthesized in Reference Example 55 (64.8 mg, 0.213 mmol) was used in the same manner as in Example 26 to obtain the title compound (hereinafter referred to as the compound of Example 74) as a white solid (62.6 mg, 0.203 mmol, yield: 95%).

$^1$H-NMR ($CDCl_3$) δ: 7.39-7.32 (4H, m), 7.30-7.27 (1H, m), 7.26-7.24 (1H, m), 7.12 (1H, brs), 7.04 (1H, dd, J=8.5, 2.5 Hz), 6.50 (1H, d, J=8.7 Hz), 4.41 (1H, dd, J=9.1, 3.2 Hz), 4.00 (1H, brs), 2.90 (1H, ddd, J=16.0, 10.1, 5.5 Hz), 2.71 (1H, ddd, J=16.5, 5.0, 5.0 Hz), 2.14-2.08 (1H, m), 2.02-1.92 (1H, m), 1.30 (9H, s).

MS(ESI) [M+H]$^+$: 309.

Reference Example 56: Synthesis of N-(2-phenylquinolin-6-yl)methanesulfonamide

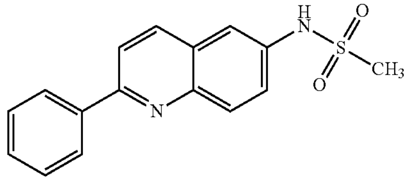 [SMILES: CS(=O)(=O)Nc1ccc2nc(-c3ccccc3)ccc2c1]

The 2-phenylquinoline-6-amine synthesized in Reference Example 53 (40.0 mg, 0.182 mmol) was dissolved in dichloromethane (1.8 mL), and the resulting solution was cooled to 0° C., and triethylamine (38.0 μL, 0.272 mmol) and methanesulfonyl chloride (14.1 μL, 0.182 mmol) were added to the solution, and the resulting mixture was stirred at 0° C. for 2 hours under argon atmosphere. Triethylamine (25.3 μL, 0.182 mmol) and methanesulfonyl chloride (16.9 μL, 0.218 mmol) were then added to the mixture, and the resulting mixture was stirred at room temperature for 18 hours under argon atmosphere. An 8 mol/L aqueous solution of sodium hydroxide (230 μL, 1.81 mmol) was further added to the mixture, and the resulting mixture was stirred at room temperature for 7 hours. An 8 mol/L aqueous solution of sodium hydroxide (230 μL, 1.81 mmol) was finally added to the mixture, and the resulting mixture was stirred at room temperature for 2 hours. After the reaction was completed, a saturated aqueous solution of ammonium chloride was added to the reaction mixture, and the resulting mixture was extracted with ethyl acetate. The organic layers were combined, washed with saturated brine, and dried over anhydrous sodium sulfate, and the filtrate was then concentrated under reduced pressure. The obtained crude product was purified by column chromatography (silica gel, hexane/ethyl acetate) to obtain the title compound as a white solid (48.7 mg, 0.163 mmol, yield: 90%).

$^1$H-NMR ($CDCl_3$) δ: 8.20-8.14 (4H, m), 7.92 (1H, d, J=8.6 Hz), 7.73 (1H, d, J=2.3 Hz), 7.56-7.46 (4H, m), 6.59 (1H, brs), 3.10 (3H, s).

MS(ESI) [M+H]$^+$: 299.

Example 75: Synthesis of N-(2-phenyl-1,2,3,4-tetrahydroquinolin-6-yl)methanesulfonamide (a Novel Compound)

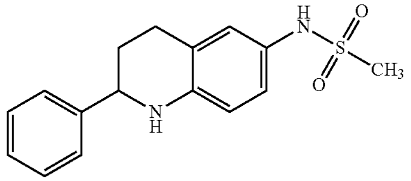 [SMILES: CS(=O)(=O)Nc1ccc2c(c1)CCC(c1ccccc1)N2]

The N-(2-phenylquinolin-6-yl)methanesulfonamide synthesized in Reference Example 56 (48.7 mg, 0.163 mmol) was used in the same manner as in Example 4 to obtain the title compound (hereinafter referred to as the compound of Example 75) as a white solid (20.2 mg, 66.8 μmol, yield: 41%).

$^1$H-NMR ($CDCl_3$) δ: 7.38-7.27 (5H, m), 6.93-6.90 (2H, m), 6.51 (1H, d, J=8.6 Hz), 6.07-6.07 (1H, brm), 4.46-4.43 (1H, m), 4.13 (1H, brs), 2.96-2.86 (4H, m), 2.76-2.69 (1H, m), 2.16-2.09 (1H, m), 2.02-1.92 (1H, m).

MS(ESI) [M+H]$^+$: 303.

Reference Example 57: Synthesis of 1-(tert-butyl)-3-(2-phenylquinolin-6-yl)urea

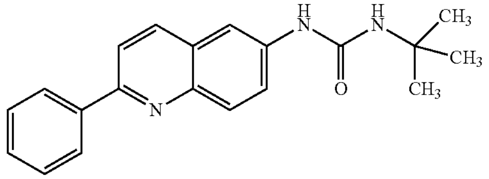 [SMILES: CC(C)(C)NC(=O)Nc1ccc2nc(-c3ccccc3)ccc2c1]

The 2-phenylquinoline-6-amine synthesized in Reference Example 53 (40.0 mg, 0.182 mmol) and potassium carbonate (201 mg, 1.45 mmol) were suspended in acetonitrile (1.8 mL), and tert-butyl isocyanate (0.150 mL, 1.27 mmol) was added to the resulting suspension, and the resulting mixture was stirred at 85° C. for 2 hours under argon atmosphere. Furthermore, tert-butyl isocyanate (0.150 mL, 1.27 mL) was added to the mixture, and the resulting mixture was stirred at 85° C. for 16 hours under argon atmosphere. After the reaction was completed, water was added to the reaction mixture, and the resulting mixture was extracted with ethyl acetate. The organic layers were combined, washed with saturated brine, and dried over anhydrous sodium sulfate, and the filtrate was then concentrated under reduced pressure. The obtained crude product was purified by column chromatography (silica gel, hexane/ethyl acetate) to obtain the title compound as a white solid (58.0 mg, 0.182 mmol, yield: 100%).

$^1$H-NMR ($CDCl_3$) δ: 8.13-8.10 (4H, m), 8.04 (1H, d, J=9.1 Hz), 7.81 (1H, d, J=8.6 Hz), 7.51 (2H, dd, J=8.0, 10.8 Hz), 7.46-7.39 (2H, m), 6.94 (1H, brs), 4.98 (1H, brs), 1.41 (9H, s).

MS(ESI) [M+H]$^+$: 320.

Example 76: Synthesis of 1-(tert-butyl)-3-(2-phenyl-1,2,3,4-tetrahydroquinolin-6-yl)urea (a Novel Compound)

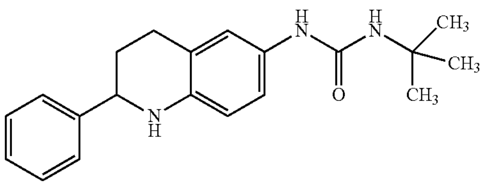 [SMILES: CC(C)(C)NC(=O)Nc1ccc2c(c1)CCC(c1ccccc1)N2]

The 1-(tert-butyl)-3-(2-phenylquinolin-6-yl)urea synthesized in Reference Example 57 (58.0 mg, 0.182 mmol) was used in the same manner as in Example 4 to obtain the title compound (hereinafter referred to as the compound of Example 76) as a purple amorphous (27.2 mg, 84.1 μmol, yield: 46%).

$^1$H-NMR ($CDCl_3$) δ: 7.40-7.27 (5H, m), 6.88 (1H, d, J=1.8 Hz), 6.83 (1H, dd, J=8.8, 2.0 Hz), 6.50 (1H, d, J=8.6 Hz), 5.77 (1H, brs), 4.54 (1H, brs), 4.43 (1H, dd, J=9.5, 3.2 Hz), 4.07 (1H, brs), 2.94-2.86 (1H, m), 2.75-2.68 (1H, m), 2.15-2.09 (1H, m), 2.02-1.93 (1H, m), 1.34 (9H, s).

MS(ESI) [M+H]$^+$: 324.

Reference Example 58: Synthesis of 1-(2-phenylquinolin-6-yl)urea

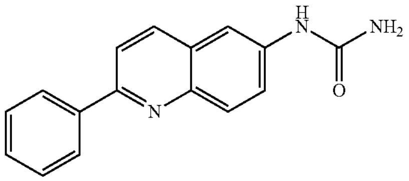 [SMILES: NC(=O)Nc1ccc2nc(-c3ccccc3)ccc2c1]

The 2-phenylquinoline-6-amine synthesized in Reference Example 53 (40.0 mg, 0.182 mmol) was suspended in THF (2.2 mL), and trichloroacetyl isocyanate (29.6 μL, 0.250 mmol) was added to the resulting suspension, and the resulting mixture was stirred at 0° C. for 1 hour under argon atmosphere. Methanol/triethylamine (2.2 mL/1.1 mL) was then added to the mixture, and the resulting mixture was stirred at room temperature for 2 hours. After the reaction was completed, the filtrate was concentrated under reduced pressure. The obtained crude product was purified by slurry washing (hexane/chloroform) to obtain the title compound as a reddish purple solid (49.3 mg, 0.187 mmol, yield: 83%).

$^1$H-NMR (DMSO-$d_6$) δ: 8.92 (1H, brs), 8.30 (1H, d, J=8.7 Hz), 8.23 (2H, d, J=6.9 Hz), 8.13 (1H, d, J=2.3 Hz), 8.04 (1H, d, J=8.7 Hz), 7.94 (1H, d, J=9.1 Hz), 7.67 (1H, dd, J=9.1, 2.3 Hz), 7.54 (2H, dd, J=7.2, 7.2 Hz), 7.49-7.45 (1H, m), 6.02 (2H, brs).

MS(ESI) [M+H]$^+$: 264.

Example 77: Synthesis of 1-(2-phenyl-1,2,3,4-tetrahydroquinolin-6-yl)urea (a Novel Compound)

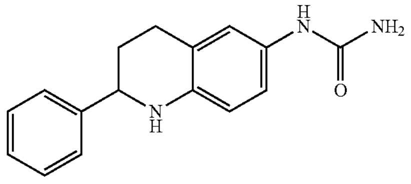 [SMILES: NC(=O)Nc1ccc2c(c1)CCC(c1ccccc1)N2]

The 1-(2-phenylquinolin-6-yl)urea synthesized in Reference Example 58 (47.9 mg, 0.182 mmol) was used in the same manner as in Example 4 to obtain the title compound (hereinafter referred to as the compound of Example 77) as a white amorphous (40.6 mg, 0.152 mmol, yield: 84%).

$^1$H-NMR ($CDCl_3$) δ: 7.37-7.28 (5H, m), 6.91-6.88 (2H, m), 6.52 (1H, d, J=8.0 Hz), 6.14 (1H, brs), 4.64 (2H, brs), 4.45 (1H, dd, J=9.1, 3.6 Hz), 2.93-2.85 (1H, m), 2.75-2.68 (1H, m), 2.16-2.09 (1H, m), 2.02-1.93 (1H, m).

MS(ESI) [M+H]$^+$: 268.

Reference Example 59: Synthesis of 3,3-dimethyl-N-(2-phenylquinolin-6-yl)butanamide

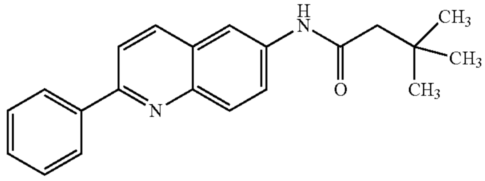 [SMILES: CC(C)(C)CC(=O)Nc1ccc2nc(-c3ccccc3)ccc2c1]

The 2-phenylquinoline-6-amine synthesized in Reference Example 53 (40.0 mg, 0.182 mmol) was dissolved in dichloromethane (0.90 mL), and 3,3-dimethylbutyryl chloride (26.5 μL, 0.191 mmol) was added to the resulting solution, and the resulting mixture was stirred at room temperature for 2 hours under argon atmosphere. Furthermore, tert-butyl isocyanate (0.150 mL, 1.27 mL) was added to the mixture, and the resulting mixture was stirred at room temperature for 2 hours under argon atmosphere. After the reaction was completed, water was added to the reaction mixture, and the resulting mixture was extracted with chloroform. The organic layers were combined and dried over anhydrous sodium sulfate, and the filtrate was then concentrated under reduced pressure. The obtained crude product was purified by column chromatography (silica gel, hexane/ethyl acetate) to obtain the title compound as a white solid (53.7 mg, 0.169 mmol, yield: 93%).

$^1$H-NMR ($CDCl_3$) δ: 8.41 (1H, d, J=2.4 Hz), 8.20-8.09 (4H, m), 7.87 (1H, d, J=8.6 Hz), 7.55-7.51 (3H, m), 7.48-7.44 (1H, m), 2.31 (2H, s), 1.16 (9H, s).

MS(ESI) [M+H]$^+$: 319.

Example 78: Synthesis of 3,3-dimethyl-N-(2-phenyl-1,2,3,4-tetrahydroquinolin-6-yl)butanamide (a Novel Compound)

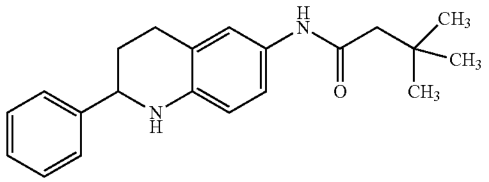 [SMILES: CC(C)(C)CC(=O)Nc1ccc2c(c1)CCC(c1ccccc1)N2]

The 3,3-dimethyl-N-(2-phenylquinolin-6-yl)butanamide synthesized in Reference Example 59 (53.7 mg, 0.169 mmol) was used in the same manner as in Example 4 to obtain the title compound (hereinafter referred to as the compound of Example 78) as a white amorphous (18.7 mg, 58.0 μmol, yield: 34%).

$^1$H-NMR ($CDCl_3$) δ: 7.39-7.27 (5H, m), 7.22 (1H, d, J=2.3 Hz), 7.02 (1H, dd, J=8.8, 2.8 Hz), 6.85 (1H, brs), 6.49 (1H, d, J=8.2 Hz), 4.41 (1H, dd, J=9.1, 3.2 Hz), 2.94-2.86 (1H, m), 2.75-2.68 (1H, m), 2.18 (2H, s), 2.14-2.97 (1H, m), 2.01-1.92 (1H, m), 1.10 (9H, s).

MS(ESI) $[M+H]^+$: 323.

Reference Example 60: Synthesis of 8-chloro-2-phenylquinoline

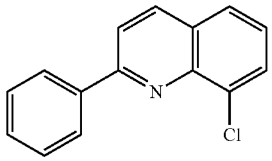 [SMILES: Clc1cccc2ccc(-c3ccccc3)nc12]

2-Chloroaniline (0.325 mL, 3.91 mmol) and cinnamaldehyde (0.493 mmol, 3.91 mmol) were dissolved in DMSO (2 mL), and palladium(II) acetate (87.9 mg, 0.391 mmol) was added to the resulting solution, and the resulting mixture was stirred at 130° C. for 18 hours under oxygen atmosphere. After the reaction was completed, water was added to the reaction mixture, and the resulting mixture was extracted with ethyl acetate. The organic layers were combined, washed with water and saturated brine, and dried over anhydrous sodium sulfate, and the filtrate was then concentrated under reduced pressure. The obtained crude product was purified by column chromatography (silica gel, hexane/ethyl acetate) to obtain the title compound as a pale yellow solid (109 mg, 0.456 mmol, yield: 12%).

$^1$H-NMR ($CDCl_3$) δ: 8.31-8.28 (2H, m), 8.24 (1H, d, J=8.6 Hz), 7.99 (1H, d, J=8.6 Hz), 7.85 (1H, dd, J=7.5, 1.1 Hz), 7.76 (1H, dd, J=8.2, 1.4 Hz), 7.57-7.42 (4H, m).

MS(ESI) $[M+H]^+$: 240.

Example 79: Synthesis of 8-chloro-2-phenyl-1,2,3,4-tetrahydroquinoline (a Novel Compound)

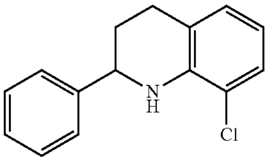 [SMILES: Clc1cccc2c1NC(c1ccccc1)CC2]

The 8-chloro-2-phenylquinoline synthesized in Reference Example 60 (109 mg, 0.456 mmol) was used in the same manner as in Example 26 to obtain the title compound (hereinafter referred to as the compound of Example 79) as a pale yellow oily substance (93.8 mg, 0.385 mmol, yield: 84%).

$^1$H-NMR ($CDCl_3$) δ: 7.41-7.29 (4H, m), 7.12 (1H, d, J=7.3 Hz), 6.91 (1H, d, J=7.3 Hz), 6.56 (1H, dd, J=8.0, 7.6 Hz), 4.67 (1H, brs), 4.53 (1H, ddd, J=9.2, 3.6, 1.2), 2.91 (1H, ddd, J=16.0, 10.4, 5.2 Hz), 2.74 (1H, ddd, J=16.8, 5.2, 4.7 Hz), 2.16-2.12 (1H, m), 2.02-1.93 (1H, m).

MS(ESI) $[M+H]^+$: 244.

Reference Example 61: Synthesis of 8-fluoro-2-phenylquinoline

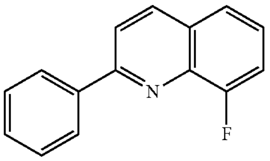 [SMILES: Fc1cccc2ccc(-c3ccccc3)nc12]

2-Fluoroaniline (0.325 mL, 4.50 mmol) and cinnamaldehyde (0.566 mmol, 4.50 mmol) were used in the same manner as in Reference Example 60 to obtain the title compound as a pale yellow solid (68.9 mg, 0.309 mmol, yield: 7%).

$^1$H-NMR ($CDCl_3$) δ: 8.25 (1H, dd, J=8.7, 1.8 Hz), 8.23-8.20 (2H, m), 7.96 (1H, d, J=8.7 Hz), 7.62 (1H, dd, J=7.1, 1.6 Hz), 7.56-7.39 (5H, m).

MS(ESI) $[M+H]^+$: 224.

Example 80: Synthesis of 8-fluoro-2-phenyl-1,2,3,4-tetrahydroquinoline (a Novel Compound)

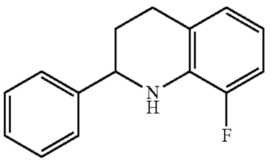 [SMILES: Fc1cccc2c1NC(c1ccccc1)CC2]

The 8-fluoro-2-phenylquinoline synthesized in Reference Example 61 (68.9 mg, 0.309 mmol) was used in the same manner as in Example 26 to obtain the title compound (hereinafter referred to as the compound of Example 80) as a pale yellow oily substance (51.2 mg, 0.225 mmol, yield: 73%).

$^1$H-NMR ($CDCl_3$) δ: 7.41-7.28 (5H, m), 6.84 (1H, dd, J=11.4, 8.2 Hz), 6.79 (1H, d, J=7.3 Hz), 6.55 (1H, ddd, J=8.0, 5.2, 5.2 Hz), 4.46 (1H, ddd, J=9.2, 3.2, 1.2 Hz), 4.26 (1H, brs), 2.93 (1H, ddd, J=16.0, 10.8, 5.6 Hz), 2.76 (1H, ddd, J=16.4, 5.2, 4.4 Hz), 2.16-2.13 (1H, m), 2.05-1.96 (1H, m).

MS(ESI) $[M+H]^+$: 228.

Reference Example 62: Synthesis of 2-phenyl-6-(trifluoromethoxy)quinoline

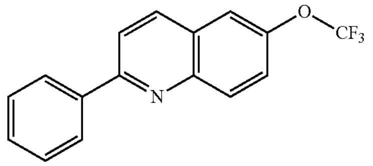 [SMILES: FC(F)(F)Oc1ccc2nc(-c3ccccc3)ccc2c1]

4-(Trifluoromethoxy)aniline (0.325 mL, 2.82 mmol) and cinnamaldehyde (0.355 mmol, 2.82 mmol) were used in the same manner as in Reference Example 60 to obtain the title compound as a pale yellow solid (70.1 mg, 0.242 mmol, yield: 9%).

$^1$H-NMR ($CDCl_3$) δ: 8.23-8.21 (2H, m), 8.18-8.15 (2H, m), 7.95 (1H, d, J=8.6 Hz), 7.66 (1H, s), 7.60-7.47 (4H, m).

MS(ESI) $[M+H]^+$: 290.

Example 81: Synthesis of 2-phenyl-6-(trifluoromethoxy)-1,2,3,4-tetrahydroquinoline (a Novel Compound)

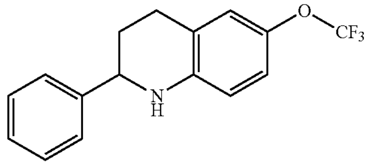 [SMILES: FC(F)(F)Oc1ccc2c(c1)CCC(c1ccccc1)N2]

The 2-phenyl-6-(trifluoromethoxy)quinoline synthesized in Reference Example 62 (83.1 mg, 0.287 mmol) was used in the same manner as in Example 26 to obtain the title compound (hereinafter referred to as the compound of Example 81) as a pale yellow oily substance (83.1 mg, 0.283 mmol, yield: 99%).

$^1$H-NMR ($CDCl_3$) δ: 7.38-7.28 (5H, m), 6.89-6.86 (2H, m), 6.49-6.48 (1H, m), 4.44 (1H, dd, J=9.4, 3.4 Hz), 4.11 (1H, brs), 2.91 (1H, ddd, J=16.5, 10.5, 5.9 Hz), 2.73 (1H, ddd, J=16.5, 4.6, 5.0 Hz), 2.16-2.09 (1H, m), 2.02-1.93 (1H, m).

MS(ESI) $[M+H]^+$: 294.

Reference Example 63: Synthesis of 6-fluoro-2-phenylquinoline

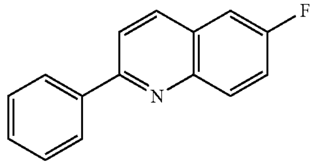 [SMILES: Fc1ccc2nc(-c3ccccc3)ccc2c1]

4-Fluoroaniline (0.431 mL, 4.50 mmol) and cinnamaldehyde (0.566 mmol, 4.50 mmol) were used in the same manner as in Reference Example 60 to obtain the title compound as a pale yellow solid (48.2 mg, 0.216 mmol, yield: 5%).

$^1$H-NMR ($CDCl_3$) δ: 8.20-8.13 (3H, m), 7.91-7.89 (2H, m), 7.57-7.44 (5H, m).

MS(ESI) $[M+H]^+$: 224.

Example 82: Synthesis of 6-fluoro-2-phenyl-1,2,3,4-tetrahydroquinoline

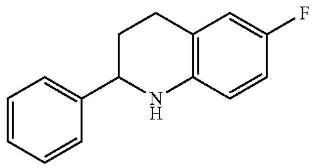 [SMILES: Fc1ccc2c(c1)CCC(c1ccccc1)N2]

The 6-fluoro-2-phenylquinoline synthesized in Reference Example 63 (48.2 mg, 0.216 mmol) was used in the same manner as in Example 26 to obtain the title compound (hereinafter referred to as the compound of Example 82) as a pale yellow oily substance (29.7 mg, 0.131 mmol, yield: 61%).

$^1$H-NMR ($CDCl_3$) δ: 7.40-7.32 (5H, m), 6.74-6.71 (2H, m), 6.47 (1H, dd, J=9.1, 5.0 Hz), 4.39 (1H, dd, J=9.1, 3.2 Hz), 3.94 (1H, brs), 2.92 (1H, ddd, J=16.5, 10.5, 5.5 Hz), 2.72 (1H, ddd, J=16.9, 4.6, 4.6 Hz), 2.14-2.08 (1H, m), 2.02-1.93 (1H, m).

MS(ESI) $[M+H]^+$: 228.

Reference Example 64: Synthesis of 6-chloro-2-phenylquinoline

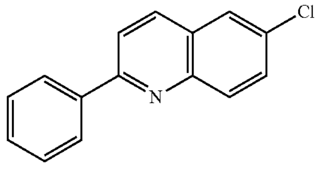 [SMILES: Clc1ccc2nc(-c3ccccc3)ccc2c1]

4-Chloroaniline (100 mg, 0.784 mmol) and (E)-cinnamyl alcohol (105 mg, 0.784 mmol) were used in the same manner as in Reference Example 60 to obtain the title compound as an orange solid (28.0 mg, 0.117 mmol, yield: 15%).

$^1$H-NMR ($CDCl_3$) δ: 8.17-8.14 (3H, m), 8.11 (1H, d, J=9.1 Hz), 7.91 (1H, d, J=8.2 Hz), 7.82 (1H, d, J=2.3 Hz), 7.67 (1H, dd, J=8.9, 2.5 Hz), 7.56-7.46 (3H, m).

MS(ESI) $[M+H]^+$: 240.

Example 83: Synthesis of 6-chloro-2-phenyl-1,2,3,4-tetrahydroquinoline

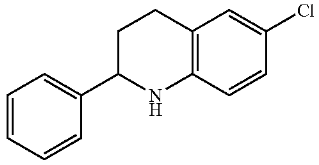 [SMILES: Clc1ccc2c(c1)CCC(c1ccccc1)N2]

The 6-chloro-2-phenylquinoline synthesized in Reference Example 64 (28.0 mg, 0.117 mmol) was used in the same manner as in Example 26 to obtain the title compound (hereinafter referred to as the compound of Example 83) as a pale yellow oily substance (28.0 mg, 0.114 mmol, yield: 98%).

$^1$H-NMR ($CDCl_3$) δ: 7.35-7.31 (5H, m), 6.96-6.95 (2H, m), 6.46 (1H, d, J=8.2 Hz), 4.43 (1H, dd, J=9.1, 3.2 Hz), 4.06 (1H, brs), 2.88 (1H, ddd, J=15.9, 10.4, 5.4 Hz), 2.70 (1H, ddd, J=16.3, 5.0, 5.0 Hz), 2.14-2.08 (1H, m), 2.01-1.91 (1H, m).

MS(ESI) [M+H]$^+$: 244.

Reference Example 65: Synthesis of 2-phenyl-6-(trifluoromethyl)quinoline

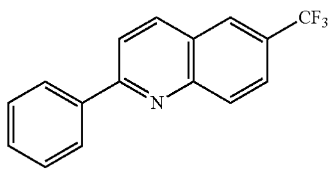 [SMILES: FC(F)(F)c1ccc2nc(-c3ccccc3)ccc2c1]

4-(Trifluoromethyl)aniline (76.9 μL, 0.621 mmol) and (E)-cinnamyl alcohol (83.3 mg, 0.621 mmol) were used in the same manner as in Reference Example 60 to obtain the title compound as an orange solid (42.0 mg, 0.154 mmol, yield: 25%).

$^1$H-NMR ($CDCl_3$) δ: 8.32 (1H, d, J=8.7 Hz), 8.28 (1H, d, J=8.7 Hz), 8.19 (2H, d, J=7.8 Hz), 8.15 (1H, s), 7.99 (1H, d, J=8.7 Hz), 7.90 (1H, dd, J=8.9, 1.6 Hz), 7.56-7.51 (3H, m).

MS(ESI) [M+H]$^+$: 274.

Example 84: Synthesis of 2-phenyl-6-(trifluoromethyl)-1,2,3,4-tetrahydroquinoline (a Novel Compound)

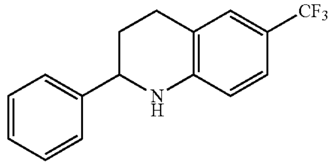 [SMILES: FC(F)(F)c1ccc2c(c1)CCC(c1ccccc1)N2]

The 2-phenyl-6-(trifluoromethyl)quinoline synthesized in Reference Example 65 (42.0 mg, 0.154 mmol) was used in the same manner as in Example 26 to obtain the title compound (hereinafter referred to as the compound of Example 84) as a pale yellow oily substance (30.8 mg, 0.111 mmol, yield: 72%).

$^1$H-NMR ($CDCl_3$) δ: 7.37-7.29 (5H, m), 7.25-7.23 (2H, m), 6.54 (1H, d, J=9.1 Hz), 4.51 (1H, dd, J=8.7, 2.3 Hz), 4.38 (1H, brs), 2.90 (1H, ddd, J=15.6, 10.1, 5.0 Hz), 2.74 (1H, ddd, J=16.5, 5.0, 5.0 Hz), 2.18-2.12 (1H, m), 2.06-1.93 (1H, m).

MS(ESI) [M+H]$^+$: 278.

Reference Example 66: Synthesis of 6,7-difluoro-2-phenylquinoline

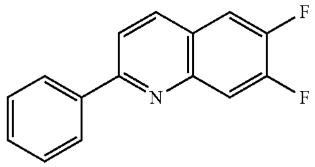 [SMILES: Fc1cc2ccc(-c3ccccc3)nc2cc1F]

3,4-Difluoroaniline (150 mg, 1.16 mmol) and (E)-cinnamyl alcohol (156 mg, 1.16 mmol) were used in the same manner as in Reference Example 60 to obtain the title compound as an orange solid (57.7 mg, 0.239 mmol, yield: 21%).

$^1$H-NMR ($CDCl_3$) δ: 8.16-8.14 (3H, m), 7.92 (1H, dd, J=11.6, 7.6 Hz), 7.89 (1H, d, J=8.4 Hz), 7.56-7.46 (4H, m).

MS(ESI) [M+H]$^+$: 242.

Example 85: Synthesis of 6,7-difluoro-2-phenyl-1,2,3,4-tetrahydroquinoline (a Novel Compound)

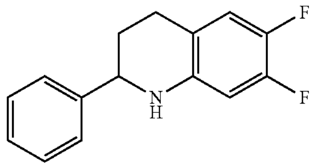 [SMILES: Fc1cc2c(cc1F)NC(c1ccccc1)CC2]

The 6,7-difluoro-2-phenylquinoline synthesized in Reference Example 66 (57.7 mg, 0.239 mmol) was used in the same manner as in Example 26 to obtain the title compound (hereinafter referred to as the compound of Example 85) as a colorless clear oily substance (41.6 mg, 0.170 mmol, yield: 71%).

$^1$H-NMR ($CDCl_3$) δ: 7.38-7.28 (5H, m), 6.78 (1H, dd, J=10.6, 8.8 Hz), 6.31 (1H, dd, J=12.0, 7.0 Hz), 4.39 (1H, ddd, J=9.1, 3.2, 0.9 Hz), 3.97 (1H, brs), 2.83 (1H, ddd, J=16.3, 10.9, 5.4 Hz), 2.65 (1H, ddd, J=16.3, 5.0, 5.0 Hz), 2.13-2.07 (1H, m), 2.00-1.90 (1H, m).

MS(ESI) [M+H]$^+$: 246.

Reference Example 67: Synthesis of 6,8-difluoro-2-phenylquinoline

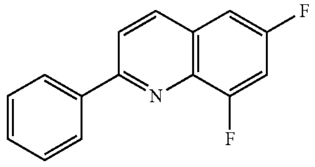 [SMILES: Fc1cc(F)c2nc(-c3ccccc3)ccc2c1]

2,4-Difluoroaniline (150 mg, 1.16 mmol) and (E)-cinnamyl alcohol (156 mg, 1.16 mmol) were used in the same manner as in Reference Example 60 to obtain the title compound as a yellow solid (13.5 mg, 56.0 μmol, yield: 5%).

$^1$H-NMR ($CDCl_3$) δ: 8.21-8.17 (3H, m), 7.98 (1H, d, J=8.7 Hz), 7.93-7.88 (1H, m), 7.56-7.44 (4H, m).

MS(ESI) $[M+H]^+$: 242.

Example 86: Synthesis of 6,8-difluoro-2-phenyl-1,2,3,4-tetrahydroquinoline (a Novel Compound)

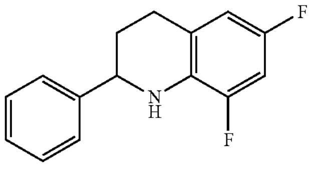 [SMILES: Fc1cc(F)c2c(c1)CCC(c1ccccc1)N2]

The 6,8-difluoro-2-phenylquinoline synthesized in Reference Example 67 (13.5 mg, 56.0 μmol) was used in the same manner as in Example 26 to obtain the title compound (hereinafter referred to as the compound of Example 86) as an orange solid (7.70 mg, 31.4 μmol, yield: 56%).

$^1$H-NMR ($CDCl_3$) δ: 7.41-7.30 (5H, m), 6.65 (1H, ddd, J=11.3, 8.6, 3.2 Hz), 6.57 (1H, d, J=9.1 Hz), 4.41 (1H, dd, J=9.5, 3.2 Hz), 4.07 (1H, brs), 2.92 (1H, ddd, J=16.3, 10.4, 5.9 Hz), 2.74 (1H, ddd, J=17.2, 5.0, 5.0 Hz), 2.16-2.13 (1H, m), 2.05-1.95 (1H, m).

MS(ESI) $[M+H]^+$: 246.

Reference Example 68: Synthesis of 4-(6-nitroquinolin-2-yl)benzonitrile

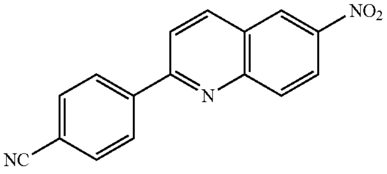 [SMILES: N#Cc1ccc(-c2ccc3cc([N+](=O)[O-])ccc3n2)cc1]

2-Chloro-6-nitroquinoline (700 mg, 3.36 mmol), 4-cyanophenylboronic acid (641 mg, 4.36 mmol), tetrakis(triphenylphosphine)palladium(0) (77.5 mg, 0.0671 mmol), and potassium carbonate (1.39 g, 10.1 mmol) were dissolved in 1,4-dioxane/water (5/1, v/v, 17 mL), and the resulting mixture was then stirred with heating at 100° C. for 16 hours. After the reaction mixture was cooled down to room temperature, water was poured into the reaction mixture, and the resulting solid was filtered to obtain the title compound as a gray solid (647 mg, 2.35 mmol, yield: 70%).

$^1$H-NMR (DMSO-$d_6$) δ: 9.14 (1H, d, J=2.7 Hz), 8.90 (1H, d, J=8.7 Hz), 8.56-8.51 (3H, m), 8.49 (1H, d, J=8.7 Hz), 8.31 (1H, d, J=9.1 Hz), 8.09 (2H, dt, J=8.2, 1.8 Hz).

MS(ESI) $[M+H]^+$: 276.

Reference Example 69: Synthesis of 4-(6-aminoquinolin-2-yl)benzonitrile

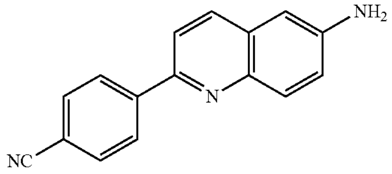 [SMILES: N#Cc1ccc(-c2ccc3cc(N)ccc3n2)cc1]

The 4-(6-nitroquinolin-2-yl)benzonitrile synthesized in Reference Example 68 (100 mg, 0.363 mmol) was dissolved in acetic acid (3.6 mL), and iron powder (81.2 mg, 1.45 mmol) was then added to the resulting solution, and the resulting mixture was stirred at 50° C. for 14 hours. After the reaction mixture was cooled down to room temperature, the reaction mixture was concentrated under reduced pressure, adjusted to pH 12 by addition of a 1 mol/L aqueous solution of sodium hydroxide, and extracted with ethyl acetate. After the resulting reddish brown solid was removed by filtration, the filtrate was dried over anhydrous sodium sulfate and then concentrated under reduced pressure. The obtained crude product was purified by column chromatography (silica gel, chloroform/methanol) to obtain the title compound as a yellow solid (31.8 mg, 0.131 mmol, yield: 36%).

$^1$H-NMR ($CDCl_3$) δ: 8.24 (2H, dt, J=8.4, 1.8 Hz), 8.01 (1H, d, J=8.9 Hz), 7.97 (1H, d, J=8.9 Hz), 7.80-7.76 (3H, m), 7.20 (1H, dd, J=8.9, 2.6 Hz), 6.93 (1H, d, J=2.6 Hz), 4.05 (2H, brs).

MS(ESI) $[M+H]^+$: 246.

Reference Example 70: Synthesis of 1-(tert-butyl)-3-(2-(4-cyanophenyl)quinolin-6-yl)urea

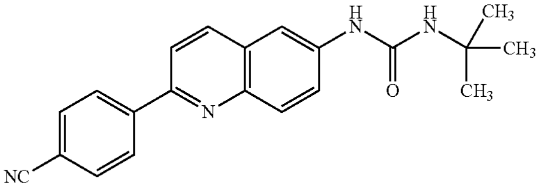 [SMILES: CC(C)(C)NC(=O)Nc1ccc2nc(-c3ccc(C#N)cc3)ccc2c1]

The 4-(6-aminoquinolin-2-yl)benzonitrile synthesized in Reference Example 69 (30.0 mg, 0.122 mmol) was dissolved in acetonitrile/THF (2/1, v/v, 1.8 mL), and potassium carbonate (33.8 mg, 0.245 mmol) and tert-butyl isocyanate (86.6 μL, 0.733 mmol) were then added to the resulting solution, and the resulting mixture was heated to reflux for 23 hours. After the reaction mixture was cooled down to room temperature, water was added to the reaction mixture, and the resulting mixture was extracted with ethyl acetate. The organic layer was dried over anhydrous sodium sulfate and then concentrated under reduced pressure. The obtained crude product was purified by column chromatography (amino-silica gel, chloroform/methanol) to obtain the title compound as a pale orange solid (37.2 mg, 0.107 mmol, yield: 88%).

$^1$H-NMR ($CDCl_3$) δ: 8.23 (2H, dt, J=8.5, 1.7 Hz), 8.15-8.12 (2H, m), 8.02 (1H, d, J=9.1 Hz), 7.80-7.77 (3H, m), 7.42 (1H, dd, J=9.1, 2.7 Hz), 6.72 (1H, brs), 4.84 (1H, brs), 1.43 (9H, s).

MS(ESI) $[M+H]^+$: 345.

Reference Example 71: Synthesis of 4-(6-(3-(tert-butyl)ureido)quinolin-2-yl)benzamide

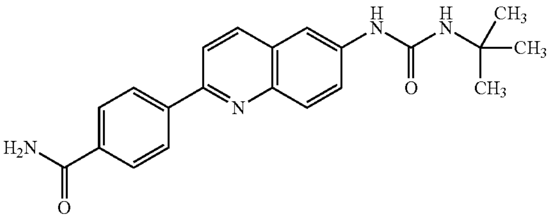 [SMILES: CC(C)(C)NC(=O)Nc1ccc2nc(-c3ccc(C(N)=O)cc3)ccc2c1]

The 1-(tert-butyl)-3-(2-(4-cyanophenyl)quinolin-6-yl) urea synthesized in Reference Example 70 (37.0 mg, 0.107 mmol) was dissolved in THE (1.1 mL), and a 1 mol/L aqueous solution of sodium hydroxide (60 μL, 0.453 mmol) and a 30% aqueous solution of hydrogen peroxide (37 μL, 0.453 mmol) were then added to the resulting solution, and the resulting mixture was stirred at room temperature for 3 hours. A 10% aqueous solution of sodium thiosulfate was added to the reaction mixture, and the resulting mixture was extracted with ethyl acetate. The organic layer was dried over anhydrous sodium sulfate and then concentrated under reduced pressure. The obtained crude product was subjected to slurry washing (hexane/ethyl acetate) to obtain the title compound as a pale yellow solid (32.4 mg, 0.0888 mmol, yield: 83%).

$^1$H-NMR (DMSO-$d_6$) δ: 8.71 (1H, brs), 8.32-8.30 (3H, m), 8.16 (1H, d, J=2.3 Hz), 8.11 (1H, d, J=9.1 Hz), 8.10 (1H, brs), 8.02 (2H, d, J=8.7 Hz), 7.95 (1H, d, J=9.1 Hz), 7.59 (1H, dd, J=9.1, 2.3 Hz), 7.44 (1H, brs), 6.21 (1H, brs), 1.33 (9H, s).

MS(ESI) [M+H]$^+$: 363.

Example 87: Synthesis of 4-(6-(3-(tert-butyl)ureido)-1,2,3,4-tetrahydroquinolin-2-yl)benzamide (a Novel Compound)

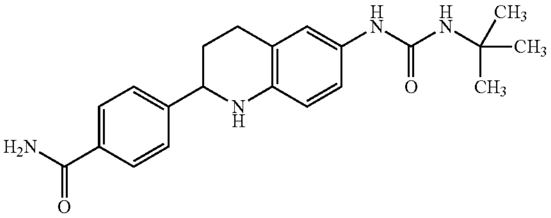 [SMILES: CC(C)(C)NC(=O)Nc1ccc2c(c1)CCC(c1ccc(C(N)=O)cc1)N2]

The 4-(6-(3-(tert-butyl)ureido)quinolin-2-yl)benzamide synthesized in Reference Example 71 (31.0 mg, 0.0855 mmol) was suspended in THF/methanol (1/1, v/v, 0.85 mL), and acetic acid (0.015 mL, 0.26 mmol) and platinum(IV) oxide (3.0 mg, 0.13 mmol) were added to the resulting suspension, and the resulting mixture was stirred at room temperature and normal pressure for 48 hours under hydrogen atmosphere. After the reaction was completed, the hydrogen was replaced with nitrogen, and the reaction mixture was filtered using celite. The filtrate was concentrated under reduced pressure, and the obtained crude product was purified by column chromatography (silica gel, chloroform/methanol) to obtain the title compound (hereinafter referred to as the compound of Example 87) as a white solid (26.1 mg, 0.0564 mmol, yield: 66%).

$^1$H-NMR ($CDCl_3$) δ: 7.92 (2H, dt, J=8.7, 1.8 Hz), 7.60 (2H, dt, J=8.7, 1.8 Hz), 7.06-7.00 (2H, m), 6.69 (1H, td, J=7.3, 0.9 Hz), 6.59 (1H, dd, J=7.8, 0.9 Hz), 4.57 (1H, dd, J=8.7, 3.2 Hz), 4.09 (1H, brs), 3.06 (3H, s), 2.95-2.87 (1H, m), 2.70 (1H, td, J=10.9, 5.5 Hz), 2.19-2.12 (1H, m), 2.01-1.97 (1H, m).

MS(ESI) [M+H]$^+$: 288.

Example 88: Synthesis of methyl (2R*, 4R*)-2-phenyl-1,2,3,4-tetrahydroquinolin-4-carboxylate (a Novel Compound)

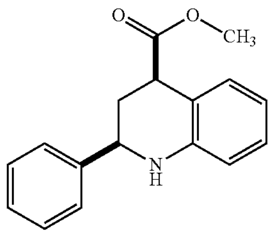 [SMILES: COC(=O)[C@@H]1C[C@H](c2ccccc2)Nc2ccccc21]

Methyl 2-phenylquinoline-4-carboxylate (300 mg, 1.14 mmol) was dissolved in THF/ethanol (1/1, v/v, 5.7 mL), and acetic acid (0.197 mL, 3.42 mmol) and platinum(IV) oxide (30 mg, 0.043 mmol) were then added to the resulting solution, and the resulting mixture was stirred at room temperature and normal pressure for 23 hours under hydrogen atmosphere. After the reaction was completed, the hydrogen was replaced with nitrogen, and the reaction mixture was filtered using celite. The filtrate was concentrated under reduced pressure, and the obtained crude product was purified by column chromatography (silica gel, hexane/ethyl acetate) to obtain the title compound (hereinafter referred to as the compound of Example 88) as a pale yellow oily substance (274 mg, 1.03 mmol, yield: 90%).

$^1$H-NMR ($CDCl_3$) δ: 7.44-7.42 (2H, m), 7.39-7.35 (2H, m), 7.33-7.29 (1H, m), 7.08-7.02 (2H, m), 6.70 (1H, td, J=7.5, 1.1 Hz), 6.57 (1H, dd, J=8.2, 1.1 Hz), 4.42 (1H, dd, J=10.5, 3.2 Hz), 4.11 (1H, dd, J=11.2, 6.2 Hz), 4.05 (1H, brs), 3.71 (3H, s), 2.40-2.31 (2H, m).

MS(ESI) [M+H]$^+$: 268.

Example 89: Synthesis of ((2R*,4R*)-2-phenyl-1,2,3,4-tetrahydroquinolin-4-yl)methanol (a Novel Compound)

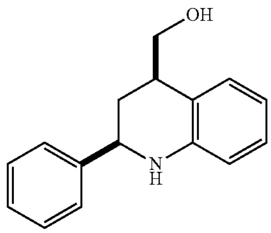 [SMILES: OC[C@@H]1C[C@H](c2ccccc2)Nc2ccccc21]

The methyl (2R*,4R*)-2-phenyl-1,2,3,4-tetrahydroquinolin-4-carboxylate synthesized in Example 88 (70.0 mg, 0.262 mmol) was dissolved in THF (2.6 mL), and a 2 mol/L THF solution of lithium borohydride (0.656 mL, 1.31 mmol)

was then added dropwise to the resulting solution, and the resulting mixture was stirred at room temperature for 6 hours. After the reaction was completed, saturated aqueous solution of sodium potassium tartrate was added to the reaction mixture, and the resulting mixture was stirred at room temperature for 1 hour. The obtained reaction mixture was extracted with ethyl acetate. The organic layers were combined and dried over anhydrous sodium sulfate, and the filtrate was then concentrated under reduced pressure. The obtained crude product was purified by column chromatography (silica gel, hexane/ethyl acetate) to obtain the title compound (hereinafter referred to as the compound of Example 89) as a white solid (32.3 mg, 0.135 mmol, yield: 52%).

$^1$H-NMR ($CDCl_3$) δ: 7.45-7.42 (2H, m), 7.39-7.35 (2H, m), 7.33-7.28 (1H, m), 7.23 (1H, d, J=7.4 Hz), 7.05 (1H, t, J=7.4 Hz), 6.73 (1H, td, J=7.4, 1.2 Hz), 6.58 (1H, dd, J=8.0, 1.2 Hz), 4.44 (1H, dd, J=11.0, 2.7 Hz), 4.01-3.93 (3H, m), 3.28-3.25 (1H, m), 2.26-2.23 (1H, m), 2.04 (1H, dt, J=12.8, 11.0 Hz), 1.41 (1H, dd, J=7.3, 4.6 Hz).

MS(ESI) $[M+H]^+$: 240.

Reference Example 72: Synthesis of 4-methyl-2-phenylquinoline

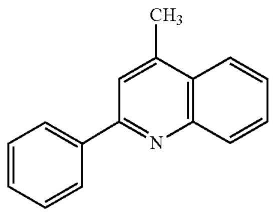 [SMILES: Cc1cc(-c2ccccc2)nc2ccccc12]

2-Chloro-4-methylquinoline (300 mg, 1.69 mmol) and phenylboronic acid (227 mg, 1.86 mmol) were used in the same manner as in Reference Example 6 to obtain the title compound as a colorless oily substance (360 mg, 1.64 mmol, 97%).

$^1$H-NMR ($CDCl_3$) δ: 8.18-8.15 (3H, m), 8.01 (1H, d, J=8.2 Hz), 7.74-7.71 (2H, m), 7.56-7.53 (3H, m), 7.47-7.45 (1H, m), 2.78 (3H, s).

MS(ESI) $[M+H]^+$: 220.

Example 90: Synthesis of (2R*,4R*)-4-methyl-2-phenyl-1,2,3,4-tetrahydroquinoline

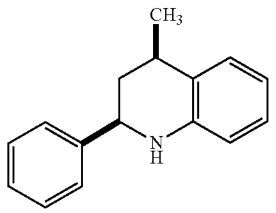 [SMILES: C[C@@H]1C[C@H](c2ccccc2)Nc2ccccc21]

The 4-methyl-2-phenylquinoline synthesized in Reference Example 72 (100 mg, 0.456 mmol) was used in the same manner as in Example 26 to obtain the title compound (hereinafter referred to as the compound of Example 90) as a pale yellow oily substance (46.1 mg, 0.206 mmol, 45%).

$^1$H-NMR ($CDCl_3$) δ: 7.43-7.42 (2H, m), 7.38-7.34 (2H, m), 7.30-7.28 (1H, m), 7.19 (1H, d, J=7.7 Hz), 7.01 (1H, ddd, J=7.2, 7.2, 0.9 Hz), 6.71 (1H, ddd, J=7.2, 7.2, 0.9 Hz), 6.53 (1H, dd, J=8.2, 0.9 Hz), 4.47 (1H, dd, J=11.3, 2.7 Hz), 3.97 (1H, brs), 3.13 (1H, ddd, J=6.3, 12.2, 6.3 Hz), 2.11 (1H, ddd, J=12.7, 5.0, 2.7 Hz), 1.76 (1H, ddd, J=11.8, 11.8, 11.8 Hz), 1.35 (3H, d, J=6.8 Hz).

MS(ESI) $[M+H]^+$: 224.

Reference Example 73: Synthesis of tert-butyl 2-phenyl-3,4-dihydroquinoline-1(2H)-carboxylate

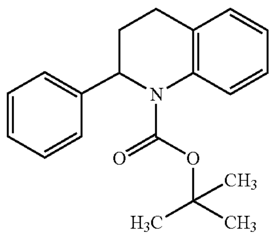 [SMILES: CC(C)(C)OC(=O)N1c2ccccc2CCC1c1ccccc1]

2-Phenyl-1,2,3,4-tetrahydroquinoline (30.0 mg, 0.143 mmol) was dissolved in tetrahydrofuran (1 mL), and a 1.64 mol/L hexane solution of n-butyl lithium (0.140 mL, 0.229 mmol) was added at −78° C. to the resulting solution under argon atmosphere, and the resulting mixture was stirred for 0.5 hour. Subsequently, a tetrahydrofuran solution (1 mL) of di-tert-butyl dicarbonate (93.9 mg, 0.430 mmol) was added to the mixture, and the resulting mixture was stirred at room temperature for 16 hours. After the reaction was completed, a saturated aqueous solution of sodium bicarbonate was added to the reaction mixture, and the organic layer was separated off. The obtained aqueous phase was extracted with diethyl ether. The organic layers were combined, washed with saturated brine, and dried over anhydrous sodium sulfate, and the filtrate was then concentrated under reduced pressure. The obtained crude product was purified by column chromatography (amino-silica gel, hexane/ethyl acetate) to obtain the title compound as a colorless amorphous (44.3 mg, 0.143 mmol, yield: 99%).

$^1$H-NMR ($CDCl_3$) δ: 7.80 (1H, d, J=8.2 Hz), 7.28-7.16 (6H, m), 7.08 (1H, d, J=5.9 Hz), 7.01 (1H, ddd, J=7.3, 7.3, 1.4 Hz), 5.35 (1H, dd, J=8.5, 7.1 Hz), 2.70-2.58 (2H, m), 2.45-2.41 (1H, m), 1.84-1.81 (1H, m), 1.34 (9H, s).

Reference Example 74: Synthesis of tert-butyl 2-methyl-2-phenyl-3,4-dihydroquinoline-1(2H)-carboxylate

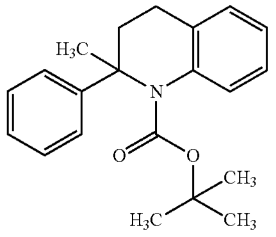 [SMILES: CC(C)(C)OC(=O)N1c2ccccc2CCC1(C)c1ccccc1]

The tert-butyl 2-phenyl-3,4-dihydroquinoline-1(2H)-carboxylate synthesized in Reference Example 73 (22.2 mg, 71.1 μmol) was dissolved in tetrahydrofuran (1.0 mL), and a 1.64 mol/L hexane solution of n-butyl lithium (73.9 μL, 0.121 mmol) was added at −78° C. to the resulting solution under argon atmosphere, and the resulting mixture was stirred for 10 hour. Subsequently, iodomethane (13.4 μL, 0.215 mmol) was added to the mixture, and the resulting mixture was stirred at room temperature for 16 hours. After the reaction was completed, methanol was added to the reaction mixture, and the resulting mixture was concentrated under reduced pressure. The obtained crude product was purified by preparative thin-layer chromatography (silica gel, hexane/ethyl acetate) to obtain the title compound as a colorless amorphous (16.5 mg, 51.0 μmol, yield: 71%).

$^1$H-NMR ($CDCl_3$) δ: 7.67 (1H, d, J=8.2 Hz), 7.36-7.29 (4H, m), 7.23-7.18 (2H, m), 7.07 (1H, d, J=7.3 Hz), 6.97 (1H, dd, J=7.8, 7.8 Hz), 2.71 (1H, ddd, J=14.2, 9.1, 4.6 Hz), 2.48 (1H, ddd, J=14.6, 5.9, 2.7 Hz), 2.01 (3H, s), 1.95-1.91 (2H, m), 1.17 (9H, s).

Example 91: Synthesis of 2-methyl-2-phenyl-1,2,3,4-tetrahydroquinoline

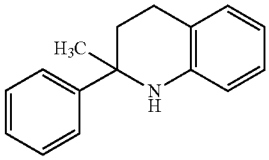 [SMILES: CC1(c2ccccc2)CCc2ccccc2N1]

The tert-butyl 2-methyl-2-phenyl-3,4-dihydroquinoline-1(2H)-carboxylate synthesized in Reference Example 74 (16.5 mg, 51.0 μmol) was dissolved in dichloromethane (1 mL), and trifluoroacetic acid (37.9 μL, 0.510 mmol) was added to the resulting solution, and the resulting mixture was stirred at room temperature for 16 hours. After the reaction was completed, the reaction mixture was concentrated under reduced pressure. The obtained crude product was purified by column chromatography (amino-silica gel, hexane/ethyl acetate) to obtain the title compound (hereinafter referred to as the compound of Example 91) as a colorless amorphous (8.10 mg, 36.3 μmol, yield: 71%).

$^1$H-NMR ($CDCl_3$) δ: 7.40-7.38 (2H, m), 7.31-7.27 (2H, m), 7.21-7.19 (1H, m), 7.03-7.01 (1H, m), 6.90 (1H, d, J=7.3 Hz), 6.61-6.59 (2H, m), 2.60 (1H, ddd, J=16.5, 4.6, 4.6 Hz), 2.32 (1H, ddd, J=16.5, 11.4, 5.5 Hz), 2.21 (1H, ddd, J=12.8, 5.0, 5.0 Hz), 1.91 (1H, ddd, J=12.8, 11.0, 5.0 Hz), 1.58 (3H, s).

MS(ESI) $[M+H]^+$: 224.

Reference Example 75: Synthesis of 1-(tert-butyl) 2-methyl 2-phenyl-3,4-dihydroquinoline-1,2(2H)-dicarboxylate

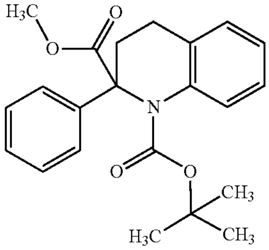 [SMILES: COC(=O)C1(c2ccccc2)CCc2ccccc2N1C(=O)OC(C)(C)C]

The tert-butyl 2-phenyl-3,4-dihydroquinoline-1(2H)-carboxylate synthesized in Reference Example 73 (300 mg, 0.970 mmol) was dissolved in tetrahydrofuran (6 mL) under argon atmosphere, and a 1.64 mol/L hexane solution of n-butyl lithium, (0.887 mL, 1.45 mmol) was added dropwise at −78° C. to the resulting solution, and the resulting mixture was stirred at −78° C. for 10 minutes. Subsequently, methyl chloroformate (0.261 mL, 3.39 mmol) was added at −78° C. to the mixture, and the resulting mixture was stirred at room temperature for 18 hours. After the reaction was completed, methanol (1 mL) was added to the reaction mixture, and the resulting mixture was concentrated under reduced pressure. The obtained crude product was purified by column chromatography (silica gel, hexane/ethyl acetate) to obtain the title compound as a colorless clear oily substance (250 mg, 0.681 mmol, yield: 70%).

$^1$H-NMR ($CDCl_3$) δ: 7.87 (1H, d, J=8.2 Hz), 7.61-7.59 (2H, m), 7.32-7.28 (2H, m), 7.23-7.21 (2H, m), 7.03-6.99 (2H, m), 3.78 (3H, s), 2.81 (1H, ddd, J=14.5, 9.9, 3.1 Hz), 2.57-2.43 (2H, m), 2.18-2.11 (1H, m), 1.29 (9H, s).

Reference Example 76: Synthesis of tert-butyl 2-(hydroxymethyl)-2-phenyl-3,4-dihydroquinoline-1(2H)-carboxylate

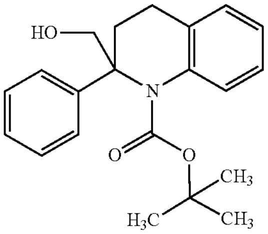 [SMILES: CC(C)(C)OC(=O)N1c2ccccc2CCC1(CO)c1ccccc1]

The 1-(tert-butyl) 2-methyl 2-phenyl-3,4-dihydroquinoline-1,2(2H)-dicarboxylate synthesized in Reference Example 75 (141 mg, 0.383 mmol) was dissolved in dichloromethane (4.0 mL) under argon atmosphere, and a 1 mol/L hexane solution of diisobutylaluminum hydride (1.53 mL, 1.53 mmol) was added at −78° C. to the resulting solution, and the resulting mixture was stirred at −78° C. for 4 hours. After the reaction was completed, the reaction mixture was allowed to warm to 0° C., and a saturated aqueous solution of potassium sodium tartrate was added to the reaction mixture, and the resulting mixture was stirred at room temperature for 16 hours. The organic layer was separated off from the obtained mixture, and the aqueous layer was extracted with ethyl acetate. The organic layers were combined, washed with saturated brine, and dried over anhydrous sodium sulfate, and the filtrate was then concentrated under reduced pressure. The obtained crude product was purified by column chromatography (silica gel, hexane/ethyl acetate) to obtain the title compound as a colorless clear oily substance (95.9 mg, 0.283 mmol, yield: 74%).

$^1$H-NMR ($CDCl_3$) δ: 7.36-7.33 (5H, m), 7.25-7.23 (1H, m), 7.17-7.15 (1H, m), 7.05 (1H, d, J=6.9 Hz), 6.99 (1H, ddd, J=7.8, 7.8, 1.4 Hz), 4.42 (1H, dd, J=11.4, 7.3 Hz), 4.29 (1H, dd, J=7.1, 4.3 Hz), 4.12-4.08 (2H, m), 2.82-2.74 (1H, m), 2.40 (1H, ddd, J=15.1, 3.7, 3.7 Hz), 2.00-1.96 (1H, m), 1.33 (9H, s).

Example 92: Synthesis of (2-phenyl-1,2,3,4-tetrahydroquinolin-2-yl)methanol (a Novel Compound)

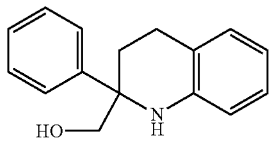 [SMILES: OCC1(c2ccccc2)CCc2ccccc2N1]

The tert-butyl 2-(hydroxymethyl)-2-phenyl-3,4-dihydroquinoline-1(2H)-carboxylate synthesized in Reference Example 76 (95.9 mg, 0.283 mmol) was dissolved in dichloromethane (2 mL), and trifluoroacetic acid (0.104 mL, 1.41 mmol) was added to the resulting solution, and the resulting mixture was stirred at room temperature for 2 hours. After the reaction was completed, a saturated aqueous solution of sodium bicarbonate was added to the reaction mixture, and the resulting mixture was extracted with dichloromethane. The organic layers were combined, washed with saturated brine, and dried over anhydrous sodium sulfate, and the filtrate was then concentrated under reduced pressure. The obtained crude product was purified by column chromatography (silica gel, hexane/ethyl acetate) to obtain the title compound (hereinafter referred to as the compound of Example 92) as a colorless clear oily substance (37.0 mg, 0.154 mmol, yield: 55%).

$^{1}$H-NMR ($CDCl_3$) δ: 7.39-7.31 (4H, m), 7.25-7.20 (1H, m), 7.07-7.01 (1H, m), 6.89 (1H, d, J=7.3 Hz), 6.70 (1H, dd, J=8.2, 0.9 Hz), 6.61 (1H, ddd, J=7.3, 7.3, 1.4 Hz), 4.70 (1H, brs), 4.42 (1H, s), 3.95 (1H, dd, J=10.7, 3.0 Hz), 3.77 (1H, t, J=10.5 Hz), 2.58 (1H, ddd, J=16.0, 4.6, 3.2 Hz), 2.31 (1H, ddd, J=16.5, 12.8, 5.0 Hz), 2.15 (1H, ddd, J=12.8, 5.0, 2.7 Hz), 2.01 (1H, ddd, J=12.8, 12.8, 5.0 Hz).

MS(ESI) $[M+H]^+$: 240.

Example 93: Synthesis of methyl 2-phenyl-1,2,3,4-tetrahydroquinoline-2-carboxylate (a Novel Compound)

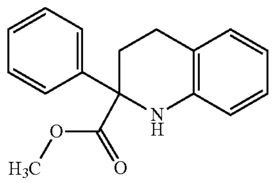 [SMILES: COC(=O)C1(c2ccccc2)CCc2ccccc2N1]

The 1-(tert-butyl) 2-methyl 2-phenyl-3,4-dihydroquinoline-1,2(2H)-dicarboxylate synthesized in Reference Example 75 (100 mg, 0.272 mmol) was used in the same manner as in Example 92 to obtain the title compound (hereinafter referred to as the compound of Example 93) as a colorless clear oily substance (70.0 mg, 0.262 mmol, yield: 96%).

$^{1}$H-NMR ($CDCl_3$) δ: 7.51-7.49 (2H, m), 7.36-7.27 (3H, m), 7.06-7.04 (1H, m), 6.93 (1H, dd, J=7.5, 1.1 Hz), 6.71 (1H, dd, J=7.8, 0.9 Hz), 6.65 (1H, ddd, J=7.3, 7.3, 0.9 Hz), 3.75 (3H, s), 2.72 (1H, ddd, J=16.0, 5.9, 5.9 Hz), 2.52-2.36 (3H, m).

MS(ESI) $[M+H]^+$: 268.

Reference Example 77: Synthesis of tert-butyl 2-(2-methoxy-2-oxoethyl)-2-phenyl-3,4-dihydroquinoline-1(2H)-carboxylate

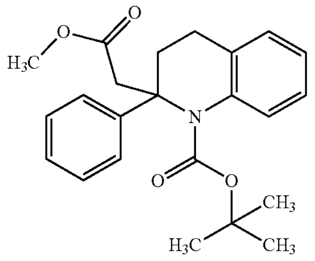 [SMILES: COC(=O)CC1(c2ccccc2)CCc2ccccc2N1C(=O)OC(C)(C)C]

Tert-butyl 2-phenyl-3,4-dihydroquinoline-1(2H)-carboxylate (600 mg, 1.94 mmol) and methyl bromoacetate (0.625 mL, 6.79 mmol) were used in the same manner as in Reference Example 75 to obtain the title compound as a colorless clear oily substance (275 mg, 0.722 mmol, yield: 37%).

$^{1}$H-NMR ($CDCl_3$) δ: 7.55 (1H, d, J=8.2 Hz), 7.36-7.27 (4H, m), 7.25-7.23 (1H, m), 7.16 (1H, ddd, J=8.2, 8.2, 1.8 Hz), 7.04 (1H, d, J=6.9 Hz), 6.95 (1H, ddd, J=7.3, 7.3, 0.9 Hz), 3.83 (1H, d, J=12.3 Hz), 3.54 (3H, s), 3.20 (1H, d, J=12.3 Hz), 2.77-2.73 (1H, m), 2.58 (1H, ddd, J=13.3, 13.3, 2.7 Hz), 2.29 (1H, ddd, J=14.6, 2.7, 2.7 Hz), 1.97 (1H, ddd, J=13.3, 3.2, 3.2 Hz), 1.19 (9H, s).

Example 94: Synthesis of 2-(2-phenyl-1,2,3,4-tetrahydroquinolin-2-yl)methyl acetate

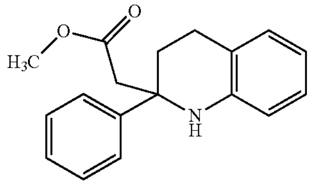 [SMILES: COC(=O)CC1(c2ccccc2)CCc2ccccc2N1]

The tert-butyl 2-(2-methoxy-2-oxoethyl)-2-phenyl-3,4-dihydroquinoline-1(2H)-carboxylate synthesized in Reference Example 77 (57.4 mg, 0.150 mmol) was used in the same manner as in Example 93 to obtain the title compound (hereinafter referred to as the compound of Example 94) as a colorless oily substance (34.4 mg, 0.262 mmol, yield: 81%).

$^{1}$H-NMR ($CDCl_3$) δ: 7.37-7.34 (2H, m), 7.30-7.28 (2H, m), 7.20-7.19 (1H, m), 7.05-7.03 (1H, m), 6.88 (1H, d, J=7.3 Hz), 6.70 (1H, dd, J=8.2, 0.9 Hz), 6.60 (1H, ddd, J=7.3, 7.3, 0.9 Hz), 5.58 (1H, brs), 3.49 (3H, s), 3.09 (1H, d, J=15.6 Hz), 2.86 (1H, d, J=15.6 Hz), 2.57 (1H, ddd, J=16.0, 4.1, 4.1 Hz), 2.31 (1H, ddd, J=16.0, 11.4, 5.0 Hz), 2.22-2.17 (1H, m), 2.02 (1H, ddd, J=12.3, 11.4, 4.6 Hz).

MS(ESI) $[M+H]^+$: 282.

Reference Example 78: Synthesis of 5-(6-chloroquinolin-2-yl)indolin-2-one

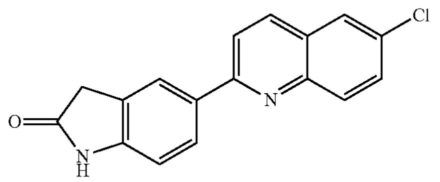 [SMILES: O=C1Cc2cc(-c3ccc4cc(Cl)ccc4n3)ccc2N1]

2,6-Dichloroquinoline (200.0 mg, 1.010 mmol), 5-(4,4,5,5-tetramethyl-1,3,2-dioxaborolan-2-yl)indolin-2-one (287.8 mg, 1.111 mmol), tetrakis(triphenylphosphine)palladium(0) (35.0 mg, 0.030 mmol), and potassium carbonate (348.9 mg, 2.525 mmol) were dissolved in DMF/water (4/1, v/v, 10 mL), and the resulting solution was then stirred with heating at 100° C. for 4 hours. After the reaction mixture was cooled down to room temperature, water was poured into the reaction mixture, and the resulting mixture was filtered. The obtained solid was washed with water, acetone, and chloroform/hexane (9/1) to obtain the title compound as a colorless clear oily substance (243.4 mg, 0.828 mmol, yield: 82%).

$^1$H-NMR (DMSO-$d_6$) δ: 10.63 (1H, s), 8.39 (1H, d, J=8.2 Hz), 8.19-8.14 (3H, m), 8.11 (1H, d, J=2.3 Hz), 8.03 (1H, d, J=9.1 Hz), 7.76 (1H, dd, J=9.1, 2.3 Hz), 6.97 (1H, d, J=8.2 Hz), 3.62 (2H, s).

MS(ESI) $[M+H]^+$: 295.

Example 95: Synthesis of 5-(6-chloro-2,3,4,4-tetrahydroquinolin-2-yl)indolin-2-one (a Novel Compound)

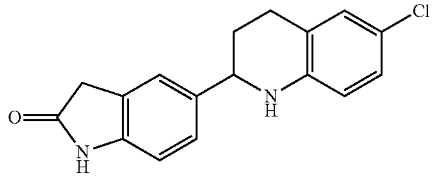 [SMILES: O=C1Cc2cc(C3CCc4cc(Cl)ccc4N3)ccc2N1]

The 5-(6-chloroquinolin-2-yl)indolin-2-one synthesized in Reference Example 78 (243.0 mg, 0.824 mmol) was dissolved in THE (8 mL), and diethyl 1,4-dihydro-2,6-dimethyl-3,5-pyridinedicarboxylate (501 mg, 1.98 mmol) and iodine (20.9 mg, 0.082 mmol) were then added to the resulting solution, and the resulting mixture was stirred at 60° C. for 2 hours. After the reaction was completed, the reaction mixture was concentrated under reduced pressure. The obtained crude product was subjected to column chromatography (silica gel, chloroform/methanol) and suspended and washed with chloroform (6.0 mL) to obtain the title compound (hereinafter referred to as the compound of Example 95) as a pale red solid (157 mg, 0.526 mmol, yield: 64%).

$^1$H-NMR (DMSO-$d_6$) δ: 10.35 (1H, s), 7.18 (1H, s), 7.13 (1H, d, J=7.8 Hz), 6.90-6.89 (2H, m), 6.77 (1H, d, J=7.8 Hz), 6.57 (1H, dd, J=6.6, 2.5 Hz), 6.18 (1H, s), 4.35-4.33 (1H, m), 3.45 (2H, s), 2.79-2.58 (1H, m), 2.58-2.52 (1H, m), 1.95-1.91 (1H, m), 1.82-1.73 (1H, m).

MS(ESI) $[M+H]^+$: 299.

Reference Example 79: Synthesis of 6-chloro-2-(1H-pyrazol-4-yl)quinoline

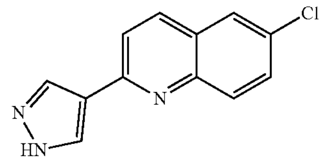 [SMILES: Clc1ccc2nc(-c3cn[nH]c3)ccc2c1]

2,6-Dichloroquinoline (200.0 mg, 1.010 mmol), (1H-pyrazol-4-yl)boronic acid (212.0 mg, 1.616 mmol), tetrakis(triphenylphosphine)palladium(0) (70.0 mg, 0.060 mmol), and potassium carbonate (348.9 mg, 2.525 mmol) were dissolved in DMF/water (5/1, v/v, 10 mL), and the resulting solution was then stirred with heating at 100° C. for 18 hours. After the reaction was completed, water was added to the reaction mixture, and the resulting mixture was extracted with ethyl acetate. The organic layers were combined, washed with saturated brine, and dried over anhydrous sodium sulfate, and the filtrate was then concentrated under reduced pressure. The obtained crude product was purified by column chromatography (silica gel, chloroform/methanol) to obtain the title compound as a pale yellow solid (49.7 mg, 0.214 mmol, yield: 21%).

$^1$H-NMR ($CDCl_3$) δ: 8.27 (2H, s), 8.07 (1H, d, J=8.7 Hz), 7.99 (1H, d, J=9.1 Hz), 7.77 (1H, d, J=2.7 Hz), 7.67 (1H, d, J=8.7 Hz), 7.63 (1H, dd, J=9.1, 2.3 Hz).

MS(ESI) $[M+H]^+$: 230.

Example 96: Synthesis of 6-chloro-2-(1H-pyrazol-4-yl)-1,2,3,4-tetrahydroquinoline (a Novel Compound)

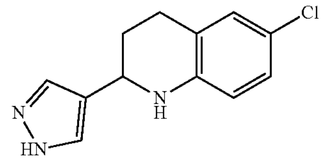 [SMILES: Clc1ccc2c(c1)CCC(c1cn[nH]c1)N2]

The 6-chloro-2-(1H-pyrazol-4-yl)quinoline synthesized in Reference Example 79 (49.7 mg, 0.216 mmol) was dissolved in THF (2.16 mL), and diethyl 1,4-dihydro-2,6-dimethyl-3,5-pyridinedicarboxylate (131.6 mg, 0.519 mmol) and iodine (5.5 mg, 0.022 mmol) were then added to the resulting solution, and the resulting mixture was stirred at 60° C. for 2 hours. After the reaction was completed, the reaction mixture was concentrated under reduced pressure. The obtained crude product was purified by column chromatography (silica gel, chloroform/methanol) to obtain the title compound (hereinafter referred to as the compound of Example 96) as a pale yellow amorphous (37.4 mg, 0.160 mmol, yield: 74%).

$^1$H-NMR ($CDCl_3$) δ: 7.57 (2H, s), 7.00-6.93 (2H, m), 6.44 (1H, d, J=8.2 Hz), 4.48 (1H, dd, J=9.4, 3.0 Hz), 3.98 (1H, brs), 2.92-2.84 (1H, m), 2.73 (1H, dt, J=16.8, 4.9 Hz), 2.16-2.09 (1H, m), 2.01-1.92 (1H, m).

MS(ESI) $[M+H]^+$: 234.

Reference Example 80: Synthesis of 6-methyl-2-(1H-pyrazol-4-yl)quinoline

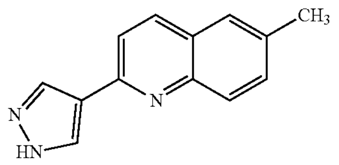 [SMILES: Cc1ccc2nc(-c3cn[nH]c3)ccc2c1]

2-Chloro-6-methylquinoline (200.0 mg, 1.126 mmol), (1H-pyrazol-4-yl)boronic acid (278.0 mg, 2.484 mmol), tetrakis(triphenylphosphine)palladium(0) (70.0 mg, 0.060 mmol), and potassium carbonate (348.9 mg, 2.525 mmol) were dissolved in DMF/water (5/1, v/v, 10 mL), and the resulting solution was then stirred with heating at 100° C. for 18 hours. After the reaction was completed, water was added to the reaction mixture, and the resulting mixture was extracted with ethyl acetate. The organic layers were combined, washed with saturated brine, and dried over anhydrous sodium sulfate, and the filtrate was then concentrated under reduced pressure. The obtained crude product was purified by column chromatography (silica gel, chloro-form/methanol) to obtain the title compound as a pale yellow solid (49.9 mg, 0.236 mmol, yield: 21%).

$^1$H-NMR ($CDCl_3$) δ: 8.26 (1H, s), 8.26 (1H, s), 8.06 (1H, d, J=8.7 Hz), 7.95 (1H, d, J=8.7 Hz), 7.62-7.52 (3H, m), 2.53 (3H, s).

MS(ESI) $[M+H]^+$: 210.

Example 97: Synthesis of 6-methyl-2-(1H-pyrazol-4-yl)-1,2,3,4-tetrahydroquinoline (a Novel Compound)

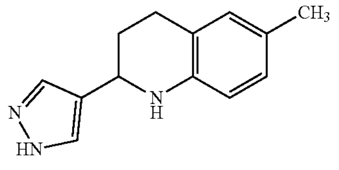 [SMILES: Cc1ccc2c(c1)CCC(c1cn[nH]c1)N2]

The 6-methyl-2-(1H-pyrazol-4-yl)quinoline synthesized in Reference Example 80 (49.9 mg, 0.238 mmol) was dissolved in THF (2.38 mL), and diethyl 1,4-dihydro-2,6-dimethyl-3,5-pyridinedicarboxylate (145.0 mg, 0.572 mmol) and iodine (6.1 mg, 0.024 mmol) were then added to the resulting solution, and the resulting mixture was stirred at 60° C. for 2 hours. After the reaction was completed, the reaction mixture was concentrated under reduced pressure. The obtained crude product was purified by column chromatography (silica gel, chloroform/methanol) to obtain the title compound (hereinafter referred to as the compound of Example 97) as a pale yellow solid (37.2 mg, 0.174 mmol, yield: 73%).

$^1$H-NMR ($CDCl_3$) δ: 7.58 (2H, s), 6.82-6.81 (2H, m), 6.45 (1H, d, J=8.7 Hz), 4.46 (1H, dd, J=9.4, 3.0 Hz), 2.94-2.85 (1H, m), 2.73 (1H, dt, J=16.5, 4.8 Hz), 2.22 (3H, s), 2.16-2.09 (1H, m), 2.03-1.93 (1H, m).

MS(ESI) $[M+H]^+$: 214.

Reference Example 81: Synthesis of 6-fluoro-2-(1H-pyrazol-4-yl)quinoline

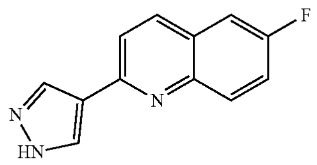 [SMILES: Fc1ccc2nc(-c3cn[nH]c3)ccc2c1]

2-Chloro-6-fluoroquinoline (200.0 mg, 1.101 mmol), (1H-pyrazol-4-yl)boronic acid (272.0 mg, 2.431 mmol), tetrakis(triphenylphosphine)palladium(0) (70.0 mg, 0.060 mmol), and potassium carbonate (348.9 mg, 2.525 mmol) were dissolved in DMF/water (5/1, v/v, 10 mL), and the resulting solution was then stirred with heating at 100° C. for 18 hours. After the reaction was completed, water was added to the reaction mixture, and the resulting mixture was extracted with ethyl acetate. The organic layers were combined, washed with saturated brine, and dried over anhydrous sodium sulfate, and the filtrate was then concentrated under reduced pressure. The obtained crude product was purified by column chromatography (silica gel, chloroform/methanol) to obtain the title compound as a pale yellow solid (69.9 mg, 0.330 mmol, yield: 30%).

$^1$H-NMR ($CDCl_3$) δ: 8.27 (2H, s), 8.10 (1H, d, J=8.7 Hz), 8.05 (1H, dd, J=9.1, 5.5 Hz), 7.66 (1H, d, J=8.7 Hz), 7.47 (1H, td, J=8.7, 3.0 Hz), 7.40 (1H, dd, J=8.7, 3.0 Hz).

MS(ESI) $[M+H]^+$: 214.

Example 98: Synthesis of 6-fluoro-2-(1H-pyrazol-4-yl)-1,2,3,4-tetrahydroquinoline (a Novel Compound)

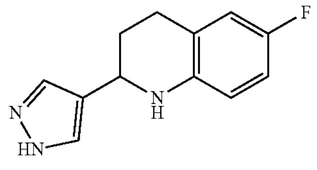 [SMILES: Fc1ccc2c(c1)CCC(c1cn[nH]c1)N2]

The 6-fluoro-2-(1H-pyrazol-4-yl)quinoline synthesized in Reference Example 81 (69.9 mg, 0.328 mmol) was dissolved in THF (3.28 mL), and diethyl 1,4-dihydro-2,6-dimethyl-3,5-pyridinedicarboxylate (199.3 mg, 0.787 mmol) and iodine (8.3 mg, 0.033 mmol) were then added to the resulting solution, and the resulting mixture was stirred at 60° C. for 3.5 hours. After the reaction was completed, the reaction mixture was concentrated under reduced pressure. The obtained crude product was purified by column chromatography (silica gel, chloroform/methanol) to obtain the title compound (hereinafter referred to as the compound of Example 98) as a pale yellow amorphous (49.9 mg, 0.230 mmol, yield: 70%).

$^1$H-NMR ($CDCl_3$) δ: 7.58 (2H, s), 6.74-6.69 (2H, m), 6.47-6.43 (1H, m), 4.45 (1H, dd, J=9.4, 3.0 Hz), 2.95-2.87 (1H, m), 2.74 (1H, dt, J=16.8, 4.8 Hz), 2.16-2.10 (1H, m), 2.02-1.93 (1H, m).

MS(ESI) $[M+H]^+$: 218.

Reference Example 82: Synthesis of 4-(6-methylquinolin-2-yl)benzamide

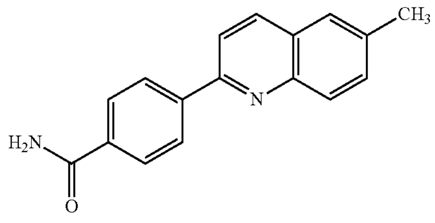 [SMILES: Cc1ccc2nc(-c3ccc(C(N)=O)cc3)ccc2c1]

2-Chloro-6-methylquinoline (250 mg, 1.41 mmol), 4-aminocarbonylphenylboronic acid (348 mg, 2.11 mmol), tetrakis(triphenylphosphine)palladium(0) (48.8 mg, 0.0422 mmol), and potassium carbonate (486 mg, 3.52 mmol) were dissolved in DMF/water (5/1, v/v, 12 mL), and the resulting solution was then stirred with heating at 100° C. for 3 hours. Water was added at room temperature to the reaction mixture, and the precipitated solid was filtered. The obtained solid was washed with chloroform/hexane and filtered to obtain the title compound as a pale brown solid (283 mg, 1.08 mmol, yield: 77%).

$^1$H-NMR ($CDCl_3$) δ: 8.26 (2H, d, J=8.2 Hz), 8.18 (1H, d, J=8.2 Hz), 8.07 (1H, d, J=8.2 Hz), 7.97 (2H, d, J=8.2 Hz), 7.88 (1H, d, J=8.2 Hz), 7.62 (1H, d, J=2.0 Hz), 7.59 (1H, dd, J=8.2, 2.0 Hz), 6.15 (1H, brs), 5.62 (1H, brs), 2.57 (3H, s).

MS(ESI) $[M+H]^+$: 262.

Example 99: Synthesis of 4-(6-methyl-1,2,3,4-tetrahydroquinolin-2-yl)benzamide (a Novel Compound)

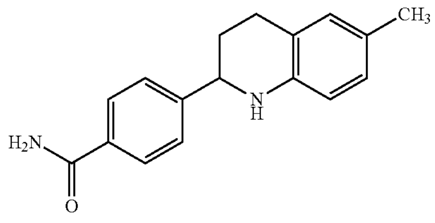 [SMILES: Cc1ccc2c(c1)CCC(c1ccc(C(N)=O)cc1)N2]

The 4-(6-methylquinolin-2-yl)benzamide synthesized in Reference Example 82 (280 mg, 1.07 mmol) was dissolved in tetrahydrofuran (8.0 mL), and diethyl 1,4-dihydro-2,6-dimethyl-3,5-pyridinedicarboxylate (649 mg, 2.56 mmol) and iodine (27.1 mg, 0.107 mmol) were then added to the resulting solution, and the resulting mixture was stirred at 50° C. for 17 hours. After the reaction was completed, the reaction mixture was concentrated under reduced pressure. The obtained crude product was purified by column chromatography (silica gel, chloroform/methanol) to obtain the title compound (hereinafter referred to as the compound of Example 99) as a white solid (188 mg, 0.706 mmol, yield: 66%).

$^1$H-NMR ($CDCl_3$) δ: 7.79 (2H, d, J=8.2 Hz), 7.48 (2H, d, J=8.2 Hz), 6.86-6.83 (2H, m), 6.51 (1H, d, J=8.2 Hz), 6.06 (1H, brs), 5.56 (1H, brs), 4.48 (1H, dd, J=8.8, 3.4 Hz), 4.02 (1H, brs), 2.93-2.85 (1H, m), 2.68 (1H, td, J=10.8, 5.6 Hz), 2.24 (3H, s), 2.15-2.09 (1H, m), 2.02-1.93 (1H, m).

MS(ESI) $[M+H]^+$: 267.

Reference Example 83: Synthesis of 4-(6-methylquinolin-2-yl)benzenesulfonamide

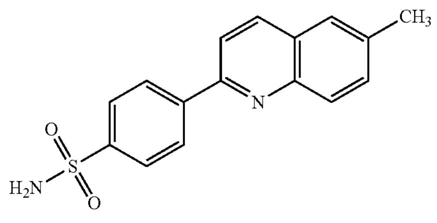 [SMILES: Cc1ccc2nc(-c3ccc(S(N)(=O)=O)cc3)ccc2c1]

2-Chloro-6-methylquinoline (250 mg, 1.41 mmol), 4-aminosulfonylphenylboronic acid (424 mg, 2.11 mmol), tetrakis(triphenylphosphine)palladium(0) (48.8 mg, 0.0422 mmol), and potassium carbonate (486 mg, 3.52 mmol) were dissolved in DMF/water (5/1, v/v, 12 mL), and the resulting solution was then stirred with heating at 100° C. for 3 hours. Water was added at room temperature to the reaction mixture, and the precipitated solid was filtered and washed with hexane/chloroform to obtain the title compound as a pale brown solid (320 mg, 1.07 mmol, yield: 76%).

$^1$H-NMR ($CDCl_3$) δ: 8.32 (2H, d, J=8.6 Hz), 8.20 (1H, d, J=8.6 Hz), 8.07 (3H, d, J=8.6 Hz), 7.87 (1H, d, J=8.6 Hz), 7.63-7.59 (2H, m), 4.82 (2H, brs), 2.57 (3H, s).

MS(ESI) $[M+H]^+$: 299.

Example 100: Synthesis of 4-(6-methyl-1,2,3,4-tetrahydroquinolin-2-yl)benzenesulfonamide (a Novel Compound)

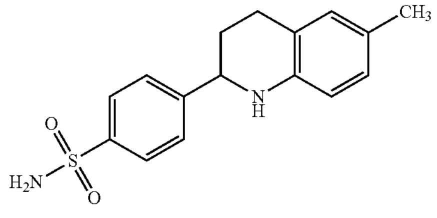 [SMILES: Cc1ccc2c(c1)CCC(c1ccc(S(N)(=O)=O)cc1)N2]

The 4-(6-methylquinolin-2-yl)benzenesulfonamide synthesized in Reference Example 83 (310 mg, 1.04 mmol) was dissolved in tetrahydrofuran (10 mL), and diethyl 1,4-dihydro-2,6-dimethyl-3,5-pyridinedicarboxylate (631 mg, 2.49 mmol) and iodine (26.4 mg, 0.104 mmol) were then added to the resulting solution, and the resulting mixture was stirred at 50° C. for 18 hours. After the reaction was completed, the reaction mixture was concentrated under reduced pressure. The obtained crude product was purified by column chromatography (silica gel, hexane/ethyl acetate) to obtain the title compound (hereinafter referred to as the compound of Example 100) as a white solid (186 mg, 0.615 mmol, yield: 59%).

$^1$H-NMR ($CDCl_3$) δ: 7.90 (2H, d, J=8.6 Hz), 7.55 (2H, d, J=8.6 Hz), 6.87-6.84 (2H, m), 6.51 (1H, d, J=7.7 Hz), 4.77 (2H, s), 4.51 (1H, dd, J=8.8, 3.4 Hz), 3.96 (1H, s), 2.92-2.84 (1H, m), 2.66 (1H, td, J=10.8, 5.6 Hz), 2.15-2.09 (1H, m), 2.01-1.92 (1H, m).

MS(ESI) $[M+H]^+$: 303.

Reference Example 84: Synthesis of 6-methyl-3',4'-dihydro-[2,6'-biquinolin]-2'(1'H)-one

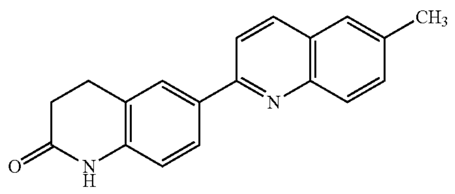 [SMILES: Cc1ccc2nc(-c3ccc4c(c3)CCC(=O)N4)ccc2c1]

2-Chloro-6-methylquinoline (250 mg, 1.41 mmol), 6-(4,4,5,5-tetramethyl-1,3,2-dioxaborolan-2-yl)-3,4-dihydroquinolin-2(1H)-one (576 mg, 2.11 mmol), tetrakis(triphenylphosphine)palladium(0) (48.8 mg, 0.0422 mmol), and potassium carbonate (486 mg, 3.52 mmol) were dissolved in DMF/water (5/1, v/v, 12 mL), and the resulting solution was then stirred with heating at 100° C. for 3 hours. Water was added at room temperature to the reaction mixture, and the precipitated solid was filtered and washed with chloroform/hexane to obtain the title compound (357 mg, 1.24 mmol, yield: 88%) as a pale brown solid.

$^1$H-NMR ($CDCl_3$) δ: 8.12 (1H, d, J=8.6 Hz), 8.06-8.02 (2H, m), 7.94 (1H, dd, J=8.2, 1.8 Hz), 7.80 (1H, d, J=8.6 Hz), 7.72 (1H, brs), 7.59 (1H, s), 7.56 (1H, dd, J=8.6, 1.8 Hz), 6.87 (1H, d, J=8.2 Hz), 3.11 (2H, t, J=7.5 Hz), 2.71 (2H, t, J=7.5 Hz), 2.55 (3H, s).

MS(ESI) $[M+H]^+$: 289.

Example 101: Synthesis of 6-methyl-1,2,3,3',4,4'-hexahydro-[2,6'-biquinolin]-2'(1'H)-one (a Novel Compound)

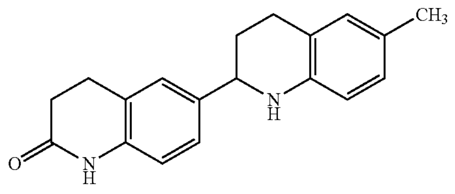 [SMILES: Cc1ccc2c(c1)CCC(c1ccc3c(c1)CCC(=O)N3)N2]

The 6-methyl-3',4'-dihydro-[2,6'-biquinolin]-2'(1'H)-one synthesized in Reference Example 84 (240 mg, 0.832 mmol) was dissolved in tetrahydrofuran (8 mL), and diethyl 1,4-dihydro-2,6-dimethyl-3,5-pyridinedicarboxylate (506 mg, 2.00 mmol) and iodine (21.1 mg, 0.0832 mmol) were then added to the resulting solution, and the resulting mixture was stirred at 50° C. for 26 hours. After the reaction was completed, the reaction mixture was concentrated under reduced pressure. The obtained crude product was purified by column chromatography (silica gel, hexane/ethyl acetate) to obtain the title compound (hereinafter referred to as the compound of Example 101) as a white solid (200 mg, 0.684 mmol, yield: 82%).

$^1$H-NMR ($CDCl_3$) δ: 7.49 (1H, brs), 7.22-7.17 (2H, m), 6.84-6.83 (2H, m), 6.70 (1H, d, J=8.2 Hz), 6.50-6.47 (1H, m), 4.34 (1H, dd, J=9.5, 3.2 Hz), 3.88 (1H, brs), 2.98-2.87 (3H, m), 2.75-2.68 (1H, m), 2.63 (2H, dd, J=8.4, 6.6 Hz), 2.23 (3H, s), 2.11-1.93 (2H, m).

MS(ESI) $[M+H]^+$: 293.

Reference Example 85: Synthesis of 2-(furan-3-yl)-6-methylquinoline

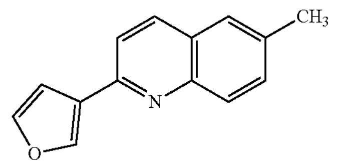 [SMILES: Cc1ccc2nc(-c3ccoc3)ccc2c1]

2-Chloro-6-methylquinoline (100 mg, 0.563 mmol), 3-furylboronic acid (94.5 mg, 0.844 mmol), tetrakis(triphenylphosphine)palladium(0) (19.5 mg, 0.0169 mmol), and potassium carbonate (195 mg, 1.41 mmol) were dissolved in DMF/water (5/1, v/v, 3.6 mL), and the resulting solution was then stirred with heating at 100° C. for 4 hours. After the reaction mixture was cooled down to room temperature, water was poured into the reaction mixture, and the resulting mixture was extracted with ethyl acetate. The organic layer was dried over anhydrous sodium sulfate and then concentrated under reduced pressure. The obtained crude product was purified by column chromatography (silica gel, hexane/ethyl acetate) to obtain the title compound as a white solid (118 mg, 0.563 mmol, yield: 100%).

$^1$H-NMR ($CDCl_3$) δ: 8.12 (1H, dd, J=1.8, 0.9 Hz), 8.03 (1H, d, J=9.1 Hz), 7.97 (1H, d, J=9.1 Hz), 7.56-7.51 (4H, m), 7.09 (1H, dd, J=1.8, 0.9 Hz), 2.52 (3H, s).

MS(ESI) $[M+H]^+$: 210.

Example 102: Synthesis of 2-(furan-3-yl)-6-methyl-1,2,3,4-tetrahydroquinoline (a Novel Compound)

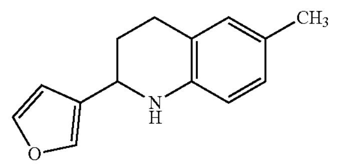 [SMILES: Cc1ccc2c(c1)CCC(c1ccoc1)N2]

The 2-(furan-3-yl)-6-methylquinoline synthesized in Reference Example 85 (115 mg, 0.550 mmol) was used in the same manner as in Example 72 to obtain the title compound (hereinafter referred to as the compound of Example 102) as a white solid (113 mg, 0.531 mmol, yield: 97%).

$^1$H-NMR ($CDCl_3$) δ: 7.39-7.38 (2H, m), 6.82-6.80 (2H, m), 6.45 (1H, d, J=8.6 Hz), 6.41 (1H, dd, J=1.6, 1.1 Hz), 4.37 (1H, dd, J=9.1, 3.2 Hz), 2.92-2.83 (1H, m), 2.72 (1H, dt, J=16.5, 4.8 Hz), 2.22 (3H, s), 2.13-2.06 (1H, m), 2.01-1.91 (1H, m).

MS(ESI) $[M+H]^+$: 214.

Reference Example 86: Synthesis of 4-(6-methylquinolin-2-yl)thiazole

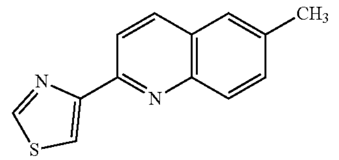 [SMILES: Cc1ccc2nc(-c3cscn3)ccc2c1]

2-Chloro-6-methylquinoline (70.0 mg, 0.394 mmol), thiazol-4-ylboronic acid (76.2 mg, 0.591 mmol), 1,1'-bis(diphenylphosphino)ferrocenepalladium(II) dichloride (32.2 mg, 0.0394 mmol), and potassium carbonate (109 mg, 0.788 mmol) were dissolved in 1,2-dimethoxyethane/water (8/1, v/v, 2.25 mL), and the resulting solution was then stirred with heating at 90° C. for 5 hours. After the reaction mixture was cooled down to room temperature, the reaction mixture was concentrated under reduced pressure. The obtained crude product was purified by column chromatography (silica gel, hexane/ethyl acetate) to obtain the title compound as a white solid (5.00 mg, 0.0221 mmol, yield: 5.6%).

$^1$H-NMR ($CDCl_3$) δ: 8.94 (1H, d, J=1.8 Hz), 8.34 (1H, s), 8.27 (1H, d, J=8.6 Hz), 8.17 (1H, d, J=8.6 Hz), 8.04 (1H, d, J=8.6 Hz), 7.60 (1H, s), 7.56 (1H, dd, J=8.6, 1.8 Hz), 2.55 (3H, s).

MS(ESI) $[M+H]^+$: 227.

Example 103: Synthesis of 4-(6-methyl-1,2,3,4-tetrahydroquinolin-2-yl)thiazole (a Novel Compound)

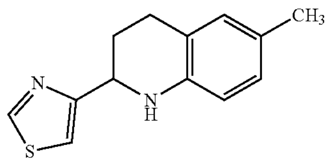 [SMILES: Cc1ccc2c(c1)CCC(c1cscn1)N2]

The 4-(6-methylquinolin-2-yl)thiazole synthesized in Reference Example 86 (5.00 mg, 0.0221 mmol) was used in the same manner as in Example 72 to obtain the title compound (hereinafter referred to as the compound of Example 103) as a pale yellow oily substance (2.00 mg, 0.00869 mmol, yield: 39%).

$^1$H-NMR ($CDCl_3$) δ: 8.80 (1H, d, J=2.0 Hz), 7.22 (1H, dd, J=2.0, 1.1 Hz), 6.85-6.82 (2H, m), 6.54 (1H, d, J=7.7 Hz), 4.73 (1H, dd, J=8.2, 3.6 Hz), 2.91-2.83 (1H, m), 2.66 (1H, td, J=11.1, 5.4 Hz), 2.34-2.26 (1H, m), 2.23 (3H, s), 2.19-2.10 (1H, m).

MS(ESI) $[M+H]^+$: 231.

Reference Example 87: Synthesis of 4-(6-methylquinolin-2-yl)isoxazole

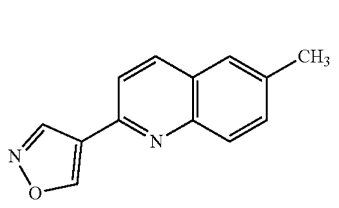 [SMILES: Cc1ccc2nc(-c3cnoc3)ccc2c1]

2-Chloro-6-methylquinoline (70.0 mg, 0.394 mmol), 4-(4,4,5,5-tetramethyl-1,3,2-dioxaborolan-2-ylisoxazole (115 mg, 0.591 mmol), 1,1'-bis(diphenylphosphino)ferrocenepalladium(II) dichloride (32.2 mg, 0.0394 mmol), and potassium carbonate (109 mg, 0.788 mmol) were dissolved in DMF/water (5/1, v/v, 3.6 mL), and the resulting solution was then stirred with heating at 90° C. for 5 hours. After the reaction mixture was cooled down to room temperature, the reaction mixture was concentrated under reduced pressure. The obtained crude product was purified by column chromatography (silica gel, hexane/ethyl acetate) to obtain the title compound as a white solid (17.0 mg, 0.0808 mmol, yield: 21%).

$^1$H-NMR ($CDCl_3$) δ: 9.05 (1H, brs), 8.97 (1H, s), 8.12 (1H, d, J=8.6 Hz), 7.99 (1H, d, J=8.6 Hz), 7.59-7.55 (3H, m), 2.55 (3H, s).

MS(ESI) $[M+H]^+$: 211.

Example 104: Synthesis of 4-(6-methyl-1,2,3,4-tetrahydroquinolin-2-yl)isoxazole (a Novel Compound)

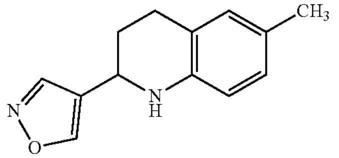 [SMILES: Cc1ccc2c(c1)CCC(c1cnoc1)N2]

The 4-(6-methylquinolin-2-yl)isoxazole synthesized in Reference Example 87 (17.0 mg, 0.0808 mmol) was used in the same manner as in Example 72 to obtain the title compound (hereinafter referred to as the compound of Example 104) as a white solid (12.0 mg, 0.0560 mmol, yield: 69%).

$^1$H-NMR ($CDCl_3$) δ: 8.38 (1H, s), 8.30 (1H, s), 6.85-6.83 (2H, m), 6.47 (1H, d, J=8.6 Hz), 4.47 (1H, dd, J=9.1, 3.2 Hz), 2.93-2.84 (1H, m), 2.71 (1H, td, J=10.9, 5.7 Hz), 2.23 (3H, s), 2.17-2.10 (1H, m), 2.03-1.93 (1H, m).

MS(ESI) $[M+H]^+$: 215.

Reference Example 88: Synthesis of 4-(7-methylquinolin-2-yl)benzenesulfonamide

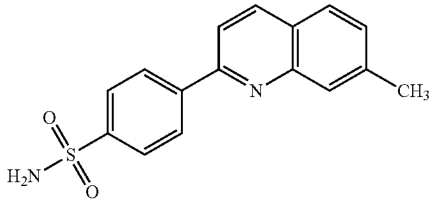 [SMILES: Cc1ccc2ccc(-c3ccc(S(N)(=O)=O)cc3)nc2c1]

2-Chloro-7-methylquinoline (110 mg, 0.619 mmol) and (4-sulfamoylphenyl)boronic acid (187 mg, 0.929 mmol) were used in the same manner as in Reference Example 11 to obtain the title compound as a white solid (185 mg, 0.619 mmol, yield: 100%).

$^1$H-NMR (DMSO-$d_6$) δ: 8.46 (1H, d, J=8.7 Hz), 8.44-8.40 (2H, m), 8.15 (1H, d, J=8.7 Hz), 7.99-7.95 (2H, m), 7.94-7.90 (2H, m), 7.48 (1H, dd, J=8.2, 1.8 Hz), 2.56 (3H, s).

MS(ESI) $[M+H]^+$: 299.

Example 105: Synthesis of 4-(7-methyl-1,2,3,4-tetrahydroquinolin-2-yl)benzenesulfonamide (a Novel Compound)

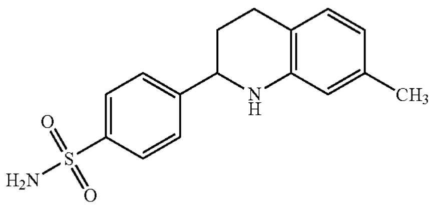 [SMILES: Cc1ccc2c(c1)NC(c1ccc(S(N)(=O)=O)cc1)CC2]

The 4-(7-methylquinolin-2-yl)benzenesulfonamide synthesized in Reference Example 88 (185 mg, 0.619 mmol) was used in the same manner as in Example 72 to obtain the title compound (hereinafter referred to as the compound of Example 105) as a white solid (135 mg, 0.447 mmol, yield: 72%).

$^1$H-NMR ($CDCl_3$) δ: 7.92-7.88 (2H, m), 7.56-7.52 (4H, m), 6.90 (1H, d, J=7.8 Hz), 6.52 (1H, dd, J=7.8, 0.9 Hz), 6.42-6.41 (1H, m), 4.81 (2H, s), 4.53 (1H, dd, J=8.7, 3.7 Hz), 4.01 (1H, brs), 2.90-2.81 (1H, m), 2.69-2.61 (1H, m), 2.26 (3H, s), 2.16-2.08 (1H, m), 2.00-1.90 (1H, m).

MS(ESI) $[M+H]^+$: 303.

Reference Example 89: Synthesis of 4-(7-methylquinolin-2-yl)benzamide

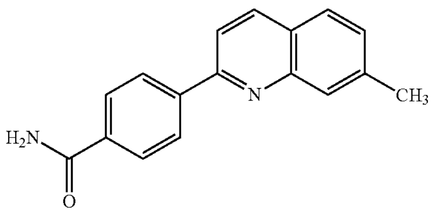 [SMILES: Cc1ccc2ccc(-c3ccc(C(N)=O)cc3)nc2c1]

2-Chloro-7-methylquinoline (126 mg, 0.709 mmol) and (4-carbamoylphenyl)boronic acid (176 mg, 1.06 mmol) were used in the same manner as in Reference Example 11 to obtain the title compound as a white solid (173 mg, 0.658 mmol, yield: 93%).

$^1$H-NMR (DMSO-$d_6$) δ: 8.44 (1H, d, J=8.5 Hz), 8.36-8.33 (2H, m), 8.15 (1H, d, J=8.5 Hz), 8.12-8.09 (1H, m), 8.06-8.03 (2H, m), 7.93-7.90 (2H, m), 7.49-7.46 (2H, m), 2.56 (3H, s).

MS(ESI) $[M+H]^+$: 263.

Example 106: Synthesis of 4-(7-methyl-1,2,3,4-tetrahydroquinolin-2-yl)benzamide (a Novel Compound)

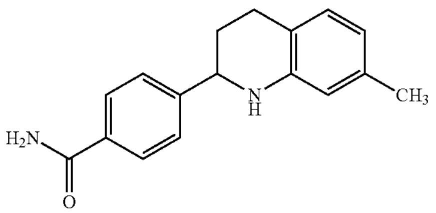 [SMILES: Cc1ccc2c(c1)NC(c1ccc(C(N)=O)cc1)CC2]

The 4-(7-methylquinolin-2-yl)benzamide synthesized in Reference Example 89 (170 mg, 0.648 mmol) was used in the same manner as in Example 72 to obtain the title compound (hereinafter referred to as the compound of Example 106) as a white solid (170 mg, 0.638 mmol, yield: 98%).

$^1$H-NMR ($CDCl_3$) δ: 7.81-7.77 (2H, m), 7.48-7.45 (2H, m), 6.90 (1H, d, J=7.8 Hz), 6.52-6.49 (1H, m), 6.42-6.40 (1H, m), 6.07 (1H, brs), 5.64 (1H, brs), 4.50 (1H, dd, J=8.7, 3.2 Hz), 4.01 (1H, brs), 2.91-2.82 (1H, m), 2.70-2.63 (1H, m), 2.25 (3H, s), 2.15-2.08 (1H, m), 2.01-1.91 (1H, m).

MS(ESI) $[M+H]^+$: 367.

Reference Example 90: Synthesis of 4-(6-fluoroquinolin-2-yl)benzenesulfonamide

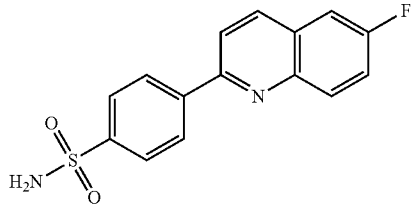 [SMILES: NS(=O)(=O)c1ccc(-c2ccc3cc(F)ccc3n2)cc1]

2-Chloro-6-fluoroquinoline (300 mg, 1.65 mmol) and (4-sulfamoylphenyl)boronic acid (498 mg, 2.48 mmol) were used in the same manner as in Reference Example 11 to obtain the title compound as a white solid (267 mg, 0.883 mmol, yield: 54%).

$^1$H-NMR (DMSO-$d_6$) δ: 8.53 (1H, d, J=8.9 Hz), 8.47-8.43 (2H, m), 8.29 (1H, d, J=8.9 Hz), 8.21-8.16 (1H, m), 8.01-7.98 (2H, m), 7.88-7.85 (1H, m), 7.77-7.71 (1H, m), 7.40 (2H, brs).

MS(ESI) $[M+H]^+$: 267.

Example 107: Synthesis of 4-(6-fluoro-1,2,3,4-tetrahydroquinolin-2-yl)benzenesulfonamide (a Novel Compound)

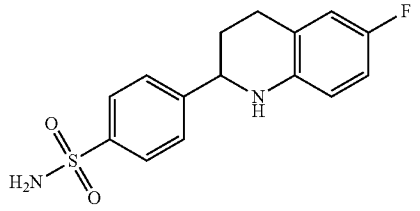 [SMILES: NS(=O)(=O)c1ccc(C2CCc3cc(F)ccc3N2)cc1]

The 4-(6-fluoroquinolin-2-yl)benzenesulfonamide synthesized in Reference Example 90 (265 mg, 0.877 mmol) was used in the same manner as in Example 72 to obtain the title compound (hereinafter referred to as the compound of Example 107) as a white solid (211 mg, 0.689 mmol, yield: 70%).

$^1$H-NMR ($CDCl_3$) δ: 7.93-7.89 (2H, m), 7.56-7.52 (2H, m), 6.78-6.72 (2H, m), 6.53-6.49 (1H, m), 4.84-4.81 (2H, m), 4.50 (1H, dd, J=9.1, 3.2 Hz), 3.97 (1H, brs), 2.95-2.86 (1H, m), 2.72-2.65 (1H, m), 2.16-2.09 (1H, m), 2.01-1.92 (1H, m).

MS(ESI) $[M+H]^+$: 307.

Example 108: Obtainment of One of the Optical Isomers of 4-(6-fluoro-1,2,3,4-tetrahydroquinolin-2-yl)benzenesulfonamide (a Novel Compound)

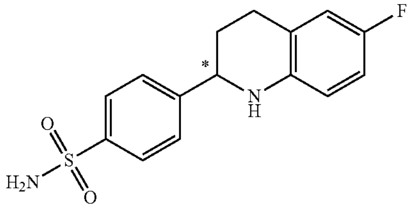 [SMILES: NS(=O)(=O)c1ccc(C2CCc3cc(F)ccc3N2)cc1]

In the formula, the carbon atom marked with an asterisk (*) is an asymmetric center.

The 4-(6-fluoro-1,2,3,4-tetrahydroquinolin-2-yl)benzenesulfonamide synthesized in Example 107 (58.0 mg, 0.189 mmol) was dissolved in propan-2-ol (5.8 mL) and optically resolved using HPLC under the following conditions to obtain the title compound (hereinafter referred to as the compound of Example 108) as a white solid (24.0 mg, 0.0783 mmol, yield: 41%, enantiomeric excess: 99.8% ee).

$^1$H-NMR ($CDCl_3$) δ: 7.93-7.89 (2H, m), 7.56-7.52 (2H, m), 6.78-6.72 (2H, m), 6.53-6.49 (1H, m), 4.84-4.81 (2H, m), 4.50 (1H, dd, J=9.1, 3.2 Hz), 3.97 (1H, brs), 2.95-2.86 (1H, m), 2.72-2.65 (1H, m), 2.16-2.09 (1H, m), 2.01-1.92 (1H, m).

MS(ESI) $[M+H]^+$: 307.

Conditions for optical resolution using HPLC:

Column: Daicel Chiralcel OZ-H chiral column (inner diameter: 20 mm, length: 250 mm, particle size: 5 μm)

Column temperature: 40° C.

Mobile phase: propan-2-ol:hexane=70:30

Total injection volume: 6.8 mL (0.80 to 1.0 mL/injection)

Flow rate: 10 mL/min

Detection: UV (254 nm)

Rt: 11.34 min

HPLC analysis conditions:

Column: Daicel Chiralcel OZ-3 chiral column (inner diameter: 4.6 mm, length: 150 mm, particle size: 3 μm)

Column temperature: 40° C.

Mobile phase: propan-2-ol:hexane=40:60

Flow rate: 0.6 mL/min

Detection: UV (254 nm)

Rt: 9.26 min

Example 109: Obtainment of the Other of the Optical Isomers of 4-(6-fluoro-1,2,3,4-tetrahydro-quinolin-2-yl)benzenesulfonamide (a Novel Compound)

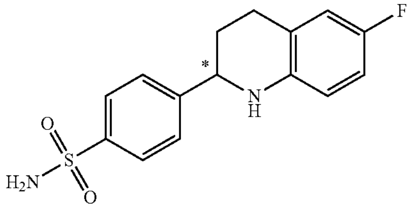 [SMILES: NS(=O)(=O)c1ccc(C2CCc3cc(F)ccc3N2)cc1]

In the formula, the carbon atom marked with an asterisk (*) is an asymmetric center.

The 4-(6-fluoro-1,2,3,4-tetrahydroquinolin-2-yl)benzenesulfonamide synthesized in Example 107 (58.0 mg, 0.189 mmol) was dissolved in propan-2-ol (5.8 mL) and optically resolved using HPLC under the following conditions to obtain the title compound (hereinafter referred to as the compound of Example 109) as a white solid (23.2 mg, 0.0757 mmol, yield: 39%, enantiomeric excess: 99.9% ee).

$^1$H-NMR ($CDCl_3$) δ: 7.93-7.89 (2H, m), 7.56-7.52 (2H, m), 6.78-6.72 (2H, m), 6.53-6.49 (1H, m), 4.84-4.81 (2H, m), 4.50 (1H, dd, J=9.1, 3.2 Hz), 3.97 (1H, brs), 2.95-2.86 (1H, m), 2.72-2.65 (1H, m), 2.16-2.09 (1H, m), 2.01-1.92 (1H, m).

MS(ESI) $[M+H]^+$: 307.

Conditions for optical resolution using HPLC:

Column: Daicel Chiralcel OZ-H chiral column (inner diameter: 20 mm, length: 250 mm, particle size: 5 μm)

Column temperature: 40° C.

Mobile phase: propan-2-ol:hexane=70:30

Total injection volume: 6.8 mL (0.80 to 1.0 mL/injection)

Flow rate: 10 mL/min

Detection: UV (254 nm)

Rt: 16.55 min

HPLC analysis conditions:

Column: Daicel Chiralcel OZ-3 chiral column (inner diameter: 4.6 mm, length: 150 mm, particle size: 3 μm)

Column temperature: 40° C.

Mobile phase: propan-2-ol:hexane=40:60

Flow rate: 0.6 mL/min

Detection: UV (254 nm)

Rt: 15.96 min

Example 110: Obtainment of One of the Optical Isomers of 4-(6-methyl-1,2,3,4-tetra-hydroquinolin-2-yl)benzamide (a Novel Compound)

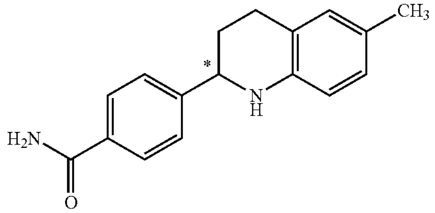 [SMILES: Cc1ccc2c(c1)CCC(c1ccc(C(N)=O)cc1)N2]

In the formula, the carbon atom marked with an asterisk (*) is an asymmetric center.

The 4-(6-methyl-1,2,3,4-tetrahydroquinolin-2-yl)benzamide synthesized in Example 99 (60.0 mg, 0.225 mmol) was dissolved in propan-2-ol (30 mL) and optically resolved using HPLC under the following conditions to obtain the title compound (hereinafter referred to as the compound of Example 110) as a white solid (21.0 mg, 0.0788 mmol, yield: 35%, enantiomeric excess: 100% ee).

$^1$H-NMR ($CDCl_3$) δ: 7.79 (2H, d, J=8.2 Hz), 7.48 (2H, d, J=8.2 Hz), 6.86-6.83 (2H, m), 6.51 (1H, d, J=8.2 Hz), 6.06 (1H, brs), 5.56 (1H, brs), 4.48 (1H, dd, J=8.8, 3.4 Hz), 4.02 (1H, brs), 2.93-2.85 (1H, m), 2.68 (1H, td, J=10.8, 5.6 Hz), 2.24 (3H, s), 2.15-2.09 (1H, m), 2.02-1.93 (1H, m).

MS(ESI) $[M+H]^+$: 267.

Conditions for optical resolution using HPLC:
Column: Daicel Chiralcel OD-H chiral column
(inner diameter: 20 mm, length: 250 mm, particle size: 5 μm)
Column temperature: 40° C.
Mobile phase: propan-2-ol:hexane=70:30
Total injection volume: 30 mL (1.0 to 5.0 mL/injection)
Flow rate: 10 mL/min
Detection: UV (254 nm)
Rt: 12.51 min
HPLC analysis conditions:
Column: Daicel Chiralcel OD-H chiral column
(inner diameter: 4.6 mm, length: 250 mm, particle size: 5 μm)
Column temperature: 40° C.
Mobile phase: propan-2-ol:hexane=40:60
Flow rate: 0.6 mL/min
Detection: UV (254 nm)
Rt: 11.30 min

Example 111: Obtainment of the Other of the Optical Isomers of 4-(6-methyl-1,2,3,4-tetrahydroquinolin-2-yl)benzamide (a Novel Compound)

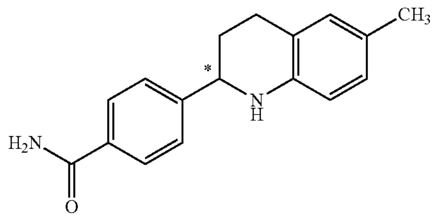 [SMILES: Cc1ccc2c(c1)CCC(c1ccc(C(N)=O)cc1)N2]

In the formula, the carbon atom marked with an asterisk (*) is an asymmetric center.

The 4-(6-methyl-1,2,3,4-tetrahydroquinolin-2-yl)benzamide synthesized in Example 99 (60.0 mg, 0.225 mmol) was dissolved in propan-2-ol (30 mL) and optically resolved using HPLC under the following conditions to obtain the title compound (hereinafter referred to as the compound of Example 111) as a white solid (25.5 mg, 0.0957 mmol, yield: 43%, enantiomeric excess: 99.9% ee).

$^1$H-NMR ($CDCl_3$) δ: 7.79 (2H, d, J=8.2 Hz), 7.48 (2H, d, J=8.2 Hz), 6.86-6.83 (2H, m), 6.51 (1H, d, J=8.2 Hz), 6.06 (1H, brs), 5.56 (1H, brs), 4.48 (1H, dd, J=8.8, 3.4 Hz), 4.02 (1H, brs), 2.93-2.85 (1H, m), 2.68 (1H, td, J=10.8, 5.6 Hz), 2.24 (3H, s), 2.15-2.09 (1H, m), 2.02-1.93 (1H, m).

MS(ESI) [M+H]$^+$: 267.

Conditions for optical resolution using HPLC:
Column: Daicel Chiralcel OD-H chiral column
(inner diameter: 20 mm, length: 250 mm, particle size: 5 μm)
Column temperature: 40° C.
Mobile phase: propan-2-ol:hexane=70:30
Total injection volume: 30 mL (1.0 to 5.0 mL/injection)
Flow rate: 10 mL/min
Detection: UV (254 nm)
Rt: 15.51 min
HPLC analysis conditions:
Column: Daicel Chiralcel OD-H chiral column
(inner diameter: 4.6 mm, length: 150 mm, particle size: 5 μm)
Column temperature: 40° C.
Mobile phase: propan-2-ol:hexane=40:60
Flow rate: 0.6 mL/min
Detection: UV (254 nm)
Rt: 15.51 min

Reference Example 91: Synthesis of 4-(5-methylquinolin-2-yl)benzenesulfonamide

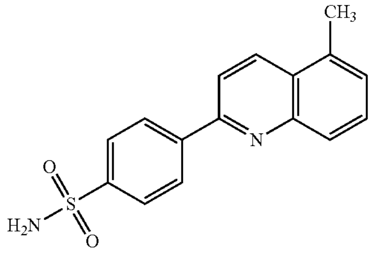

2-Chloro-5-methylquinoline (30.0 mg, 0.169 mmol) and (4-sulfamoylphenyl)boronic acid (37.3 mg, 0.186 mmol) were used in the same manner as in Reference Example 11 to obtain the title compound as a white solid (46.3 mg, 0.155 mmol, yield: 92%).

$^1$H-NMR (DMSO-$d_6$) δ: 8.61 (1H, d, J=8.7 Hz), 8.50-8.46 (2H, m), 8.25 (1H, d, J=8.7 Hz), 8.02-7.98 (2H, m), 7.97-7.94 (1H, m), 7.72-7.68 (2H, m), 7.49-7.47 (3H, m), 2.71 (3H, s).

MS(ESI) [M+H]$^+$: 299.

Example 112: Synthesis of 4-(5-methyl-1,2,3,4-tetrahydroquinolin-2-yl)benzenesulfonamide (a Novel Compound)

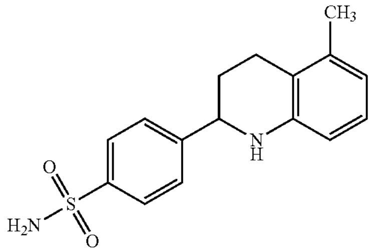

The 4-(5-methylquinolin-2-yl)benzenesulfonamide synthesized in Reference Example 91 (44.0 mg, 0.147 mmol) was used in the same manner as in Example 72 to obtain the title compound (hereinafter referred to as the compound of Example 112) as a white solid (23.3 mg, 0.0771 mmol, yield: 52%).

$^1$H-NMR ($CDCl_3$) δ: 7.92-7.89 (2H, m), 7.57-7.53 (2H, m), 6.95 (1H, dd, J=7.6, 7.6 Hz), 6.59 (1H, d, J=7.6 Hz), 6.47 (1H, d, J=7.6 Hz), 4.81 (2H, s), 4.50-4.46 (1H, m), 4.04 (1H, brs), 2.79-2.71 (1H, m), 2.67-2.60 (1H, m), 2.20 (3H, s), 2.19-2.13 (1H, m), 2.04-1.94 (1H, m).

MS(ESI) [M+H]$^+$: 303.

Reference Example 92: Synthesis of 2-fluoro-4-(6-methylquinolin-2-yl)benzenesulfonamide

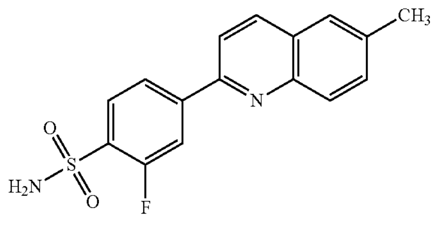 [SMILES: Cc1ccc2nc(-c3ccc(S(N)(=O)=O)c(F)c3)ccc2c1]

2-Chloro-6-methylquinoline (30.0 mg, 0.169 mmol) and (3-fluoro-4-sulfamoylphenyl)boronic acid (40.7 mg, 0.186 mmol) were used in the same manner as in Reference Example 11 to obtain the title compound as a white solid (30.4 mg, 0.0961 mmol, yield: 92%).

$^1$H-NMR (DMSO-$d_6$) δ: 8.46-8.42 (1H, m), 8.31-8.20 (2H, m), 8.05-8.00 (1H, m), 7.98-7.93 (1H, m), 7.84-7.76 (3H, m), 7.70-7.65 (1H, m), 2.54 (3H, s).

MS(ESI) $[M+H]^+$: 317.

Example 113: Synthesis of 2-fluoro-4-(6-methyl-1,2,3,4-tetrahydroquinolin-2-yl)benzenesulfonamide (a Novel Compound)

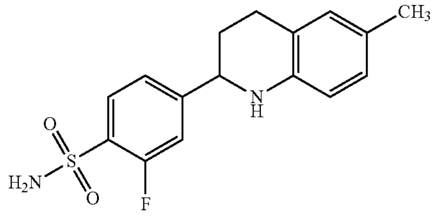 [SMILES: Cc1ccc2c(c1)CCC(c1ccc(S(N)(=O)=O)c(F)c1)N2]

The 2-fluoro-4-(6-methylquinolin-2-yl)benzenesulfonamide synthesized in Reference Example 92 (38.0 mg, 0.120 mmol) was used in the same manner as in Example 72 to obtain the title compound (hereinafter referred to as the compound of Example 113) as a white solid (21.0 mg, 0.0655 mmol, yield: 55%).

$^1$H-NMR ($CDCl_3$) δ: 7.88-7.83 (1H, m), 7.31-7.27 (2H, m), 6.87-6.82 (2H, m), 6.52 (1H, d, J=8.2 Hz), 5.07 (2H, s), 4.52-4.48 (1H, m), 3.97 (1H, brs), 2.90-2.81 (1H, m), 2.68-2.60 (1H, m), 2.23 (3H, s), 2.16-2.07 (1H, m), 1.99-1.89 (1H, m).

MS(ESI) $[M+H]^+$: 321.

Reference Example 93: Synthesis of N-(4-(6-methylquinolin-2-yl)phenyl)sulfamoylamine

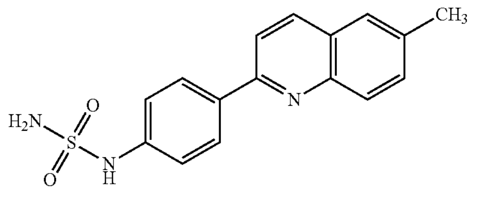 [SMILES: Cc1ccc2nc(-c3ccc(NS(N)(=O)=O)cc3)ccc2c1]

Chlorosulfonyl isocyanate (36.2 mg, 0.256 mmol) was added at 0° C. to a dichloromethane solution (0.70 mL) of 2-methylpropan-2-ol (21.5 mg, 0.290 mmol), and the resulting mixture was stirred at the same temperature for 30 minutes. The reaction mixture was added to a dichloromethane solution (1.0 mL) of 4-(6-methylquinolin-2-yl)aniline (40.0 mg, 0.171 mmol) and triethylamine (0.0432 mL, 0.307 mmol), and the resulting mixture was stirred at room temperature for 1 hour. After the reaction was completed, a saturated aqueous solution of sodium bicarbonate was added to the reaction mixture, and the resulting mixture was extracted with ethyl acetate. The organic layer was dried over anhydrous sodium sulfate, and the filtrate was then concentrated under reduced pressure. The obtained crude product was dissolved in dichloromethane (1 mL), and trifluoroacetic acid (0.0916 mL) was then added to the resulting solution, and the resulting mixture was stirred at room temperature for 18 hours. After the reaction was completed, the reaction mixture was concentrated under reduced pressure. The obtained crude product was purified by column chromatography (silica gel, chloroform/methanol) to obtain the title compound as a yellow solid (37.8 mg, 0.121 mmol, yield: 71%).

$^1$H-NMR ($CD_3OD$) δ: 8.25 (1H, d, J=8.7 Hz), 8.06-8.02 (2H, m), 7.98 (1H, d, J=8.7 Hz), 7.88 (1H, d, J=8.7 Hz), 7.68-7.66 (1H, m), 7.60 (1H, dd, J=8.7, 1.8 Hz), 7.39-7.35 (2H, m), 2.55 (3H, s).

MS(ESI) $[M+H]^+$: 314.

Example 114: Synthesis of N-(4-(6-methyl-1,2,3,4-tetrahydroquinolin-2-yl)phenyl)sulfamoylamine (a Novel Compound)

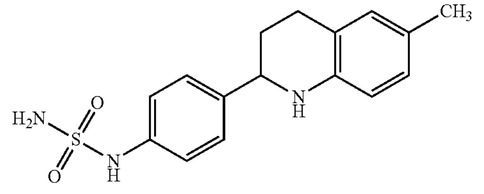

The N-(4-(6-methylquinolin-2-yl)phenyl)sulfamoylamine synthesized in Reference Example 93 (37.8 mg, 0.121 mmol) was used in the same manner as in Example 72 to obtain the title compound (hereinafter referred to as the compound of Example 114) as a white solid (17.3 mg, 0.0545 mmol, yield: 45%).

$^1$H-NMR (DMSO-$d_6$) δ: 9.40 (1H, s), 7.26-7.22 (2H, m), 7.13-7.10 (2H, m), 7.04 (2H, s), 6.70-6.67 (2H, m), 6.48 (1H, d, J=8.2 Hz), 5.70 (1H, s), 4.30-4.26 (1H, m), 2.79-2.70 (1H, m), 2.54-2.47 (1H, m), 2.12 (3H, s), 1.96-1.89 (1H, m), 1.83-1.73 (1H, m).

MS(ESI) $[M+H]^+$: 318.

Reference Example 94: Synthesis of 4-(6-chloroquinolin-2-yl)benzenesulfonamide

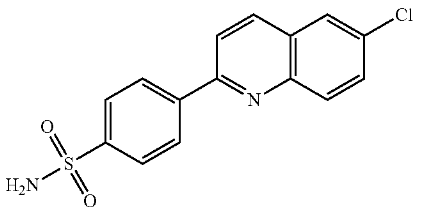 [SMILES: NS(=O)(=O)c1ccc(-c2ccc3cc(Cl)ccc3n2)cc1]

2,6-Dichloroquinoline (1.00 g, 5.05 mmol) and (4-sulfamoylphenyl)boronic acid (964 mg, 4.80 mmol) were used in the same manner as in Reference Example 11 to obtain the title compound as a pale pink solid (1.38 g, 4.34 mmol, yield: 86%).

$^1$H-NMR (DMSO-$d_6$) δ: 8.52 (1H, d, J=8.7 Hz), 8.47 (2H, d, J=8.7 Hz), 8.30 (1H, d, J=8.7 Hz), 8.20 (1H, d, J=2.3 Hz), 8.13 (1H, d, J=9.1 Hz), 8.00 (2H, d, J=8.2 Hz), 7.83 (1H, dd, J=9.1, 2.3 Hz), 7.50 (2H, s).

MS(ESI) $[M+H]^+$: 319.

Example 115: Synthesis of 4-(6-chloro-1,2,3,4-tetrahydroquinolin-2-yl)benzenesulfonamide (a Novel Compound)

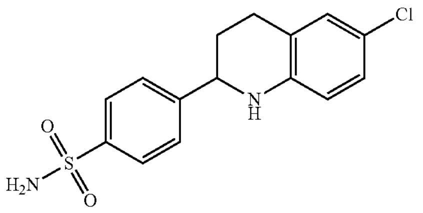 [SMILES: NS(=O)(=O)c1ccc(C2CCc3cc(Cl)ccc3N2)cc1]

The 4-(6-chloroquinolin-2-yl)benzenesulfonamide synthesized in Reference Example 94 (200 mg, 0.627 mmol) was used in the same manner as in Example 72 to obtain the title compound (hereinafter referred to as the compound of Example 115) as a pale pink solid (127 mg, 0.394 mmol, yield: 63%).

$^1$H-NMR ($CDCl_3$) δ: 7.91 (2H, d, J=8.2 Hz), 7.52 (2H, d, J=8.2 Hz), 6.99-6.98 (2H, m), 6.51 (1H, d, J=9.1 Hz), 4.79 (2H, brs), 4.54 (1H, ddd, J=8.7, 3.2, 1.8 Hz), 4.09 (1H, brs), 2.86 (1H, ddd, J=15.6, 9.6, 5.5 Hz), 2.66 (1H, ddd, J=16.5, 5.5, 5.5 Hz), 2.15-2.11 (1H, m), 2.00-1.91 (1H, m).

MS(ESI) $[M+H]^+$: 323.

Example 116: Synthesis of One of the Optical Isomers of 4-(6-chloro-1,2,3,4-tetrahydro-quinolin-2-yl)benzenesulfonamide (a Novel Compound)

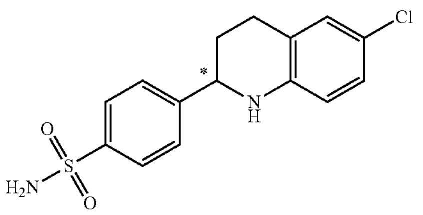 [SMILES: NS(=O)(=O)c1ccc(C2CCc3cc(Cl)ccc3N2)cc1]

In the formula, the carbon atom marked with an asterisk (*) is an asymmetric center.

The 4-(6-chloroquinolin-2-yl)benzenesulfonamide synthesized in Reference Example 94 (600 mg, 1.88 mmol) and (R)-3,3'-bis(2,4,6-triisopropylphenyl)-1,1'-binaphthyl-2,2'-diyl hydrogen phosphate (28.3 mg, 0.0376 mmol) were used in the same manner as in Example 37 to obtain the title compound (hereinafter referred to as the compound of Example 116) as a pale pink solid (431 mg, 1.34 mmol, yield: 71%, enantiomeric excess: 94.8% ee).

$^1$H-NMR ($CDCl_3$) δ: 7.91 (2H, d, J=8.7 Hz), 7.52 (2H, d, J=8.2 Hz), 6.99-6.98 (2H, m), 6.51 (1H, dd, J=5.9, 3.2 Hz), 4.79 (2H, s), 4.54 (1H, dd, J=11.0, 3.7 Hz), 4.09 (1H, brs), 2.86 (1H, ddd, J=15.6, 9.6, 5.0 Hz), 2.66 (1H, ddd, J=16.5, 5.0, 5.9 Hz), 2.16-2.09 (1H, m), 1.97-1.94 (1H, m).

MS(ESI) $[M+H]^+$: 323.

HPLC analysis conditions:

Column: Daicel Chiralcel OD-H chiral column (inner diameter: 0.46 mm, length: 250 mm, particle size: 5 μm)

Column temperature: 40° C.

Mobile phase: propan-2-ol:hexane=50:50

Flow rate: 0.6 mL/min

Detection: UV (254 nm)

Rt: 15.47 min

Example 117: Synthesis of the Other of the Optical Isomers of 4-(6-chloro-1,2,3,4-tetrahydroquinolin-2-yl)benzenesulfonamide (a Novel Compound)

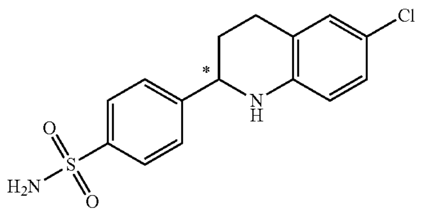 [SMILES: NS(=O)(=O)c1ccc(C2CCc3cc(Cl)ccc3N2)cc1]

In the formula, the carbon atom marked with an asterisk (*) is an asymmetric center.

The 4-(6-chloroquinolin-2-yl)benzenesulfonamide synthesized in Reference Example 94 (600 mg, 1.88 mmol) and (S)-3,3'-bis(2,4,6-triisopropylphenyl)-1,1'-binaphthyl-2,2'-diyl hydrogen phosphate (28.3 mg, 0.0376 mmol) were used in the same manner as in Example 37 to obtain the title compound (hereinafter referred to as the compound of Example 117) as a pale pink solid (380 mg, 1.18 mmol, yield: 63%, enantiomeric excess: 99.1% ee).

$^1$H-NMR ($CDCl_3$) δ: 7.91 (2H, d, J=8.7 Hz), 7.52 (2H, d, J=8.2 Hz), 7.00-6.96 (2H, m), 6.51 (1H, dd, J=5.9, 3.2 Hz), 4.79 (2H, s), 4.56-4.52 (1H, m), 4.09 (1H, brs), 2.86 (1H, ddd, J=15.6, 9.6, 4.6 Hz), 2.66 (1H, ddd, J=16.5, 5.0, 5.0 Hz), 2.16-2.09 (1H, m), 2.00-1.90 (1H, m).

MS(ESI) $[M+H]^+$: 323.

HPLC analysis conditions:

Column: Daicel Chiralcel OD-H chiral column (inner diameter: 0.46 mm, length: 250 mm, particle size: 5 μm)

Column temperature: 40° C.

Mobile phase: propan-2-ol:hexane=50:50

Flow rate: 0.6 mL/min

Detection: UV (254 nm)

Rt: 18.58 min

Reference Example 95: Synthesis of 4-(7-fluoroquinolin-2-yl)benzenesulfonamide

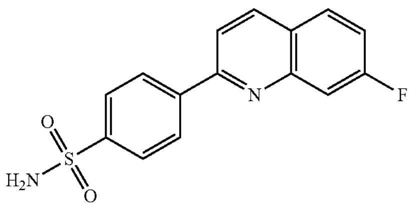 [SMILES: NS(=O)(=O)c1ccc(-c2ccc3ccc(F)cc3n2)cc1]

2-Chloro-7-fluoroquinoline (200 mg, 1.10 mmol) and (4-sulfamoylphenyl)boronic acid (266 mg, 1.32 mmol) were used in the same manner as in Reference Example 11 to obtain the title compound as a yellowish brown solid (297 mg, 0.982 mmol, yield: 89%).

$^1$H-NMR ($CDCl_3$) δ: 8.33 (2H, d, J=8.6 Hz), 8.29 (1H, d, J=8.6 Hz), 8.09 (2H, d, J=8.6 Hz), 7.89-7.86 (2H, m), 7.81 (1H, dd, J=10.0, 2.7 Hz), 7.38 (1H, ddd, J=8.2, 8.2, 2.3 Hz), 4.84 (2H, brs).

MS(ESI) $[M+H]^+$: 303.

Example 118: Synthesis of 4-(7-fluoro-1,2,3,4-tetrahydroquinolin-2-yl)benzenesulfonamide (a Novel Compound)

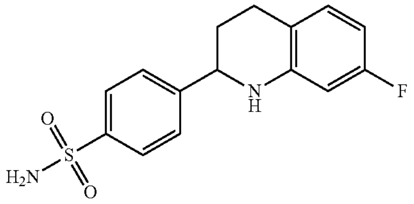 [SMILES: NS(=O)(=O)c1ccc(C2CCc3ccc(F)cc3N2)cc1]

The 4-(7-fluoroquinolin-2-yl)benzenesulfonamide synthesized in Reference Example 95 was used in the same manner as in Example 72 to obtain the title compound (hereinafter referred to as the compound of Example 118) as a white solid (182 mg, 0.595 mmol, yield: 90%).

$^1$H-NMR ($CDCl_3$) δ: 7.91 (2H, d, J=7.8 Hz), 7.52 (2H, d, J=8.2 Hz), 6.92 (1H, dd, J=6.9, 7.3 Hz), 6.37 (1H, ddd, J=8.2, 8.2, 2.3 Hz), 6.28 (1H, dd, J=10.5, 2.3 Hz), 4.80 (2H, brs), 4.55 (1H, d, J=8.2 Hz), 4.17 (1H, brs), 2.83 (1H, ddd, J=15.1, 9.6, 5.0 Hz), 2.63 (1H, ddd, J=16.0, 5.5, 5.5 Hz), 2.17-2.10 (1H, m), 1.97-1.94 (1H, m).

MS(ESI) $[M+H]^+$: 307.

Example 119: Synthesis of One of the Optical Isomers of 4-(6-methyl-1,2,3,4-tetrahydro-quinolin-2-yl)benzenesulfonamide (a Novel Compound)

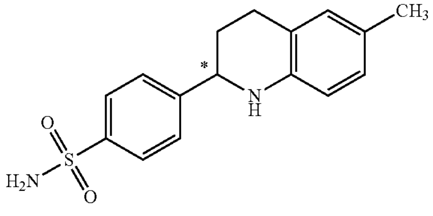 [SMILES: Cc1ccc2c(c1)CCC(c1ccc(S(N)(=O)=O)cc1)N2]

In the formula, the carbon atom marked with an asterisk (*) is an asymmetric center.

The 4-(6-methylquinolin-2-yl)benzenesulfonamide synthesized in Reference Example 83 (600 mg, 2.01 mmol) and (R)-3,3'-bis(2,4,6-triisopropylphenyl)-1,1'-binaphthyl-2,2'-diyl hydrogen phosphate ((R)-TRIP, 30.3 mg, 0.0402 mmol) were suspended in 1,4-dioxane (6.7 mL), and diethyl 1,4-dihydro-2,6-dimethyl-3,5-pyridinedicarboxylate (1.53 g, 6.03 mmol) was added to the resulting suspension, and the resulting mixture was stirred at 60° C. for 24 hours under argon atmosphere. After the reaction was completed, the reaction mixture was concentrated under reduced pressure. The obtained crude product was purified by column chromatography (silica gel, hexane/ethyl acetate) to obtain the title compound (hereinafter referred to as the compound of Example 119) as a white solid (443 mg, 1.47 mmol, yield: 73%, enantiomeric excess: 99.4% ee).

$^1$H-NMR ($CDCl_3$) δ: 7.90 (2H, d, J=8.6 Hz), 7.55 (2H, d, J=8.6 Hz), 6.87-6.84 (2H, m), 6.51 (1H, d, J=7.7 Hz), 4.77 (2H, s), 4.51 (1H, dd, J=8.8, 3.4 Hz), 3.96 (1H, s), 2.92-2.84 (1H, m), 2.66 (1H, td, J=10.8, 5.6 Hz), 2.15-2.09 (1H, m), 2.01-1.92 (1H, m).

MS(ESI) $[M+H]^+$: 303.

Rt: 6.92 min

HPLC analysis conditions:

Column: Daicel Chiralcel OZ-H chiral column (inner diameter: 20 mm, length: 250 mm, particle size: 5 μm)

Column temperature: 40° C.

Mobile phase: propan-2-ol:hexane=50:50

Flow rate: 0.6 mL/min

Detection: UV (254 nm)

Example 120: Synthesis of the Other of the Optical Isomers of 4-(6-methyl-1,2,3,4-tetrahydroquinolin-2-yl)benzenesulfonamide (a Novel Compound)

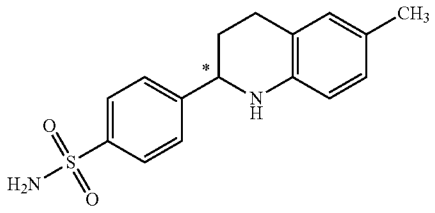 [SMILES: Cc1ccc2c(c1)CCC(c1ccc(S(N)(=O)=O)cc1)N2]

In the formula, the carbon atom marked with an asterisk (*) is an asymmetric center.

The 4-(6-methyl-1,2,3,4-tetrahydroquinolin-2-yl)benzenesulfonamide synthesized in Example 100 (40.5 mg, 0.134 mmol) was dissolved in propan-2-ol (4.2 mL) and optically resolved using HPLC under the following conditions to obtain the title compound (hereinafter referred to as the compound of Example 120) as a white solid (14.9 mg, 49.3 μmol, yield: 37%, enantiomeric excess: 99.9%).

$^1$H-NMR ($CDCl_3$) δ: 7.90 (2H, d, J=8.6 Hz), 7.55 (2H, d, J=8.6 Hz), 6.87-6.84 (2H, m), 6.51 (1H, d, J=7.7 Hz), 4.77 (2H, s), 4.51 (1H, dd, J=8.8, 3.4 Hz), 3.96 (1H, s), 2.92-2.84 (1H, m), 2.66 (1H, td, J=10.8, 5.6 Hz), 2.15-2.09 (1H, m), 2.01-1.92 (1H, m).

MS(ESI) $[M+H]^+$: 303.

MS(ESI) $[M+H]^+$: 303.

Conditions for optical resolution using HPLC:

Column: Daicel Chiralcel OZ-H chiral column (inner diameter: 20 mm, length: 250 mm, particle size: 5 μm)

Column temperature: 40° C.

Mobile phase: propan-2-ol:hexane=70:30

Total injection volume: 4.0 mL (1.0 mL×4)

Flow rate: 10 mL/min

Detection: UV (254 nm)

Rt: 17.00 to 22.00 min

HPLC analysis conditions:

Column: Daicel Chiralcel OZ-3 chiral column (inner diameter: 0.46 mm, length: 150 mm, particle size: 3 μm)

Column temperature: 40° C.

Mobile phase: propan-2-ol:hexane=50:50

Flow rate: 0.6 mL/min

Detection: UV (254 nm)

Rt: 12.17 min

Example 121: Synthesis of One of the Optical Isomers of 4-(6-chloro-1,2,3,4-tetrahydroquinolin-2-yl) benzamide (a Novel Compound)

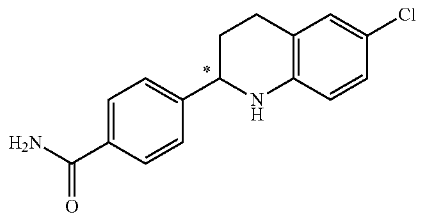 [SMILES: NC(=O)c1ccc(C2CCc3cc(Cl)ccc3N2)cc1]

In the formula, the carbon atom marked with an asterisk (*) is an asymmetric center.

The 4-(6-chloro-1,2,3,4-tetrahydroquinolin-2-yl)benzamide synthesized in Example 131 (40.8 mg, 0.125 mmol) was dissolved in propan-2-ol (13 mL) and optically resolved using HPLC under the following conditions to obtain the title compound (hereinafter referred to as the compound of Example 121) as a white solid (17.1 mg, 50.2 μmol, yield: 42%, enantiomeric excess: 99.9%).

$^1$H-NMR ($CDCl_3$) δ: 7.80 (2H, d, J=8.2 Hz), 7.45 (2H, d, J=8.2 Hz), 6.97 (2H, d, J=5.9 Hz), 6.50 (1H, d, J=4.5 Hz), 4.51 (1H, d, J=6.8 Hz), 4.11 (1H, brs), 2.91-2.83 (1H, m), 2.72-2.63 (1H, m), 2.16-2.08 (1H, m), 2.11-1.90 (1H, m).

MS(ESI) $[M+H]^+$: 287.

Conditions for optical resolution using HPLC:

Column: Daicel Chiralcel OD-H chiral column (inner diameter: 20 mm, length: 250 mm, particle size: 5 μm)

Column temperature: 40° C.

Mobile phase: propan-2-ol:hexane=70:30

Total injection volume: 12.0 mL (5.0 mL×2, 1.0 mL×2)

Flow rate: 10 mL/min

Detection: UV (254 nm)

Rt: 9.00 to 13.50 min

HPLC analysis conditions:

Column: Daicel Chiralcel OD-H chiral column (inner diameter: 0.46 mm, length: 150 mm, particle size: 5 μm)

Column temperature: 40° C.

Mobile phase: propan-2-ol:hexane=50:50

Flow rate: 0.6 mL/min

Detection: UV (254 nm)

Rt: 11.26 min

Example 122: Synthesis of the Other of the Optical Isomers of 4-(6-chloro-1,2,3,4-tetrahydroquinolin-2-yl)benzamide (a Novel Compound)

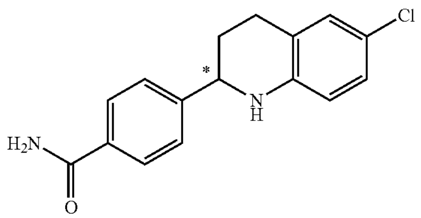 [SMILES: NC(=O)c1ccc(C2CCc3cc(Cl)ccc3N2)cc1]

In the formula, the carbon atom marked with an asterisk (*) is an asymmetric center.

The 4-(6-chloro-1,2,3,4-tetrahydroquinolin-2-yl)benzamide synthesized in Example 131 (40.8 mg, 0.125 mmol) was dissolved in propan-2-ol (13 mL) and optically resolved using HPLC under the following conditions to obtain the title compound (hereinafter referred to as the compound of Example 122) as a white solid (17.0 mg, 44.0 μmol, yield: 42%, enantiomeric excess: 99.9%).

$^1$H-NMR ($CDCl_3$) δ: 7.80 (2H, d, J=8.2 Hz), 7.45 (2H, d, J=8.2 Hz), 6.97 (2H, d, J=5.9 Hz), 6.50 (1H, d, J=4.5 Hz), 4.51 (1H, d, J=6.8 Hz), 4.11 (1H, brs), 2.91-2.83 (1H, m), 2.72-2.63 (1H, m), 2.16-2.08 (1H, m), 2.11-1.90 (1H, m).

MS(ESI) $[M+H]^+$: 287.

Conditions for optical resolution using HPLC:

Column: Daicel Chiralcel OD-H chiral column (inner diameter: 20 mm, length: 250 mm, particle size: 5 μm)

Column temperature: 40° C.

Mobile phase: propan-2-ol:hexane=70:30

Total injection volume: 12.0 mL (5.0 mL×2, 1.0 mL×2)

Flow rate: 10 mL/min

Detection: UV (254 nm)

Rt: 14.00 to 18.00 min

HPLC analysis conditions:

Column: Daicel Chiralcel OD-H chiral column (inner diameter: 0.46 mm, length: 150 mm, particle size: 5 μm)

Column temperature: 40° C.

Mobile phase: propan-2-ol:hexane=50:50

Flow rate: 0.6 mL/min

Detection: UV (254 nm)

Rt: 18.55 min

Example 123: Synthesis of One of the Optical Isomers of 5-(1,2,3,4-tetrahydroquinolin-2-yl)isoindolin-1-one (a Novel Compound)

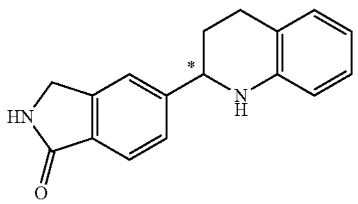 [SMILES: O=C1NCc2cc(C3CCc4ccccc4N3)ccc21]

In the formula, the carbon atom marked with an asterisk (*) is an asymmetric center.

The 5-(quinolin-2-yl)isoindolin-1-one synthesized in Reference Example 17 (100 mg, 0.384 mmol) and (R)-3,3'-bis(2,4,6-triisopropylphenyl)-1,1'-binaphthyl-2,2'-diyl hydrogen phosphate (5.79 mg, 0.00768 mmol) were suspended in 1,4-dioxane (4 mL), and diethyl 1,4-dihydro-2,6-dimethyl-3,5-pyridinedicarboxylate (234 mg, 0.922 mmol) was added to the resulting suspension, and the resulting mixture was stirred at room temperature for 24 hours and at 60° C. for 24 hours under argon atmosphere. After the reaction was completed, the reaction mixture was concentrated under reduced pressure. The obtained crude product was purified by column chromatography (silica gel, hexane/ethyl acetate) to obtain the title compound (hereinafter referred to as the compound of Example 123) as a white solid (49.3 mg, 0.187 mmol, yield: 49%, enantiomeric excess: 97.0% ee).

$^1$H-NMR ($CDCl_3$) δ: 7.85 (1H, d, J=7.7 Hz), 7.53 (1H, s), 7.49 (1H, d, J=8.8 Hz), 7.04 (2H, dd, J=12.9, 7.0 Hz), 6.69 (1H, dd, J=7.2, 7.2 Hz), 6.59 (1H, d, J=7.7 Hz), 6.49 (1H, s), 4.62-4.55 (1H, m), 4.44 (2H, s), 4.12 (1H, s), 2.96-2.88 (1H, m), 2.72 (1H, dd, J=10.6, 5.4, 5.4 Hz), 2.21-2.11 (1H, m), 2.06-1.96 (1H, m).

MS(ESI) $[M+H]^+$: 265.

Rt: 22.04 min

HPLC analysis conditions:

Column: Daicel Chiralcel OD-H chiral column (inner diameter: 4.6 mm, length: 250 mm, particle size: 5 μm)

Column temperature: 40° C.

Mobile phase: propan-2-ol:hexane=40:60

Flow rate: 0.6 mL/min

Detection: UV (254 nm)

Example 124: Synthesis of the Other of the Optical Isomers of 5-(1,2,3,4-tetrahydroquinolin-2-yl)isoindolin-1-one (a Novel Compound)

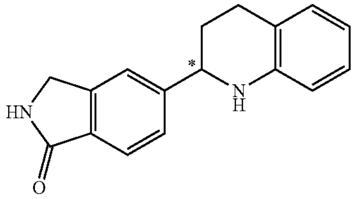 [SMILES: O=C1NCc2cc(C3CCc4ccccc4N3)ccc21]

In the formula, the carbon atom marked with an asterisk (*) is an asymmetric center.

The 5-(quinolin-2-yl)isoindolin-1-one synthesized in Reference Example 17 (50.0 mg, 0.192 mmol) and (S)-3,3'-bis(2,4,6-triisopropylphenyl)-1,1'-binaphthyl-2,2'-diyl hydrogen phosphate (2.89 mg, 0.00384 mmol) were suspended in 1,4-dioxane (2 mL), and diethyl 1,4-dihydro-2,6-dimethyl-3,5-pyridinedicarboxylate (117 mg, 0.461 mmol) was added to the resulting suspension, and the resulting mixture was stirred at room temperature for 18 hours and at 60° C. for 4 hours under argon atmosphere. After the reaction was completed, the reaction mixture was concentrated under reduced pressure. The obtained crude product was purified by column chromatography (silica gel, hexane/ethyl acetate) to obtain the title compound (hereinafter referred to as the compound of Example 124) as a white amorphous (32.9 mg, 0.187 mmol, yield: 65%, enantiomeric excess: 97.0% ee).

$^1$H-NMR ($CDCl_3$) δ: 7.85 (1H, d, J=7.7 Hz), 7.53 (1H, s), 7.49 (1H, d, J=8.8 Hz), 7.04 (2H, dd, J=12.9, 7.0 Hz), 6.69 (1H, dd, J=7.2, 7.2 Hz), 6.59 (1H, d, J=7.7 Hz), 6.49 (1H, s), 4.62-4.55 (1H, m), 4.44 (2H, s), 4.12 (1H, s), 2.96-2.88 (1H, m), 2.72 (1H, dd, J=10.6, 5.4, 5.4 Hz), 2.21-2.11 (1H, m), 2.06-1.96 (1H, m).

MS(ESI) $[M+H]^+$: 265.

Rt: 26.97 min

HPLC analysis conditions:

Column: Daicel Chiralcel OD-H chiral column (inner diameter: 4.6 mm, length: 250 mm, particle size: 5 μm)

Column temperature: 40° C.

Mobile phase: propan-2-ol:hexane=40:60

Flow rate: 0.6 mL/min

Detection: UV (254 nm)

Example 125: Synthesis of One of the Optical Isomers of 1,2,3,3',4,4'-hexahydro-[2,6'-biquinolin]-2'(1'H)-one (a Novel Compound)

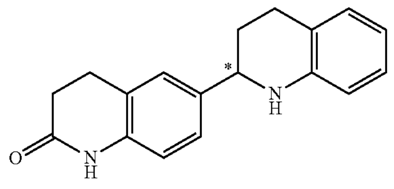 [SMILES: O=C1CCc2cc(C3CCc4ccccc4N3)ccc2N1]

In the formula, the carbon atom marked with an asterisk (*) is an asymmetric center.

The 3',4'-dihydro-[2,6'-biquinolin]-2'(1'H)-one synthesized in Reference Example 15 (100 mg, 0.364 mmol) and (R)-3,3'-bis(2,4,6-triisopropylphenyl)-1,1'-binaphthyl-2,2'-diyl hydrogen phosphate (5.49 mg, 0.00729 mmol) were suspended in 1,4-dioxane (4 mL), and diethyl 1,4-dihydro-2,6-dimethyl-3,5-pyridinedicarboxylate (222 mg, 0.875 mmol) was added to the resulting suspension, and the resulting mixture was stirred at room temperature for 18 hours under argon atmosphere. After the reaction was completed, the reaction mixture was concentrated under reduced pressure. The obtained crude product was purified by column chromatography (silica gel, hexane/ethyl acetate) to obtain the title compound (hereinafter referred to as the compound of Example 125) as a white solid (74.0 mg, 0.266 mmol, yield: 73%, enantiomeric excess: 99.1% ee).

$^1$H-NMR ($CDCl_3$) δ: 7.63 (1H, s), 7.24-7.17 (2H, m), 7.04-7.68 (2H, m), 6.72-6.64 (2H, m), 6.54 (1H, d, J=7.7 Hz), 4.38 (1H, dd, J=9.3, 2.9 Hz), 3.98 (1H, s), 2.99-2.89 (3H, m), 2.79-2.70 (1H, m), 2.68-2.60 (2H, m), 2.11-2.07 (1H, m), 2.02-1.90 (1H, m).

MS(ESI) $[M+H]^+$: 279.

Rt: 27.76 min

HPLC analysis conditions:

Column: Daicel Chiralcel OZ-3 chiral column (inner diameter: 4.6 mm, length: 150 mm, particle size: 5 μm)

Column temperature: 40° C.

Mobile phase: propan-2-ol:hexane=10:90

Flow rate: 0.6 mL/min

Detection: UV (254 nm)

Example 126: Synthesis of the Other of the Optical Isomers of 1,2,3,3',4,4'-hexahydro-[2,6'-biquinolin]-2'(1'H)-one (a Novel Compound)

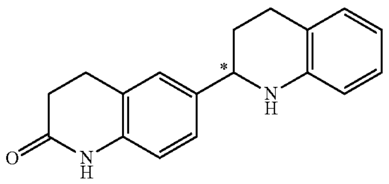 [SMILES: O=C1CCc2cc(C3CCc4ccccc4N3)ccc2N1]

In the formula, the carbon atom marked with an asterisk (*) is an asymmetric center.

The 3',4'-dihydro-[2,6'-biquinolin]-2'(1'H)-one synthesized in Reference Example 15 (90.0 mg, 0.328 mmol) and (S)-3,3'-bis(2,4,6-triisopropylphenyl)-1,1'-binaphthyl-2,2'-diyl hydrogen phosphate (4.94 mg, 0.00656 mmol) were suspended in 1,4-dioxane (2 mL), and diethyl 1,4-dihydro-2,6-dimethyl-3,5-pyridinedicarboxylate (199 mg, 0.787 mmol) was added to the resulting suspension, and the resulting mixture was stirred at room temperature for 18 hours under argon atmosphere. After the reaction was completed, the reaction mixture was concentrated under reduced pressure. The obtained crude product was purified by column chromatography (silica gel, hexane/ethyl acetate) to obtain the title compound (hereinafter referred to as the compound of Example 126) as a white solid (41.0 mg, 0.147 mmol, yield: 45%, enantiomeric excess: 99.0% ee).

$^1$H-NMR ($CDCl_3$) δ: 7.63 (1H, s), 7.24-7.17 (2H, m), 7.04-7.68 (2H, m), 6.72-6.64 (2H, m), 6.54 (1H, d, J=7.7 Hz), 4.38 (1H, dd, J=9.3, 2.9 Hz), 3.98 (1H, s), 2.99-2.89 (3H, m), 2.79-2.70 (1H, m), 2.68-2.60 (2H, m), 2.11-2.07 (1H, m), 2.02-1.90 (1H, m).

MS(ESI) $[M+H]^+$: 279.

Rt: 21.04 min

HPLC analysis conditions:

Column: Daicel Chiralcel OZ-3 chiral column (inner diameter: 4.6 mm, length: 150 mm, particle size: 5 μm)

Column temperature: 40° C.

Mobile phase: propan-2-ol:hexane=10:90

Flow rate: 0.6 mL/min

Detection: UV (254 nm)

Example 127: Synthesis of One of the Optical Isomers of 1-(tert-butyl)-3-(2-phenyl-1,2,3,4-tetrahydroquinolin-6-yl)urea (a Novel Compound)

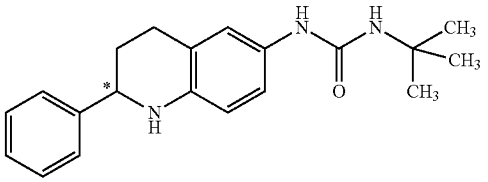 [SMILES: CC(C)(C)NC(=O)Nc1ccc2c(c1)CCC(c1ccccc1)N2]

In the formula, the carbon atom marked with an asterisk (*) is an asymmetric center.

The 1-(tert-butyl)-3-(2-phenylquinolin-6-yl)urea synthesized in Reference Example 57 (75.0 mg, 0.235 mmol) and (R)-3,3'-bis(2,4,6-triisopropylphenyl)-1,1'-binaphthyl-2,2'- diyl hydrogen phosphate (3.54 mg, 0.00470 mmol) were suspended in 1,4-dioxane (3 mL), and diethyl 1,4-dihydro-2,6-dimethyl-3,5-pyridinedicarboxylate (143 mg, 0.564 mmol) was added to the resulting suspension, and the resulting mixture was stirred at room temperature for 18 hours and at 60° C. for 8 hours under argon atmosphere. After the reaction was completed, the reaction mixture was concentrated under reduced pressure. The obtained crude product was purified by column chromatography (amine-silica gel, hexane/ethyl acetate) to obtain the title compound (hereinafter referred to as the compound of Example 127) as a white amorphous (73.0 mg, 0.226 mmol, yield: 96%, enantiomeric excess: 97.3% ee).

$^1$H-NMR ($CDCl_3$) δ: 7.40-7.25 (5H, m), 6.88-6.82 (2H, m), 6.50 (1H, d, J=8.6 Hz), 5.69 (1H, s), 4.50 (1H, s), 4.43 (1H, dd, J=9.5, 3.2 Hz), 4.09 (1H, s), 2.94-2.86 (1H, m), 2.72 (1H, dt, J=16.5, 4.8 Hz), 2.15-2.10 (1H, m), 2.05-1.93 (1H, m), 1.34 (9H, s).

MS(ESI) $[M+H]^+$: 324.

Rt: 8.64 min

HPLC analysis conditions:

Column: Daicel Chiralcel OD-H chiral column (inner diameter: 4.6 mm, length: 250 mm, particle size: 5 μm)

Column temperature: 40° C.

Mobile phase: propan-2-ol:hexane=50:50

Flow rate: 0.6 mL/min

Detection: UV (254 nm)

Example 128: Synthesis of the Other of the Optical Isomers of 1-(tert-butyl)-3-(2-phenyl-1,2,3,4-tetrahydroquinolin-6-yl)urea (a Novel Compound)

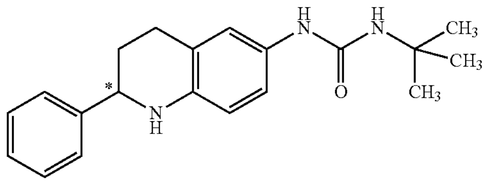 [SMILES: CC(C)(C)NC(=O)Nc1ccc2c(c1)CCC(c1ccccc1)N2]

In the formula, the carbon atom marked with an asterisk (*) is an asymmetric center.

The 1-(tert-butyl)-3-(2-phenylquinolin-6-yl)urea synthesized in Reference Example 57 (52.0 mg, 0.163 mmol) and (S)-3,3'-bis(2,4,6-triisopropylphenyl)-1,1'-binaphthyl-2,2'-diyl hydrogen phosphate (2.45 mg, 0.00326 mmol) were suspended in 1,4-dioxane (2 mL), and diethyl 1,4-dihydro-2,6-dimethyl-3,5-pyridinedicarboxylate (99.0 mg, 0.391 mmol) was added to the resulting suspension, and the resulting mixture was stirred at room temperature for 18 hours and at 60° C. for 8 hours under argon atmosphere. After the reaction was completed, the reaction mixture was concentrated under reduced pressure. The obtained crude product was purified by column chromatography (amine-silica gel, hexane/ethyl acetate) to obtain the title compound (hereinafter referred to as the compound of Example 128) as a white amorphous (50.0 mg, 0.155 mmol, yield: 95%, enantiomeric excess: 97.1% ee).

$^1$H-NMR ($CDCl_3$) δ: 7.40-7.25 (5H, m), 6.88-6.82 (2H, m), 6.50 (1H, d, J=8.6 Hz), 5.69 (1H, s), 4.50 (1H, s), 4.43 (1H, dd, J=9.5, 3.2 Hz), 4.09 (1H, s), 2.94-2.86 (1H, m), 2.72 (1H, dt, J=16.5, 4.8 Hz), 2.15-2.10 (1H, m), 2.05-1.93 (1H, m), 1.34 (9H, s).

MS(ESI) $[M+H]^+$: 324.

Rt: 24.37 min

HPLC analysis conditions:

Column: Daicel Chiralcel OD-H chiral column (inner diameter: 4.6 mm, length: 250 mm, particle size: 5 μm)

Column temperature: 40° C.

Mobile phase: propan-2-ol:hexane=50:50

Flow rate: 0.6 mL/min

Detection: UV (254 nm)

Example 129: Synthesis of One of the Optical Isomers of 3,3-dimethyl-N-(2-phenyl-1,2,3,4-tetrahydroquinolin-6-yl)butanamide (a Novel Compound)

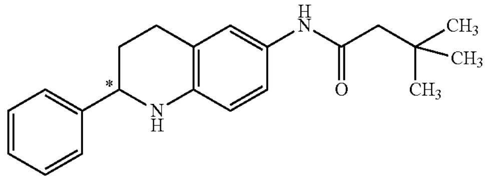 [SMILES: CC(C)(C)CC(=O)Nc1ccc2c(c1)CCC(c1ccccc1)N2]

In the formula, the carbon atom marked with an asterisk (*) is an asymmetric center.

The 3,3-dimethyl-N-(2-phenylquinolin-6-yl)butanamide synthesized in Reference Example 59 (100 mg, 0.314 mmol) and (R)-3,3'-bis(2,4,6-triisopropylphenyl)-1,1'-binaphthyl-2,2'-diyl hydrogen phosphate (4.73 mg, 0.00628 mmol) were suspended in 1,4-dioxane (3 mL), and diethyl 1,4-dihydro-2,6-dimethyl-3,5-pyridinedicarboxylate (191 mg, 0.736 mmol) was added to the resulting suspension, and the resulting mixture was stirred at room temperature for 18 hours under argon atmosphere. After the reaction was completed, the reaction mixture was concentrated under reduced pressure. The obtained crude product was purified by column chromatography (silica gel, hexane/ethyl acetate) to obtain the title compound (hereinafter referred to as the compound of Example 129) as a white solid (57.7 mg, 0.179 mmol, yield: 57%, enantiomeric excess: 99.3% ee).

$^1$H-NMR ($CDCl_3$) δ: 7.38-7.32 (3H, m), 7.30-7.25 (2H, m), 7.23-7.20 (1H, m), 7.04-7.00 (1H, m), 6.85 (1H, s), 6.49 (1H, d, J=8.2 Hz), 4.42 (1H, dd, J=9.1, 3.2 Hz), 4.01 (1H, s), 2.94-2.86 (1H, m), 2.72 (1H, dt, J=16.5, 4.8 Hz), 2.20 (2H, s), 2.14-2.07 (1H, m), 2.02-1.92 (1H, m), 1.12 (9H, s).

MS(ESI) $[M+H]^+$: 323.

Rt: 10.36 min

HPLC analysis conditions:

Column: Daicel Chiralcel OD-H chiral column (inner diameter: 4.6 mm, length: 250 mm, particle size: 5 μm)

Column temperature: 40° C.

Mobile phase: propan-2-ol:hexane=50:50

Flow rate: 0.6 mL/min

Detection: UV (254 nm)

Example 130: Synthesis of the Other of the Optical Isomers of 3,3-dimethyl-N-(2-phenyl-1,2,3,4-tetrahydroquinolin-6-yl)butanamide (a Novel Compound)

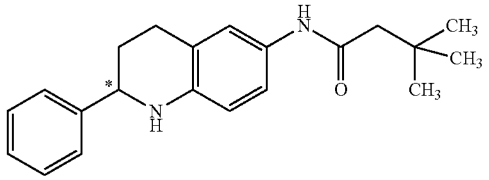 [SMILES: CC(C)(C)CC(=O)Nc1ccc2c(c1)CCC(c1ccccc1)N2]

In the formula, the carbon atom marked with an asterisk (*) is an asymmetric center.

The 3,3-dimethyl-N-(2-phenylquinolin-6-yl)butanamide synthesized in Reference Example 59 (100 mg, 0.314 mmol) and (S)-3,3'-bis(2,4,6-triisopropylphenyl)-1,1'-binaphthyl-2,2'-diyl hydrogen phosphate (4.73 mg, 0.00628 mmol) were suspended in 1,4-dioxane (3 mL), and diethyl 1,4-dihydro-2,6-dimethyl-3,5-pyridinedicarboxylate (191 mg, 0.736 mmol) was added to the resulting suspension, and the resulting mixture was stirred at room temperature for 18 hours under argon atmosphere. After the reaction was completed, the reaction mixture was concentrated under reduced pressure. The obtained crude product was purified by column chromatography (silica gel, hexane/ethyl acetate) to obtain the title compound (hereinafter referred to as the compound of Example 130) as a white amorphous (41.2 mg, 0.128 mmol, yield: 40%, enantiomeric excess: 99.0% ee).

$^1$H-NMR ($CDCl_3$) δ: 7.38-7.32 (3H, m), 7.30-7.25 (2H, m), 7.23-7.20 (1H, m), 7.04-7.00 (1H, m), 6.85 (1H, s), 6.49 (1H, d, J=8.2 Hz), 4.42 (1H, dd, J=9.1, 3.2 Hz), 4.01 (1H, s), 2.94-2.86 (1H, m), 2.72 (1H, dt, J=16.5, 4.8 Hz), 2.20 (2H, s), 2.14-2.07 (1H, m), 2.02-1.92 (1H, m), 1.12 (9H, s).

MS(ESI) $[M+H]^+$: 323.

Rt: 12.89 min

HPLC analysis conditions:

Column: Daicel Chiralcel OD-H chiral column (inner diameter: 4.6 mm, length: 250 mm, particle size: 5 μm)

Column temperature: 40° C.

Mobile phase: propan-2-ol:hexane=50:50

Flow rate: 0.6 mL/min

Detection: UV (254 nm)

Reference Example 96: Synthesis of 4-(6-chloroquinolin-2-yl)benzamide

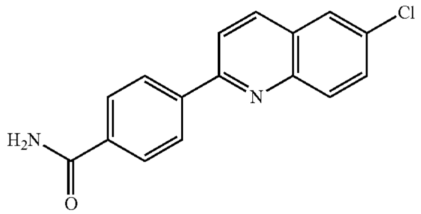 [SMILES: NC(=O)c1ccc(-c2ccc3cc(Cl)ccc3n2)cc1]

2,6-Dichloroquinoline (300 mg, 1.51 mmol), (4-carbamoylphenyl)boronic acid (325 mg, 1.97 mmol), tetrakis(triphenylphosphine)palladium(0) (17.5 mg, 0.0151 mmol), and potassium carbonate (419 mg, 3.03 mmol) were dissolved in 1,4-dioxane/water (5/1, v/v, 7 mL), and the resulting solution was then stirred with heating at 100° C. for 3 hours. After the reaction mixture was cooled down to room temperature, water was poured into the reaction mixture, and the precipitated solid was filtered. The obtained crude product was washed with water, acetone, and hexane/chloroform to obtain the title compound as a brown solid (338 mg, 1.20 mmol, yield: 79%).

$^1$H-NMR (DMSO-$d_6$) δ: 8.50 (1H, d, J=8.6 Hz), 8.36 (2H, d, J=8.2 Hz), 8.30 (1H, d, J=9.1 Hz), 8.19 (1H, d, J=5.2 Hz), 8.12 (2H, d, J=9.1 Hz), 8.06 (2H, d, J=8.6 Hz), 7.82 (1H, dd, J=8.8, 2.5 Hz), 7.50 (1H, brs).

MS(ESI) $[M+H]^+$: 283.

Example 131: Synthesis of 4-(6-chloro-1,2,3,4-tetrahydroquinolin-2-yl)benzamide (a Novel Compound)

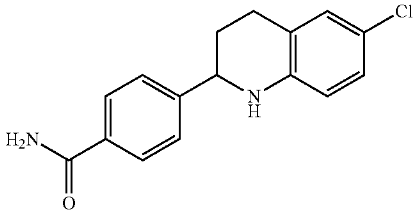 [SMILES: NC(=O)c1ccc(C2CCc3cc(Cl)ccc3N2)cc1]

The 4-(6-chloroquinolin-2-yl)benzamide synthesized in Reference Example 96 (280 mg, 0.990 mmol) was dissolved in THE (10.0 mL), and diethyl 1,4-dihydro-2,6-dimethyl-3,5-pyridinedicarboxylate (602 mg, 2.38 mmol) and iodine (25.1 mg, 0.0990 mmol) were then added to the resulting solution, and the resulting mixture was stirred at room temperature for 18 hours. After the reaction was completed, the reaction mixture was concentrated under reduced pressure. The obtained crude product was purified by column chromatography (silica gel, hexane/ethyl acetate) to obtain the title compound (hereinafter referred to as the compound of Example 131) as a pale pink solid (230 mg, 0.909 mmol, yield: 81%).

$^1$H-NMR ($CDCl_3$) δ: 7.80 (2H, d, J=8.2 Hz), 7.45 (2H, d, J=8.2 Hz), 6.97 (2H, d, J=5.9 Hz), 6.50 (1H, d, J=4.5 Hz), 4.51 (1H, d, J=6.8 Hz), 4.11 (1H, brs), 2.91-2.83 (1H, m), 2.72-2.63 (1H, m), 2.16-2.08 (1H, m), 2.11-1.90 (1H, m).

MS(ESI) $[M+H]^+$: 287.

Reference Example 97: Synthesis of 4-(6-fluoroquinolin-2-yl)benzamide

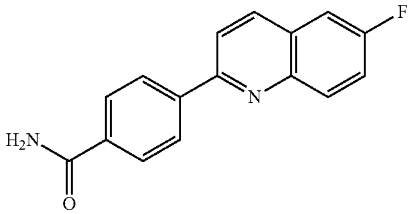 [SMILES: NC(=O)c1ccc(-c2ccc3cc(F)ccc3n2)cc1]

2-Chloro-6-fluoroquinoline (250 mg, 1.38 mmol), (4-carbamoylphenyl)boronic acid (295 mg, 1.79 mmol), tetrakis (triphenylphosphine)palladium(0) (31.3 mg, 0.0275 mmol), and potassium carbonate (381 mg, 2.75 mmol) were dissolved in 1,4-dioxane/water (5/1, v/v, 7 mL), and the resulting solution was then stirred with heating at 100° C. for 5 hours. After the reaction mixture was cooled down to room temperature, water was poured into the reaction mixture, and the precipitated solid was filtered. The obtained crude product was washed with water, acetone, and hexane/chloroform to obtain the title compound as a gray solid (280 mg, 1.05 mmol, yield: 77%).

$^1$H-NMR (DMSO-$d_6$) δ: 8.50 (1H, d, J=8.6 Hz), 8.36-8.34 (2H, m), 8.28 (1H, d, J=8.6 Hz), 8.17 (1H, dd, J=9.1, 5.4 Hz), 8.12 (1H, brs), 8.07-8.04 (2H, m), 7.85 (1H, dd, J=9.3, 2.9 Hz), 7.73 (1H, dd, J=8.9, 3.0 Hz), 7.49 (1H, s).

MS(ESI) $[M+H]^+$: 267.

Example 132: Synthesis of 4-(6-fluoro-1,2,3,4-tetrahydroquinolin-2-yl)benzamide (a Novel Compound)

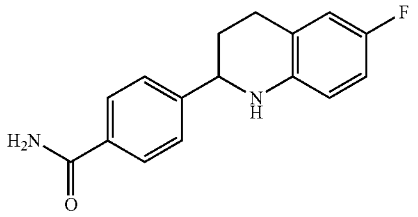 [SMILES: NC(=O)c1ccc(C2CCc3cc(F)ccc3N2)cc1]

The 4-(6-fluoroquinolin-2-yl)benzamide synthesized in Reference Example 97 (180 mg, 0.676 mmol) was dissolved in THE (7.0 mL), and diethyl 1,4-dihydro-2,6-dimethyl-3,5-pyridinedicarboxylate (620 mg, 2.45 mmol) and iodine (34.2 mg, 0.135 mmol) were then added to the resulting solution, and the resulting mixture was stirred at 60° C. for 24 hours. After the reaction was completed, the reaction mixture was concentrated under reduced pressure. The obtained crude product was purified by column chromatography (silica gel, hexane/ethyl acetate) to obtain the title compound (hereinafter referred to as the compound of Example 132) as a pale pink solid (141 mg, 0.522 mmol, yield: 77%).

$^1$H-NMR ($CDCl_3$) δ: 7.80 (2H, dd, J=8.2, 1.8 Hz), 7.47 (2H, d, J=8.2 Hz), 6.75 (2H, dd, J=13.4, 5.7 Hz), 6.54-6.46 (1H, m), 4.47 (1H, d, J=6.8 Hz), 3.97 (1H, brs), 2.95-2.86 (1H, m), 2.74-2.65 (1H, m), 2.15-2.09 (1H, m), 2.02-1.92 (1H, m).

MS(ESI) $[M+H]^+$: 271.

Reference Example 98: Synthesis of 6-fluoro-3',4'-dihydro-[2,6'-biquinolin]-2'(1'H)-one

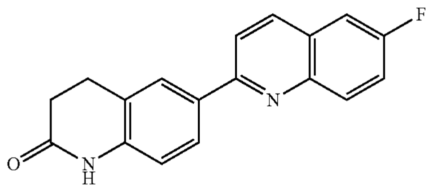 [SMILES: O=C1CCc2cc(-c3ccc4cc(F)ccc4n3)ccc2N1]

2-Chloro-6-fluoroquinoline (200 mg, 1.10 mmol), 6-(4,4,5,5-tetramethyl-1,3,2-dioxaborolan-2-yl)-3,4-dihydroquinolin-2(1H)-one (325 mg, 1.65 mmol), tetrakis(triphenylphosphine)palladium(0) (40.5 mg, 0.0350 mmol), and potassium carbonate (304 mg, 2.21 mmol) were dissolved in 1,4- dioxane/water (5/1, v/v, 7 mL), and the resulting solution was then stirred with heating at 100° C. for 18 hours. After the reaction mixture was cooled down to room temperature, water was poured into the reaction mixture, and the precipitated solid was filtered. The obtained crude product was washed with water, acetone, and hexane/chloroform to obtain the title compound as a brown solid (234 mg, 0.801 mmol, yield: 73%).

$^{1}$H-NMR (DMSO-$d_6$) δ: 10.31 (1H, s), 8.40 (1H, d, J=8.6 Hz), 8.16-8.06 (4H, m), 7.78 (1H, dd, J=9.3, 2.9 Hz), 7.67 (1H, dd, J=8.9, 3.0 Hz), 7.00 (1H, d, J=8.2 Hz), 3.05-2.97 (2H, m), 2.55-2.45 (2H, m).

MS(ESI) $[M+H]^+$: 293.

Example 133: Synthesis of 6-fluoro-1,2,3,3',4,4'-hexahydro-[2,6'-biquinolin]-2'(1'H)-one (a Novel Compound)

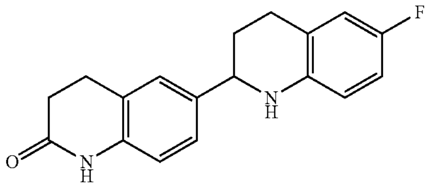 [SMILES: O=C1CCc2cc(C3CCc4cc(F)ccc4N3)ccc2N1]

The 6-fluoro-3',4'-dihydro-[2,6'-biquinolin]-2'(1'H)-one synthesized in Reference Example 98 (200 mg, 0.684 mmol) was dissolved in THE (7 mL), and diethyl 1,4-dihydro-2,6-dimethyl-3,5-pyridinedicarboxylate (516 mg, 2.04 mmol) and iodine (17.4 mg, 0.0684 mmol) were then added to the resulting solution, and the resulting mixture was stirred at 60° C. for 48 hours. After the reaction was completed, the reaction mixture was concentrated under reduced pressure. The obtained crude product was purified by column chromatography (silica gel, hexane/ethyl acetate) to obtain the title compound (hereinafter referred to as the compound of Example 133) as a pale pink solid (144 mg, 0.486 mmol, yield: 71%).

$^{1}$H-NMR ($CDCl_3$) δ: 7.54-7.68 (1H, m), 7.22-7.15 (2H, m), 6.76-6.70 (3H, m), 6.47 (1H, dd, J=9.5, 5.0 Hz), 4.33 (1H, dd, J=9.7, 2.9 Hz), 3.87 (1H, brs), 3.00-2.89 (3H, m), 2.77-2.68 (1H, m), 2.66-2.62 (2H, m), 2.10-2.03 (1H, m), 2.00-1.89 (1H, m).

MS(ESI) $[M+H]^+$: 297.

Reference Example 99: Synthesis of 4-(5-chloroquinolin-2-yl)benzenesulfonamide

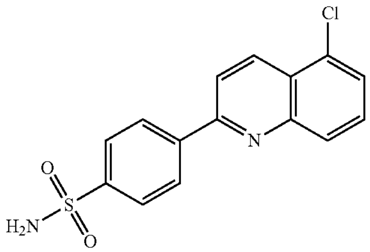

2,5-Dichloroquinoline (180 mg, 0.909 mmol), (4-sulfamoylphenyl)boronic acid (274 mg, 1.36 mmol), tetrakis (triphenylphosphine)palladium(0) (31.5 mg, 0.0273 mmol), and potassium carbonate (251 mg, 1.82 mmol) were dissolved in DMF/water (5/1, v/v, 7 mL), and the resulting solution was then stirred with heating at 100° C. for 4 hours. After the reaction mixture was cooled down to room temperature, water was poured into the reaction mixture, and the precipitated solid was filtered. The obtained crude product was washed with water, acetone, and hexane/chloroform to obtain the title compound as a gray solid (160 mg, 0.503 mmol, yield: 55%).

$^{1}$H-NMR (DMSO-$d_6$) δ: 8.71 (1H, d, J=4.5 Hz), 8.48 (3H, dd, J=10.4, 3.6 Hz), 8.40 (1H, d, J=9.1 Hz), 8.14-8.11 (1H, m), 8.02 (2H, d, J=8.6 Hz), 7.85-7.80 (3H, m).

MS(ESI) $[M+H]^+$: 319.

Example 134: Synthesis of 4-(5-chloro-1,2,3,4-tetrahydroquinolin-2-yl)benzenesulfonamide (a Novel Compound)

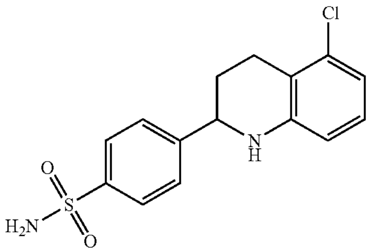

The 4-(5-chloroquinolin-2-yl)benzamide synthesized in Reference Example 99 (160 mg, 0.502 mmol) was dissolved in THE (5.0 mL), and diethyl 1,4-dihydro-2,6-dimethyl-3,5-pyridinedicarboxylate (305 mg, 1.20 mmol) and iodine (12.7 mg, 0.0502 mmol) were then added to the resulting solution, and the resulting mixture was stirred at room temperature for 18 hours. After the reaction was completed, the reaction mixture was concentrated under reduced pressure. The obtained crude product was purified by column chromatography (silica gel, hexane/ethyl acetate) to obtain the title compound (hereinafter referred to as the compound of Example 134) as a pale yellow solid (105 mg, 0.326 mmol, yield: 65%).

$^{1}$H-NMR ($CDCl_3$) δ: 7.93-7.90 (2H, m), 7.55-7.50 (2H, m), 6.97 (1H, dd, J=14.7, 6.6 Hz), 6.76 (1H, dd, J=7.9, 1.1 Hz), 6.49 (1H, dd, J=3.9, 3.9 Hz), 4.77 (2H, brs), 4.50 (1H, d, J=7.7 Hz), 4.18 (1H, brs), 2.86-2.80 (2H, m), 2.20-2.14 (1H, m), 2.05-1.94 (1H, m).

MS(ESI) $[M+H]^+$: 323.

Reference Example 100: Synthesis of 4-(5-fluoroquinolin-2-yl)benzenesulfonamide

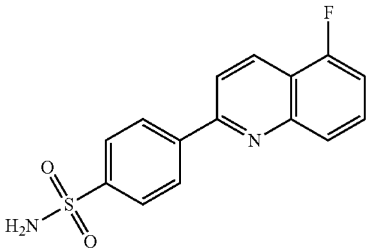 [SMILES: NS(=O)(=O)c1ccc(-c2ccc3c(F)cccc3n2)cc1]

2-Chloro-5-fluoroquinoline (160 mg, 0.881 mmol), (4-sulfamoylphenyl)boronic acid (266 mg, 1.32 mmol), tetrakis(triphenylphosphine)palladium(0) (30.5 mg, 0.0264 mmol), and potassium carbonate (243 mg, 1.76 mmol) were dissolved in DMF/water (5/1, v/v, 6 mL), and the resulting solution was then stirred with heating at 100° C. for 4 hours. After the reaction mixture was cooled down to room temperature, water was poured into the reaction mixture, and the precipitated solid was filtered. The obtained crude product was washed with water, acetone, and hexane/chloroform to obtain the title compound as a gray solid (215 mg, 0.712 mmol, yield: 81%).

$^{1}$H-NMR (DMSO-$d_6$) δ: 8.65 (1H, d, J=9.1 Hz), 8.48 (2H, dd, J=6.8, 1.8 Hz), 8.34 (1H, dd, J=7.5, 7.5 Hz), 8.05-7.90 (4H, m), 7.86-7.79 (1H, m), 7.55-7.45 (2H, m).

MS(ESI) $[M+H]^+$: 303.

Example 135: Synthesis of 4-(5-fluoro-1,2,3,4-tetrahydroquinolin-2-yl)benzenesulfonamide (a Novel Compound)

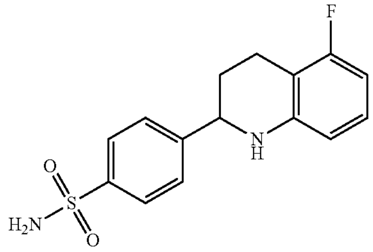 [SMILES: NS(=O)(=O)c1ccc(C2CCc3c(F)cccc3N2)cc1]

The 4-(5-fluoroquinolin-2-yl)benzamide synthesized in Reference Example 100 (210 mg, 0.660 mmol) was dissolved in THE (12.0 mL), and diethyl 1,4-dihydro-2,6-dimethyl-3,5-pyridinedicarboxylate (401 mg, 1.58 mmol) and iodine (16.7 mg, 0.0660 mmol) were then added to the resulting solution, and the resulting mixture was stirred at room temperature for 18 hours. After the reaction was completed, the reaction mixture was concentrated under reduced pressure. The obtained crude product was purified by column chromatography (silica gel, hexane/ethyl acetate) to obtain the title compound (hereinafter referred to as the compound of Example 135) as a pale yellow solid (155 mg, 0.507 mmol, yield: 77%).

$^{1}$H-NMR ($CDCl_3$) δ: 7.93-7.90 (2H, m), 7.56-7.50 (2H, m), 7.00-6.95 (1H, m), 6.44-6.36 (2H, m), 4.79 (2H, brs), 4.52 (1H, d, J=8.6 Hz), 4.19 (1H, brs), 2.85-2.70 (2H, m), 2.20-2.10 (1H, m), 2.00-1.90 (1H, m).

MS(ESI) $[M+H]^+$: 307.

Reference Example 101: Synthesis of N-(4-(quinolin-2-yl)phenyl)methanesulfonamide

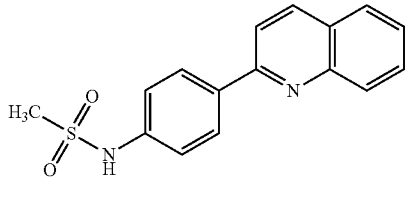 [SMILES: CS(=O)(=O)Nc1ccc(-c2ccc3ccccc3n2)cc1]

2-Chloroquinoline (140 mg, 0.859 mmol), (4-(methylsulfonamide)phenyl)boronic acid (256 mg, 1.19 mmol), tetrakis(triphenylphosphine)palladium(0) (27.5 mg, 0.0238 mmol), and potassium carbonate (275 mg, 1.99 mmol) were dissolved in DMF/water (5/1, v/v, 5 mL), and the resulting solution was then stirred with heating at 100° C. for 4 hours. After the reaction mixture was cooled down to room temperature, water was poured into the reaction mixture, and the resulting mixture was extracted with hexane/ethyl acetate. The organic layer was washed with water and saturated brine. The organic layer was dried over anhydrous sodium sulfate and then concentrated under reduced pressure. The obtained crude product was purified by column chromatography (silica gel, hexane/ethyl acetate) to obtain the title compound as a white solid (267 mg, 0.896 mmol, yield: quantitative).

$^{1}$H-NMR ($CDCl_3$) δ: 8.23 (1H, d, J=8.6 Hz), 8.20-8.14 (2H, m), 7.86-7.83 (2H, m), 7.76-7.65 (2H, m), 7.57-7.52 (1H, m), 7.50-7.47 (1H, m), 7.40-7.35 (1H, m), 6.69 (1H, s), 3.06 (3H, s).

MS(ESI) $[M+H]^+$: 299.

Example 136: Synthesis of N-(4-(1,2,3,4-tetrahydroquinolin-2-yl)phenyl)methanesulfonamide (a Novel Compound)

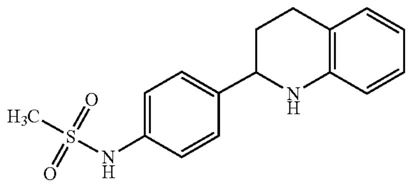 [SMILES: CS(=O)(=O)Nc1ccc(C2CCc3ccccc3N2)cc1]

The N-(4-(quinolin-2-yl)phenyl)methanesulfonamide synthesized in Reference Example 101 (180 mg, 0.573 mmol) was dissolved in THE (6.0 mL), and diethyl 1,4-dihydro-2,6-dimethyl-3,5-pyridinedicarboxylate (348 mg, 1.38 mmol) and iodine (14.5 mg, 0.0573 mmol) were then added to the resulting solution, and the resulting mixture was stirred at room temperature for 24 hours. After the reaction was completed, the reaction mixture was concentrated under reduced pressure. The obtained crude product was purified by column chromatography (silica gel, hexane/ethyl acetate) to obtain the title compound (hereinafter referred to as the compound of Example 136) as a pale yellow solid (113 mg, 0.374 mmol, yield: 65%).

$^{1}$H-NMR ($CDCl_3$) δ: 7.40-7.37 (2H, m), 7.21-7.18 (2H, m), 7.05-7.68 (2H, m), 6.66 (1H, dd, J=7.5, 1.1 Hz), 6.55 (1H, d, J=8.2 Hz), 6.39 (1H, s), 4.46-4.40 (1H, m), 4.00 (1H, s), 3.02 (3H, s), 2.96-2.88 (1H, m), 2.77-2.68 (1H, m), 2.13-2.07 (1H, m), 2.01-1.91 (1H, m).

MS(ESI) $[M+H]^+$: 303.

Reference Example 102: Synthesis of 4-(5-fluoroquinolin-2-yl)benzamide

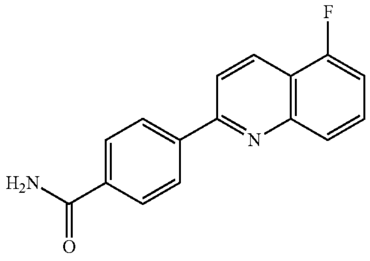 [SMILES: NC(=O)c1ccc(-c2ccc3c(F)cccc3n2)cc1]

2-Chloro-5-fluoroquinoline (150 mg, 0.826 mmol), (4-carbamoylphenyl)boronic acid (204 mg, 1.24 mmol), tetrakis(triphenylphosphine)palladium(0) (28.6 mg, 0.0248 mmol), and potassium carbonate (228 mg, 1.65 mmol) were dissolved in DMF/water (5/1, v/v, 6 mL), and the resulting solution was then stirred with heating at 100° C. for 4 hours. After the reaction mixture was cooled down to room temperature, water was poured into the reaction mixture, and the precipitated solid was filtered. The obtained crude product was washed with water, acetone, and hexane/chloroform to obtain the title compound as a gray solid (206 mg, 0.774 mmol, yield: 94%).

$^1$H-NMR (DMSO-$d_6$) δ: 8.61 (1H, d, J=8.6 Hz), 8.38 (2H, dd, J=4.3, 4.3 Hz), 8.33 (1H, d, J=8.6 Hz), 8.15-8.05 (3H, m), 7.98 (2H, dd, J=8.4, 2.9 Hz), 7.85-7.78 (1H, m), 7.50-7.43 (1H, m).

MS(ESI) $[M+H]^+$: 267.

Example 137: Synthesis of 4-(5-fluoro-1,2,3,4-tetrahydroquinolin-2-yl)benzamide (a Novel Compound)

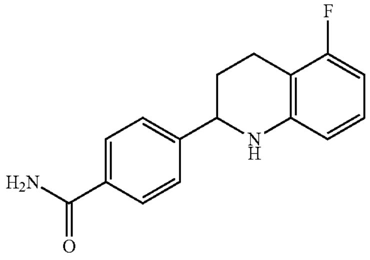 [SMILES: NC(=O)c1ccc(C2CCc3c(F)cccc3N2)cc1]

The 4-(5-fluoroquinolin-2-yl)benzamide synthesized in Reference Example 102 (180 mg, 0.642 mmol) was dissolved in THE (6.0 mL), and diethyl 1,4-dihydro-2,6-dimethyl-3,5-pyridinedicarboxylate (390 mg, 1.54 mmol) and iodine (16.3 mg, 0.0642 mmol) were then added to the resulting solution, and the resulting mixture was stirred at room temperature for 18 hours. After the reaction was completed, the reaction mixture was concentrated under reduced pressure. The obtained crude product was purified by column chromatography (silica gel, hexane/ethyl acetate) to obtain the title compound (hereinafter referred to as the compound of Example 137) as a white solid (131 mg, 0.485 mmol, yield: 76%).

$^1$H-NMR ($CDCl_3$) δ: 7.80 (2H, dd, J=8.5, 1.9 Hz), 7.48-7.45 (2H, m), 6.99-6.93 (1H, m), 6.43-6.35 (2H, m), 4.51-4.45 (1H, m), 4.20 (1H, brs), 2.80-2.75 (2H, m), 2.18-2.11 (1H, m), 2.00-1.90 (1H, m).

MS(ESI) $[M+H]^+$: 271.

Reference Example 103: Synthesis of 4-(5-chloroquinolin-2-yl)benzamide

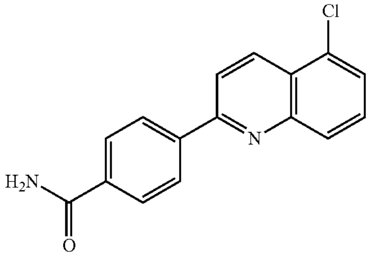

2,5-Dichloroquinoline (150 mg, 0.757 mmol), (4-carbamoylphenyl)boronic acid (149 mg, 0.903 mmol), tetrakis (triphenylphosphine)palladium(0) (26.2 mg, 0.0227 mmol), and potassium carbonate (209 mg, 1.51 mmol) were dissolved in DMF/water (5/1, v/v, 7 mL), and the resulting solution was then stirred with heating at 100° C. for 4 hours. After the reaction mixture was cooled down to room temperature, water was poured into the reaction mixture, and the precipitated solid was filtered. The obtained crude product was washed with water, acetone, and hexane/chloroform to obtain the title compound as a gray solid (209 mg, 0.741 mmol, yield: 98%).

$^1$H-NMR (DMSO-$d_6$) δ: 8.68 (1H, d, J=4.5 Hz), 8.40-8.36 (3H, m), 8.15-8.05 (4H, m), 7.81 (2H, dd, J=11.2, 4.1 Hz), 7.48 (1H, brs).

MS(ESI) $[M+H]^+$: 283.

Example 138: Synthesis of 4-(5-chloro-1,2,3,4-tetrahydroquinolin-2-yl)benzamide (a Novel Compound)

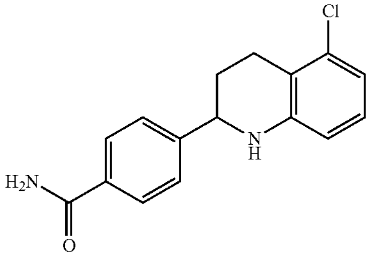

The 4-(5-chloroquinolin-2-yl)benzamide synthesized in Reference Example 103 (180 mg, 0.605 mmol) was dissolved in THE (6.0 mL), and diethyl 1,4-dihydro-2,6-dimethyl-3,5-pyridinedicarboxylate (547 mg, 2.16 mmol) and iodine (15.3 mg, 0.0605 mmol) were then added to the resulting solution, and the resulting mixture was stirred at 60° C. for 48 hours. After the reaction was completed, the reaction mixture was concentrated under reduced pressure. The obtained crude product was purified by column chromatography (silica gel, hexane/ethyl acetate) to obtain the title compound (hereinafter referred to as the compound of Example 138) as a white solid (155 mg, 0.542 mmol, yield: 89%).

$^1$H-NMR ($CDCl_3$) δ: 7.82-7.79 (2H, m), 7.48-7.42 (2H, m), 6.95 (1H, dd, J=8.0, 8.0 Hz), 6.75 (1H, dd, J=8.0, 1.1

Hz), 6.48 (1H, dd, J=8.2, 0.9 Hz), 4.50-4.45 (1H, m), 4.17 (1H, brs), 2.84 (2H, dd, J=7.5, 5.3 Hz), 2.21-2.15 (1H, m), 2.05-1.93 (1H, m).

MS(ESI) $[M+H]^+$: 287.

Reference Example 104: Synthesis of 7-fluoro-3',4'-dihydro-[2,6'-biquinolin]-2'(1'H)-one

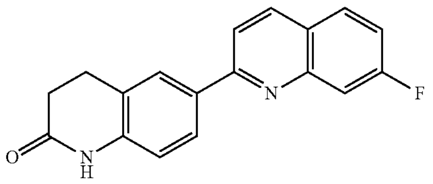 [SMILES: O=C1CCc2cc(-c3ccc4ccc(F)cc4n3)ccc2N1]

2-Chloro-7-fluoroquinoline (60.0 mg, 0.330 mmol), 6-(4,4,5,5-tetramethyl-1,3,2-di-oxaborolan-2-yl)-3,4-dihydroquinolin-2(1H)-one (135 mg, 0.496 mmol), tetrakis(triphenylphos-phine)palladium(0) (11.4 mg, 0.00991 mmol), and potassium carbonate (91.3 mg, 0.660 mmol) were dissolved in 1,4-dioxane/water (5/1, v/v, 3 mL), and the resulting solution was then stirred with heating at 100° C. for 4 hours. After the reaction mixture was cooled down to room temperature, water was poured into the reaction mixture, and the precipitated solid was filtered. The obtained crude product was washed with water, acetone, and hexane/chloroform to obtain the title compound as a gray solid (96.7 mg, 0.331 mmol, yield: 100%).

$^1$H-NMR (DMSO-$d_6$) δ: 10.32 (1H, s), 8.46 (1H, d, J=8.6 Hz), 8.14-8.05 (4H, m), 7.75 (1H, dd, J=10.4, 2.7 Hz), 7.50 (1H, dd, J=8.8, 2.4 Hz), 7.01 (1H, d, J=8.6 Hz), 3.05-2.99 (2H, m), 2.55-2.45 (2H, m).

MS(ESI) $[M+H]^+$: 293.

Example 139: Synthesis of 7-fluoro-1,2,3,3',4,4'-hexahydro-[2,6'-biquinolin]-2'(1'H)-one (a Novel Compound)

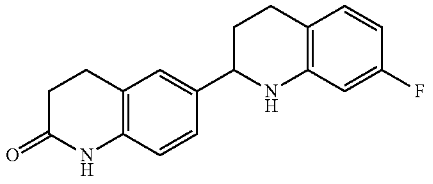 [SMILES: O=C1CCc2cc(C3CCc4ccc(F)cc4N3)ccc2N1]

The 7-fluoro-3',4'-dihydro-[2,6'-biquinolin]-2'(1'H)-one synthesized in Reference Example 104 (71.0 mg, 0.231 mmol) was dissolved in THE (3.0 mL), and diethyl 1,4-dihydro-2,6-dimethyl-3,5-pyridinedicarboxylate (140 mg, 0.554 mmol) and iodine (5.8 mg, 0.023 mmol) were then added to the resulting solution, and the resulting mixture was stirred at 60° C. for 18 hours. After the reaction was completed, the reaction mixture was concentrated under reduced pressure. The obtained crude product was purified by column chromatography (silica gel, hexane/ethyl acetate) to obtain the title compound (hereinafter referred to as the compound of Example 139) as a white solid (35.7 mg, 0.121 mmol, yield: 52%).

$^1$H-NMR ($CDCl_3$) δ: 7.81 (1H, brs), 7.20-7.12 (2H, m), 6.91 (1H, dd, J=7.2, 7.2 Hz), 6.72 (1H, d, J=7.7 Hz), 6.34 (1H, dd, J=8.5, 2.6 Hz), 6.24 (1H, dd, J=10.9, 2.7 Hz), 4.40-4.35 (1H, m), 4.07 (1H, s), 3.00-2.93 (2H, m), 2.89-2.81 (1H, m), 2.73-2.62 (3H, m), 2.11-2.05 (1H, m), 1.98-1.88 (1H, m).

MS(ESI) $[M+H]^+$: 297.

Reference Example 105: Synthesis of 7-fluoro-2-(1H-pyrazol-4-yl)quinoline

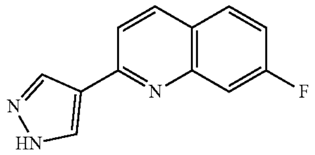

2-Chloro-7-fluoroquinoline (70.0 mg, 0.385 mmol), 1H-pyrazol-4-yl)boronic acid (64.0 mg, 0.576 mmol), tetrakis(triphenylphosphine)palladium(0) (13.3 mg, 0.0115 mmol), and potassium carbonate (106 mg, 0.768 mmol) were dissolved in DMF/water (5/1, v/v, 2 mL), and the resulting solution was then stirred with heating at 100° C. for 6 hours. After the reaction mixture was cooled down to room temperature, water was poured into the reaction mixture, and the precipitated solid was filtered. The obtained crude product was washed with water, acetone, and hexane/chloroform to obtain the title compound as a gray solid (20.0 mg, 0.0938 mmol, yield: 24%).

$^1$H-NMR ($CDCl_3$) δ: 8.28 (2H, s), 8.14 (1H, d, J=8.6 Hz), 7.77 (1H, dd, J=9.1, 5.9 Hz), 7.69 (1H, dd, J=10.4, 2.3 Hz), 7.62 (1H, d, J=8.6 Hz), 7.30-7.25 (1H, m).

MS(ESI) $[M+H]^+$: 214.

Example 140: Synthesis of 7-fluoro-(1H-pyrazol-4-yl)-1,2,3,4-tetrahydroquinoline (a Novel Compound)

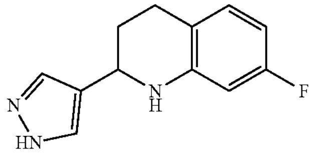

The 7-fluoro-2-(1H-pyrazol-4-yl)quinoline synthesized in Reference Example 105 (20.0 mg, 0.0891 mmol) was dissolved in THF (2.0 mL), and diethyl 1,4-dihydro-2,6-dimethyl-3,5-pyridinedicarboxylate (54.2 mg, 0.214 mmol) and iodine (2.26 mg, 0.00891 mmol) were then added to the resulting solution, and the resulting mixture was stirred at 60° C. for 18 hours. After the reaction was completed, the reaction mixture was concentrated under reduced pressure. The obtained crude product was purified by column chromatography (silica gel, hexane/ethyl acetate) to obtain the title compound (hereinafter referred to as the compound of Example 140) as a yellow oily substance (14.1 mg, 0.0650 mmol, yield: 73%).

$^1$H-NMR ($CDCl_3$) δ: 7.57 (2H, s), 6.92-6.89 (1H, m), 6.34 (1H, dd, J=8.5, 2.4 Hz), 6.21 (1H, dd, J=10.6, 2.5 Hz), 4.50 (1H, dd, J=9.1, 3.2 Hz), 2.89-2.80 (1H, m), 2.75-2.67 (1H, m), 2.16-2.10 (1H, m), 2.02-1.92 (1H, m).

MS(ESI) $[M+H]^+$: 218.

Reference Example 106: Synthesis of 2-fluoro-4-(quinolin-2-yl)benzonitrile

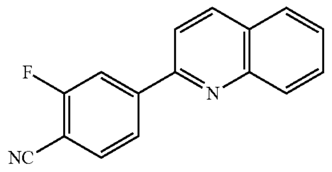 [SMILES: N#Cc1ccc(-c2ccc3ccccc3n2)cc1F]

2-Chloroquinoline (70.0 mg, 0.428 mmol), (4-cyano-3-fluorophenyl)boronic acid (106 mg, 0.642 mmol), tetrakis (triphenylphosphine)palladium(0) (14.8 mg, 0.0128 mmol), and potassium carbonate (118 mg, 0.856 mmol) were dissolved in 1,4-dioxane/water (5/1, v/v, 3 mL), and the resulting solution was then stirred with heating at 100° C. for 3 hours. After the reaction mixture was cooled down to room temperature, water was poured into the reaction mixture, and the resulting mixture was extracted with chloroform. The organic layer was washed with saturated brine, dried over anhydrous sodium sulfate, and then concentrated under reduced pressure. The obtained crude product was purified by column chromatography (silica gel, hexane/ethyl acetate) to obtain the title compound as a white solid (92.0 mg, 0.371 mmol, yield: 86%).

$^1$H-NMR ($CDCl_3$) δ: 8.31 (1H, d, J=8.6 Hz), 8.19-8.07 (3H, m), 7.88 (2H, d, J=8.6 Hz), 7.81-7.76 (2H, m), 7.63-7.59 (1H, m).

MS(ESI) $[M+H]^+$: 249.

Example 141: Synthesis of 4-fluoro-4-(1,2,3,4-tetrahydroquinolin-2-yl)benzonitrile (a Novel Compound)

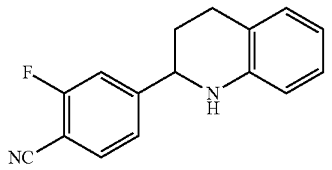 [SMILES: N#Cc1ccc(C2CCc3ccccc3N2)cc1F]

The 2-fluoro-4-(quinolin-2-yl)benzonitrile synthesized in Reference Example 106 (50.0 mg, 0.201 mmol) was dissolved in THE (2.0 mL), and diethyl 1,4-dihydro-2,6-dimethyl-3,5-pyridinedicarboxylate (122 mg, 0.483 mmol) and iodine (5.11 mg, 0.0201 mmol) were then added to the resulting solution, and the resulting mixture was stirred at room temperature for 18 hours. After the reaction was completed, the reaction mixture was concentrated under reduced pressure. The obtained crude product was purified by column chromatography (silica gel, hexane/ethyl acetate) to obtain the title compound (hereinafter referred to as the compound of Example 141) as a yellow oily substance (36.6 mg, 0.145 mmol, yield: 72%).

$^1$H-NMR ($CDCl_3$) δ: 7.61-7.58 (1H, m), 7.31-7.25 (2H, dd, J=7.7, 5.4 Hz), 7.08-7.68 (2H, m), 6.72-6.66 (1H, m), 6.61-6.57 (1H, m), 4.57-4.50 (1H, m), 4.10 (1H, brs), 2.93-2.83 (1H, m), 2.70-2.62 (1H, m), 2.18-2.10 (1H, m), 2.00-1.90 (1H, m).

MS(ESI) $[M+H]^+$: 253.

Reference Example 107: Synthesis of 4-(6-(trifluoromethyl)quinolin-2-yl)benzenesulfonamide

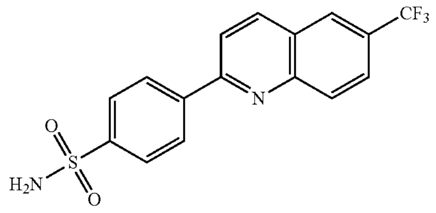 [SMILES: NS(=O)(=O)c1ccc(-c2ccc3cc(C(F)(F)F)ccc3n2)cc1]

2-Chloro-6-(trifluoromethyl)quinoline (200 mg, 0.864 mmol), (4-sulfamoyl-phenyl)boronic acid (260 mg, 1.30 mmol), tetrakis(triphenylphosphine)palladium(0) (29.9 mg, 0.0259 mmol), and potassium carbonate (239 mg, 1.73 mmol) were dissolved in DMF/water (5/1, v/v, 4.3 mL), and the resulting solution was then stirred with heating at 100° C. for 17 hours. After the reaction mixture was cooled down to room temperature, water was poured into the reaction mixture, and the resulting mixture was extracted with ethyl acetate. The organic layer was dried over anhydrous sodium sulfate and then concentrated under reduced pressure. The obtained crude product was purified by recrystallization (hexane/chloroform) to obtain the title compound as a pale yellow solid (220 mg, 0.624 mmol, yield: 72%).

$^1$H-NMR (DMSO-$d_6$) δ: 8.75 (1H, d, J=8.7 Hz), 8.59 (1H, s), 8.52 (2H, dt, J=8.7, 1.8 Hz), 8.41 (1H, d, J=8.7 Hz), 8.31 (1H, d, J=8.7 Hz), 8.07 (1H, dd, J=8.9, 2.1 Hz), 8.02 (2H, d, J=8.7 Hz), 7.52 (2H, s).

MS(ESI) $[M+H]^+$: 353.

Example 142: Synthesis of 4-(6-(trifluoromethyl)-1,2,3,4-tetrahydroquinolin-2-yl)benzenesulfonamide (a Novel Compound)

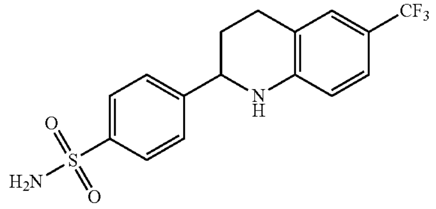 [SMILES: NS(=O)(=O)c1ccc(C2CCc3cc(C(F)(F)F)ccc3N2)cc1]

The 4-(6-(trifluoromethyl)quinolin-2-yl)benzenesulfonamide synthesized in Reference Example 107 (218 mg, 0.619 mmol) was dissolved in THF (6.2 mL), and diethyl 1,4-dihydro-2,6-dimethyl-3,5-pyridinedicarboxylate (376 mg, 1.49 mmol) and iodine (15.7 mg, 0.0619 mmol) were then added to the resulting solution, and the resulting mixture was stirred at 60° C. for 16 hours. After the reaction was completed, the reaction mixture was concentrated under reduced pressure. The obtained crude product was purified by column chromatography (silica gel, hexane/ethyl acetate) to obtain the title compound (hereinafter referred to as the compound of Example 142) as a white solid (166 mg, 0.466 mmol, yield: 75%).

$^1$H-NMR ($CDCl_3$) δ: 7.92 (2H, ddd, J=8.5, 8.5, 1.8 Hz), 7.51 (2H, d, J=8.5 Hz), 7.28-7.24 (2H, m), 6.60 (1H, d, J=8.2 Hz), 4.79 (2H, s), 4.63 (1H, d, J=7.8 Hz), 4.41 (1H, brs), 2.93-2.85 (1H, m), 2.73-2.68 (1H, m), 2.20-2.15 (1H, m), 2.02-1.96 (1H, m).

MS(ESI) $[M+H]^+$: 357.

Reference Example 108: Synthesis of ethyl 2-(2-phenylquinolin-6-yl)acetate

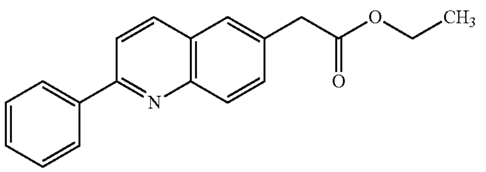 [SMILES: CCOC(=O)Cc1ccc2nc(-c3ccccc3)ccc2c1]

Ethyl 2-(4-aminophenyl)acetate (10.0 g, 55.8 mmol) was dissolved in acetonitrile (56 mL), and benzaldehyde (6.2 mL, 61 mmol) was then added to the resulting solution, and the resulting mixture was stirred at 50° C. for 19 hours with nitrogen gas flow in open air. After the complete dissolution of the raw material was confirmed, the solution was allowed to cool down to room temperature. Acetonitrile/dichloromethane (1/1, v/v, 56 mL) was added to the solution, and ethyl vinyl ether (0.75 mL, 67 mmol) and ytterbium(III) triflate hydrate (769 mg, 1.12 mmol) were added to the resulting mixture under ice cooling, and the resulting mixture was stirred for 1 hour. Subsequently, the reaction mixture was distilled under reduced pressure. The obtained crude product was purified by column chromatography (silica gel, hexane/ethyl acetate) to obtain a mixture as a white solid (14.9 g, crude yield: 79%), which contains ethyl 2-(4-ethoxy-2-phenyl-1,2,3,4-tetrahydroquinolin-6-yl)acetate as a main component.

The obtained mixture (14.9 g) was dissolved in acetic acid/toluene (1/2, v/v, 220 mL), and the resulting solution was then stirred at 60° C. for 20 hours in open air. Subsequently, the reaction mixture was distilled under reduced pressure. The obtained crude product was purified by column chromatography (silica gel, hexane/ethyl acetate) to obtain the title compound as a pale yellow solid (6.31 g, 21.7 mmol, yield in 2 steps: 39%).

$^1$H-NMR ($CDCl_3$) δ: 8.19-8.13 (4H, m), 7.87 (1H, d, J=8.7 Hz), 7.73 (1H, d, J=1.6 Hz), 7.66 (1H, dd, J=8.7, 1.6 Hz), 7.55-7.50 (2H, m), 7.46 (1H, tt, J=7.3, 1.8 Hz), 4.19 (2H, q, J=7.2 Hz), 3.81 (2H, s), 1.27 (3H, t, J=7.2 Hz).

MS(ESI) $[M+H]^+$: 292.

Reference Example 109: Synthesis of 2-(2-phenylquinolin-6-yl)acetic acid

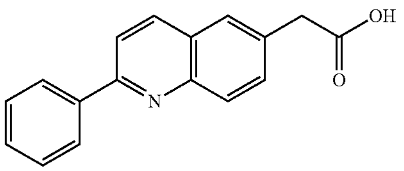 [SMILES: O=C(O)Cc1ccc2nc(-c3ccccc3)ccc2c1]

The ethyl 2-(2-phenylquinolin-6-yl)acetate synthesized in Reference Example 108 (6.31 g, 21.7 mmol) was dissolved in ethanol/tetrahydrofuran (1/1, v/v, 86 mL), and a 1 mol/L aqueous solution of sodium hydroxide (45.5 mL, 45.5 mmol) was then added to the resulting solution, and the resulting mixture was stirred at room temperature for 1 hour. The reaction mixture was adjusted to pH 6 by addition of 1 mol/L hydrochloric acid (about 30 mL) and then diluted with ethyl acetate (86 mL). After the organic layer was separated off, the aqueous phase was extracted three times with ethyl acetate (170 mL). The organic layers were combined, washed with water (170 mL) and saturated brine (85 mL), dried over anhydrous sodium sulfate, and then distilled under reduced pressure to obtain the title compound as a yellow solid (6.31 g, 21.7 mmol, yield: 39%).

$^1$H-NMR ($CDCl_3$) δ: 8.19-8.12 (4H, m), 7.87 (1H, d, J=8.5 Hz), 7.74 (1H, d, J=1.8 Hz), 7.66 (1H, dd, J=8.5, 1.8 Hz), 7.54-7.50 (2H, m), 7.48-7.44 (1H, m), 3.85 (2H, s).

MS(ESI) $[M+H]^+$: 264.

Reference Example 110: Synthesis of 1-(3-hydroxyazetidin-1-yl)-2-(2-phenylquinolin-6-yl)ethan-1-one

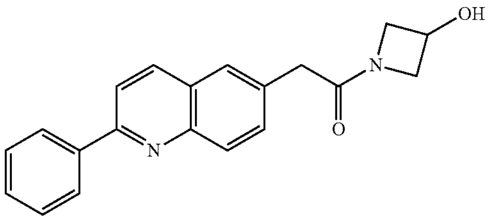 [SMILES: O=C(Cc1ccc2nc(-c3ccccc3)ccc2c1)N1CC(O)C1]

The 2-(2-phenylquinolin-6-yl)acetic acid synthesized in Reference Example 109 (4.90 g, 18.6 mmol) was dissolved in DMF (93 mL), and N,N-diisopropylethylamine (11.3 mL, 65.1 mmol) and 1-[bis(dimethylamino)methylene]-1H-1,2,3-triazolo[4,5-b]pyridinium 3-oxide hexafluorophosphate (HATU, 10.6 g, 27.9 mmol) were then added to the resulting solution, and the resulting mixture was stirred at room temperature for 20 minutes. Subsequently, 3-hydroxyazetidin hydrochloride (2.65 g, 24.2 mmol) was added to the mixture, and the resulting mixture was stirred at room temperature for further 15 hours. Water (280 mL) was added to the reaction mixture, and the resulting mixture was stirred for 30 minutes, and the obtained suspension was then filtrated. The filtrate was extracted three times with ethyl acetate (180 mL) and further extracted four times with ethyl acetate (90 mL). The organic layer was washed twice with saturated brine (180 mL), dried over anhydrous sodium sulfate, and then distilled under reduced pressure. The obtained crude product was purified by column chromatography (silica gel, chloroform/methanol) and column chromatography (silica gel, ethyl acetate/methanol) to obtain the title compound as a pale yellow solid (1.43 g, 4.50 mmol, yield: 24%).

$^1$H-NMR ($CDCl_3$) δ: 8.19-8.11 (4H, m), 7.87 (1H, d, J=8.2 Hz), 7.72 (1H, s), 7.63 (1H, dd, J=8.5, 2.1 Hz), 7.55-7.47 (3H, m), 4.62 (1H, brs), 4.34 (1H, dd, J=8.0, 6.6 Hz), 4.27 (1H, dd, J=10.3, 6.6 Hz), 4.01 (1H, dd, J=9.6, 3.8 Hz), 3.89 (1H, dd, J=10.7, 3.8 Hz), 3.65 (2H, s), 2.60 (1H, brs).

MS(ESI) $[M+H]^+$: 319.

Example 143: Synthesis of One of the Optical Isomers of 1-(3-hydroxyazetidin-1-yl)-2-(2-phenyl-1,2,3,4-tetrahydroquinolin-6-yl)ethan-1-one hydrochloride (a Novel Compound)

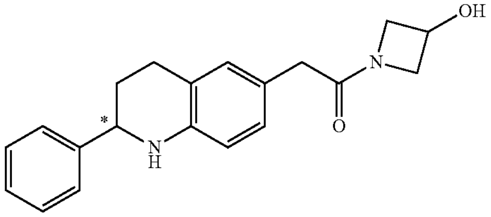 [SMILES: O=C(Cc1ccc2c(c1)CCC(c1ccccc1)N2)N1CC(O)C1]

In the formula, the carbon atom marked with an asterisk (*) is an asymmetric center.

The 1-(3-hydroxyazetidin-1-yl)-2-(2-phenylquinolin-6-yl)ethan-1-one synthesized in Reference Example 110 (50.0 mg, 0.157 mmol) and (S)-3,3'-bis(2,4,6-triisopropylphenyl)-1,1'-binaphthyl-2,2'-diyl hydrogen phosphate ((S)-TRIP, 2.4 mg, 0.0031 mmol) were suspended in 1,4-dioxane (0.8 mL), and diethyl 1,4-dihydro-2,6-dimethyl-3,5-pyridinedicarboxylate (87.5 mg, 0.346 mmol) was then added to the resulting suspension, and the resulting mixture was stirred at room temperature for 17 hours. The reaction mixture was distilled under reduced pressure, and the obtained crude product was purified by column chromatography (silica gel, chloroform/methanol) to obtain one of the optical isomers of 1-(3-hydroxyazetidin-1-yl)-2-(2-phenyl-1,2,3,4-tetrahydroquinolin-6-yl)ethan-1-one as a pale yellow amorphous (44.7 mg).

The obtained optical isomer of 1-(3-hydroxyazetidin-1-yl)-2-(2-phenyl-1,2,3,4-tetrahydroquinolin-6-yl)ethan-1-one (44.7 mg), which is one of the optical isomers, was dissolved in ethyl acetate (2 mL), and a 4 mol/L hydrogen chloride-ethyl acetate solution (0.136 mL) was then added to the resulting solution with stirring. The resulting mixture was further stirred at room temperature for 30 minutes, and the resulting solid was then filtered to obtain the title compound (hereinafter referred to as the compound of Example 143) as a white solid (40.5 mg, 0.113 mmol, yield: 72%, enantiomeric excess: 95.6% ee).

$^1$H-NMR (DMSO-$d_6$) δ: 7.49-7.47 (2H, m), 7.41-7.39 (2H, m), 7.34-7.31 (1H, m), 6.93 (2H, brs), 6.83 (1H, brs), 4.51-4.49 (1H, brm), 4.44-4.43 (1H, m), 4.34 (1H, dd, J=8.5, 6.8 Hz), 4.01 (1H, dd, J=10.3, 6.8 Hz), 3.88 (1H, dd, J=8.5, 4.4 Hz), 3.56 (1H, dd, J=10.3, 4.4 Hz), 3.29 (2H, s), 2.88-2.85 (1H, brm), 2.71-2.67 (1H, brm), 2.09-2.03 (2H, m).

MS(ESI) $[M+H]^+$: 323.

Rt: 12.27 min

HPLC analysis conditions:

Column: Daicel Chiralcel OD-H chiral column (inner diameter: 4.6 mm, length: 250 mm, particle size: 5 μm)

Column temperature: 40° C.

Mobile phase: propan-2-ol:hexane=60:40

Flow rate: 0.6 mL/min

Injection volume: 10 μL

Detection: UV (254 nm)

Example 144: Synthesis of the Other of the Optical Isomers of 1-(3-hydroxyazetidin-1-yl)-2-(2-phenyl-1,2,3,4-tetrahydroquinolin-6-yl)ethan-1-one hydrochloride (a Novel Compound)

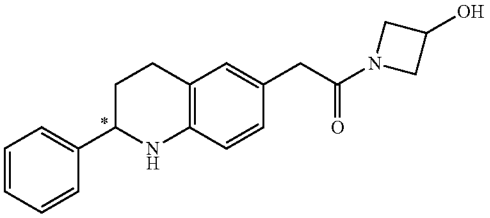 [SMILES: O=C(Cc1ccc2c(c1)CCC(c1ccccc1)N2)N1CC(O)C1]

In the formula, the carbon atom marked with an asterisk (*) is an asymmetric center.

The 1-(3-hydroxyazetidin-1-yl)-2-(2-phenylquinolin-6-yl)ethan-1-one synthesized in Reference Example 110 (1.43 g, 4.49 mmol) and (R)-3,3'-bis(2,4,6-triisopropylphenyl)-1,1'-binaphthyl-2,2'-diyl hydrogen phosphate ((R)-TRIP, 67.6 mg, 0.0898 mmol) were suspended in 1,4-dioxane (22 mL), and diethyl 1,4-dihydro-2,6-dimethyl-3,5-pyridinedicarboxylate (2.50 g, 9.88 mmol) was then added to the resulting suspension, and the resulting mixture was stirred at room temperature for 18 hours. The reaction mixture was distilled under reduced pressure, and the obtained crude product was purified by column chromatography (amino-silica gel, chloroform/methanol) and column chromatography (silica gel, ethyl acetate/methanol) to obtain the other of the optical isomers of 1-(3-hydroxyazetidin-1-yl)-2-(2-phenyl-1,2,3,4-tetrahydroquinolin-6-yl)ethan-1-one as a pale yellow amorphous (1.13 g).

The obtained optical isomer of 1-(3-hydroxyazetidin-1-yl)-2-(2-phenyl-1,2,3,4-tetrahydroquinolin-6-yl)ethan-1-one (1.13 g), which is the other of the optical isomers, was dissolved in ethyl acetate (45 mL), and a 4 mol/L hydrogen chloride-ethyl acetate solution (3.5 mL) was then added to the resulting solution with stirring. The resulting mixture was further stirred at room temperature for 30 minutes, and the resulting solid was then filtered to obtain the title compound (hereinafter referred to as the compound of Example 144) as a white solid (1.13 g, 3.15 mmol, yield: 70%, enantiomeric excess: 95.4% ee).

$^1$H-NMR (DMSO-$d_6$) δ: 7.49-7.47 (2H, m), 7.41-7.39 (2H, m), 7.34-7.31 (1H, m), 6.93 (2H, brs), 6.83 (1H, brs), 4.51-4.49 (1H, brm), 4.44-4.43 (1H, m), 4.34 (1H, dd, J=8.5, 6.8 Hz), 4.01 (1H, dd, J=10.3, 6.8 Hz), 3.88 (1H, dd, J=8.5, 4.4 Hz), 3.56 (1H, dd, J=10.3, 4.4 Hz), 3.29 (2H, s), 2.88-2.85 (1H, brm), 2.71-2.67 (1H, brm), 2.09-2.03 (2H, m).

MS(ESI) $[M+H]^+$: 323.

Rt: 9.30 min

HPLC analysis conditions:

Column: Daicel Chiralcel OD-H chiral column (inner diameter: 4.6 mm, length: 250 mm, particle size: 5 μm)

Column temperature: 40° C.

Mobile phase: propan-2-ol:hexane=60:40

Flow rate: 0.6 mL/min

Injection volume: 10 μL

Detection: UV (254 nm)

Example 145: Synthesis of 1-morpholino-2-(2-phenyl-1,2,3,4-tetrahydroquinolin-6-yl)ethan-1-one (a Novel Compound)

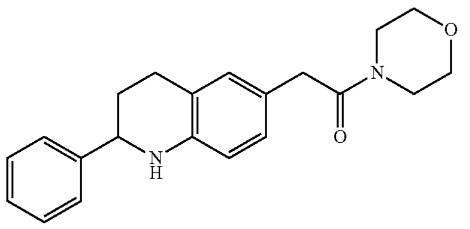 [SMILES: O=C(Cc1ccc2c(c1)CCC(c1ccccc1)N2)N1CCOCC1]

The 2-(2-phenyl-1,2,3,4-tetrahydroquinolin-6-yl)acetic acid synthesized in Reference Example 40 (92.0 mg, 0.344 mmol) was dissolved in DMF (0.75 mL), and N,N-diisopropylethylamine (89.8 μL, 0.516 mmol), morpholine (24.8 μL, 0.413 mmol), and 1-[bis(dimethyl-amino)methylene]-1H-1,2,3-triazolo[4,5-b]pyridinium 3-oxide hexafluorophosphate (HATU, 157 mg, 0.413 mmol) were then added to the resulting solution, and the resulting mixture was stirred at room temperature for 2 hours. Water was added to the reaction mixture, and the resulting mixture was extracted with ethyl acetate. The organic layer was washed with saturated brine, dried over anhydrous sodium sulfate, and then distilled under reduced pressure. The obtained crude product was purified by column chromatography (silica gel, chloroform/methanol) and column chromatography (amino-silica gel, hexane/ethyl acetate) to obtain the title compound (hereinafter referred to as the compound of Example 145) as a colorless clear oily substance (83.3 mg, 0.248 mmol, yield: 72%).

$^1$H-NMR ($CDCl_3$) δ: 7.39-7.33 (4H, m), 7.31-7.27 (1H, m), 6.89-6.84 (2H, m), 6.50 (1H, d, J=8.2 Hz), 4.42 (1H, dd, J=9.1, 3.2 Hz), 4.02 (1H, brs), 3.65 (4H, s), 3.60 (2H, s), 3.54-3.52 (2H, m), 3.48-3.46 (2H, m), 2.94-2.86 (1H, m), 2.71 (1H, dt, J=16.5, 4.8 Hz), 2.14-2.08 (1H, m), 2.02-1.93 (1H, m).

MS(ESI) $[M+H]^+$: 337.

Example 146: Synthesis of 1-(3,3-dimethylazetidin-1-yl)-2-(2-phenyl-1,2,3,4-tetrahy-dro-quin-olin-6-yl) ethan-1-one (a Novel Compound)

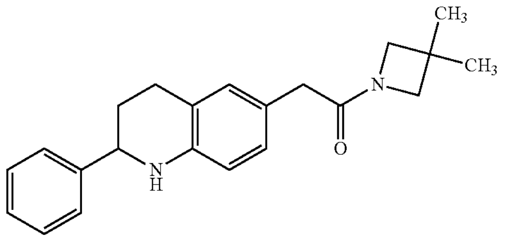 [SMILES: CC1(C)CN(C(=O)Cc2ccc3c(c2)CCC(c2ccccc2)N3)C1]

The 2-(2-phenyl-1,2,3,4-tetrahydroquinolin-6-yl)acetic acid synthesized in Reference Example 40 (20.0 mg, 0.0748 mmol), N,N-diisopropylethylamine (39.0 μL, 0.224 mmol), 3,3-dimethylazetidine (10.9 mg, 0.0898 mmol), and 1-[bis(dimethylamino)methylene]-1H-1,2,3-triazolo[4,5-b]pyridinium 3-oxide hexafluorophosphate (HATU, 34.1 mg, 0.0898 mmol) were used in the same manner as in Example 145 to obtain the title compound (hereinafter referred to as the compound of Example 146) as a colorless clear oily substance (20.0 mg, 0.0598 mmol, yield: 80%).

$^1$H-NMR ($CDCl_3$) δ: 7.40-7.32 (4H, m), 7.30-7.27 (1H, m), 6.92 (1H, d, J=2.3 Hz), 6.89 (1H, dd, J=8.2, 2.3 Hz), 6.49 (1H, d, J=8.2 Hz), 4.42 (1H, dd, J=9.5, 3.2 Hz), 4.01 (1H, brs), 3.78 (2H, s), 3.69 (2H, s), 3.33 (2H, s), 2.96-2.86 (1H, m), 2.72 (1H, dt, J=16.3, 4.8 Hz), 2.14-2.07 (1H, m), 2.02-1.93 (1H, m), 1.25 (6H, s).

MS(ESI) $[M+H]^+$: 335.

Example 147: Synthesis of 1-(3-methoxyazetidin-1-yl)-2-(2-phenyl-1,2,3,4-tetrahydroquinolin-6-yl) ethan-1-one (a Novel Compound)

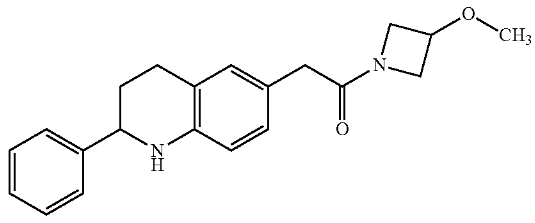 [SMILES: COC1CN(C(=O)Cc2ccc3c(c2)CCC(c2ccccc2)N3)C1]

The 2-(2-phenyl-1,2,3,4-tetrahydroquinolin-6-yl)acetic acid synthesized in Reference Example 40 (20.0 mg, 0.0748 mmol), N,N-diisopropylethylamine (19.5 μL, 0.112 mmol), 3-methoxyazetidine (7.82 mg, 0.0898 mmol), and 1-[bis(dimethylamino)methylene]-1H-1,2,3-triazolo[4,5-b]pyridinium 3-oxide hexafluorophosphate (HATU, 34.1 mg, 0.0898 mmol) were used in the same manner as in Example 145 to obtain the title compound (hereinafter referred to as the compound of Example 147) as a colorless clear oily substance (8.00 mg, 0.0238 mmol, yield: 32%).

$^1$H-NMR ($CDCl_3$) δ: 7.39-7.33 (4H, m), 7.30-7.27 (1H, m), 6.91 (1H, d, J=2.0 Hz), 6.88 (1H, dd, J=8.2, 2.0 Hz), 6.49 (1H, d, J=8.2 Hz), 4.42 (1H, dd, J=8.8, 3.4 Hz), 4.26-4.22 (1H, m), 4.18-4.13 (2H, m), 3.98 (1H, dd, J=8.8, 2.9 Hz), 3.91-3.86 (1H, m), 3.35 (2H, s), 3.28 (3H, s), 2.94-2.86 (1H, m), 2.71 (1H, dt, J=16.6, 4.8 Hz), 2.14-2.07 (1H, m), 2.02-1.92 (1H, m).

MS(ESI) $[M+H]^+$: 337.

Example 148: Synthesis of N-(oxetan-3-yl)-2-(2-phenyl-1,2,3,4-tetrahydroquinolin-6-yl)acetamide (a Novel Compound)

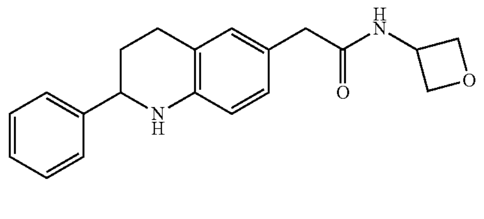 [SMILES: O=C(Cc1ccc2c(c1)CCC(c1ccccc1)N2)NC1COC1]

The 2-(2-phenyl-1,2,3,4-tetrahydroquinolin-6-yl)acetic acid synthesized in Reference Example 40 (20.0 mg, 0.0748 mmol), N,N-diisopropylethylamine (19.5 μL, 0.112 mmol), oxetane-3-amine (6.56 mg, 0.0898 mmol), and 1-[bis(dimethylamino)methylene]-1H-1,2,3-triazolo[4,5-b]pyridinium 3-oxide hexafluorophosphate (HATU, 34.1 mg, 0.0898 mmol) were used in the same manner as in Example 145 to obtain the title compound (hereinafter referred to as the compound of Example 148) as a white solid (2.50 mg, 0.00775 mmol, yield: 10%).

$^1$H-NMR (DMSO-$d_6$) δ: 7.37-7.31 (4H, m), 7.27-7.23 (1H, m), 6.73-6.70 (2H, m), 6.52 (1H, dd, J=8.2, 3.6 Hz), 5.95 (1H, brs), 4.98-4.87 (1H, m), 4.48-4.36 (2H, m), 3.99-3.86 (1H, m), 3.71-3.64 (1H, m), 3.49-3.34 (4H, m), 2.80-2.69 (1H, m), 2.02-1.94 (1H, m), 1.86-1.77 (1H, m).

MS(ESI) $[M+H]^+$: 323.

Example 149: Synthesis of 1-(3,3-difluoroazetidin-1-yl)-2-(2-phenyl-1,2,3,4-tetrahydroquinolin-6-yl) ethan-1-one (a Novel Compound)

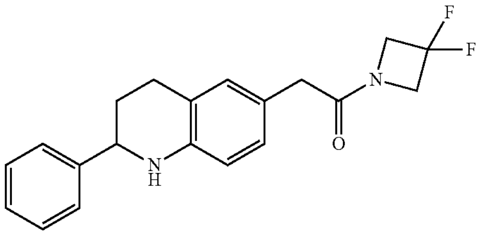 [SMILES: O=C(Cc1ccc2c(c1)CCC(c1ccccc1)N2)N1CC(F)(F)C1]

The 2-(2-phenyl-1,2,3,4-tetrahydroquinolin-6-yl)acetic acid synthesized in Reference Example 40 (19.1 mg, 0.0715 mmol), N,N-diisopropylethylamine (37 μL, 0.21 mmol), 3,3-difluoroazetidine hydrochloride (18.5 mg, 0.143 mmol), and 1-[bis(dimethylamino)methylene]-1H-1,2,3-triazolo[4,5-b]pyridinium 3-oxide hexafluorophosphate (HATU, 32.6 mg, 0.0857 mmol) were used in the same manner as in Example 145 to obtain the title compound (hereinafter referred to as the compound of Example 149) as a colorless clear oily substance (15.4 mg, 0.0715 mmol, yield: 63%).

$^1$H-NMR ($CDCl_3$) δ: 7.40-7.33 (4H, m), 7.31-7.27 (1H, m), 6.89-6.86 (2H, m), 6.50 (1H, d, J=8.2 Hz), 4.43 (1H, dd, J=9.1, 3.2 Hz), 4.34 (4H, q, J=11.4 Hz), 4.06 (1H, brs), 3.43 (2H, s), 2.94-2.86 (1H, m), 2.72 (1H, dt, J=16.6, 4.7 Hz), 2.15-2.09 (1H, m), 2.01-1.96 (1H, m).

MS(ESI) $[M+H]^+$: 343.

Example 150: Synthesis of N-(2-hydroxyethyl)-N-methyl-2-(2-phenyl-1,2,3,4-tetrahydroquino-lin-6-yl) acetamide (a Novel Compound)

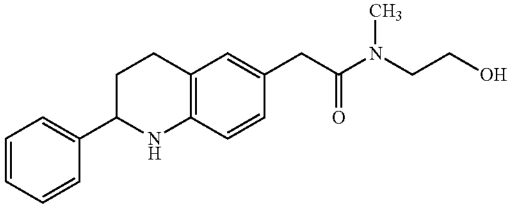 [SMILES: CN(CCO)C(=O)Cc1ccc2c(c1)CCC(c1ccccc1)N2]

The 2-(2-phenyl-1,2,3,4-tetrahydroquinolin-6-yl)acetic acid synthesized in Reference Example 40 (18.0 mg, 0.0673 mmol), N,N-diisopropylethylamine (35 μL, 0.20 mmol), 2-(methylamino)ethanol (10.1 mg, 0.135 mmol), and 1-[bis(dimethylamino)methylene]-1H-1,2,3-triazolo[4,5-b]pyridinium 3-oxide hexafluorophosphate (HATU, 30.7 mg, 0.0808 mmol) were used in the same manner as in Example 145 to obtain the title compound (hereinafter referred to as the compound of Example 150) as a white solid (20.1 mg, 0.0620 mmol, yield: 92%).

$^1$H-NMR was employed to observe a mixture of two rotamers.

Major Rotamer:

$^1$H-NMR ($CDCl_3$) δ: 7.40-7.33 (4H, m), 7.30-7.28 (1H, m), 6.92-6.87 (2H, m), 6.51 (1H, d, J=7.9 Hz), 4.42 (1H, dd, J=9.4, 3.0 Hz), 4.02 (1H, brs), 3.79 (2H, q, J=5.0 Hz), 3.61 (2H, s), 3.57 (2H, t, J=5.0 Hz), 3.19 (1H, t, J=5.0 Hz), 3.08 (3H, s), 2.95-2.87 (1H, m), 2.75-2.70 (1H, m), 2.13-2.09 (1H, m), 2.00-1.95 (1H, m).

Minor Rotamer:

$^1$H-NMR ($CDCl_3$) δ: 7.40-7.33 (4H, m), 7.30-7.28 (1H, m), 6.92-6.87 (2H, m), 6.50 (1H, d, J=7.9 Hz), 4.42 (1H, dd, J=9.4, 3.0 Hz), 4.02 (1H, brs), 3.72 (2H, q, J=5.6 Hz), 3.67 (2H, s), 3.50 (2H, t, J=5.6 Hz), 3.19 (1H, t, J=5.0 Hz), 2.98 (3H, s), 2.95-2.87 (1H, m), 2.75-2.70 (1H, m), 2.13-2.09 (1H, m), 2.00-1.95 (1H, m).

MS(ESI) $[M+H]^+$: 325.

Example 151: Synthesis of 1-(azetidin-1-yl)-2-(2-phenyl-1,2,3,4-tetrahydroquinolin-6-yl)ethan-1-one (a Novel Compound)

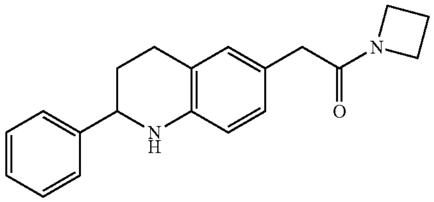 [SMILES: O=C(Cc1ccc2c(c1)CCC(c1ccccc1)N2)N1CCC1]

The 2-(2-phenyl-1,2,3,4-tetrahydroquinolin-6-yl)acetic acid synthesized in Reference Example 40 (18.5 mg, 0.0692 mmol), N,N-diisopropylethylamine (36 μL, 0.21 mmol), azetidine hydrochloride (12.9 mg, 0.138 mmol), and 1-[bis(dimethylamino)methylene]-1H-1,2,3-triazolo[4,5-b]pyridinium 3-oxide hexafluorophosphate (HATU, 31.6 mg, 0.0830 mmol) were used in the same manner as in Example 145 to obtain the title compound (hereinafter referred to as the compound of Example 151) as a colorless clear oily substance (21.0 mg, 0.0685 mmol, yield: 99%).

$^1$H-NMR ($CDCl_3$) δ: 7.39-7.33 (4H, m), 7.30-7.27 (1H, m), 6.93 (1H, s), 6.90 (1H, dd, J=7.9, 2.1 Hz), 6.49 (1H, d, J=7.9 Hz), 4.42 (1H, dd, J=9.1, 3.2 Hz), 4.14 (2H, t, J=7.5 Hz), 4.03 (2H, t, J=7.8 Hz), 4.02 (1H, brs), 3.32 (2H, s), 2.94-2.88 (1H, m), 2.72 (1H, dt, J=16.3, 4.7 Hz), 2.26-2.18 (2H, m), 2.14-2.08 (1H, m), 2.02-1.92 (1H, m).

MS(ESI) $[M+H]^+$: 307.

Example 152: Synthesis of N-cyclopropyl-2-(2-phenyl-1,2,3,4-tetrahydroquinolin-6-yl)acetamide (a Novel Compound)

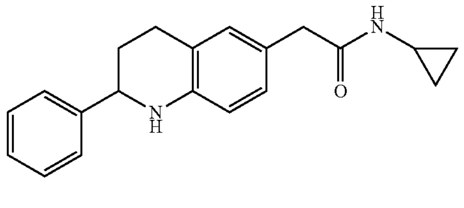 [SMILES: O=C(Cc1ccc2c(c1)CCC(c1ccccc1)N2)NC1CC1]

The 2-(2-phenyl-1,2,3,4-tetrahydroquinolin-6-yl)acetic acid synthesized in Reference Example 40 (20.7 mg, 0.0774 mmol), N,N-diisopropylethylamine (20.2 μL, 0.116 mmol), cyclopropylamine (6.5 μL, 0.093 mmol), and 1-[bis(dimethylamino)methylene]-1H-1,2,3-triazolo[4,5-b]pyridinium 3-oxide hexafluorophosphate (HATU, 35.3 mg, 0.0929 mmol) were used in the same manner as in Example 145 to obtain the title compound (hereinafter referred to as the compound of Example 152) as a white amorphous (20.2 mg, 0.0658 mmol, yield: 85%).

$^1$H-NMR ($CDCl_3$) δ: 7.40-7.30 (5H, m), 6.84-6.83 (2H, m), 6.51 (1H, d, J=8.7 Hz), 5.55 (1H, brs), 4.44 (1H, dd, J=9.1, 3.2 Hz), 4.08 (1H, brs), 3.42 (2H, s), 2.91-2.88 (1H, m), 2.73-2.65 (2H, m), 2.16-2.11 (1H, m), 2.04-1.97 (1H, m), 0.73 (2H, td, J=7.0, 5.3 Hz), 0.43-0.39 (2H, m).

MS(ESI) $[M+H]^+$: 307.

Example 153: Synthesis of N-(cyclopropylmethyl)-2-(2-phenyl-1,2,3,4-tetrahydroquin-olin-6-yl)acetamide (a Novel Compound)

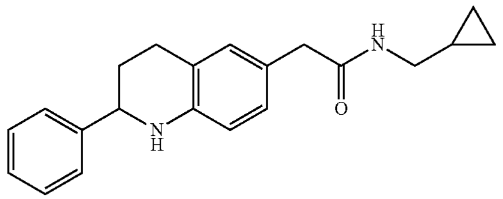 [SMILES: O=C(Cc1ccc2c(c1)CCC(c1ccccc1)N2)NCC1CC1]

The 2-(2-phenyl-1,2,3,4-tetrahydroquinolin-6-yl)acetic acid synthesized in Reference Example 40 (20.9 mg, 0.0782 mmol), N,N-diisopropylethylamine (20.4 μL, 0.117 mmol), cyclo-propylmethylamine (8.0 μL, 0.094 mmol), and 1-[bis(dimethylamino)methylene]-1H-1,2,3-triazolo[4,5-b]pyridinium 3-oxide hexafluorophosphate (HATU, 35.7 mg, 0.0938 mmol) were used in the same manner as in Example 145 to obtain the title compound (hereinafter referred to as the compound of Example 153) as a pale yellow amorphous (13.0 mg, 0.0407 mmol, yield: 52%).

$^1$H-NMR ($CDCl_3$) δ: 7.40-7.28 (5H, m), 6.89-6.88 (2H, m), 6.53 (1H, d, J=8.7 Hz), 5.58 (1H, brs), 4.45 (1H, dd, J=9.1, 2.7 Hz), 4.08 (1H, brs), 3.45 (2H, s), 3.09 (2H, dd, J=6.9, 5.9 Hz), 2.96-2.88 (1H, m), 2.73 (1H, dt, J=16.9, 5.0 Hz), 2.16-2.10 (1H, m), 2.04-1.98 (1H, m), 0.91-0.87 (1H, m), 0.47-0.43 (2H, m), 0.16-0.12 (2H, m).

MS(ESI) $[M+H]^+$: 321.

Example 154: Synthesis of N-(oxetan-3-ylmethyl)-2-(2-phenyl-1,2,3,4-tetrahydroquin-olin-6-yl)acetamide (a Novel Compound)

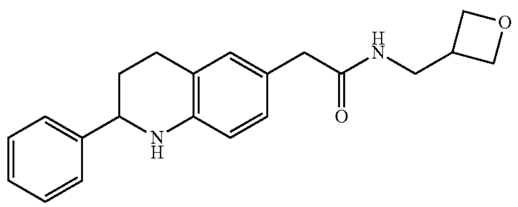 [SMILES: O=C(Cc1ccc2c(c1)CCC(c1ccccc1)N2)NCC1COC1]

The 2-(2-phenyl-1,2,3,4-tetrahydroquinolin-6-yl)acetic acid synthesized in Reference Example 40 (20.9 mg, 0.0782 mmol), N,N-diisopropylethylamine (20.4 μL, 0.117 mmol), 3-(aminomethyl)oxetane (8.1 μL, 0.094 mmol), and 1-[bis(dimethylamino)methylene]-1H-1,2,3-triazolo[4,5-b]pyridinium 3-oxide hexafluorophosphate (HATU, 35.7 mg, 0.0938 mmol) were used in the same manner as in Example 145 to obtain the title compound (hereinafter referred to as the compound of Example 154) as a pale yellow amorphous (19.1 mg, 0.0571 mmol, yield: 73%).

$^1$H-NMR ($CDCl_3$) δ: 7.40-7.26 (5H, m), 6.87-6.85 (2H, m), 6.53 (1H, d, J=8.7 Hz), 5.68 (1H, brs), 4.73 (2H, dd, J=7.8, 6.4 Hz), 4.45 (1H, dd, J=9.1, 3.2 Hz), 4.34 (2H, dd, J=5.9, 6.4 Hz), 4.09 (1H, brs), 3.46 (2H, s), 3.19-3.12 (1H, m), 2.96-2.86 (1H, m), 2.80 (2H, s), 2.72 (1H, dt, J=16.5, 4.8 Hz), 2.17-2.10 (1H, m), 2.03-1.94 (1H, m).

MS(ESI) $[M+H]^+$: 337.

Example 155: Synthesis of N-cyclobutyl-2-(2-phenyl-1,2,3,4-tetrahydroquinolin-6-yl)acetamide (a Novel Compound)

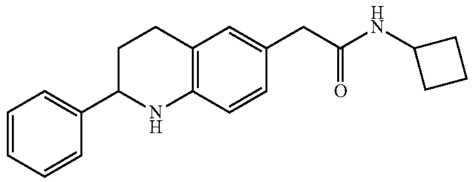 [SMILES: O=C(Cc1ccc2c(c1)CCC(c1ccccc1)N2)NC1CCC1]

The 2-(2-phenyl-1,2,3,4-tetrahydroquinolin-6-yl)acetic acid synthesized in Reference Example 40 (18.0 mg, 0.0673 mmol), N,N-diisopropylethylamine (17.5 μL, 0.101 mmol), cyclobutylamine (23.9 μL, 0.336 mmol), and 1-[bis(dimethylamino)methylene]-1H-1,2,3-triazolo[4,5-b]pyridinium 3-oxide hexafluorophosphate (HATU, 33.2 mg, 0.0875 mmol) were used in the same manner as in Example 145 to obtain the title compound (hereinafter referred to as the compound of Example 155) as a white amorphous (11.4 mg, 0.0356 mmol, yield: 53%).

$^1$H-NMR ($CDCl_3$) δ: 7.41-7.34 (4H, m), 7.30 (1H, tt, J=6.8, 2.0 Hz), 6.86 (2H, d, J=5.9 Hz), 6.53 (1H, dd, J=5.7, 2.9 Hz), 5.57 (1H, d, J=5.4 Hz), 4.41 (2H, ddd, J=25.5, 13.0, 5.8 Hz), 4.08 (1H, brs), 3.40 (2H, s), 2.97-2.88 (1H, m), 2.74 (1H, dt, J=16.5, 4.6 Hz), 2.29 (2H, ddt, J=14.2, 7.7, 2.5 Hz), 2.15 (1H, td, J=8.8, 4.2 Hz), 2.05-1.95 (1H, m), 1.80-1.61 (4H, m).

MS(ESI) $[M+H]^+$: 321.

Example 156: Synthesis of 2-(2-phenyl-1,2,3,4-tetrahydroquinolin-6-yl)-1-(pyrrolidin-1-yl)ethan-1-one (a Novel Compound)

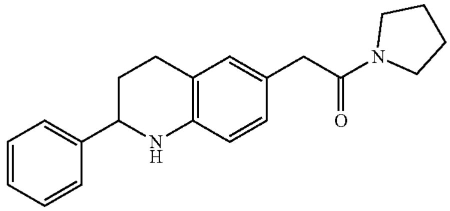 [SMILES: O=C(Cc1ccc2c(c1)CCC(c1ccccc1)N2)N1CCCC1]

The 2-(2-phenyl-1,2,3,4-tetrahydroquinolin-6-yl)acetic acid synthesized in Reference Example 40 (20.0 mg, 0.0748 mmol), N,N-diisopropylethylamine (65.1 μL, 0.374 mmol), pyrrolidine (12.2 μL, 0.150 mmol), and 1-[bis(dimethylamino)methylene]-1H-1,2,3-triazolo[4,5-b]pyridinium 3-oxide hexafluorophosphate (HATU, 56.9 mg, 0.150 mmol) were used in the same manner as in Example 145 to obtain the title compound (hereinafter referred to as the compound of Example 156) as a colorless clear oily substance (24.0 mg, 0.0748 mmol, yield: 100%).

$^1$H-NMR ($CDCl_3$) δ: 7.39-7.31 (4H, m), 7.30-7.27 (1H, m), 6.94-6.89 (2H, m), 6.49 (1H, d, J=7.8 Hz), 4.43-4.39 (1H, m), 4.01 (1H, brs), 3.52-3.42 (6H, m), 2.96-2.85 (1H, m), 2.75-2.67 (1H, m), 2.13-2.06 (1H, m), 2.02-1.88 (3H, m), 1.86-1.79 (2H, m).

MS(ESI) $[M+H]^+$: 321.

Example 157: Synthesis of 2-(2-(2-phenyl-1,2,3,4-tetrahydroquinolin-6-yl)acetyl)piperazin-2-one (a Novel Compound)

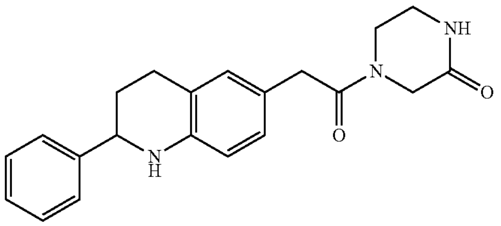 [SMILES: O=C1CN(C(=O)Cc2ccc3c(c2)CCC(c2ccccc2)N3)CCN1]

The 2-(2-phenyl-1,2,3,4-tetrahydroquinolin-6-yl)acetic acid synthesized in Reference Example 40 (20.0 mg, 0.0748 mmol), N,N-diisopropylethylamine (65.1 μL, 0.374 mmol), piperazin-2-one (15.0 mg, 0.150 mmol), and 1-[bis(dimethylamino)methylene]-1H-1,2,3-triazolo[4,5-b]pyridinium 3-oxide hexafluorophosphate (HATU, 56.9 mg, 0.150 mmol) were used in the same manner as in Example 145 to obtain the title compound (hereinafter referred to as the compound of Example 157) as a colorless clear oily substance (22.8 mg, 0.0652 mmol, yield: 87%).

$^1$H-NMR ($CDCl_3$) δ: 7.39-7.32 (4H, m), 7.31-7.27 (1H, m), 6.98 (OH, s), 6.89-6.83 (2H, m), 6.77 (1H, brs), 6.49 (1H, d, J=8.2 Hz), 4.44-4.40 (1H, m), 4.26 (1H, s), 4.14 (1H, s), 4.06 (1H, brs), 3.83-3.80 (1H, m), 3.67-3.58 (3H, m), 3.38-3.34 (1H, m), 3.22-3.18 (1H, m), 2.93-2.84 (1H, m), 2.74-2.66 (1H, m), 2.14-2.07 (1H, m), 2.01-1.91 (1H, m).

MS(ESI) $[M+H]^+$: 350.

Example 158: Synthesis of 2-(2-phenyl-1,2,3,4-tetrahydroquinolin-6-yl)-1-(piperazin-1-yl)ethan-1-one (a Novel Compound)

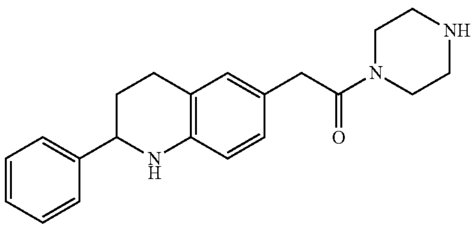 [SMILES: O=C(Cc1ccc2c(c1)CCC(c1ccccc1)N2)N1CCNCC1]

The 2-(2-phenyl-1,2,3,4-tetrahydroquinolin-6-yl)acetic acid synthesized in Reference Example 40 (18.0 mg, 0.0673 mmol), N,N-diisopropylethylamine (35 μL, 0.20 mmol), piperazine (116.0 mg, 1.35 mmol), and 1-[bis(dimethylamino)methylene]-1H-1,2,3-triazolo[4,5-b]pyridinium 3-oxide hexafluorophosphate (HATU, 30.7 mg, 0.0808 mmol) were used in the same manner as in Example 145 to obtain the title compound (hereinafter referred to as the compound of Example 158) as a colorless clear oily substance (17.7 mg, 0.0528 mmol, yield: 78%).

$^1$H-NMR ($CDCl_3$) δ: 7.39-7.33 (4H, m), 7.30-7.28 (1H, m), 6.89-6.85 (2H, m), 6.49 (1H, d, J=7.8 Hz), 4.42 (1H, dd, J=9.6, 3.2 Hz), 4.00 (1H, brs), 3.63-3.60 (2H, m), 3.60 (2H, s), 3.44 (2H, t, J=5.0 Hz), 2.94-2.86 (1H, m), 2.82 (2H, t, J=5.3 Hz), 2.73-2.68 (3H, m), 2.14-2.07 (1H, m), 2.02-1.92 (1H, m).

MS(ESI) $[M+H]^+$: 336.

Example 159: Synthesis of N-methyl-2-(2-phenyl-1,2,3,4-tetrahydroquinolin-6-yl)acetamide (a Novel Compound)

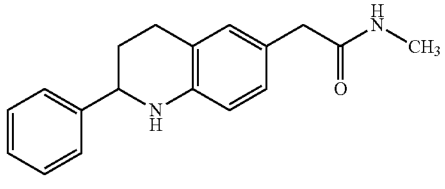 [SMILES: CNC(=O)Cc1ccc2c(c1)CCC(c1ccccc1)N2]

The 2-(2-phenyl-1,2,3,4-tetrahydroquinolin-6-yl)acetic acid synthesized in Reference Example 40 (25.0 mg, 0.0935 mmol), N,N-diisopropylethylamine (97.6 μL, 0.561 mmol), methylamine hydrochloride (31.6 mg, 0.468 mmol), and 1-[bis(dimethylamino)methylene]-1H-1,2,3-triazolo[4,5-b]pyridinium 3-oxide hexafluorophosphate (HATU, 42.7 mg, 0.112 mmol) were used in the same manner as in Example 145 to obtain the title compound (hereinafter referred to as the compound of Example 159) as a colorless clear oily substance (24.9 mg, 0.0888 mmol, yield: 95%).

$^1$H-NMR ($CDCl_3$) δ: 7.39-7.35 (4H, m), 7.31-7.28 (1H, m), 6.87-6.86 (2H, m), 6.53 (1H, d, J=8.7 Hz), 5.47 (1H, brs), 4.44 (1H, dd, J=9.6, 3.2 Hz), 4.09 (1H, brs), 3.45 (2H, s), 2.95-2.87 (1H, m), 2.77-2.69 (2H, m), 2.76 (2H, d, J=5.0 Hz), 2.16-2.12 (1H, m), 2.03-1.94 (1H, m).

MS(ESI) $[M+H]^+$: 281.

Example 160: Obtainment of One of the Optical Isomers of (a Novel Compound) 1-(3,3-difluoroazetidin-1-yl)-2-(2-phenyl-1,2,3,4-tetrahydroquinolin-6-yl)ethan-1-one

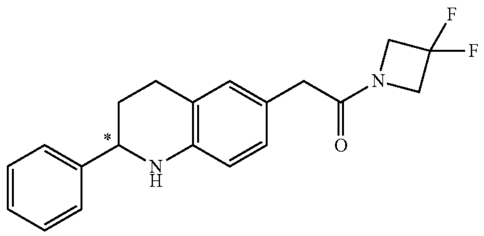 [SMILES: O=C(Cc1ccc2c(c1)CCC(c1ccccc1)N2)N1CC(F)(F)C1]

In the formula, the carbon atom marked with an asterisk (*) is an asymmetric center.

The 1-(3,3-difluoroazetidin-1-yl)-2-(2-phenyl-1,2,3,4-tetrahydroquinolin-6-yl)ethan-1-one synthesized in Example 149 (91.2 mg, 0.266 mmol) was dissolved in propan-2-ol (4.8 mL) and optically resolved using HPLC under the following conditions to obtain the title compound (hereinafter referred to as the compound of Example 160) as a white solid (33.4 mg, 0.0975 mmol, yield: 37%, enantiomeric excess: 100% ee).

$^1$H-NMR ($CDCl_3$) δ: 7.40-7.33 (4H, m), 7.31-7.27 (1H, m), 6.89-6.86 (2H, m), 6.50 (1H, d, J=8.2 Hz), 4.43 (1H, dd, J=9.1, 3.2 Hz), 4.34 (4H, q, J=11.4 Hz), 4.06 (1H, brs), 3.43 (2H, s), 2.94-2.86 (1H, m), 2.72 (1H, dt, J=16.6, 4.7 Hz), 2.15-2.09 (1H, m), 2.01-1.96 (1H, m).

MS(ESI) $[M+H]^+$: 343.

Conditions for optical resolution using HPLC:

Column: Daicel Chiralcel OD-H chiral column (inner diameter: 20 mm, length: 250 mm, particle size: 5 μm)

Column temperature: 40° C.

Mobile phase: propan-2-ol:hexane=90:10

Total injection volume: 4.8 mL (0.8 to 1.0 mL/injection)

Flow rate: 10 mL/min

Detection: UV (254 nm)

Rt: 15.45 min

HPLC analysis conditions:

Column: Daicel Chiralcel OD-H chiral column (inner diameter: 4.6 mm, length: 250 mm, particle size: 5 μm)

Column temperature: 40° C.

Mobile phase: propan-2-ol:hexane=50:50

Flow rate: 0.6 mL/min

Detection: UV (254 nm)

Rt: 14.54 min

Example 161: Obtainment of the Other of the Optical Isomers of 1-(3,3-difluoroazetidin-1-yl)-2-(2-phenyl-1,2,3,4-tetrahydroquinolin-6-yl)ethan-1-one (a Novel Compound)

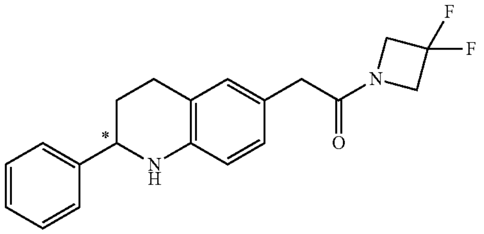 [SMILES: O=C(Cc1ccc2c(c1)CCC(c1ccccc1)N2)N1CC(F)(F)C1]

In the formula, the carbon atom marked with an asterisk (*) is an asymmetric center.

The 1-(3,3-difluoroazetidin-1-yl)-2-(2-phenyl-1,2,3,4-tetrahydroquinolin-6-yl)ethan-1-one synthesized in Example 149 (91.2 mg, 0.266 mmol) was dissolved in propan-2-ol (4.8 mL) and optically resolved using HPLC under the following conditions to obtain the title compound (hereinafter referred to as the compound of Example 161) as a white solid (31.0 mg, 0.0905 mmol, yield: 34%, enantiomeric excess: 99.6% ee).

$^1$H-NMR ($CDCl_3$) δ: 7.40-7.33 (4H, m), 7.31-7.27 (1H, m), 6.89-6.86 (2H, m), 6.50 (1H, d, J=8.2 Hz), 4.43 (1H, dd, J=9.1, 3.2 Hz), 4.34 (4H, q, J=11.4 Hz), 4.06 (1H, brs), 3.43 (2H, s), 2.94-2.86 (1H, m), 2.72 (1H, dt, J=16.6, 4.7 Hz), 2.15-2.09 (1H, m), 2.01-1.96 (1H, m).

MS(ESI) $[M+H]^+$: 343.

Conditions for optical resolution using HPLC:

Column: Daicel Chiralcel OD-H chiral column (inner diameter: 20 mm, length: 250 mm, particle size: 5 μm)

Column temperature: 40° C.

Mobile phase: propan-2-ol:hexane=90:10

Total injection volume: 4.8 mL (0.8 to 1.0 mL/injection)

Flow rate: 10 mL/min

Detection: UV (254 nm)

Rt: 21.67 min

HPLC analysis conditions:

Column: Daicel Chiralcel OD-H chiral column (inner diameter: 4.6 mm, length: 150 mm, particle size: 5 μm)

Column temperature: 40° C.

Mobile phase: propan-2-ol:hexane=50:50

Flow rate: 0.6 mL/min

Detection: UV (254 nm)

Rt: 21.44 min

Example 162: Obtainment and synthesis of 3-phenyl-1,2,3,4-tetrahydroquinoline

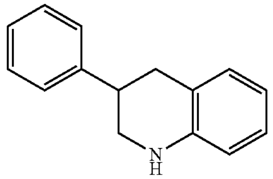 [SMILES: c1ccc(C2CNc3ccccc3C2)cc1]

For 3-phenyl-1,2,3,4-tetrahydroquinoline (hereinafter referred to as the compound of Example 162), a commercial product from, for example, Enamine Ltd. can be used, or the compound can be synthesized according to a known method or equivalent methods.

Reference Example 111: Synthesis of 6-chloro-3-phenylquinoline

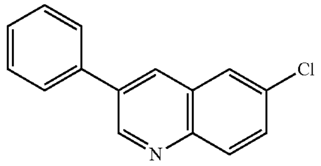 [SMILES: Clc1ccc2ncc(-c3ccccc3)cc2c1]

4-Chloroaniline (0.202 mL, 1.57 mmol) was dissolved in DMSO (4 mL), and 2-phenylacetaldehyde (0.264 mL, 2.35 mmol), copper(I) bromide (22.5 mg, 0.157 mmol), and trifluoromethanesulfonic acid (13.9 μL, 0.157 mmol) were added to the resulting solution, and the resulting mixture was stirred at 110° C. for 1 hour. After the reaction was completed, ethyl acetate was added to the reaction mixture. The obtained reaction mixture was washed with saturated brine and dried over anhydrous sodium sulfate, and the filtrate was then concentrated under reduced pressure. The obtained crude product was purified by column chromatography (silica gel, hexane/ethyl acetate) and preparative thin-layer chromatography (silica gel, hexane/ethyl acetate) to obtain the title compound as a pale yellow solid (41.8 mg, 0.174 mmol, yield: 11%).

$^1$H-NMR ($CDCl_3$) δ: 9.17 (1H, d, J=2.3 Hz), 8.22 (1H, d, J=2.3 Hz), 8.08 (1H, d, J=9.1 Hz), 7.88 (1H, d, J=2.3 Hz), 7.72-7.69 (2H, m), 7.66 (1H, dd, J=8.8, 2.5 Hz), 7.55-7.54 (2H, m), 7.47-7.46 (1H, m).

MS(ESI) $[M+H]^+$: 240.

Example 163: Synthesis of 6-chloro-3-phenyl-1,2,3,4-tetrahydroquinoline

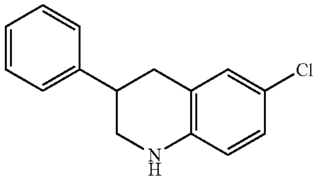 [SMILES: Clc1ccc2c(c1)CC(c1ccccc1)CN2]

The 6-chloro-3-phenylquinoline synthesized in Reference Example 111 (20.0 mg, 83.4 μmol) was used in the same manner as in Example 26 to obtain the title compound (hereinafter referred to as the compound of Example 163) as a pale yellow solid (18.9 mg, 77.5 μmol, yield: 93%).

$^1$H-NMR ($CDCl_3$) δ: 7.36-7.33 (2H, m), 7.28-7.27 (1H, m), 7.24-7.22 (2H, m), 7.00-6.94 (2H, m), 6.47 (1H, d, J=8.2 Hz), 4.04 (1H, brs), 3.46 (1H, ddd, J=11.0, 3.2, 1.4 Hz), 3.32 (1H, dd, J=11.4, 11.0 Hz), 3.15-3.07 (1H, m), 3.02-2.90 (2H, m).

MS(ESI) $[M+H]^+$: 244.

Reference Example 112: Synthesis of 7-chloro-3-phenylquinoline

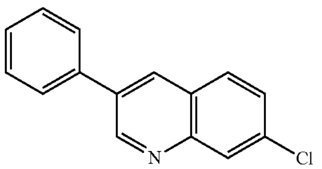 [SMILES: Clc1ccc2cc(-c3ccccc3)cnc2c1]

(2-Amino-4-chlorophenyl)methanol (100 mg, 0.635 mmol) was dissolved in 1,4-dioxane (3 mL), and 2-phenylacetaldehyde (0.141 mL, 1.27 mmol) and potassium tert-butoxide (107 mg, 0.952 mmol) were added to the resulting solution, and the resulting mixture was stirred at 80° C. for 4 hours. After the reaction was completed, the reaction mixture was filtered using celite, and the filtrate was concentrated under reduced pressure. The obtained residue was purified by column chromatography (silica gel, hexane/ethyl acetate) to obtain the title compound as a pale yellow solid (7.20 mg, 30.0 μmol, yield: 5%).

$^1$H-NMR ($CDCl_3$) δ: 9.19 (1H, d, J=2.3 Hz), 8.29 (1H, d, J=2.3 Hz), 8.14 (1H, d, J=2.3 Hz), 7.83 (1H, d, J=8.7 Hz), 7.72-7.69 (2H, m), 7.56-7.52 (3H, m), 7.47-7.45 (1H, m).

MS(ESI) $[M+H]^+$: 240.

Example 164: Synthesis of 7-chloro-3-phenyl-1,2,3,4-tetrahydroquinoline

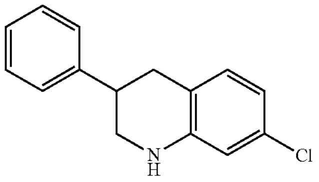 [SMILES: Clc1ccc2c(c1)NCC(c1ccccc1)C2]

The 7-chloro-3-phenylquinoline synthesized in Reference Example 112 (7.20 mg, 30.0 μmol) was used in the same manner as in Example 26 to obtain the title compound (hereinafter referred to as the compound of Example 164) as a pale yellow solid (6.20 mg, 25.4 μmol, yield: 85%).

$^1$H-NMR ($CDCl_3$) δ: 7.37-7.33 (2H, m), 7.26-7.24 (3H, m), 6.90 (1H, d, J=7.8 Hz), 6.59 (1H, dd, J=8.0, 2.1 Hz), 6.52 (1H, d, J=1.8 Hz), 4.10 (1H, brs), 3.46 (1H, dd, J=11.0, 3.2 Hz), 3.32 (1H, dd, J=11.0, 11.0 Hz), 3.12-3.09 (1H, m), 2.95-2.93 (2H, m).

MS(ESI) $[M+H]^+$: 244.

Reference Example 113: Synthesis of (4-(quinolin-3-yl)phenyl)methanol

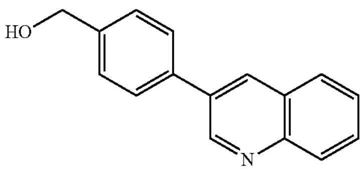 [SMILES: OCc1ccc(-c2cnc3ccccc3c2)cc1]

3-Chloroquinoline (200 mg, 1.22 mmol) and (4-(hydroxymethyl)phenyl)boronic acid (186 mg, 1.22 mmol) were dissolved in toluene (5 mL), and palladium(II) acetate (5.49 mg, 24.5 μmol), 2-dicyclohexylphosphino-2',6'-diisopropoxybiphenyl (RuPhos, 22.8 mg, 48.9 μmol), potassium carbonate (507 mg, 3.67 mmol), and water (0.5 mL) were added to the resulting solution, and the resulting mixture was stirred at 80° C. for 17 hours under argon atmosphere. After the reaction was completed, water was added to the reaction mixture, and the resulting mixture was extracted with ethyl acetate. The organic layers were combined, washed with saturated brine, and dried over anhydrous sodium sulfate, and the filtrate was then concentrated under reduced pressure. The obtained crude product was purified by column chromatography (silica gel, hexane/ethyl acetate) to obtain the title compound as a white solid (111 mg, 0.471 mol, yield: 39%).

$^1$H-NMR ($CDCl_3$) δ: 9.15 (1H, d, J=2.3 Hz), 8.31 (1H, d, J=2.3 Hz), 8.14 (1H, d, J=8.2 Hz), 7.89 (1H, dd, J=8.2, 1.4 Hz), 7.76-7.71 (3H, m), 7.59 (1H, ddd, J=8.2, 6.9, 0.9 Hz), 7.55-7.52 (2H, m), 4.80 (2H, d, J=5.5 Hz), 1.91 (1H, t, J=5.5 Hz).

MS(ESI) $[M+H]^+$: 236.

Example 165: Synthesis of (4-(1,2,3,4-tetrahydroquinolin-3-yl)phenyl)methanol (a Novel Compound)

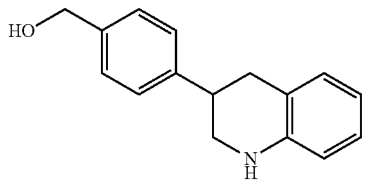 [SMILES: OCc1ccc(C2CNc3ccccc3C2)cc1]

The (4-(quinolin-3-yl)phenyl)methanol synthesized in Reference Example 113 (30.0 mg, 0.128 mmol) was used in the same manner as in Example 4 to obtain the title compound (hereinafter referred to as the compound of Example 165) as a white solid (16.2 mg, 67.7 μmol, yield: 53%).

$^1$H-NMR ($CDCl_3$) δ: 7.35 (2H, d, J=8.2 Hz), 7.25-7.23 (2H, m), 7.03-7.01 (2H, m), 6.65 (1H, ddd, J=7.3, 7.3, 0.9 Hz), 6.56-6.55 (1H, m), 4.69 (2H, s), 4.03 (1H, brs), 3.45 (1H, ddd, J=11.4, 3.7, 1.8 Hz), 3.33 (1H, dd, J=11.4, 11.4 Hz), 3.20-3.12 (1H, m), 3.06-2.94 (2H, m), 1.63 (1H, brs).

MS(ESI) $[M+H]^+$: 240.

Reference Example 114: Synthesis of 4-(quinolin-3-yl)benzamide

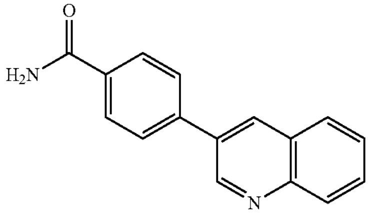 [SMILES: NC(=O)c1ccc(-c2cnc3ccccc3c2)cc1]

3-Boromoquinoline (150 mg, 0.721 mmol) and (4-carbamoylphenyl)boronic acid (178 mg, 1.08 mmol) were used in the same manner as in Reference Example 6 to obtain the title compound as a white solid (32.7 mg, 0.132 mol, yield: 18%).

$^1$H-NMR ($CDCl_3$) δ: 9.20 (1H, d, J=2.3 Hz), 8.37 (1H, d, J=2.3 Hz), 8.17-8.15 (1H, m), 8.00-7.98 (2H, m), 7.92 (1H, dd, J=8.2, 1.4 Hz), 7.84-7.81 (2H, m), 7.77 (1H, ddd, J=8.7, 6.9, 1.8 Hz), 7.62 (1H, ddd, J=7.8, 6.9, 0.9 Hz).

MS(ESI) $[M+H]^+$: 249.

Example 166: Synthesis of 4-(1,2,3,4-tetrahydroquinolin-3-yl)benzamide (a Novel Compound)

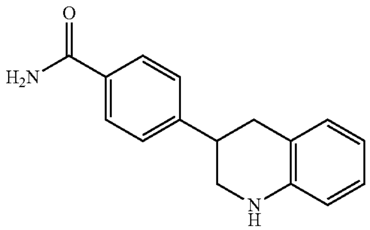 [SMILES: NC(=O)c1ccc(C2CNc3ccccc3C2)cc1]

The 4-(quinolin-3-yl)benzamide synthesized in Reference Example 114 (32.7 mg, 0.132 mol) was used in the same manner as in Example 4 to obtain the title compound (hereinafter referred to as the compound of Example 166) as a white solid (11.1 mg, 44.0 μmol, yield: 33%).

$^1$H-NMR ($CDCl_3$) δ: 7.81-7.77 (2H, m), 7.34-7.32 (2H, m), 7.04-7.02 (2H, m), 6.66 (1H, ddd, J=7.3, 7.3, 0.9 Hz), 6.56 (1H, d, J=7.8 Hz), 5.59-5.56 (2H, brm), 4.74 (1H, brs), 3.49-3.47 (1H, m), 3.36 (1H, dd, J=10.5, 11.0 Hz), 3.24-3.20 (1H, m), 3.07-2.98 (2H, m).

MS(ESI) $[M+H]^+$: 253.

Reference Example 115: Synthesis of 4-(quinolin-3-yl)benzenesulfonamide

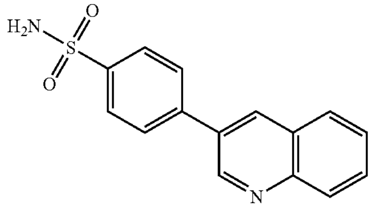 [SMILES: NS(=O)(=O)c1ccc(-c2cnc3ccccc3c2)cc1]

3-Boromoquinoline (5.00 g, 24.0 mmol) and (4-sulfamoylphenyl)boronic acid (6.76 g, 33.6 mmol) were used in the same manner as in Reference Example 11 to obtain the title compound as a pale brown solid (6.10 g, 21.5 mmol, yield: 89%).

$^1$H-NMR (DMSO-$d_6$) δ: 9.29 (1H, d, J=2.3 Hz), 8.74 (1H, d, J=2.3 Hz), 8.09-8.06 (4H, m), 7.97-7.95 (2H, m), 7.80 (1H, ddd, J=8.2, 6.9, 1.4 Hz), 7.67-7.65 (1H, m).

MS(ESI) $[M+H]^+$: 285.

Example 167: Synthesis of 4-(1,2,3,4-tetrahydroquinolin-3-yl)benzenesulfonamide (a Novel Compound)

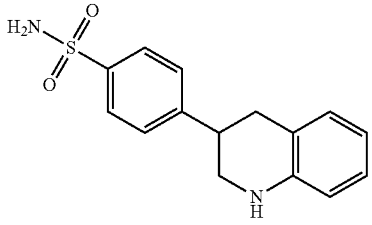 [SMILES: NS(=O)(=O)c1ccc(C2CNc3ccccc3C2)cc1]

The 4-(quinolin-3-yl)benzenesulfonamide synthesized in Reference Example 115 (500 mg, 1.75 mmol) was used in the same manner as in Example 72 to obtain the title compound (hereinafter referred to as the compound of Example 167) as a white solid (363 mg, 1.26 mmol, yield: 72%).

$^1$H-NMR ($CDCl_3$) δ: 7.89 (2H, d, J=8.7 Hz), 7.40 (2H, d, J=8.2 Hz), 7.05-7.00 (2H, m), 6.68-6.66 (1H, m), 6.56 (1H, d, J=9.1 Hz), 4.75 (2H, s), 3.49 (1H, dd, J=10.7, 3.4 Hz), 3.36 (1H, dd, J=11.0, 12.8 Hz), 3.27-3.25 (1H, m), 3.03-3.01 (2H, m).

MS(ESI) $[M+H]^+$: 289.

Reference Example 116: Synthesis of N-(4-(quinolin-3-yl)phenyl)acetamide

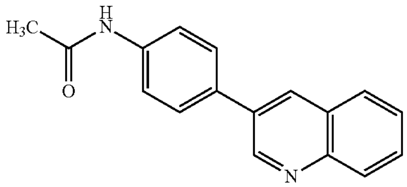 [SMILES: CC(=O)Nc1ccc(-c2cnc3ccccc3c2)cc1]

3-Boromoquinoline (150 mg, 0.721 mmol) and (4-acetamidophenyl)boronic acid (194 mg, 1.08 mmol) were used in the same manner as in Reference Example 11 to obtain the title compound as a white solid (178 mg, 0.680 mmol, yield: 94%).

$^1$H-NMR (DMSO-$d_6$) δ: 10.13 (1H, s), 9.25 (1H, d, J=2.3 Hz), 8.61 (1H, d, J=2.3 Hz), 8.04 (2H, d, J=9.1 Hz), 7.85 (2H, d, J=8.7 Hz), 7.76 (3H, dd, J=12.1, 4.8 Hz), 7.64 (1H, dd, J=7.8, 7.8 Hz), 2.09 (3H, s).

MS(ESI) $[M+H]^+$: 263.

Example 168: Synthesis of N-(4-(1,2,3,4-tetrahydroquinolin-3-yl)phenyl)acetamide (a Novel Compound)

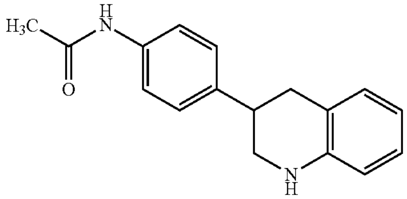 [SMILES: CC(=O)Nc1ccc(C2CNc3ccccc3C2)cc1]

The N-(4-(quinolin-3-yl)phenyl)acetamide synthesized in Reference Example 116 (50.0 mg, 0.191 mmol) was used in the same manner as in Example 4 to obtain the title compound (hereinafter referred to as the compound of Example 168) as a white solid (17.5 mg, 65.7 μmol, yield: 34%).

$^1$H-NMR ($CDCl_3$) δ: 7.45 (2H, d, J=8.7 Hz), 7.20 (2H, d, J=8.2 Hz), 7.11 (1H, brs), 7.02-7.00 (2H, m), 6.65 (1H, ddd, J=7.3, 7.3, 1.4 Hz), 6.55 (1H, d, J=7.8 Hz), 3.44 (1H, ddd, J=11.0, 3.2, 1.4 Hz), 3.30 (1H, dd, J=11.0, 10.5 Hz), 3.13-3.12 (1H, m), 2.99-2.97 (2H, m), 2.18 (3H, s).

MS(ESI) $[M+H]^+$: 267.

Reference Example 117: Synthesis of 3-(4-(methylsulfonyl)phenyl)quinoline

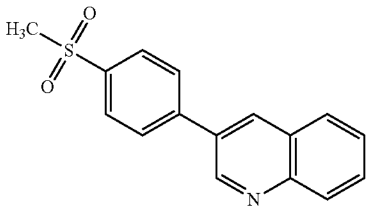

3-Boromoquinoline (90.8 mg, 0.437 mmol) and (4-(methylsulfonyl)phenyl)boronic acid (131 mg, 0.655 mmol) were used in the same manner as in Reference Example 11 to obtain the title compound as a white solid (124 mg, 0.437 mmol, yield: 99%).

$^1$H-NMR ($CDCl_3$) δ: 9.19 (1H, d, J=2.3 Hz), 8.38 (1H, d, J=2.3 Hz), 8.18 (1H, d, J=8.7 Hz), 8.11 (2H, d, J=8.7 Hz), 7.94-7.92 (3H, m), 7.80 (1H, ddd, J=8.2, 6.9, 1.4 Hz), 7.64 (1H, ddd, J=8.2, 6.9, 1.4 Hz), 3.13 (3H, s).

MS(ESI) $[M+H]^+$: 284.

Example 169: Synthesis of 3-(4-(methylsulfonyl)phenyl)-1,2,3,4-tetrahydroquinoline (a Novel Compound)

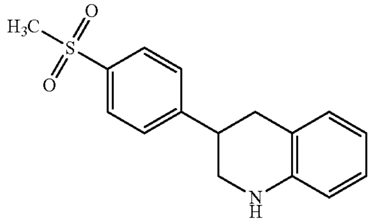

The 3-(4-(methylsulfonyl)phenyl)quinoline synthesized in Reference Example 117 (124 mg, 0.437 mmol) was used in the same manner as in Example 26 to obtain the title compound (hereinafter referred to as the compound of Example 169) as a white solid (94.1 mg, 0.327 mmol, yield: 75%).

$^1$H-NMR ($CDCl_3$) δ: 7.91 (2H, d, J=8.2 Hz), 7.45 (2H, d, J=8.2 Hz), 7.05-7.01 (2H, m), 6.67 (1H, ddd, J=7.3, 7.3, 0.5 Hz), 6.57 (1H, dd, J=7.8, 0.9 Hz), 4.05 (1H, brs), 3.49-3.47 (1H, m), 3.37 (1H, dd, J=10.5, 10.5 Hz), 3.28-3.25 (1H, m), 3.06 (3H, s), 3.03 (2H, d, J=7.8 Hz).

MS(ESI) $[M+H]^+$: 288.

Reference Example 118: Synthesis of 3-(pyridin-3-yl)quinoline

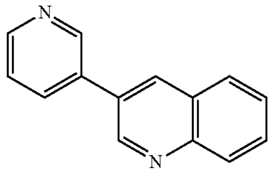 [SMILES: c1cncc(-c2cnc3ccccc3c2)c1]

3-Boromoquinoline (200 mg, 0.961 mmol) and pyridin-3-ylboronic acid (177 mg, 1.44 mmol) were used in the same manner as in Reference Example 11 to obtain the title compound as a white solid (196 mg, 0.949 mol, yield: 99%).

$^1$H-NMR ($CDCl_3$) δ: 9.17 (1H, d, J=2.3 Hz), 8.99 (1H, d, J=1.8 Hz), 8.70 (1H, dd, J=5.0, 1.4 Hz), 8.35 (1H, d, J=1.8 Hz), 8.17 (1H, d, J=8.2 Hz), 8.04-8.02 (1H, m), 7.92 (1H, d, J=8.2 Hz), 7.78 (1H, ddd, J=8.7, 6.9, 1.8 Hz), 7.63 (1H, ddd, J=8.2, 6.9, 0.9 Hz), 7.48-7.47 (2H, m).

MS(ESI) $[M+H]^+$: 207.

Example 170: Synthesis of 3-(pyridin-3-yl)-1,2,3,4-tetrahydroquinoline

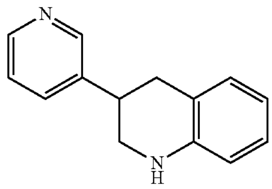 [SMILES: c1cncc(C2CNc3ccccc3C2)c1]

The 3-(pyridin-3-yl)quinoline synthesized in Reference Example 118 (100 mg, 0.484 mmol) was used in the same manner as in Example 4 to obtain the title compound (hereinafter referred to as the compound of Example 170) as a pale yellow solid (52.3 mg, 0.249 mol, yield: 52%).

$^1$H-NMR ($CDCl_3$) δ: 8.54 (1H, d, J=2.3 Hz), 8.50 (1H, dd, J=4.8, 1.6 Hz), 7.55 (1H, ddd, J=7.8, 1.8, 1.8 Hz), 7.30-7.26 (1H, m), 7.04-7.02 (2H, m), 6.67 (1H, ddd, J=7.3, 7.3, 0.9 Hz), 6.56 (1H, dd, J=8.2, 0.9 Hz), 3.51-3.48 (1H, m), 3.35 (1H, dd, J=11.2, 9.8 Hz), 3.24-3.17 (1H, m), 3.02-2.99 (2H, m), 2.10 (1H, s).

MS(ESI) $[M+H]^+$: 211.

Example 171: Synthesis of One of the Optical Isomers of 4-(1,2,3,4-tetrahydroquinolin-3-yl)benzenesulfonamide (a Novel Compound)

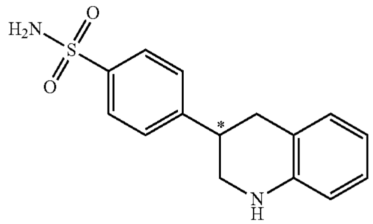 [SMILES: NS(=O)(=O)c1ccc(C2CNc3ccccc3C2)cc1]

In the formula, the carbon atom marked with an asterisk (*) is an asymmetric center.

The 4-(1,2,3,4-tetrahydroquinolin-3-yl)benzenesulfonamide synthesized in Example 167 (1.00 g, 3.47 mmol) was dissolved in propan-2-ol (1.0 L) and optically resolved using HPLC under the following conditions to obtain the title compound (hereinafter referred to as the compound of Example 171) as a white solid (394.9 mg, 1.37 mmol, yield: 39%, enantiomeric excess: 97.9%).

$^1$H-NMR ($CDCl_3$) δ: 7.89 (2H, d, J=8.7 Hz), 7.40 (2H, d, J=8.2 Hz), 7.05-7.00 (2H, m), 6.68-6.66 (1H, m), 6.56 (1H, d, J=9.1 Hz), 4.75 (2H, s), 3.49 (1H, dd, J=10.7, 3.4 Hz), 3.36 (1H, dd, J=11.0, 12.8 Hz), 3.27-3.25 (1H, m), 3.03-3.01 (2H, m).

MS(ESI) $[M+H]^+$: 289.

Conditions for optical resolution using HPLC:
Column: Daicel Chiralcel OZ-H chiral column
(inner diameter: 20 mm, length: 250 mm, particle size: 5 μm)
Column temperature: 40° C.
Mobile phase: propan-2-ol:hexane=90:10
Total injection volume: 975 mL (5.0 mL/injection)
Flow rate: 5 mL/min
Detection: UV (254 nm)
Rt: 23.00 to 26.00 min
HPLC analysis conditions:
Column: Daicel Chiralcel OZ-3 chiral column
(inner diameter: 0.46 mm, length: 150 mm, particle size: 3 μm)
Column temperature: 40° C.
Mobile phase: propan-2-ol:hexane=50:50
Flow rate: 0.6 mL/min
Detection: UV (254 nm)
Rt: 18.83 min Example 172: Synthesis of the Other of the Optical Isomers of 4-(1,2,3,4-tetrahydroquinolin-3-yl)benzenesulfonamide (a Novel Compound)

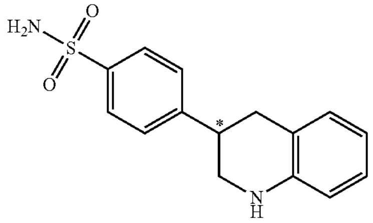 [SMILES: NS(=O)(=O)c1ccc(C2CNc3ccccc3C2)cc1]

In the formula, the carbon atom marked with an asterisk (*) is an asymmetric center.

The 4-(1,2,3,4-tetrahydroquinolin-3-yl)benzenesulfonamide synthesized in Reference Example 167 (1.00 g, 3.47 mmol) was dissolved in propan-2-ol (1.0 L) and optically resolved using HPLC under the following conditions to obtain the title compound (hereinafter referred to as the compound of Example 172) as a white solid (378.6 mg, 1.31 mmol, yield: 38%, enantiomeric excess: 94.0%).

$^1$H-NMR ($CDCl_3$) δ: 7.89 (2H, d, J=8.7 Hz), 7.40 (2H, d, J=8.2 Hz), 7.05-7.00 (2H, m), 6.68-6.66 (1H, m), 6.56 (1H, d, J=9.1 Hz), 4.75 (2H, s), 3.49 (1H, dd, J=10.7, 3.4 Hz), 3.36 (1H, dd, J=11.0, 12.8 Hz), 3.27-3.25 (1H, m), 3.03-3.01 (2H, m).

MS(ESI) $[M+H]^+$: 289.

Conditions for optical resolution using HPLC:
Column: Daicel Chiralcel OZ-H chiral column
(inner diameter: 20 mm, length: 250 mm, particle size: 5 μm)
Column temperature: 40° C.
Mobile phase: propan-2-ol:hexane=90:10
Total injection volume: 975 mL (5.0 mL/injection)
Flow rate: 5 mL/min
Detection: UV (254 nm)
Rt: 26.50 to 31.50 min
HPLC analysis conditions:
Column: Daicel Chiralcel OZ-3 chiral column
(inner diameter: 0.46 mm, length: 150 mm, particle size: 3 μm)
Column temperature: 40° C.
Mobile phase: propan-2-ol:hexane=50:50
Flow rate: 0.6 mL/min
Detection: UV (254 nm)
Rt: 22.46 min Comparative Example 1: Obtainment and synthesis of 2-phenyl-1,2,3,4-tetrahydroquinoxaline

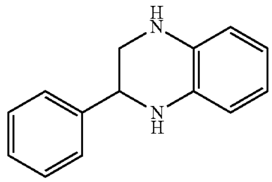 [SMILES: c1ccc(C2CNc3ccccc3N2)cc1]

For 2-phenyl-1,2,3,4-tetrahydroquinoxaline (hereinafter referred to as the compound of Comparative Example 1), a commercial product from, for example, Enamine Ltd. can be used, or the compound can be synthesized according to a known method or equivalent methods.

Example 173: In Vitro Inhibitory Action Against Ferroptosis

The inhibitory action against ferroptosis of the tetrahydroquinoline derivative (I) or a pharmaceutically acceptable salt thereof was evaluated with Human fibrosarcoma cells (HT-1080 cells), by using, as an index, the inhibitory action against the cell death induced by treatment with a ferroptosis inducer, Erastin.

HT-1080 cells (ATCC) were cultured in a mixture (hereinafter referred to as vehicle) composed of DMEM/F12 (Thermo Fisher Scientific, Inc.), a final concentration of 10% fetal bovine serum (Thermo Fisher Scientific, Inc.), and a final concentration of 1% penicillin-streptomycin solution (Nacalai Tesque, Inc.). Cells were seeded into 96-well plates (Corning Inc.) at $5\times10^4$ cells/well and cultured overnight.

A test compound was dissolved in DMSO, and the resulting solution was diluted in the vehicle to a final concentration of 1% DMSO and then used. On the day after seeding the cells, the test compound diluted in the vehicle was added to wells to a final test concentration of 25, 30, or 50 μmol/L. Thirty minutes after the addition of the test compound, Erastin (Cayman Chemical Co.) diluted in the vehicle at a final concentration of 3 μmol/L was added to wells. The wells added with the test compound and Erastin were grouped as "test compound," and the wells added with no test compound and no Erastin were grouped as "background," and the wells added with no test compound but with Erastin were grouped as "control." Twenty-four hours after the addition of Erastin, 5 μL of Cell Counting Kit-8 (Dojindo Laboratories) was added to each well and incubated for 4 hours, and the absorbance at 450 nm was then measured for each well (N=2). The average absorbance value at 450 nm was calculated from the absorbance values of the wells, and the inhibition rate of ferroptosis by the test compound (hereinafter referred to as ferroptosis inhibition rate, %) was then calculated based on the equation 1 below.

Ferroptosis inhibition rate (%)=[1−{(Average absorbance value at 450 nm measured when a test compound is added)−(Average absorbance value at 450 nm measured in the background)}/{(Average absorbance value at 450 nm measured in the control)−(Average absorbance value at 450 nm measured in the background)}]×100 Equation 1

Ferroptosis inhibition rates (%) for treatment with the test compounds are shown Tables 2-1 to 2-6.

TABLE 2-1

| Test compound | Ferroptosis inhibition rate (%) | Evaluation concentration |
|---|---|---|
| Compound of Example 1 | 110.5 | 30 μmol/L |
| Compound of Example 2 | 117.4 | 30 μmol/L |
| Compound of Example 3 | 110.2 | 30 μmol/L |
| Compound of Example 4 | 99.10 | 50 μmol/L |
| Compound of Example 5 | 99.69 | 50 μmol/L |
| Compound of Example 6 | 90.22 | 50 μmol/L |
| Compound of Example 7 | 93.95 | 50 μmol/L |
| Compound of Example 8 | 100.6 | 50 μmol/L |
| Compound of Example 9 | 88.84 | 50 μmol/L |
| Compound of Example 10 | 103.9 | 50 μmol/L |
| Compound of Example 11 | 106.0 | 50 μmol/L |
| Compound of Example 12 | 110.9 | 30 μmol/L |
| Compound of Example 13 | 119.6 | 30 μmol/L |
| Compound of Example 14 | 97.39 | 50 μmol/L |
| Compound of Example 15 | 89.22 | 30 μmol/L |
| Compound of Example 16 | 90.31 | 50 μmol/L |
| Compound of Example 17 | 98.12 | 50 μmol/L |
| Compound of Example 18 | 66.52 | 30 μmol/L |
| Compound of Example 19 | 100.5 | 30 μmol/L |
| Compound of Example 20 | 95.88 | 30 μmol/L |
| Compound of Example 21 | 88.33 | 30 μmol/L |
| Compound of Example 22 | 103.2 | 30 μmol/L |
| Compound of Example 23 | 68.45 | 30 μmol/L |
| Compound of Example 24 | 59.67 | 30 μmol/L |
| Compound of Example 25 | 105.3 | 30 μmol/L |
| Compound of Example 26 | 107.7 | 50 μmol/L |
| Compound of Example 27 | 113.1 | 50 μmol/L |
| Compound of Example 28 | 109.4 | 50 μmol/L |
| Compound of Example 29 | 95.38 | 50 μmol/L |
| Compound of Example 30 | 83.09 | 50 μmol/L |
| Compound of Example 31 | 98.99 | 50 μmol/L |
| Compound of Example 32 | 100.5 | 30 μmol/L |
| Compound of Example 33 | 84.88 | 30 μmol/L |
| Compound of Example 34 | 86.96 | 30 μmol/L |
| Compound of Example 35 | 106.5 | 30 μmol/L |
| Compound of Example 36 | 98.76 | 30 μmol/L |
| Compound of Example 37 | 98.69 | 30 μmol/L |
| Compound of Example 38 | 104.0 | 30 μmol/L |
| Compound of Example 39 | 101.5 | 30 μmol/L |
| Compound of Example 40 | 111.1 | 30 μmol/L |

TABLE 2-2

| Test compound | Ferroptosis inhibition rate (%) | Evaluation concentration |
|---|---|---|
| Compound of Example 41 | 102.2 | 30 μmol/L |
| Compound of Example 42 | 98.89 | 30 μmol/L |
| Compound of Example 43 | 107.1 | 30 μmol/L |
| Compound of Example 44 | 114.3 | 50 μmol/L |
| Compound of Example 45 | 109.1 | 30 μmol/L |
| Compound of Example 46 | 109.0 | 30 μmol/L |
| Compound of Example 47 | 85.21 | 30 μmol/L |
| Compound of Example 48 | 81.80 | 30 μmol/L |
| Compound of Example 49 | 99.20 | 30 μmol/L |
| Compound of Example 50 | 103.2 | 30 μmol/L |
| Compound of Example 51 | 84.55 | 50 μmol/L |
| Compound of Example 52 | 74.96 | 50 μmol/L |
| Compound of Example 53 | 111.3 | 50 μmol/L |
| Compound of Example 54 | 109.9 | 30 μmol/L |
| Compound of Example 55 | 93.72 | 30 μmol/L |
| Compound of Example 56 | 100.1 | 50 μmol/L |
| Compound of Example 57 | 89.18 | 30 μmol/L |
| Compound of Example 58 | 91.37 | 30 μmol/L |
| Compound of Example 59 | 76.73 | 30 μmol/L |
| Compound of Example 60 | 98.74 | 30 μmol/L |
| Compound of Example 61 | 103.9 | 30 μmol/L |
| Compound of Example 62 | 103.2 | 30 μmol/L |
| Compound of Example 63 | 68.73 | 50 μmol/L |
| Compound of Example 64 | 82.89 | 25 μmol/L |
| Compound of Example 65 | 89.25 | 30 μmol/L |
| Compound of Example 66 | 101.5 | 30 μmol/L |
| Compound of Example 67 | 102.4 | 30 μmol/L |
| Compound of Example 68 | 101.9 | 30 μmol/L |

TABLE 2-2-continued

| Test compound | Ferroptosis inhibition rate (%) | Evaluation concentration |
|---|---|---|
| Compound of Example 69 | 106.4 | 30 μmol/L |
| Compound of Example 70 | 97.10 | 30 μmol/L |
| Compound of Example 71 | 108.9 | 30 μmol/L |
| Compound of Example 72 | 110.6 | 30 μmol/L |
| Compound of Example 73 | 88.18 | 50 μmol/L |
| Compound of Example 74 | 85.08 | 30 μmol/L |
| Compound of Example 75 | 110.6 | 30 μmol/L |
| Compound of Example 76 | 85.43 | 50 μmol/L |
| Compound of Example 77 | 101.6 | 30 μmol/L |
| Compound of Example 78 | 88.56 | 25 μmol/L |
| Compound of Example 79 | 104.4 | 30 μmol/L |
| Compound of Example 80 | 103.9 | 30 μmol/L |

TABLE 2-3

| Test compound | Ferroptosis inhibition rate (%) | Evaluation concentration |
|---|---|---|
| Compound of Example 81 | 103.9 | 50 μmol/L |
| Compound of Example 82 | 112.6 | 30 μmol/L |
| Compound of Example 83 | 103.8 | 50 μmol/L |
| Compound of Example 84 | 107.1 | 50 μmol/L |
| Compound of Example 85 | 94.94 | 50 μmol/L |
| Compound of Example 86 | 98.80 | 50 μmol/L |
| Compound of Example 87 | 95.20 | 50 μmol/L |

TABLE 2-4

| Test compound | Ferroptosis inhibition rate (%) | Evaluation concentration |
|---|---|---|
| Compound of Example 88 | 97.70 | 30 μmol/L |
| Compound of Example 89 | 99.12 | 30 μmol/L |
| Compound of Example 90 | 102.4 | 30 μmol/L |
| Compound of Example 91 | 105.2 | 30 μmol/L |
| Compound of Example 92 | 66.40 | 30 μmol/L |
| Compound of Example 93 | 89.78 | 30 μmol/L |
| Compound of Example 94 | 93.68 | 30 μmol/L |
| Compound of Example 95 | 68.84 | 30 μmol/L |
| Compound of Example 96 | 98.01 | 30 μmol/L |
| Compound of Example 97 | 83.94 | 30 μmol/L |
| Compound of Example 98 | 98.95 | 30 μmol/L |
| Compound of Example 99 | 98.85 | 30 μmol/L |
| Compound of Example 100 | 103.5 | 30 μmol/L |
| Compound of Example 101 | 109.6 | 30 μmol/L |
| Compound of Example 102 | 77.96 | 30 μmol/L |
| Compound of Example 103 | 76.76 | 30 μmol/L |
| Compound of Example 104 | 64.65 | 30 μmol/L |
| Compound of Example 105 | 99.03 | 30 μmol/L |
| Compound of Example 106 | 111.7 | 30 μmol/L |
| Compound of Example 107 | 100.8 | 30 μmol/L |
| Compound of Example 108 | 83.78 | 10 μmol/L |
| Compound of Example 109 | 83.63 | 10 μmol/L |
| Compound of Example 110 | 103.0 | 10 μmol/L |
| Compound of Example 111 | 98.91 | 10 μmol/L |
| Compound of Example 112 | 105.5 | 30 μmol/L |
| Compound of Example 113 | 97.54 | 30 μmol/L |
| Compound of Example 114 | 87.04 | 30 μmol/L |
| Compound of Example 115 | 105.8 | 30 μmol/L |
| Compound of Example 116 | 80.69 | 10 μmol/L |
| Compound of Example 117 | 76.27 | 10 μmol/L |
| Compound of Example 118 | 95.28 | 30 μmol/L |
| Compound of Example 119 | 89.67 | 10 μmol/L |
| Compound of Example 120 | 87.34 | 10 μmol/L |

TABLE 2-5

| Test compound | Ferroptosis inhibition rate (%) | Evaluation concentration |
|---|---|---|
| Compound of Example 121 | 92.10 | 10 μmol/L |
| Compound of Example 122 | 97.59 | 10 μmol/L |
| Compound of Example 123 | 113.4 | 30 μmol/L |
| Compound of Example 124 | 106.3 | 30 μmol/L |
| Compound of Example 125 | 102.6 | 30 μmol/L |
| Compound of Example 126 | 97.29 | 30 μmol/L |
| Compound of Example 127 | 87.93 | 30 μmol/L |
| Compound of Example 128 | 91.83 | 30 μmol/L |
| Compound of Example 129 | 88.31 | 30 μmol/L |
| Compound of Example 130 | 104.2 | 30 μmol/L |
| Compound of Example 131 | 102.5 | 30 μmol/L |
| Compound of Example 132 | 105.6 | 30 μmol/L |
| Compound of Example 133 | 98.54 | 30 μmol/L |
| Compound of Example 134 | 77.77 | 30 μmol/L |
| Compound of Example 135 | 62.32 | 30 μmol/L |
| Compound of Example 136 | 75.50 | 30 μmol/L |
| Compound of Example 137 | 93.06 | 30 μmol/L |
| Compound of Example 138 | 65.15 | 30 μmol/L |
| Compound of Example 139 | 60.63 | 30 μmol/L |
| Compound of Example 140 | 72.81 | 30 μmol/L |
| Compound of Example 141 | 59.10 | 30 μmol/L |
| Compound of Example 142 | 64.86 | 30 μmol/L |
| Compound of Example 143 | 93.97 | 30 μmol/L |
| Compound of Example 144 | 96.14 | 30 μmol/L |
| Compound of Example 145 | 102.0 | 30 μmol/L |
| Compound of Example 146 | 112.8 | 30 μmol/L |
| Compound of Example 147 | 93.00 | 30 μmol/L |
| Compound of Example 148 | 86.55 | 30 μmol/L |
| Compound of Example 149 | 99.36 | 30 μmol/L |
| Compound of Example 150 | 106.9 | 30 μmol/L |
| Compound of Example 151 | 108.2 | 30 μmol/L |
| Compound of Example 152 | 108.1 | 30 μmol/L |
| Compound of Example 153 | 110.1 | 30 μmol/L |
| Compound of Example 154 | 114.6 | 30 μmol/L |
| Compound of Example 155 | 106.1 | 30 μmol/L |
| Compound of Example 156 | 57.76 | 30 μmol/L |
| Compound of Example 157 | 69.89 | 30 μmol/L |
| Compound of Example 158 | 55.98 | 30 μmol/L |
| Compound of Example 159 | 76.27 | 30 μmol/L |
| Compound of Example 160 | 99.11 | 10 μmol/L |

TABLE 2-6

| Test compound | Ferroptosis inhibition rate (%) | Evaluation concentration |
|---|---|---|
| Compound of Example 161 | 94.01 | 10 μmol/L |
| Compound of Example 162 | 108.4 | 50 μmol/L |
| Compound of Example 163 | 89.32 | 30 μmol/L |
| Compound of Example 164 | 72.33 | 30 μmol/L |
| Compound of Example 165 | 96.77 | 30 μmol/L |
| Compound of Example 166 | 96.52 | 30 μmol/L |
| Compound of Example 167 | 76.82 | 30 μmol/L |
| Compound of Example 168 | 86.46 | 30 μmol/L |
| Compound of Example 169 | 85.58 | 30 μmol/L |
| Compound of Example 170 | 93.41 | 30 μmol/L |
| Compound of Example 171 | 90.71 | 30 μmol/L |
| Compound of Example 172 | 92.87 | 30 μmol/L |

These results indicated that the tetrahydroquinoline derivative (I) or a pharmaceutically acceptable salt thereof had inhibitory action against ferroptosis.

Example 174: In Vitro Radical Scavenging Action

Radical scavenging action was evaluated using the DPPH method in the compound of Comparative Example 1, which is a tetrahydroquinoxaline derivative, and in the tetrahydroquinoline derivative (I) or a pharmaceutically acceptable salt thereof. The DPPH method was performed using an antioxidant capacity measurement kit (Dojindo Laboratories).

A test compound was dissolved in DMSO, and the resulting solution was then mixed with an assay buffer and a DPPH solution, which are included in the kit, to a total volume of 200 μL to obtain a final concentration of 10% DMSO, and the reaction was allowed to proceed. Wells added with 100 μmol/L ferrostatin-1, a radical scavenger, were grouped as "control," and wells added with not test compound were grouped as "background." The test compound was serially diluted 3-fold starting from a maximum concentration of 100 μmol/L, and the diluted test compound (1.2, 3.7, 11.1, 33.3, or 100 μmol/L) was added and allowed to react at room temperature. Thirty minutes after the reaction, the absorbance at 517 nm was measured, and the average absorbance value was calculated (N=2). The radical scavenging action of the test compound (hereinafter referred to as radical scavenging rate, %) was calculated based on the equation 2 below. The $EC_{50}$ value of the test compound was calculated from the radical scavenging rate.

Radical scavenging rate (%)=[1−{(Average absorbance value at 517 nm measured when a test compound is added)−(Average absorbance value at 517 nm measured in the background)}/{(Average absorbance value at 517 nm measured in the control)−(Average absorbance value at 517 nm measured in the background)}]×100 Equation 2

Radical scavenging rates (%) for treatment with the test compounds are shown in Tables 3-1 and 3-2. A note "no detection of radical scavenging action (N.D.)," is given to compounds with a $EC_{50}$ of >100 μmol/L.

TABLE 3-1

| Test compound | Radical-scavenging action $EC_{50}$ (μmol/L) |
|---|---|
| Compound of Comparative Example 1 | 8.54 |
| Compound of Example 1 | N.D. |
| Compound of Example 2 | N.D. |
| Compound of Example 3 | N.D. |
| Compound of Example 16 | N.D. |
| Compound of Example 21 | N.D. |
| Compound of Example 26 | N.D. |
| Compound of Example 29 | N.D. |
| Compound of Example 31 | N.D. |
| Compound of Example 32 | N.D. |
| Compound of Example 33 | N.D. |
| Compound of Example 34 | N.D. |
| Compound of Example 35 | N.D. |
| Compound of Example 36 | N.D. |
| Compound of Example 37 | N.D. |
| Compound of Example 38 | N.D. |
| Compound of Example 58 | N.D. |
| Compound of Example 60 | N.D. |
| Compound of Example 61 | N.D. |
| Compound of Example 62 | N.D. |
| Compound of Example 66 | N.D. |
| Compound of Example 67 | N.D. |
| Compound of Example 68 | N.D. |
| Compound of Example 69 | N.D. |
| Compound of Example 81 | N.D. |
| Compound of Example 82 | N.D. |
| Compound of Example 83 | N.D. |
| Compound of Example 85 | N.D. |
| Compound of Example 99 | N.D. |
| Compound of Example 105 | N.D. |
| Compound of Example 106 | N.D. |
| Compound of Example 107 | N.D. |
| Compound of Example 108 | N.D. |
| Compound of Example 109 | N.D. |
| Compound of Example 112 | N.D. |
| Compound of Example 115 | N.D. |

TABLE 3-2

| Test compound | Radical-scavenging action $EC_{50}$ (μmol/L) |
|---|---|
| Compound of Example 116 | N.D. |
| Compound of Example 117 | N.D. |
| Compound of Example 118 | N.D. |
| Compound of Example 119 | N.D. |
| Compound of Example 120 | N.D. |
| Compound of Example 121 | N.D. |
| Compound of Example 122 | N.D. |
| Compound of Example 131 | N.D. |
| Compound of Example 132 | N.D. |
| Compound of Example 134 | N.D. |
| Compound of Example 135 | N.D. |
| Compound of Example 136 | N.D. |
| Compound of Example 137 | N.D. |
| Compound of Example 138 | N.D. |
| Compound of Example 143 | N.D. |
| Compound of Example 144 | N.D. |
| Compound of Example 145 | N.D. |
| Compound of Example 146 | N.D. |
| Compound of Example 147 | N.D. |
| Compound of Example 148 | N.D. |
| Compound of Example 149 | N.D. |
| Compound of Example 150 | N.D. |
| Compound of Example 151 | N.D. |
| Compound of Example 152 | N.D. |
| Compound of Example 155 | N.D. |
| Compound of Example 157 | N.D. |
| Compound of Example 158 | N.D. |
| Compound of Example 160 | N.D. |
| Compound of Example 161 | N.D. |

These results indicated that the compound of Comparative Example 1, which is a tetrahydroquinoxaline derivative, exhibited radical scavenging action. In contrast, the tetrahydroquinoline derivative (I) or a pharmaceutically acceptable salt thereof had no radical scavenging action.

Example 175: Activity Assessment 1 in MOG-Induced Experimental Autoimmune Encephalomyelitis Mouse Model The effect of the compound of Example 1 on increase of neurological score was assessed in the MOG-induced experimental autoimmune encephalomyelitis mouse model. The MOG-induced experimental autoimmune encephalomyelitis mouse model was produced according to the method of Jianfeng et al. (The Journal of Immunology, 2009, vol. 182, p. 4036-4045) with partial modification.

A PBS solution prepared to contain a synthetic partial peptide of MOG (MOG35-55; CSBio) at a concentration of 4 mg/mL was mixed with an equal volume of Freund's complete adjuvant, and a total of 0.1 mL (0.05 mL per flank) of the resulting MOG35-55 dosing solution was inoculated intradermally into the bilateral flanks of C57BL/6J mice (male, 10 weeks old, Charles River Laboratories Japan, Inc.). On the day of inoculation of the MOG35-55 dosing solution and on the second day after the inoculation, 200 μL of pertussis toxin (Sigma Co. LLC) prepared at a concentration of 1 μg/mL was further administered intraperitoneally to the mice.

A test compound was administered orally at a dose of 30 mg/kg twice daily for a period of 15 days starting 55 days after the inoculation of the MOG35-55 dosing solution. The test compound was suspended in a 0.5% methylcellulose solution (hereinafter referred to as vehicle), and the resulting suspension was used. A group of mice administered with the compound of Example 1 was termed the compound of Example 1—dosing group. Additionally, a group of mice administered with the vehicle was termed the vehicle-dosing group. The vehicle was administered for the vehicle-dosing group, with the same volume, number and method of administrations as those for the test compound-dosing group.

Determination of the neurological score (0: normal, 1: tail relaxation or hind-limb weakness, 2: tail relaxation and hind-limb weakness, 3: hind-limb partial paralysis, 4: hind-limb complete paralysis, 5: moribund condition) started 15 days after the inoculation of the MOG35-55 dosing solution to evaluate paralytic symptoms in the mice. The determination of the score was performed according to the method of Jianfeng et al. (The Journal of Immunology, 2009, vol. 182, p. 4036-4045) with partial modification.

FIG. 1 shows the neurological score determined on the next day after the last administration of the test compound. The vertical axis represents neurological score (mean±standard error, n=7). On the horizontal axis, "Vehicle" represents the vehicle-dosing group, and "Compound of Example 1" represents the compound of Example 1—dosing group.

The inoculation of the MOG35-55 dosing solution increased the average neurological score to 2.43 in the vehicle-dosing group. In contrast, the neurological score of the Example 1-dosing group was 1.29, indicating a reduction in neurological score compared with the neurological score in the vehicle-dosing group. The neurological score reduction rate was 46.9%.

This result indicated that the compound of Example 1 exerts a mitigating effect on the neurological symptoms of multiple sclerosis.

Example 176: Activity Assessment 2 in MOG-Induced Experimental Autoimmune Encephalomyelitis Mouse Model The compound of Example 11, the compound of Example 32, and the compound of Example 36 were used as test compounds to assess the effect of the test compounds on increase of neurological score in the MOG-induced experimental autoimmune encephalomyelitis mouse model. The study was performed in the same manner as in Example 175, except that the start day for administrating a test compound, the scoring method, and the timing of determining the neurological score were changed from those in Example 175. Each test compound was administered orally at a dose of 30 mg/kg twice daily for a period of 15 days starting 50 days after the inoculation of the MOG35-55 dosing solution. In addition, the score was determined by the following criteria: 0, normal; 0.5, partial drooping tail; 1, full drooping tail or hind-limb weakness; 2, full drooping tail and hind-limb weakness; 3, hind-limb partial paralysis; 4, hind-limb complete paralysis; 5, fore- and hind-limb complete paralysis.

Figure 2:
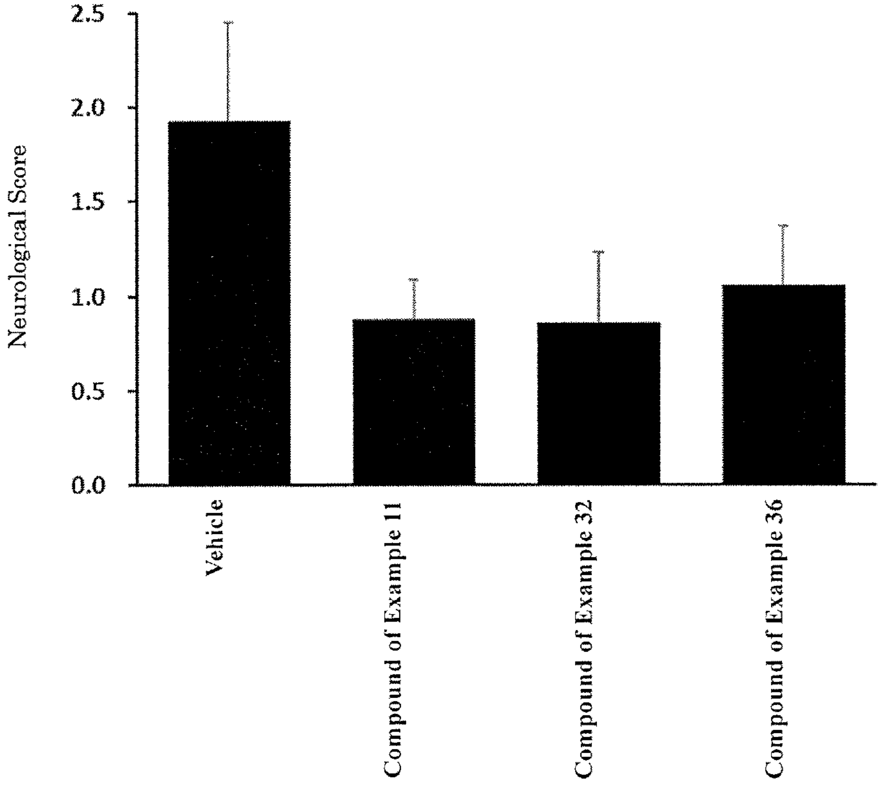
FIG. 2 shows the inhibitory effects of the compounds of Examples 11, 32, and 36 on an increase in neurological score in a myelin oligodendrocyte glycoprotein-induced experimental autoimmune encephalomyelitis mouse model.

FIG. 2 shows the neurological score determined on the next day after the last administration of the test compound. The vertical axis represents neurological score (mean±standard error, n=7 or 8). On the horizontal axis, "Vehicle" represents the vehicle-dosing group, and "Compound of Example 11" represents the compound of Example 11—dosing group, and "Compound of Example 32" represents the compound of Example 32—dosing group, and "Compound of Example 36" represents the compound of Example 36—dosing group.

The inoculation of the MOG35-55 dosing solution increased the average neurological score to 1.93 in the vehicle-dosing group. In contrast, the neurological score was decreased in the compound of Example 11—dosing group, the compound of Example 32—dosing group, and the compound of Example 36—dosing group. The neurological score reduction rate by the test compounds were 54.4% in the compound of Example 11, 55.4% in the compound of Example 32, and 45.1% in the compound of Example 36.

This result indicated that the compound of Example 11, the compound of Example 32 and the compound of Example 36 exert a mitigating effect on the neurological symptoms of multiple sclerosis.

Example 177: Activity assessment 3 in MOG-induced experimental autoimmune encephalomyelitis mouse model The compound of Example 144, the compound of Example 171, and the compound of Example 172 were used as test compounds to assess the effect of the test compounds on increase of neurological score in the MOG-induced experimental autoimmune encephalomyelitis mouse model. The study was performed in the same manner as in Example 176, except for the start day for administrating a test compound, the administered dose of a test compound, and the number of days for administering a test compound. Each test compound was administered orally at a dose of 10 mg/kg twice daily for a period of 10 days starting 53 days after the inoculation of the MOG35-55 dosing solution. A group of mice administered with the compound of Example 144 was termed the compound of Example 144—dosing group, and a group of mice administered with the compound of Example 171 was termed the compound of Example 171—dosing group, and a group of mice administered with the compound of Example 172 was termed the compound of Example 172—dosing group. Additionally, a group of mice administered with the vehicle was termed the vehicle-dosing group.

Figure 3:
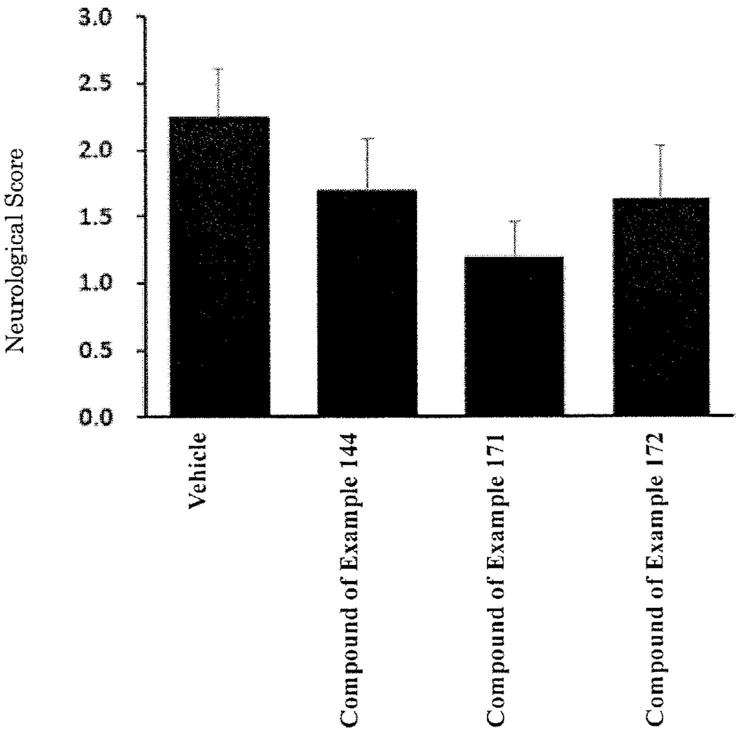
FIG. 3 shows the inhibitory effects of the compounds of Examples 144, 171, and 172 on an increase in neurological score in a myelin oligodendrocyte glycoprotein-induced experimental autoimmune encephalomyelitis mouse model.

FIG. 3 shows the neurological score determined on the next day after the last administration of the test compound. The vertical axis represents neurological score (mean±standard error, n=8). On the horizontal axis, "Vehicle" represents the vehicle-dosing group, and "Compound of Example 144" represents the compound of Example 144—dosing group, and "Compound of Example 171" represents the compound of Example 171—dosing group, and "Compound of Example 172" represents the compound of Example 172—dosing group.

The inoculation of the MOG35-55 dosing solution increased the average neurological score to 2.25 in the vehicle-dosing group. In contrast, the neurological score was decreased in the compound of Example 144—dosing group, the compound of Example 171—dosing group, and the compound of Example 172—dosing group. The neurological score reduction rate by the test compounds were 25.0% in the compound of Example 144, 47.2% in the compound of Example 171, and 27.8% in the compound of Example 172.

This result indicated that the compound of Example 144, the compound of Example 171 and the compound of Example 172 exert a mitigating effect on the neurological symptoms of multiple sclerosis.

Example 178: Activity Assessment 4 in MOG-Induced Experimental Autoimmune Encephalomyelitis Mouse Model The compound of Example 38 and the compound of Example 119 were used as test compounds to assess the effect of the test compounds on increase of neurological score in the MOG-induced experimental autoimmune encephalomyelitis mouse model. The study was performed in the same manner as in Example 176, except for the start day for administrating a test compound, the administered dose of a test compound, and the number of days for administering a test compound.

Each test compound was administered orally at a dose of 10 mg/kg twice daily for a period of 16 days starting 52 days after the inoculation of the MOG35-55 dosing solution. A group of mice administered with the compound of Example 38 was termed the compound of Example 38—dosing group, and a group of mice administered with the compound of Example 119 was termed the compound of Example 119—dosing group. Additionally, a group of mice administered with the vehicle was termed the vehicle-dosing group.

Figure 4:
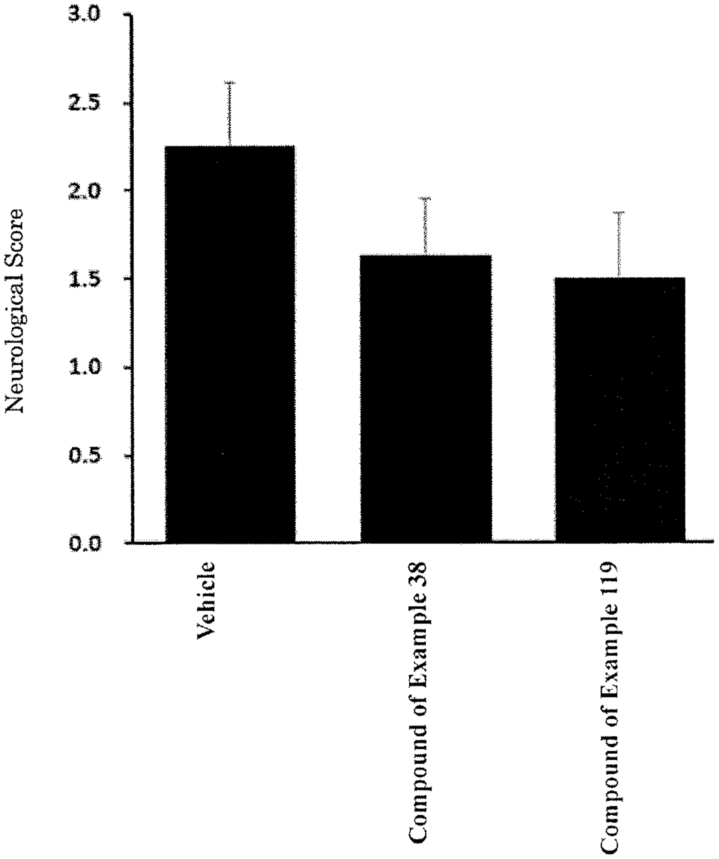
FIG. 4 shows the inhibitory effects of the compounds of Examples 38 and 119 on an increase in neurological score in a myelin oligodendrocyte glycoprotein-induced experimental autoimmune encephalomyelitis mouse model.

FIG. 4 shows the neurological score determined on the next day after the last administration of the test compound. The vertical axis represents neurological score (mean±standard error, n=8). On the horizontal axis, "Vehicle" represents the vehicle-dosing group, and "Compound of Example 38" represents the compound of Example 38—dosing group, and "Compound of Example 119" represents the compound of Example 119—dosing group.

The inoculation of the MOG35-55 dosing solution increased the average neurological score to 2.25 in the vehicle-dosing group. In contrast, the neurological score was decreased in the compound of Example 38—dosing group and the compound of Example 119—dosing group. The neurological score reduction rate by the test compounds were 27.8% in the compound of Example 38 and 33.3% in the compound of Example 119.

This result indicated that the compound of Example 38 and the compound of Example 119 exert a mitigating effect on the neurological symptoms of multiple sclerosis.

Example 179: Activity Assessment 5 in MOG-Induced Experimental Autoimmune Encephalomyelitis Mouse Model The compound of Example 33 was used as a test compound to assess the effect of the test compound on increase of neurological score in the MOG-induced experimental autoimmune encephalomyelitis mouse model. The study was performed in the same manner as in Example 176, except for the start day for administrating a test compound, the administered dose of a test compound, and the number of days for administering a test compound.

The test compound was administered orally at a dose of 10 mg/kg twice daily for a period of 15 days starting 52 days after the inoculation of the MOG35-55 dosing solution. A group of mice administered with the compound of Example 33 was termed the compound of Example 33—dosing group. Additionally, a group of mice administered with the vehicle was termed the vehicle-dosing group.

Figure 5:
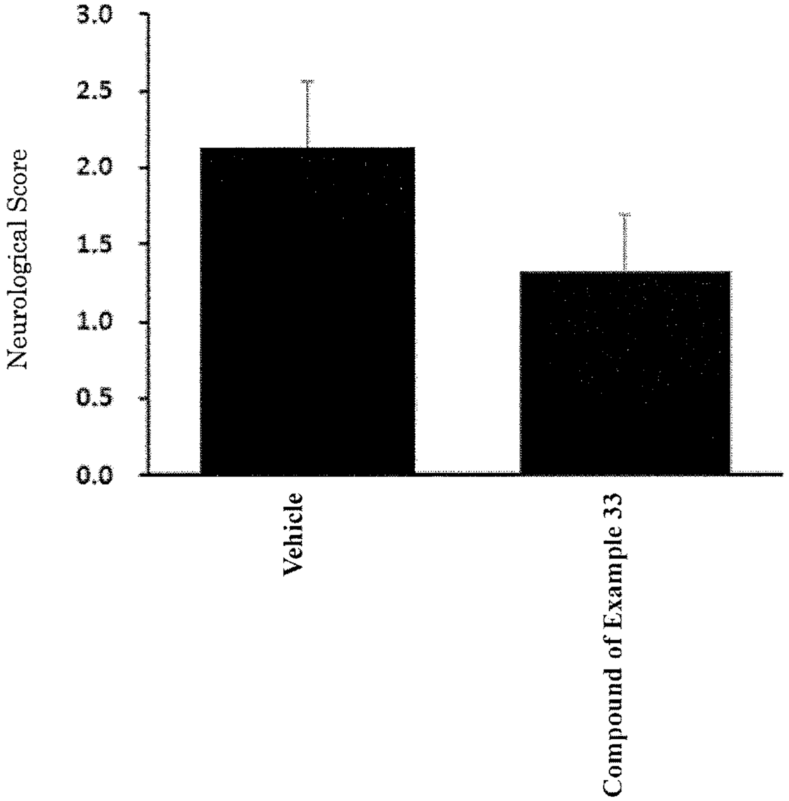
FIG. 5 shows the inhibitory effect of Example 33 on an increase in neurological score in a myelin oligodendrocyte glycoprotein-induced experimental autoimmune encephalomyelitis mouse model.

FIG. 5 shows the neurological score determined on the next day after the last administration of the test compound. The vertical axis represents neurological score (mean±standard error, n=8). On the horizontal axis, "Vehicle" represents the vehicle-dosing group, and "Compound of Example 33" represents the compound of Example 33—dosing group.

The inoculation of the MOG35-55 dosing solution increased the average neurological score to 2.13 in the vehicle-dosing group. In contrast, the neurological score was decreased in the compound of Example 33—dosing group. The neurological score reduction rate by the compound of Example 33 was 38.2%.

This result indicated that the compound of Example 33 exerts a mitigating effect on the neurological symptoms of multiple sclerosis.

Example 180: Activity Assessment 6 in MOG-Induced Experimental Autoimmune Encephalomyelitis Mouse Model The compound of Example 108 and the compound of Example 117 were used as test compounds to assess the effect of the test compounds on increase of neurological score in the MOG-induced experimental autoimmune encephalomyelitis mouse model. The study was performed in the same manner as in Example 176, except for the start day for administrating a test compound, the administered dose of a test compound, and the number of days for administering a test compound.

Each test compound was administered orally at a dose of 10 mg/kg twice daily for a period of 12 days starting 52 days after the inoculation of the MOG35-55 dosing solution. A group of mice administered with the compound of Example 108 was termed the compound of Example 108—dosing group, and a group of mice administered with the compound of Example 117 was termed the compound of Example 117—dosing group. Additionally, a group of mice administered with the vehicle was termed the vehicle-dosing group.

Figure 6:
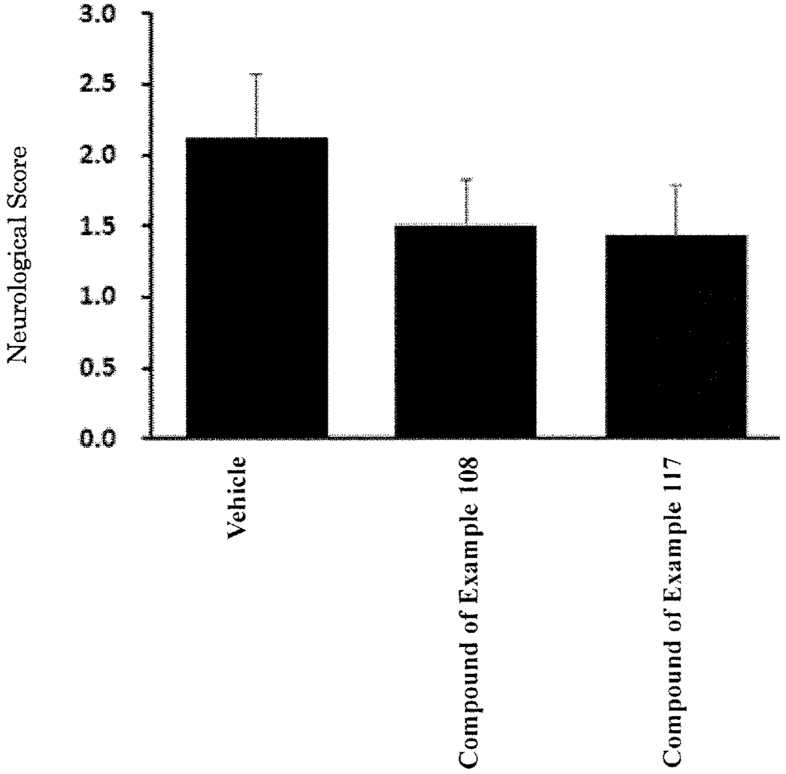
FIG. 6 shows the inhibitory effects of the compounds of Examples 108 and 117 on an increase in neurological score in a myelin oligodendrocyte glycoprotein-induced experimental autoimmune encephalomyelitis mouse model.

FIG. 6 shows the neurological score determined on the next day after the last administration of the test compound. The vertical axis represents neurological score (mean±standard error, n=8). On the horizontal axis, "Vehicle" represents the vehicle-dosing group, and "Compound of Example 108" represents the compound of Example 108—dosing group, and "Compound of Example 117" represents the compound of Example 117—dosing group.

The inoculation of the MOG35-55 dosing solution increased the average neurological score to 2.13 in the vehicle-dosing group. In contrast, the neurological score was decreased in the compound of Example 108—dosing group and the compound of Example 117—dosing group. The neurological score reduction rate by the test compounds were 29.4% in the compound of Example 108 and 32.4% in the compound of Example 117.

This result indicated that the compound of Example 108 and the compound of Example 117 exert a mitigating effect on the neurological symptoms of multiple sclerosis.

From the above results, it was indicated that the tetrahydroquinoline derivative (I) or a pharmaceutically acceptable salt thereof have inhibitory action against ferroptosis and have therapeutic or preventive effects on diseases, disorders or syndromes related to ferroptosis inhibition.

INDUSTRIAL APPLICABILITY

The tetrahydroquinoline derivative (I) or a pharmaceutically acceptable salt thereof have inhibitory action against ferroptosis and therefore can be used as therapeutic or preventive agents for diseases, disorders or syndromes related to ferroptosis inhibition such as multiple sclerosis.

The invention claimed is:

1. A tetrahydroquinoline derivative represented by general formula (I) below or a pharmaceutically acceptable salt thereof, (I)

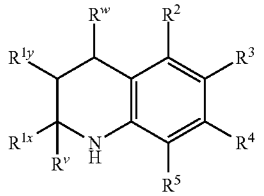

wherein for a combination of $R^2$, $R^4$, and $R^5$, all of $R^2$, $R^4$, and $R^5$ represent hydrogen; otherwise, one of $R^2$ and $R^4$ is fluorine, chlorine, methoxy, or methyl in which one hydrogen atom is optionally replaced by a hydroxy group, and both the other and $R^5$ represent hydrogen; otherwise, both $R^2$ and $R^4$ represent hydrogen, and $R^5$ is fluorine or chlorine;

$R^v$ is hydrogen; and $R^w$ is hydrogen;

when $R^{1x}$ is phenyl in which any one hydrogen atom in the phenyl group is optionally replaced by one substituent selected from the group consisting of halogen, $C_1$-$C_3$ alkyl in which any one to three hydrogen atoms are optionally replaced by a fluorine atom(s), $C_1$-$C_3$ alkoxy in which any one to three hydrogen atoms are optionally replaced by a fluorine atom(s), cyano, methoxycarbonyl, and —$NHCOR^8$, provided that m-cyanophenyl and p-(trifluoromethoxy)phenyl are excluded, or 5- or 6-membered heteroaryl in which any one hydrogen atom in the 5- or 6-membered heteroaryl is optionally replaced by a $C_1$-$C_3$ alkyl or $C_1$-$C_3$ alkoxy group, provided that 1-methyl-1H-pyrazol-4-yl and 6-methoxypyridin-3-yl are excluded, $R^3$ is $C_1$-$C_3$ alkyl in which any one to three hydrogen atoms are replaced by a fluorine atom(s), $C_1$-$C_3$ alkyl in which any one hydrogen atom is replaced by a hydroxy group, ethyl, propyl, isopropyl, 3-hydroxyoxetan-3-yl, methoxy in which any one to three hydrogen atoms are replaced by a fluorine atom(s), methoxycarbonyl, —$NR^9R^{10}$, —$CH_2NR^{11}R^{12}$, or —$CH_2CONR^{13}R^{14}$ wherein, when both $R^2$ and $R^4$ represent hydrogen and $R^5$ is fluorine or chlorine, $R^3$ is optionally hydrogen or fluorine, or when both $R^2$ and $R^5$ represent hydrogen and $R^4$ is fluorine or chlorine, $R^3$ is optionally fluorine, or when $R^2$ is methyl in which one hydrogen atom is optionally replaced by a hydroxy group, and both $R^4$ and $R^5$ represent hydrogen, $R^3$ is optionally hydrogen; or when $R^{1x}$ is hydrogen, phenyl in which any one hydrogen atom in the phenyl group is replaced by a $C_1$-$C_3$ alkyl in which any one hydrogen atom is replaced by a hydroxy group, —$CONR^6R^7$, aminosulfonyl, methylsulfonylamino, aminosulfonylamino, or $C_1$-$C_3$ alkylsulfonyl group; other-wise, the hydrogen atom at the meta-position of the phenyl group is replaced by a cyano group; otherwise, the hydrogen atom at the para-position of the phenyl group is replaced by a trifluoromethoxy group, or 1-methyl-1H-pyrazol-4-yl, or 6-methoxypyridin-3-yl, or when $R^{1x}$ is a fused ring group formed by fusing of a phenyl group and one ring selected from the group consisting of pyrrolidin-2-one, piperidin-2-one, and 1,3-dioxolane, wherein any one hydrogen atom in the fused ring group is optionally replaced by a methyl group, $R^3$ is hydrogen, fluorine, chlorine, bromine, $C_1$-$C_3$ alkyl in which any one to three hydrogen atoms are optionally replaced by a fluorine atom(s) or any one hydrogen atom is optionally replaced by a hydroxy group, 3-hydroxyoxetan-3-yl, hydroxy, methoxy in which any one to three hydrogen atoms are optionally replaced by a fluorine atom(s), methoxycarbonyl, —$NR^9R^{10}$, —$CH_2NR^{11}R^{12}$, or —$CH_2CONR^{13}R^{14}$;

$R^6$ and $R^7$ each independently represent hydrogen or $C_1$-$C_3$ alkyl, or $R^6$ and $R^7$, together with the nitrogen atom which is bound to $R^6$ and $R^7$, optionally form a piperidine ring, a morpholine ring, a piperazine ring, or an N-methylpiperazine ring;

$R^8$ is hydrogen or $C_1$-$C_3$ alkyl;

$R^9$ is hydrogen;

$R^{10}$ is hydrogen, —$COR^{15}$, or $C_1$-$C_3$ alkylsulfonyl, or $R^9$ and $R^{10}$ together represent —$(CH_2)_n$—;

n is 4 or 5;

$R^{11}$ and $R^{12}$ together represent —$(CH_2)_m$—;

m is 4 or 5, wherein any one of the methylene groups is optionally replaced by an oxygen atom;

$R^{13}$ is hydrogen or methyl;

$R^{14}$ is hydrogen, methyl, ethyl, isopropyl, tert-butyl, 2-hydroxyethyl, $C_3$ or $C_4$ cycloalkyl in which any one carbon atom is optionally replaced by an oxygen atom, or methyl which is substituted with a $C_3$ or $C_4$ cycloalkyl group in which any one carbon atom is optionally replaced by a nitrogen or oxygen atom, or $R^{13}$ and $R^{14}$, together with the nitrogen atom which is bound to $R^{13}$ and $R^{14}$, optionally form a pyrrolidine ring, a piperidine ring, a piperazine ring, a morpholine ring, a piperazinone ring, or an azetidine ring in which any two hydrogen atoms are optionally replaced by a methyl group(s) and/or a fluorine atom(s) or in which any one hydrogen atom is optionally replaced by a hydroxy or methoxy group;

$R^{15}$ is $C_1$-$C_5$ alkyl, $C_1$-$C_8$alkoxy, or —$NHR^{16}$;

$R^{16}$ is hydrogen or $C_1$-$C_5$ alkyl provided that methyl 2-(4-methoxyphenyl)-1,2,3,4-tetrahydroquinoline-6-carboxylate and 2-(benzo[d][1,3]dioxol-5-yl)-1,2,3,4-tetrahydroquinoline are excluded; and $R^{1y}$ is hydrogen, 4-hydroxymethylphenyl, 4-aminocarbonylphenyl, 4-acetamidophenyl, 4-aminosulfonylphenyl, or 4-methylsulfonylphenyl, provided that Rly is a substituent other than hydrogen when $R^{1x}$ is hydrogen, or that Rly is hydrogen when $R^{1x}$ is a substituent other than hydrogen.

2. The tetrahydroquinoline derivative or a pharmaceutically acceptable salt thereof according to claim 1, wherein for a combination of $R^2$, $R^4$, and $R^5$, all of $R^2$, $R^4$, and $R^5$ represent hydrogen; otherwise, one of $R^2$ and $R^4$ is fluorine, chlorine, methoxy, or methyl in which one hydrogen atom is optionally replaced by a hydroxy group, and both the other and $R^5$ represent hydrogen; otherwise, both $R^2$ and $R^4$ represent hydrogen, and $R^5$ is fluorine or chlorine;

$R^v$ is hydrogen; and $R^w$ is hydrogen;

wherein, when $R^{1x}$ is phenyl in which any one hydrogen atom in the phenyl group is optionally replaced by one substituent selected from the group consisting of halogen, $C_1$-$C_3$ alkyl in which any one to three hydrogen atoms are optionally replaced by a fluorine atom(s), $C_1$-$C_3$ alkoxy in which any one to three hydrogen atoms are optionally replaced by a fluorine atom(s), cyano, methoxycarbonyl, and —$NHCOR^8$, provided that m-cyanophenyl and p-(trifluoromethoxy)phenyl are excluded, or 5- or 6-membered heteroaryl in which any one hydrogen atom in the 5- or 6-membered heteroaryl is optionally replaced by a $C_1$-$C_3$ alkyl or $C_1$-$C_3$ alkoxy group, provided that 1-methyl-1H-pyrazol-4-yl and 6-methoxypyridin-3-yl are excluded, $R^3$ is $C_1$-$C_3$ alkyl in which any one to three hydrogen atoms are replaced by a fluorine atom(s), $C_1$-$C_3$ alkyl in which any one hydrogen atom is replaced by a hydroxy group, ethyl, propyl, isopropyl, 3-hydroxyoxetan-3-yl, methoxy in which any one to three hydrogen atoms are replaced by a fluorine atom(s), methoxycarbonyl, —$NR^9R^{10}$, —$CH_2NR^{11}R^{12}$, or —$CH_2CONR^{13}R$ 14 wherein, when both $R^2$ and $R^4$ represent hydrogen and $R^5$ is fluorine or chlorine, $R^3$ is optionally hydrogen or fluorine, or when both $R^2$ and $R^5$ represent hydrogen and $R^4$ is fluorine or chlorine, $R^3$ is optionally fluorine, or when $R^2$ is methyl in which one hydrogen atom is optionally replaced by a hydroxy group, and both $R^4$ and $R^5$ represent hydrogen, $R^3$ is optionally hydrogen; or when $R^{1x}$ is phenyl in which any one hydrogen atom in the phenyl group is replaced by a $C_1$-$C_3$ alkyl in which any one hydrogen atom is replaced by a hydroxy group, —$CONR^6R^7$, aminosulfonyl, or $C_1$-$C_3$ alkylsulfonyl group; otherwise, the hydrogen atom at the meta-position of the phenyl group is replaced by a cyano group; otherwise, the hydrogen atom at the para-position of the phenyl group is replaced by a trifluoromethoxy group, or 1-methyl-1H-pyrazol-4-yl, or 6-methoxypyridin-3-yl, or when $R^{1x}$ is a fused ring group formed by fusing of a phenyl group and one ring selected from the group consisting of pyrrolidin-2-one, piperidin-2-one, and 1,3-dioxolane, wherein any one hydrogen atom in the fused ring group is optionally replaced by a methyl group, $R^3$ is hydrogen, fluorine, chlorine, bromine, $C_1$-$C_3$ alkyl in which any one to three hydrogen atoms are optionally replaced by a fluorine atom(s) or any one hydrogen atom is optionally replaced by a hydroxy group, 3-hydroxyoxetan-3-yl, hydroxy, methoxy in which any one to three hydrogen atoms are optionally replaced by a fluorine atom(s), methoxycarbonyl, —$NR^9R^{10}$, $CH_2NR^{11}R^{12}$, or —$CH_2CONR^{13}R^{14}$, $R^6$ and $R^7$ each independently represent hydrogen or $C_1$-$C_3$ alkyl, or $R^6$ and $R^7$, together with the nitrogen atom which is bound to $R^6$ and $R^7$, optionally form a piperidine ring, a morpholine ring, a piperazine ring, or an N-methylpiperazine ring;

$R^8$ is hydrogen or $C_1$-$C_3$ alkyl;

$R^9$ is hydrogen;

$R^{10}$ is hydrogen, —$COR^{15}$, or $C_1$-$C_3$ alkylsulfonyl, or $R^9$ and $R^{10}$ together represent —$(CH_2)_n$—;

n is 4 or 5;

$R^{11}$ and $R^{12}$ together represent —$(CH_2)_m$—;

m is 4 or 5, wherein any one of the methylene groups is optionally replaced by an oxygen atom;

$R^{13}$ is hydrogen;

$R^{14}$ is hydrogen, methyl, ethyl, isopropyl, or tert-butyl, or $R^{13}$ and $R^{14}$, together with the nitrogen atom which is bound to $R^{13}$ and $R^{14}$, optionally form an azetidine ring in which any one hydrogen atom is optionally replaced by a hydroxy group;

$R^{15}$ is $C_1$-$C_5$ alkyl, $C_1$-$C_5$ alkoxy, or —$NHR^{16}$;

$R^{16}$ is hydrogen or $C_1$-$C_5$ alkyl provided that methyl 2-(4-methoxyphenyl)-1,2,3,4-tetra-hydroquinoline-6-carboxylate and 2-(benzo[d][1,3]dioxol-5-yl)-1,2,3,4-tetrahydroquinoline are excluded; and $R^{1y}$ is hydrogen.

3. The tetrahydroquinoline derivative or a pharmaceutically acceptable salt thereof according to claim 1, wherein the tetrahydroquinoline derivative or the pharmaceutically acceptable salt thereof is selected from the group consisting of:

(2-phenyl-1,2,3,4-tetrahydroquinolin-6-yl)methanol,
tert-butyl (2-phenyl-1,2,3,4-tetrahydroquinolin-6-yl)carbamate,
2-phenyl-1,2,3,4-tetrahydroquinoline-6-amine,
2-(benzo[d][1,3]dioxol-5-yl)-6-methoxy-1,2,3,4-tetrahydroquinoline,
(2-phenyl-1,2,3,4-tetrahydroquinolin-7-yl)methanol,
2-phenyl-6-(trifluoromethoxy)-1,2,3,4-tetrahydroquinoline,
2-(4-(trifluoromethoxy)phenyl)-1,2,3,4-tetrahydroquinoline,
(2-phenyl-1,2,3,4-tetrahydroquinolin-5-yl)methanol,
(2-(1,2,3,4-tetrahydroquinolin-2-yl)phenyl)methanol,
(3-(1,2,3,4-tetrahydroquinolin-2-yl)phenyl)methanol,
(4-(1,2,3,4-tetrahydroquinolin-2-yl)phenyl)methanol,
6,7-difluoro-2-phenyl-1,2,3,4-tetrahydroquinoline,
N-methyl-3-(1,2,3,4-tetrahydroquinolin-2-yl)benzamide,
4-(1,2,3,4-tetrahydroquinolin-2-yl)benzamide,
4-(1,2,3,4-tetrahydroquinolin-2-yl)benzenesulfonamide,
3-(1,2,3,4-tetrahydroquinolin-2-yl)benzamide,
3-(1,2,3,4-tetrahydroquinolin-2-yl)benzonitrile,
6-isopropyl-2-phenyl-1,2,3,4-tetrahydroquinoline,
2-(1-methyl-1H-pyrazol-4-yl)-1,2,3,4-tetrahydroquinoline,
2-(6-methoxypyridin-3-yl)-1,2,3,4-tetrahydroquinoline,
4-((2-phenyl-1,2,3,4-tetrahydroquinolin-6-yl)methyl)morpholine,
2-(2-phenyl-1,2,3,4-tetrahydroquinolin-6-yl)propan-2-ol,
2-(2-phenyl-1,2,3,4-tetrahydroquinolin-6-yl)acetamide,
N-(tert-butyl)-2-(2-phenyl-1,2,3,4-tetrahydroquinolin-6-yl)acetamide,
3-(2-phenyl-1,2,3,4-tetrahydroquinolin-6-yl)oxetan-3-ol,
N-(2-phenyl-1,2,3,4-tetrahydroquinolin-6-yl)acetamide,
1-(3-hydroxyazetidin-1-yl)-2-(2-phenyl-1,2,3,4-tetrahydroquinolin-6-yl) ethan-1-one,
2-phenyl-6-(piperidin-1-yl)-1,2,3,4-tetrahydroquinoline,
N-(2-phenyl-1,2,3,4-tetrahydroquinolin-6-yl)methanesulfonamide,
4-(6-(3-(tert-butyl)ureido)-1,2,3,4-tetrahydroquinolin-2-yl)benzamide,
2-(4-(methylsulfonyl)phenyl)-1,2,3,4-tetrahydroquinoline,
3,3-dimethyl-N-(2-phenyl-1,2,3,4-tetrahydroquinolin-6-yl)butanamide,
1-(tert-butyl)-3-(2-phenyl-1,2,3,4-tetrahydroquinolin-6-yl)urea,
2-(4-(1,2,3,4-tetrahydroquinolin-2-yl)phenyl)propan-2-ol,
3-(1,2,3,4-tetrahydroquinolin-2-yl)benzenesulfonamide,
2-(1,2,3,4-tetrahydroquinolin-2-yl)benzenesulfonamide,
N-(2-phenyl-1,2,3,4-tetrahydroquinolin-6-yl)pivalamide,
1-(2-phenyl-1,2,3,4-tetrahydroquinolin-6-yl)urea,
1,2,3,3',4,4'-hexahydro-[2,6'-biquinolin]-2'(1'H)-one,
1'-methyl-1,2,3,3',4,4'-hexahydro-[2,6'-biquinolin]-2'(1'H)-one,
N,N-diethyl-4-(1,2,3,4-tetrahydroquinolin-2-yl)benzamide, N-ethyl-4-(1,2,3,4-tetrahydroquinolin-2-yl)benzamide,
5-(1,2,3,4-tetrahydroquinolin-2-yl)isoindolin-1-one,
(4-methylpiperazin-1-yl)(4-(1,2,3,4-tetrahydroquinolin-2-yl)phenyl)methanone,
piperidin-1-yl(4-(1,2,3,4-tetrahydroquinolin-2-yl)phenyl) methanone, and
morpholino (4-(1,2,3,4-tetrahydroquinolin-2-yl)phenyl) methanone, and pharmaceutically acceptable salts thereof.

4. The tetrahydroquinoline derivative or a pharmaceutically acceptable salt thereof according to claim 1, wherein the tetrahydroquinoline derivative or the pharmaceutically acceptable salt thereof is selected from the group consisting of:
tert-butyl (2-phenyl-1,2,3,4-tetrahydroquinolin-6-yl)carbamate,
(4-(1,2,3,4-tetrahydroquinolin-2-yl)phenyl)methanol,
4-(1,2,3,4-tetrahydroquinolin-2-yl)benzamide,
4-(1,2,3,4-tetrahydroquinolin-2-yl)benzenesulfonamide,
4-((2-phenyl-1,2,3,4-tetrahydroquinolin-6-yl)methyl) morpholine,
2-(2-phenyl-1,2,3,4-tetrahydroquinolin-6-yl)acetamide,
N-(2-phenyl-1,2,3,4-tetrahydroquinolin-6-yl)acetamide,
1-(3-hydroxyazetidin-1-yl)-2-(2-phenyl-1,2,3,4-tetrahydroquinolin-6-yl) ethan-1-one,
N-(2-phenyl-1,2,3,4-tetrahydroquinolin-6-yl)methanesulfonamide,
4-(6-(3-(tert-butyl)ureido)-1,2,3,4-tetrahydroquinolin-2-yl)benzamide,
3,3-dimethyl-N-(2-phenyl-1,2,3,4-tetrahydroquinolin-6-yl)butanamide,
1-(tert-butyl)-3-(2-phenyl-1,2,3,4-tetrahydroquinolin-6-yl)urea,
N-(2-phenyl-1,2,3,4-tetrahydroquinolin-6-yl)pivalamide,
1-(2-phenyl-1,2,3,4-tetrahydroquinolin-6-yl)urea, and
5-(1,2,3,4-tetrahydroquinolin-2-yl)isoindolin-1-one, and pharmaceutically acceptable salts thereof.

5. The tetrahydroquinoline derivative or a pharmaceutically acceptable salt thereof according to claim 1, wherein
for a combination of $R^2$, $R^4$, and $R^5$, all of $R^2$, $R^4$, and $R^5$ represent hydrogen; otherwise, one of $R^2$ and $R^4$ is fluorine, chlorine, or methyl, and both the other and $R^5$ represent hydrogen;
$R^v$ is hydrogen; and
$R^w$ is hydrogen;
wherein, when $R^{1x}$ is phenyl in which the hydrogen atom at the para-position of the phenyl group is optionally replaced by one substituent selected from the group consisting of fluorine, trifluoromethyl, cyano, and acetamide,
$R^3$ is trifluoromethoxy, hydroxymethyl, or —$CH_2CONR^{13}R^{14}$ wherein, when $R^2$ is methyl and both $R^4$ and $R^5$ represent hydrogen, $R^3$ is optionally hydrogen; or
when $R^{1x}$ is phenyl in which the hydrogen atom at the para-position of the phenyl group is re-placed by a trifluoromethoxy, aminocarbonyl, aminosulfonyl, methylsulfonylamino, or methyl-sulfonyl group, $R^3$ is hydrogen, fluorine, chlorine, methyl, hydroxymethyl, trifluoromethoxy, or —$CH_2CONR^{13}R^{14}$;
$R^{13}$ is hydrogen or methyl;
$R^{14}$ is tert-butyl, 2-hydroxyethyl, cyclopropyl, cyclobutyl, or oxetan-3-yl, or
$R^{13}$ and $R^{14}$, together with the nitrogen atom which is bound to $R^{13}$ and $R^{14}$, optionally form a piperazine ring, a piperazin-2-one ring, an azetidine ring, a 3,3-difluoroazetidine ring, a 3,3-dimethylazetidine ring, a 3-hydroxyazetidine ring, or a 3-methoxyazetidine ring; and
$R^{1y}$ is hydrogen.

6. The tetrahydroquinoline derivative or a pharmaceutically acceptable salt thereof according to claim 1, wherein the tetrahydroquinoline derivative or the pharmaceutically acceptable salt thereof is selected from the group consisting of:
4-(1,2,3,4-tetrahydroquinolin-2-yl)benzenesulfonamide,
4-(1,2,3,4-tetrahydroquinolin-2-yl)benzamide,
1-(3-hydroxyazetidin-1-yl)-2-(2-phenyl-1,2,3,4-tetrahydroquinolin-6-yl) ethan-1-one,
4-(6-methyl-1,2,3,4-tetrahydroquinolin-2-yl)benzamide,
4-(6-methyl-1,2,3,4-tetrahydroquinolin-2-yl)benzenesulfonamide,
4-(7-methyl-1,2,3,4-tetrahydroquinolin-2-yl)benzenesulfonamide,
4-(7-methyl-1,2,3,4-tetrahydroquinolin-2-yl)benzamide,
4-(6-fluoro-1,2,3,4-tetrahydroquinolin-2-yl)benzenesulfonamide,
4-(5-methyl-1,2,3,4-tetrahydroquinolin-2-yl)benzenesulfonamide,
4-(6-chloro-1,2,3,4-tetrahydroquinolin-2-yl)benzenesulfonamide,
4-(7-fluoro-1,2,3,4-tetrahydroquinolin-2-yl)benzenesulfonamide,
4-(6-chloro-1,2,3,4-tetrahydroquinolin-2-yl)benzamide,
4-(6-fluoro-1,2,3,4-tetrahydroquinolin-2-yl)benzamide,
4-(5-chloro-1,2,3,4-tetrahydroquinolin-2-yl)benzenesulfonamide,
4-(5-fluoro-1,2,3,4-tetrahydroquinolin-2-yl)benzamide,
4-(5-chloro-1,2,3,4-tetrahydroquinolin-2-yl)benzamide,
1-(3-methoxyazetidin-1-yl)-2-(2-phenyl-1,2,3,4-tetrahydroquinolin-6-yl) ethan-1-one,
N-(oxetan-3-yl)-2-(2-phenyl-1,2,3,4-tetrahydroquinolin-6-yl)acetamide,
1-(3,3-difluoroazetidin-1-yl)-2-(2-phenyl-1,2,3,4-tetrahydroquinolin-6-yl) ethan-1-one,
N-(2-hydroxyethyl)-N-methyl-2-(2-phenyl-1,2,3,4-tetrahydroquinolin-6-yl)acetamide,
1-(azetidin-1-yl)-2-(2-phenyl-1,2,3,4-tetrahydroquinolin-6-yl) ethan-1-one,
N-cyclopropyl-2-(2-phenyl-1,2,3,4-tetrahydroquinolin-6-yl)acetamide,
N-cyclobutyl-2-(2-phenyl-1,2,3,4-tetrahydroquinolin-6-yl)acetamide,
2-(2-phenyl-1,2,3,4-tetrahydroquinolin-6-yl)-1-(piperazin-1-yl) ethan-1-one, and
4-(1,2,3,4-tetrahydroquinolin-3-yl)benzenesulfonamide, and pharmaceutically acceptable salts thereof.

7. A pharmaceutical composition containing a tetrahydroquinoline derivative represented by general formula (I) below or a pharmaceutically acceptable salt thereof as an active ingredient, (I)

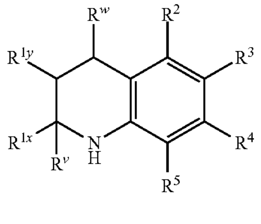

wherein $R^{1x}$ is hydrogen, aryl, or 5- or 6-membered heteroaryl having one or two heteroatoms selected from nitrogen, oxygen, and sulfur atoms, wherein any one or two hydrogen atoms in the aryl or the 5- or 6-membered heteroaryl are each independently optionally replaced by a halogen atom(s), a $C_1$-$C_3$ alkyl in which any one to three hydrogen atoms are each independently optionally replaced by a hydroxy group(s) or a fluorine atom(s), $C_1$-$C_3$ alkoxy in which any one to three hydrogen atoms are optionally replaced by a fluorine atom(s), cyano, methoxycarbonyl, —$CONR^6R^7$, —$NHCOR^8$, aminosulfonyl, $C_1$-$C_3$ alkylsulfonylamino, aminosulfonylamino, or $C_1$-$C_3$ alkylsulfonyl group(s), or when the aryl group is phenyl, $R^{1x}$ is optionally a fused ring group formed by fusing of the phenyl group and one ring selected from the group consisting of 5- or 6-membered lactam rings and 5- or 6-membered saturated heterocycles each containing one or two oxygen atoms as the atom constituting the ring, wherein any one hydrogen atom in the fused ring group is optionally replaced by a methyl group;

$R^{1y}$ is hydrogen, phenyl, 4-hydroxymethylphenyl, 4-aminocarbonylphenyl, 4-aceta-midophenyl, 4-aminosulfonylphenyl, 4-methylsulfonylphenyl, or 3-pyridyl, except that both $R^{1x}$ and $R^{1y}$ represent hydrogen;

for a combination of $R^2$, $R^4$, and $R^5$, all of $R^2$, $R^4$, and $R^5$ represent hydrogen, or one of $R^2$, $R^4$, and $R^5$ is halogen, methoxy, or methyl in which one hydrogen atom is optionally replaced by a hydroxy group, and the other two are hydrogen;

$R^3$ is hydrogen, halogen, $C_1$-$C_3$ alkyl in which any one to three hydrogen atoms are each independently optionally replaced by a hydroxy group(s) or a fluorine atom(s), 3-hydroxyoxetan-3-yl, hydroxy, $C_1$-$C_3$ alkoxy in which any one to three hydrogen atoms are optionally replaced by a fluorine atom(s), methoxycarbonyl, —$NR^9R^{10}$, —$CH_2NR^{11}R^{12}$, or —$CH_2CONR^{13}R^{14}$, $R^6$ and $R^7$ each independently represent hydrogen or $C_1$-$C_3$ alkyl, or $R^6$ and $R^7$ together represent —$(CH_2)_h$—;

h is an integer of 3 to 5, wherein any one of the methylene groups is optionally replaced by an oxygen atom, —NH—, or —$N(CH_3)$—;

$R^8$ is hydrogen or $C_1$-$C_3$ alkyl;

$R^9$ and $R^{10}$ each independently represent hydrogen, —$COR^{15}$, or $C_1$-$C_3$ alkylsulfonyl, or $R^9$ and $R^{10}$ together represent —$(CH_2)_n$—;

n is an integer of 3 to 6;

$R^{11}$ and $R^{12}$ together represent —$(CH_2)_m$—;

m is an integer of 3 to 5, wherein any one of the methylene groups is optionally replaced by an oxygen atom;

$R^{13}$ and $R^{14}$ each independently represent hydrogen, $C_1$-$C_5$ alkyl group, 2-hydroxyethyl, $C_3$ or $C_4$ cycloalkyl in which any one carbon atom is optionally replaced by an oxygen atom, or methyl which is substituted with a $C_3$ or $C_4$ cycloalkyl group in which any one carbon atom is optionally replaced by a nitrogen or oxygen atom, or $R^{13}$ and $R^{14}$ together represent —$(CH_2)_k$— in which any one or two hydrogen atoms are optionally replaced by a fluorine atom(s), a methyl group(s), a hydroxy group (s), or a methoxy group(s) or in which any one $CH_2$ group is optionally replaced by an oxygen atom, a nitrogen atom, or —CONH—;

k is an integer of 3 to 5;

$R^{15}$ is $C_1$-$C_5$ alkyl, $C_1$-$C_5$ alkoxy, or —$NHR^{16}$;

$R^{16}$ is hydrogen or $C_1$-$C_8$alkyl;

$R^v$ is hydrogen, methyl in which any one hydrogen atom is optionally replaced by a hydroxy or methoxycarbonyl group, or methoxycarbonyl; and $R^w$ is hydrogen, methyl, hydroxymethyl, or methoxycarbonyl, provided that 2-phenyl-1,2,3,4-tetrahydroquinoline and 3-phenyl-1,2,3,4-tetrahydroquinoline are excluded.

8. The pharmaceutical composition according to claim 7, containing the tetrahydroquinoline derivative or a pharmaceutically acceptable salt thereof as an active ingredient, wherein $R^{1x}$ is phenyl in which any one hydrogen atom in the phenyl group is optionally replaced by a halogen atom or a $C_1$-$C_3$ alkyl in which any one to three hydrogen atoms are optionally replaced by a fluorine atom(s) or any one hydrogen atom is optionally replaced by a hydroxy group, $C_1$-$C_3$ alkoxy in which any one to three hydrogen atoms are optionally replaced by a fluorine atom(s), cyano, methoxycarbonyl, —$CONR^6R^7$, —$NHCOR^8$, aminosulfonyl, or $C_1$-$C_3$ alkylsulfonyl group) or 5- or 6-membered heteroaryl selected from the group consisting of furyl, thienyl, pyrrolyl, imidazolyl, pyrazolyl, thiazolyl, isothiazolyl, oxazolyl, isoxazolyl, and pyridyl, wherein any one hydrogen atom in the 5- or 6-membered heteroaryl is optionally replaced by a $C_1$-$C_3$ alkyl or $C_1$-$C_3$ alkoxy group, or $R^{1x}$ is optionally a fused ring group formed by fusing of a phenyl group and one ring selected from the group consisting of pyrrolidin-2-one, piperidin-2-one, and 1,3-dioxolane, wherein any one hydrogen atom in the fused ring group is optionally replaced by a methyl group;

$R^{1y}$ is hydrogen;

for a combination of $R^2$, $R^4$, and $R^5$, all of $R^2$, $R^4$, and $R^5$ represent hydrogen; otherwise, one of $R^2$ and $R^4$ is fluorine, chlorine, methoxy, or methyl in which one hydrogen atom is optionally replaced by a hydroxy group, and both the other and $R^5$ represent hydrogen; otherwise, both $R^2$ and $R^4$ represent hydrogen, and $R^5$ is fluorine or chlorine;

$R^3$ is hydrogen, fluorine, chlorine, bromine, $C_1$-$C_3$ alkyl in which any one to three hydrogen atoms are optionally replaced by a fluorine atom(s) or any one hydrogen atom is optionally replaced by a hydroxy group, 3-hydroxyoxetan-3-yl, hydroxy, methoxy in which any one to three hydrogen atoms are optionally replaced by a fluorine atom(s), methoxycarbonyl, —$NR^9R^{10}$, —$CH_2NR^{11}R^{12}$, or —$CH_2CONR^{13}R^{14}$, $R^6$ and $R^7$ each independently represent hydrogen or $C_1$-$C_3$ alkyl, or $R^6$ and $R^7$, together with the nitrogen atom which is bound to $R^6$ and $R^7$, optionally form a piperidine ring, a morpholine ring, a piperazine ring, or an N-methylpiperazine ring;

$R^8$ is hydrogen or $C_1$-$C_3$ alkyl;

$R^9$ is hydrogen;

$R^{10}$ is hydrogen, —$COR^{15}$, or $C_1$-$C_3$ alkylsulfonyl, or $R^9$ and $R^{10}$ together represent —$(CH_2)_n$—;

n is 4 or 5;

$R^{11}$ and $R^{12}$ together represent —$(CH_2)_m$—;

m is 4 or 5, wherein any one of the methylene groups is optionally replaced by an oxygen atom;

$R^{13}$ is hydrogen;

$R^{14}$ is hydrogen, methyl, ethyl, isopropyl, or tert-butyl, or $R^{13}$ and $R^{14}$, together with the nitrogen atom which is bound to $R^{13}$ and $R^{14}$, optionally form an azetidine ring in which any one hydrogen atom is optionally replaced by a hydroxy group;

$R^{15}$ is $C_1$-$C_5$ alkyl, $C_1$-$C_5$ alkoxy, or —$NHR^{16}$;

$R^{16}$ is hydrogen or $C_1$-$C_5$ alkyl;

$R^v$ is hydrogen; and $R^w$ is hydrogen, provided that 2-phenyl-1,2,3,4-tetrahydroquinoline is excluded.

9. The pharmaceutical composition according to claim 7, containing the tetrahydroquinoline derivative or a pharmaceutically acceptable salt thereof as an active ingredient, wherein $R^{1x}$ is phenyl or 5- or 6-membered heteroaryl selected from the group consisting of furyl, thienyl, pyrrolyl, imidazolyl, pyrazolyl, thiazolyl, isothiazolyl, oxazolyl, isoxazolyl, and pyridyl;

$R^{1y}$ is hydrogen;

for a combination of $R^2$, $R^4$, and $R^5$, all of $R^2$, $R^4$, and $R^5$ represent hydrogen; otherwise, one of $R^2$ and $R^4$ is fluorine, chlorine, methoxy, or methyl in which one hydrogen atom is optionally replaced by a hydroxy group, and both the other and $R^5$ represent hydrogen; otherwise, both $R^2$ and $R^4$ represent hydrogen, and $R^5$ is fluorine or chlorine;

$R^v$ is hydrogen; and $R^w$ is hydrogen;

wherein, when $R^{1x}$ is phenyl in which any one hydrogen atom in the phenyl group is optionally replaced by one substituent selected from the group consisting of halogen, $C_1$-$C_3$ alkyl in which any one to three hydrogen atoms are optionally replaced by a fluorine atom(s), $C_1$-$C_3$ alkoxy in which any one to three hydrogen atoms are optionally replaced by a fluorine atom(s), cyano, methoxycarbonyl, and —$NHCOR^8$, provided that m-cyanophenyl and p-(trifluoromethoxy)phenyl are excluded, or 5- or 6-membered heteroaryl in which any one hydrogen atom in the 5- or 6-membered heteroaryl is optionally replaced by a $C_1$-$C_3$ alkyl or $C_1$-$C_3$ alkoxy group, provided that 1-methyl-1H-pyrazol-4-yl and 6-methoxypyridin-3-yl are excluded, $R^3$ is $C_1$-$C_3$ alkyl in which any one to three hydrogen atoms are replaced by a fluorine atom(s), $C_1$-$C_3$ alkyl in which any one hydrogen atom is replaced by a hydroxy group, ethyl, propyl, isopropyl, 3-hydroxyoxetan-3-yl, methoxy in which any one to three hydrogen atoms are replaced by a fluorine atom(s), methoxycarbonyl, —$NR^9R^{10}$, —$CH_2NR^{11}R^{12}$, or —$CH_2CONR^{13}$R 14 wherein, when both $R^2$ and $R^4$ represent hydrogen and $R^5$ is fluorine or chlorine, $R^3$ is optionally hydrogen or fluorine, or when both $R^2$ and $R^5$ represent hydrogen and $R^4$ is fluorine or chlorine, $R^3$ is optionally fluorine, or when $R^2$ is methyl in which one hydrogen atom is optionally replaced by a hydroxy group, and both $R^4$ and $R^5$ represent hydrogen, $R^3$ is optionally hydrogen;

$R^8$ is hydrogen or $C_1$-$C_3$ alkyl;

$R^9$ is hydrogen;

$R^{10}$ is hydrogen, —$COR^{15}$, or $C_1$-$C_3$ alkylsulfonyl, or $R^9$ and $R^{10}$ together represent —$(CH_2)_n$—;

n is 4 or 5;

$R^{11}$ and $R^{12}$ together represent —$(CH_2)_m$—;

m is 4 or 5, wherein any one of the methylene groups is optionally replaced by an oxygen atom;

$R^{13}$ is hydrogen;

$R^{14}$ is hydrogen, methyl, ethyl, isopropyl, or tert-butyl, or $R^{13}$ and $R^{14}$, together with the nitrogen atom which is bound to $R^{13}$ and $R^{14}$, optionally form an azetidine ring in which any one hydrogen atom is optionally replaced by a hydroxy group;

$R^{15}$ is $C_1$-$C_5$ alkyl, $C_1$-$C_5$ alkoxy, or —$NHR^{16}$, and $R^{16}$ is hydrogen or $C_1$-$C_5$ alkyl; or when $R^{1x}$ is phenyl (any one hydrogen atom in the phenyl group is replaced by a $C_1$-$C_3$ alkyl in which any one hydrogen atom is replaced by a hydroxy group, —$CONR^6R^7$, aminosulfonyl, or $C_1$-$C_3$ alkylsulfonyl group; otherwise, the hydrogen atom at the meta-position of the phenyl group is replaced by a cyano group; otherwise, the hydrogen atom at the para-position of the phenyl group is replaced by a trifluoromethoxy group), 1-methyl-1H-pyrazol-4-yl, or 6-methoxypyridin-3-yl, or when $R^{1x}$ is a fused ring group formed by fusing of a phenyl group and one ring selected from the group consisting of pyrrolidin-2-one, piperidin-2-one, and 1,3-dioxolane, wherein any one hydrogen atom in the fused ring group is optionally replaced by a methyl group, $R^3$ is hydrogen, fluorine, chlorine, bromine, $C_1$-$C_3$ alkyl in which any one to three hydrogen atoms are optionally replaced by a fluorine atom(s) or any one hydrogen atom is optionally replaced by a hydroxy group, 3-hydroxyoxetan-3-yl, hydroxy, methoxy in which any one to three hydrogen atoms are optionally replaced by a fluorine atom(s), methoxycarbonyl, —$NR^9R^{10}$, —$CH_2NR^{11}R^{12}$, or —$CH_2CONR^{13}R^{14}$, $R^6$ and $R^7$ each independently represent hydrogen or $C_1$-$C_3$ alkyl, or $R^6$ and $R^7$, together with the nitrogen atom which is bound to $R^6$ and $R^7$, optionally form a piperidine ring, a morpholine ring, a piperazine ring, or an N-methylpiperazine ring;

$R^9$ is hydrogen;

$R^{10}$ is hydrogen, —$COR^{15}$, or $C_1$-$C_3$ alkylsulfonyl, or $R^9$ and $R^{10}$ together represent —$(CH_2)_n$—;

n is 4 or 5;

$R^{11}$ and $R^{12}$ together represent —$(CH_2)_m$—;

m is 4 or 5, wherein any one of the methylene groups is optionally replaced by an oxygen atom;

$R^{13}$ is hydrogen;

$R^{14}$ is hydrogen, methyl, ethyl, isopropyl, or tert-butyl, or $R^{13}$ and $R^{14}$, together with the nitrogen atom which is bound to $R^{13}$ and $R^{14}$, optionally form an azetidine ring in which any one hydrogen atom is optionally replaced by a hydroxy group;

$R^{15}$ is $C_1$-$C_8$alkyl, $C_1$-$C_5$ alkoxy, or —$NHR^{16}$; and $R^{16}$ is hydrogen or $C_1$-$C_5$ alkyl.

10. The pharmaceutical composition according to claim 7, wherein the tetrahydroquinoline derivative or the pharmaceutically acceptable salt thereof is selected from the group consisting of:

(2-phenyl-1,2,3,4-tetrahydroquinolin-6-yl)methanol, tert-butyl (2-phenyl-1,2,3,4-tetrahydroquinolin-6-yl)carbamate, 2-phenyl-1,2,3,4-tetrahydroquinoline-6-amine, 2-(benzo[d][1,3]dioxol-5-yl)-6-methoxy-1,2,3,4-tetrahydroquinoline, (2-phenyl-1,2,3,4-tetrahydroquinolin-7-yl)methanol, 2-phenyl-6-(trifluoromethoxy)-1,2,3,4-tetrahydroquinoline, 2-(4-(trifluoromethoxy)phenyl)-1,2,3,4-tetrahydroquinoline, (2-phenyl-1,2,3,4-tetrahydroquinolin-5-yl)methanol, (2-(1,2,3,4-tetrahydroquinolin-2-yl)phenyl)methanol,
(3-(1,2,3,4-tetrahydroquinolin-2-yl)phenyl)methanol,
(4-(1,2,3,4-tetrahydroquinolin-2-yl)phenyl)methanol,
6,7-difluoro-2-phenyl-1,2,3,4-tetrahydroquinoline,
N-methyl-3-(1,2,3,4-tetrahydroquinolin-2-yl)benzamide,
4-(1,2,3,4-tetrahydroquinolin-2-yl)benzamide,
4-(1,2,3,4-tetrahydroquinolin-2-yl)benzenesulfonamide,
3-(1,2,3,4-tetrahydroquinolin-2-yl)benzamide,
3-(1,2,3,4-tetrahydroquinolin-2-yl)benzonitrile,
6-isopropyl-2-phenyl-1,2,3,4-tetrahydroquinoline,
2-(1-methyl-1H-pyrazol-4-yl)-1,2,3,4-tetrahydroquinoline,
2-(6-methoxypyridin-3-yl)-1,2,3,4-tetrahydroquinoline,
4-((2-phenyl-1,2,3,4-tetrahydroquinolin-6-yl)methyl) morpholine,
2-(2-phenyl-1,2,3,4-tetrahydroquinolin-6-yl)propan-2-ol,
2-(2-phenyl-1,2,3,4-tetrahydroquinolin-6-yl)acetamide,
N-(tert-butyl)-2-(2-phenyl-1,2,3,4-tetrahydroquinolin-6-yl)acetamide,
3-(2-phenyl-1,2,3,4-tetrahydroquinolin-6-yl)oxetan-3-ol,
N-(2-phenyl-1,2,3,4-tetrahydroquinolin-6-yl)acetamide,
1-(3-hydroxyazetidin-1-yl)-2-(2-phenyl-1,2,3,4-tetrahydroquinolin-6-yl) ethan-1-one,
2-phenyl-6-(piperidin-1-yl)-1,2,3,4-tetrahydroquinoline,
N-(2-phenyl-1,2,3,4-tetrahydroquinolin-6-yl)methanesulfonamide,
4-(6-(3-(tert-butyl)ureido)-1,2,3,4-tetrahydroquinolin-2-yl)benzamide,
2-(4-(methylsulfonyl)phenyl)-1,2,3,4-tetrahydroquinoline,
3,3-dimethyl-N-(2-phenyl-1,2,3,4-tetrahydroquinolin-6-yl)butanamide,
1-(tert-butyl)-3-(2-phenyl-1,2,3,4-tetrahydroquinolin-6-yl)urea,
2-(4-(1,2,3,4-tetrahydroquinolin-2-yl)phenyl)propan-2-ol,
3-(1,2,3,4-tetrahydroquinolin-2-yl)benzenesulfonamide,
2-(1,2,3,4-tetrahydroquinolin-2-yl)benzenesulfonamide,
N-(2-phenyl-1,2,3,4-tetrahydroquinolin-6-yl)pivalamide,
1-(2-phenyl-1,2,3,4-tetrahydroquinolin-6-yl)urea,
1,2,3,3',4,4'-hexahydro-[2,6'-biquinolin]-2' (1'H)-one,
1'-methyl-1,2,3,3',4,4'-hexahydro-[2,6'-biquinolin]-2' (1'H)-one,
N,N-diethyl-4-(1,2,3,4-tetrahydroquinolin-2-yl)benzamide,
N-ethyl-4-(1,2,3,4-tetrahydroquinolin-2-yl)benzamide,
5-(1,2,3,4-tetrahydroquinolin-2-yl)isoindolin-1-one,
(4-methylpiperazin-1-yl) (4-(1,2,3,4-tetrahydroquinolin-2-yl)phenyl)methanone,
piperidin-1-yl (4-(1,2,3,4-tetrahydroquinolin-2-yl)phenyl)methanone, and
morpholino (4-(1,2,3,4-tetrahydroquinolin-2-yl)phenyl) methanone, and pharmaceutically acceptable salts thereof.

11. The pharmaceutical composition according to claim 7, wherein the tetrahydroquinoline derivative or the pharmaceutically acceptable salt thereof is selected from the group consisting of:
tert-butyl (2-phenyl-1,2,3,4-tetrahydroquinolin-6-yl)carbamate,
(4-(1,2,3,4-tetrahydroquinolin-2-yl)phenyl)methanol,
4-(1,2,3,4-tetrahydroquinolin-2-yl)benzamide,
4-(1,2,3,4-tetrahydroquinolin-2-yl)benzenesulfonamide,
4-((2-phenyl-1,2,3,4-tetrahydroquinolin-6-yl)methyl) morpholine,
2-(2-phenyl-1,2,3,4-tetrahydroquinolin-6-yl)acetamide,
N-(2-phenyl-1,2,3,4-tetrahydroquinolin-6-yl)acetamide,
1-(3-hydroxyazetidin-1-yl)-2-(2-phenyl-1,2,3,4-tetrahydroquinolin-6-yl) ethan-1-one,
N-(2-phenyl-1,2,3,4-tetrahydroquinolin-6-yl)methanesulfonamide,
4-(6-(3-(tert-butyl)ureido)-1,2,3,4-tetrahydroquinolin-2-yl)benzamide,
3,3-dimethyl-N-(2-phenyl-1,2,3,4-tetrahydroquinolin-6-yl)butanamide,
1-(tert-butyl)-3-(2-phenyl-1,2,3,4-tetrahydroquinolin-6-yl)urea,
N-(2-phenyl-1,2,3,4-tetrahydroquinolin-6-yl)pivalamide,
1-(2-phenyl-1,2,3,4-tetrahydroquinolin-6-yl)urea, and
5-(1,2,3,4-tetrahydroquinolin-2-yl)isoindolin-1-one, and pharmaceutically acceptable salts thereof.

12. The pharmaceutical composition according to claim 7, containing the tetrahydroquinoline derivative or a pharmaceutically acceptable salt thereof as an active ingredient, wherein
$R^{1x}$ is phenyl in which the hydrogen atom at the para-position of the phenyl group is optionally replaced by a fluorine atom, a trifluoromethyl, trifluoromethoxy, cyano, aminocarbonyl, acetamide, aminosulfonyl, methylsulfonylamino, or methylsulfonyl group;
$R^{1y}$ is hydrogen;
for a combination of $R^2$, $R^4$, and $R^5$, all of $R^2$, $R^4$, and $R^5$ represent hydrogen; otherwise, one of $R^2$ and $R^4$ is fluorine, chlorine, or methyl, and both the other and $R^5$ represent hydrogen;
$R^3$ is hydrogen, fluorine, chlorine, methyl, hydroxymethyl, trifluoromethoxy, or —$CH_2CONR^{13}R^{14}$,
$R^{13}$ is hydrogen or methyl;
$R^{14}$ is tert-butyl, 2-hydroxyethyl, cyclopropyl, cyclobutyl, or oxetan-3-yl, or
$R^{13}$ and $R^{14}$, together with the nitrogen atom which is bound to $R^{13}$ and $R^{14}$, optionally form a piperazine ring, a piperazin-2-one ring, an azetidine ring, a 3,3-difluoroazetidine ring, a 3,3-dimethylazetidine ring, a 3-hydroxyazetidine ring, or a 3-methoxyazetidine ring;
$R^v$ is hydrogen; and
$R^w$ is hydrogen, provided that 2-phenyl-1,2,3,4-tetrahydroquinoline is excluded.

13. The pharmaceutical composition according to claim 7, wherein the tetrahydroquinoline derivative or the pharmaceutically acceptable salt thereof is selected from the group consisting of:
4-(1,2,3,4-tetrahydroquinolin-2-yl)benzenesulfonamide,
4-(1,2,3,4-tetrahydroquinolin-2-yl)benzamide,
1-(3-hydroxyazetidin-1-yl)-2-(2-phenyl-1,2,3,4-tetrahydroquinolin-6-yl) ethan-1-one,
4-(6-methyl-1,2,3,4-tetrahydroquinolin-2-yl)benzamide,
4-(6-methyl-1,2,3,4-tetrahydroquinolin-2-yl)benzenesulfonamide,
4-(7-methyl-1,2,3,4-tetrahydroquinolin-2-yl)benzenesulfonamide,
4-(7-methyl-1,2,3,4-tetrahydroquinolin-2-yl)benzamide,
4-(6-fluoro-1,2,3,4-tetrahydroquinolin-2-yl)benzenesulfonamide,
4-(5-methyl-1,2,3,4-tetrahydroquinolin-2-yl)benzenesulfonamide,
4-(6-chloro-1,2,3,4-tetrahydroquinolin-2-yl)benzenesulfonamide,
4-(7-fluoro-1,2,3,4-tetrahydroquinolin-2-yl)benzenesulfonamide,
4-(6-chloro-1,2,3,4-tetrahydroquinolin-2-yl)benzamide,
4-(6-fluoro-1,2,3,4-tetrahydroquinolin-2-yl)benzamide,
4-(5-chloro-1,2,3,4-tetrahydroquinolin-2-yl)benzenesulfonamide, 4-(5-fluoro-1,2,3,4-tetrahydroquinolin-2-yl)benzamide,
4-(5-chloro-1,2,3,4-tetrahydroquinolin-2-yl)benzamide,
1-(3-methoxyazetidin-1-yl)-2-(2-phenyl-1,2,3,4-tetrahydroquinolin-6-yl) ethan-1-one,
N-(oxetan-3-yl)-2-(2-phenyl-1,2,3,4-tetrahydroquinolin-6-yl)acetamide,
1-(3,3-difluoroazetidin-1-yl)-2-(2-phenyl-1,2,3,4-tetrahydroquinolin-6-yl) ethan-1-one,
N-(2-hydroxyethyl)-N-methyl-2-(2-phenyl-1,2,3,4-tetrahydroquinolin-6-yl)acetamide,
1-(azetidin-1-yl)-2-(2-phenyl-1,2,3,4-tetrahydroquinolin-6-yl) ethan-1-one,
N-cyclopropyl-2-(2-phenyl-1,2,3,4-tetrahydroquinolin-6-yl)acetamide,
N-cyclobutyl-2-(2-phenyl-1,2,3,4-tetrahydroquinolin-6-yl)acetamide,
2-(2-phenyl-1,2,3,4-tetrahydroquinolin-6-yl)-1-(piperazin-1-yl) ethan-1-one, and
4-(1,2,3,4-tetrahydroquinolin-3-yl)benzenesulfonamide, and pharmaceutically acceptable salts thereof.

14. The pharmaceutical composition according to claim 7, that inhibits ferroptosis.

15. The pharmaceutical composition according to claim 14, that treats multiple sclerosis.

16. A method of inhibiting ferroptosis in a patient in need thereof, wherein the method comprises administering an effective amount of the pharmaceutical composition according to claim 7 to a subject in need thereof.

17. The method according to claim 16, wherein the ferroptosis is patient in need thereof is diagnosed with multiple sclerosis.

* * * * *